(12) United States Patent
Kim et al.

(10) Patent No.: US 11,329,230 B2
(45) Date of Patent: May 10, 2022

(54) ORGANIC LIGHT-EMITTING DEVICE

(71) Applicant: Samsung Display Co., Ltd, Yongin-si (KR)

(72) Inventors: Younsun Kim, Yongin-si (KR); Seulong Kim, Yongin-si (KR); Dongwoo Shin, Yongin-si (KR); Jungsub Lee, Yongin-si (KR); Jino Lim, Yongin-si (KR); Hyein Jeong, Yongin-si (KR)

(73) Assignee: SAMSUNG DISPLAY CO., LTD., Yongin-si (KR)

(*) Notice: Subject to any disclaimer, the term of this patent is extended or adjusted under 35 U.S.C. 154(b) by 402 days.

(21) Appl. No.: 15/467,889

(22) Filed: Mar. 23, 2017

(65) Prior Publication Data
US 2017/0317294 A1 Nov. 2, 2017

(30) Foreign Application Priority Data

Apr. 29, 2016 (KR) .................. 10-2016-0053530

(51) Int. Cl.
*H01L 51/54* (2006.01)
*H01L 51/00* (2006.01)
*C07C 13/00* (2006.01)
*C07C 15/00* (2006.01)
*C07F 7/08* (2006.01)
*C07C 211/00* (2006.01)
*C09K 11/02* (2006.01)
*C09K 11/06* (2006.01)
*H01L 51/50* (2006.01)

(52) U.S. Cl.
CPC .......... *H01L 51/0067* (2013.01); *C07C 13/00* (2013.01); *C07C 15/00* (2013.01); *C07C 211/00* (2013.01); *C07F 7/08* (2013.01); *C09K 11/025* (2013.01); *C09K 11/06* (2013.01); *H01L 51/006* (2013.01); *H01L 51/0052* (2013.01); *H01L 51/0058* (2013.01); *H01L 51/0059* (2013.01); *H01L 51/0061* (2013.01); *H01L 51/0077* (2013.01); *H01L 51/0081* (2013.01); *H01L 51/0094* (2013.01); *C09K 2211/1007* (2013.01); *C09K 2211/1011* (2013.01); *C09K 2211/1014* (2013.01); *C09K 2211/1029* (2013.01); *C09K 2211/185* (2013.01); *H01L 51/0054* (2013.01); *H01L 51/0072* (2013.01); *H01L 51/0073* (2013.01); *H01L 51/0074* (2013.01); *H01L 51/0085* (2013.01); *H01L 51/5004* (2013.01); *H01L 51/5036* (2013.01); *H01L 51/5056* (2013.01); *H01L 51/5072* (2013.01); *H01L 51/5092* (2013.01); *H01L 2251/552* (2013.01)

(58) Field of Classification Search
CPC . C09K 11/06; C09K 2211/00; C09K 2211/10; C09K 2211/1007; C09K 2211/1014; C09K 2211/1029; C09K 2211/185; C07F 7/08; C07C 211/00; C07C 13/00; C07C 15/00; H01L 51/0032; H01L 51/005; H01L 51/0052; H01L 51/0058; H01L 51/0059; H01L 51/006; H01L 51/0061; H01L 51/0054; H01L 51/0067; H01L 51/0072; H01L 51/0073; H01L 51/0077; H01L 51/0081; H01L 51/0094; H01L 51/0085; H01L 51/0074; H01L 51/50; H01L 51/5004; H01L 51/5012; H01L 51/5016; H01L 51/5056; H01L 51/5036; H01L 51/5072; H01L 51/509; H01L 2251/552
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 6,195,142 | B1* | 2/2001 | Gyotoku | H01L 51/5243 313/504 |
| 9,196,842 | B2 | 11/2015 | Kato et al. | |
| 2003/0230980 | A1* | 12/2003 | Forrest | H01L 51/5016 313/600 |
| 2005/0064233 | A1* | 3/2005 | Matsuura | C07C 13/567 428/690 |
| 2006/0186796 | A1* | 8/2006 | Yabe | H01L 51/0058 313/504 |

(Continued)

FOREIGN PATENT DOCUMENTS

| | | |
|---|---|---|
| CN | 1668719 | 9/2005 |
| CN | 102292841 | 12/2011 |

(Continued)

OTHER PUBLICATIONS

Machine translation of KR-101493482. (Year: 2015).*

(Continued)

*Primary Examiner* — Andrew K Bohaty
(74) *Attorney, Agent, or Firm* — Kile Park Reed & Houtteman PLLC

(57) ABSTRACT

Provided is an organic light-emitting device including a first compound and a second compound that offers low driving voltage and high efficiency. The organic light-emitting device includes an emission layer between a first electrode and a second electrode, and an electron transport region between the second electrode and the emission layer. The electron transport region includes the first compound. A hole transport region between the first electrode and the emission layer includes the second compound.

22 Claims, 4 Drawing Sheets

(56) References Cited

U.S. PATENT DOCUMENTS

| | | | |
|---|---|---|---|
| 2010/0001636 A1* | 1/2010 | Yabunouchi | H01L 51/0061 313/504 |
| 2011/0284831 A1 | 11/2011 | Kaiser et al. | |
| 2012/0161119 A1* | 6/2012 | Yabunouchi | C07D 307/91 257/40 |
| 2012/0214993 A1* | 8/2012 | Aihara | C07D 239/26 544/180 |
| 2012/0248426 A1 | 10/2012 | Kato | |
| 2012/0299468 A1 | 11/2012 | Tsai et al. | |
| 2015/0065730 A1 | 3/2015 | Montenegro et al. | |
| 2015/0115239 A1 | 4/2015 | Pflumm et al. | |
| 2015/0179940 A1 | 6/2015 | Mujica-Fernaud et al. | |
| 2015/0179953 A1 | 6/2015 | Mujica-Fernaud et al. | |
| 2015/0207075 A1 | 7/2015 | Mujica-Fernaud et al. | |
| 2015/0243891 A1 | 8/2015 | Kato et al. | |
| 2015/0287921 A1 | 10/2015 | Kato et al. | |
| 2016/0064669 A1 | 3/2016 | Kato | |
| 2016/0181526 A1 | 6/2016 | Kato et al. | |
| 2018/0053900 A1* | 2/2018 | Eum | H01L 51/0052 |

FOREIGN PATENT DOCUMENTS

| | | | | |
|---|---|---|---|---|
| CN | 102574813 | | 7/2012 | |
| EP | 2 468 731 | | 6/2012 | |
| JP | 2006073581 A | * | 3/2006 | |
| JP | 2012-519944 A | | 8/2012 | |
| JP | 2014-9196 A | | 1/2014 | |
| KR | 10-2012-0052993 A | | 5/2012 | |
| KR | 10-2012-0066076 A | | 6/2012 | |
| KR | 20130102669 A | * | 9/2013 | |
| KR | 10-2014-0027389 A | | 3/2014 | |
| KR | 10-2014-0087804 A | | 7/2014 | |
| KR | 10-2014-0119731 A | | 10/2014 | |
| KR | 10-2014-0146103 A | | 12/2014 | |
| KR | 10-2015-0016325 A | | 2/2015 | |
| KR | 101493482 B1 | * | 2/2015 | H01L 51/0074 |
| KR | 10-2015-0048137 A | | 5/2015 | |
| KR | 10-2015-0065944 A | | 6/2015 | |
| KR | 10-1593368 B1 | | 2/2016 | |
| KR | 10-2016-0044299 A | | 4/2016 | |
| WO | 2015/053403 A1 | | 4/2015 | |
| WO | 2016060332 A1 | | 4/2016 | |
| WO | WO-2016105141 A2 | * | 6/2016 | H01L 51/50 |

OTHER PUBLICATIONS

Machine translation of KR-20130102669. (Year: 2013).*
Machine translation of JP-2006073581. (Year: 2006).*
Partial European Search Report for TGL/83417EP1 dated Sep. 27, 2017.
European Communication corresponding to European Patent Application No. 17168821.1 dated Nov. 28 , 2019 351 pages.

* cited by examiner

| 190 |
|-----|
| 150 |
| 110 |

| 190 |
|---|
| 150 |
| 110 |
| 210 |

| 220 |
|-----|
| 190 |
| 150 |
| 110 |

| |
|---|
| 220 |
| 190 |
| 150 |
| 110 |
| 210 |

ORGANIC LIGHT-EMITTING DEVICE

CROSS-REFERENCE TO RELATED APPLICATION

This application claims the benefit of Korean Patent Application No. 10-2016-0053530 filed on Apr. 29, 2016 in the Korean Intellectual Property Office, the disclosure of which is incorporated herein in its entirety by reference.

BACKGROUND

1. Field

This disclosure relates to an organic light-emitting device.

2. Description of the Related Art

Organic light-emitting devices are self-emission devices and have wide viewing angles, high contrast ratios, short response times, and excellent brightness, driving voltage, and response speed characteristics, compared to other devices that are currently in the market.

For example, an organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons may transit from an excited state to a ground state, thereby generating light.

SUMMARY

One or more embodiments include an organic light-emitting device having low driving voltage and high efficiency.

Additional aspects will be set forth in part in the description which follows and, in part, will be apparent from the description, or may be learned by practice of the presented embodiments.

According to one or more embodiments, an organic light-emitting device includes a first electrode, a second electrode facing the first electrode, an emission layer between the first electrode and the second electrode, a hole transport region between the first electrode and the emission layer, and an electron transport region between the emission layer and the second electrode, wherein the electron transport region includes a first compound represented by one selected from Formulae 1A to 1D, and the hole transport region includes a second compound represented by Formula 2:

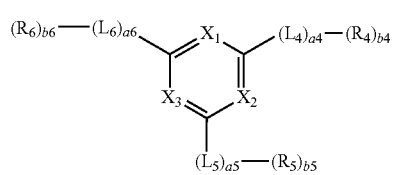
<Formula 1A>

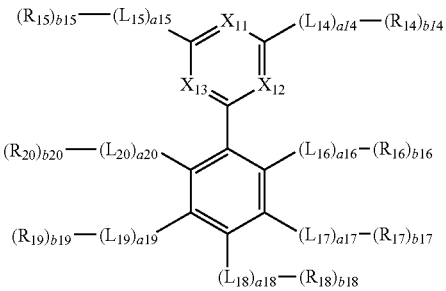
<Formula 1B>

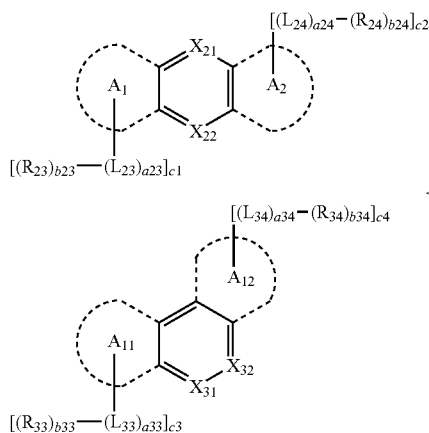
<Formula 1C>

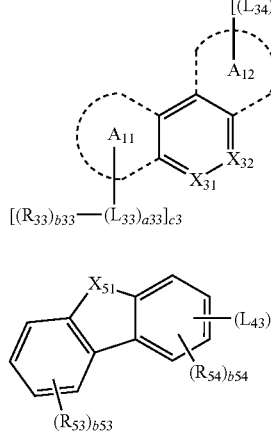
<Formula 1D>

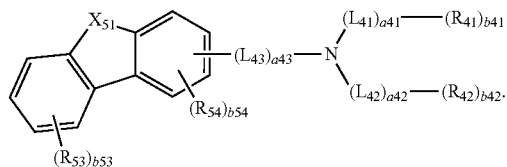
<Formula 2>

In Formulae 1A to 1D and 2, each of ring $A_1$ and ring $A_2$ is independently be a $C_5$-$C_{60}$ carbocyclic group or a $C_1$-$C_{30}$ heterocyclic group, each of ring $A_{11}$ and ring $A_{12}$ is independently be a $C_1$-$C_{30}$ heterocyclic group, $X_1$ may be selected from N and C-[$(L_1)_{a1}$-$(R_1)_{b1}$], $X_2$ may be selected from N and C-[$(L_2)_{a2}$-$(R_2)_{b2}$], and $X_3$ may be selected from N and C-[$(L_3)_{a3}$-$(R_3)_{b3}$], wherein at least one selected from $X_1$ to $X_3$ may be N, $X_{11}$ may be selected from N and C-[$(L_{11})_{a11}$-$(R_{11})_{b11}$], $X_{12}$ may be selected from N and C-[$(L_{12})_{a12}$-$(R_{12})_{b12}$], and $X_{13}$ may be selected from N and C-[$(L_{13})_{a13}$-$(R_{13})_{b13}$], wherein at least one selected from $X_{11}$ to $X_{13}$ may be N, $X_{21}$ may be selected from N and C-[$(L_{21})_{a21}$-$(R_{21})_{b21}$], and $X_{22}$ may be selected from N and C-[$(L_{22})_{a22}$-$(R_{22})_{b22}$], wherein at least one of $X_{21}$ and $X_{22}$ may be N, $X_{31}$ may be selected from N and C-[$(L_{31})_{a31}$-$(R_{31})_{b31}$], and $X_{32}$ may be selected from N and C-[$(L_{32})_{a32}$-$(R_{32})_{b32}$], $X_{51}$ may be selected from oxygen (O), sulfur (S), selenium (Se), and Si($R_{51}$)($R_{52}$), $L_1$ to $L_6$, $L_{11}$ to $L_{24}$, $L_{31}$ to $L_{34}$, and $L_{41}$ to $L_{43}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, each of a1 to a6, a11 to a24, a31 to a34, and a41 to a43 is independently an integer selected from 0 to 5, each of $R_1$ to $R_6$, $R_{11}$ to $R_{24}$, $R_{31}$ to $R_{34}$, and $R_{51}$ to $R_{54}$ is independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), each of $R_{41}$ and $R_{42}$ is selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, each of b1 to b6, b11 to b24, b31 to b34, b53, and b54 is independently ban integer selected from 0 to 5, each of b41 and b42 is independently an integer selected from 1 to 5, each of c1 to c4 is independently be an integer selected from 1 to 10, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group, wherein neither of a carbazole ring and a spiro-bifluorene ring is included in Formulae 1A to 1D, and neither of a carbazole ring and a fluorene ring is included in Formula 2.

BRIEF DESCRIPTION OF THE DRAWINGS

These and/or other aspects will become apparent and more readily appreciated from the following description of the embodiments, taken in conjunction with the accompanying drawings in which:

FIGS. 1, 2, 3, and 4 are each a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

An organic light-emitting device according to an embodiment may include: a first electrode; a second electrode facing the first electrode; an emission layer between the first electrode and the second electrode; a hole transport region between the first electrode and the emission layer; and an electron transport region between the emission layer and the second electrode, wherein the electron transport region may include a first compound, and the hole transport region may include a second compound.

The first electrode may be an anode, and the second electrode may be a cathode. The first electrode and the second electrode will be understood by referring to descriptions below.

The first compound may be represented by one selected from Formulae 1A to 1D, and the second compound may be represented by Formula 2:

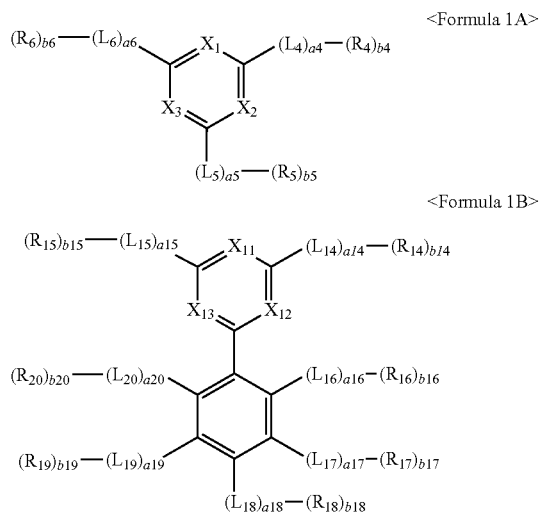

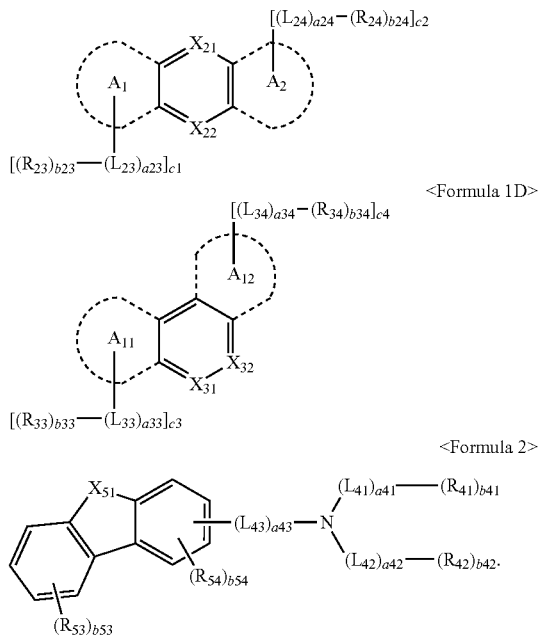

In Formulae 1C and 1D, ring $A_1$ and ring $A_2$ may each independently be a $C_5$-$C_{60}$ carbocyclic group or a $C_1$-$C_{30}$ heterocyclic group, and ring $A_{11}$ and ring $A_{12}$ may each independently be a $C_1$-$C_{30}$ heterocyclic group.

For example, ring $A_1$ and ring $A_2$ in Formula 1C may each independently be selected from a benzene group, a naphthalene group, an anthracene group, an indene group, a fluorene group, a pyridine group, a pyrimidine group, a pyrazine group, a pyridazine group, a quinoline group, and an isoquinoline group, and ring $A_{11}$ and ring $A_{12}$ in Formula 1D may each independently be selected from a pyridine group, a pyrimidine group, a pyrazine group, a pyridazine group, a quinoline group, and an isoquinoline group.

In an embodiment, ring $A_1$ and ring $A_2$ in Formula 1C may each independently be a benzene group or a naphthalene group, and ring $A_{11}$ and ring $A_{12}$ in Formula 1D may be a pyridine group or a pyrimidine group, but embodiments are not limited thereto.

In Formulae 1A to 1D, $X_1$ may be selected from N and C-[$(L_1)_{a1}$-$(R_1)_{b1}$], $X_2$ may be selected from N and C-[$(L_2)_{a2}$-$(R_2)_{b2}$], and $X_3$ may be selected from N and C-[$(L_3)_{a3}$-$(R_3)_{b3}$], wherein at least one selected from $X_1$ to $X_3$ is N. In Formulae 1A to 1D, $X_{11}$ may be N and C-[$(L_{11})_{a11}$-$(R_{11})_{b11}$], $X_{12}$ may be selected from N and C-[$(L_{12})_{a12}$-$(R_{12})_{b12}$], and $X_{13}$ may be selected from N and C-[$(L_{13})_{a13}$-$(R_{13})_{b13}$], wherein at least one selected from $X_{11}$ to $X_{13}$ is N. In Formulae 1A to 1D, $X_{21}$ may be selected from N and C-[$(L_{21})_{a21}$-$(R_{21})_{b21}$], and $X_{22}$ may be selected from N and C-[$(L_{22})_{a22}$-$(R_{22})_{b22}$], wherein at least one of $X_{21}$ and $X_{22}$ is N. In Formulae 1A to 1D, $X_{31}$ may be selected from N and C-[$(L_{31})_{a31}$-$(R_{31})_{b31}$], and $X_{32}$ may be selected from N and C-[$(L_{32})_{a32}$-$(R_{32})_{b32}$].

That is, the first compound may include a nitrogen-containing heterocyclic group having *=N—*' as a ring-forming moiety. Here, $L_1$ to $L_3$, $L_{11}$ to $L_{13}$, $L_{21}$, $L_{22}$, $L_{31}$, $L_{32}$, a1 to a3, a11 to a13, a21, a22, a31, and a32 may each independently be understood by referring to the descriptions thereof provided herein.

In one embodiment, in Formula 1A,
i) $X_1$ to $X_3$ may be N; or
ii) $X_1$ may be N, $X_2$ may be C-[$(L_2)_{a2}$-$(R_2)_{b2}$], and $X_3$ may be N,
in Formula 1B,
i) $X_{11}$ to $X_{13}$ may be N,
ii) $X_{11}$ may be C-[$(L_{11})_{a11}$-$(R_{11})_{b11}$], $X_{12}$ may be N, and $X_{13}$ may be N,
iii) $X_{11}$ may be N, $X_{12}$ may be C-[$(L_{12})_{a12}$-$(R_{12})_{b12}$], and $X_{13}$ may be N; or
iv) $X_{11}$ may be N, $X_{12}$ may be C-[$(L_{12})_{a12}$-$(R_{12})_{b12}$], and $X_{13}$ may be C-[$(L_{13})_{a13}$-$(R_{12})_{b13}$],
in Formula 1C,
i) $X_{21}$ may be C-[$(L_{21})_{a21}$-$(R_{21})_{b21}$], and $X_{22}$ may be N; or
ii) $X_{21}$ may be N, and $X_{22}$ may be C-[$(L_{22})_{a22}$-$(R_{22})_{b22}$],
in Formula 1D,
i) $X_{31}$ may be C-[$(L_{31})_{a31}$-$(R_{31})_{b31}$], and $X_{32}$ may be C-[$(L_{32})_{a32}$-$(R_{32})_{b32}$],
ii) $X_{31}$ may be N, and $X_{32}$ may be C-[$(L_{32})_{a32}$-$(R_{32})_{b32}$]; or
iii) $X_{31}$ may be C-[$(L_{31})_{a31}$-$(R_{31})_{b31}$], and $X_{32}$ may be N.

In Formula 2, $X_{51}$ may be selected from oxygen (O), sulfur (S), selenium (Se), and Si($R_{51}$)($R_{52}$). Here, $R_{51}$ and $R_{52}$ may each independently be understood by referring to the descriptions thereof provided herein.

In an embodiment, in Formula 2, $X_{51}$ may be O or S, but embodiments are not limited thereto.

In Formulae 1A to 1D and 2, $L_1$ to $L_6$, $L_{11}$ to $L_{24}$, $L_{31}$ to $L_{34}$, and $L_{41}$ to $L_{43}$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, in Formulae 1A to 1D, $L_1$ to $L_6$, $L_{11}$ to $L_{24}$, and $L_{31}$ to $L_{34}$ may each independently be selected from:

a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group; and a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), in Formula 2, $L_{41}$ to $L_{43}$ may each independently be selected from:

a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group; and a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, —Si($Q_{31}$)($Q_{32}$)($Q_{33}$), —N($Q_{31}$)($Q_{32}$), and —B($Q_{31}$)($Q_{32}$), and $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an embodiment, $L_1$ to $L_6$, $L_{11}$ to $L_{24}$, and $L_{31}$ to $L_{34}$ in Formulae 1A to 1D may each independently be a group represented by one selected from Formulae 3-1 to 3-100, and $L_{41}$ to $L_{43}$ in Formula 2 may each independently be a group represented by one selected from Formulae 3-1 to 3-30 (wherein $Y_1$ in Formulae 3-17 to 3-20 is O or S):

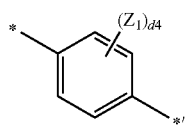

Formula 3-1

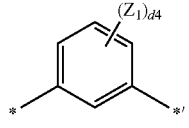

Formula 3-2

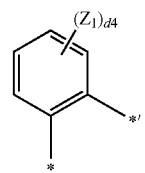

Formula 3-3

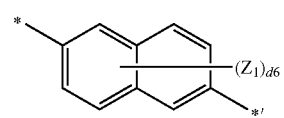

Formula 3-4

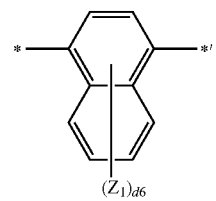

Formula 3-5

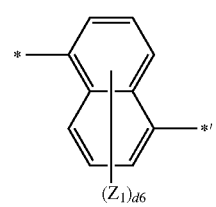

Formula 3-6

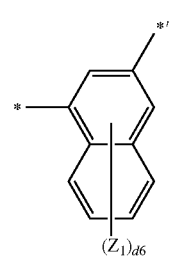

Formula 3-7

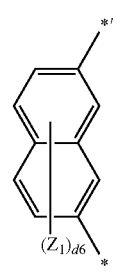

Formula 3-8

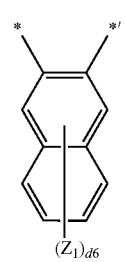

Formula 3-9

Formula 3-10 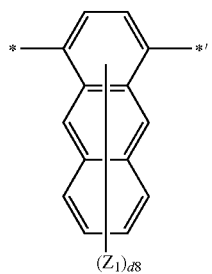
Formula 3-11 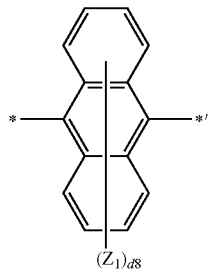
Formula 3-12 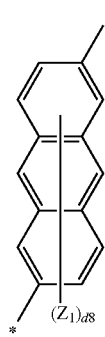
Formula 3-13 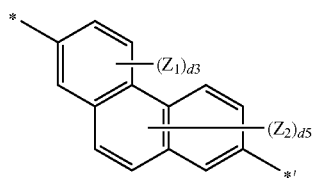
Formula 3-14 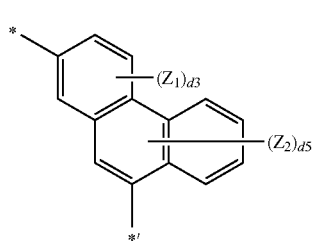
Formula 3-15 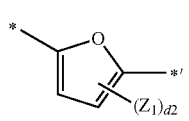
Formula 3-16 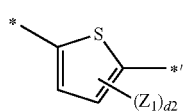
Formula 3-17 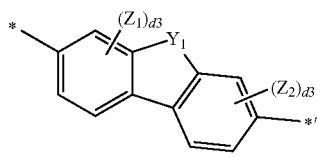
Formula 3-18 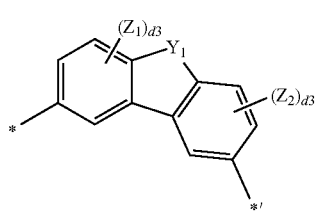
Formula 3-19 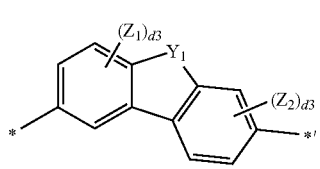
Formula 3-20 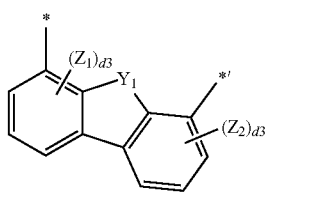
Formula 3-21 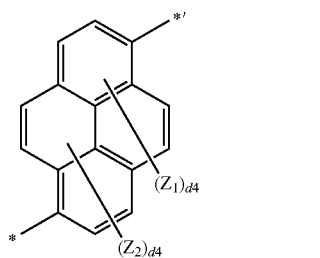
Formula 3-22 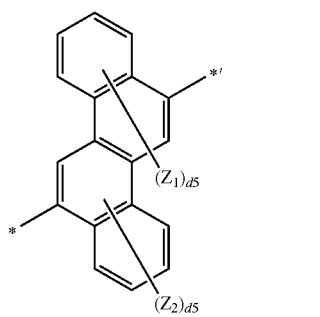
Formula 3-23 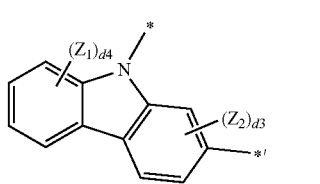

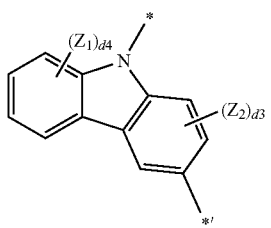
Formula 3-24
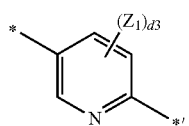
Formula 3-25
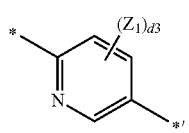
Formula 3-26
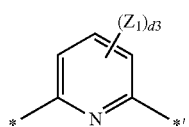
Formula 3-27
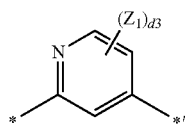
Formula 3-28
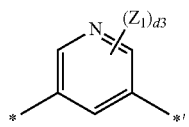
Formula 3-29
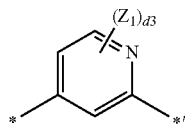
Formula 3-30
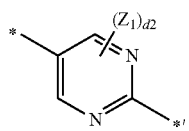
Formula 3-31
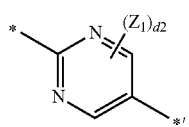
Formula 3-32
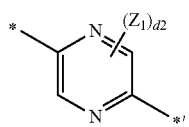
Formula 3-33
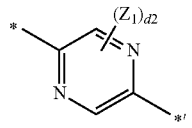
Formula 3-34
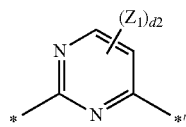
Formula 3-35
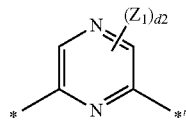
Formula 3-36
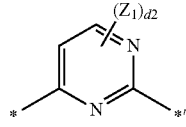
Formula 3-37
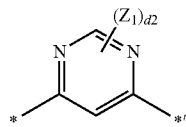
Formula 3-38
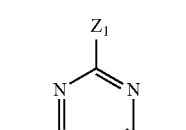
Formula 3-39
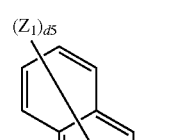
Formula 3-40
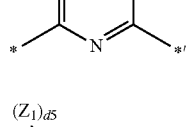
Formula 3-41
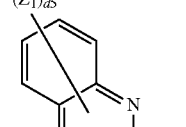
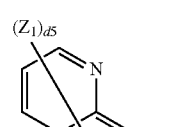
Formula 3-42

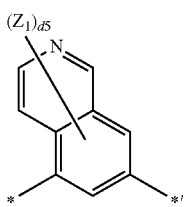
Formula 3-43
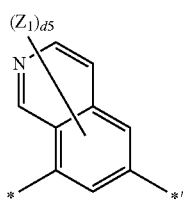
Formula 3-44
Formula 3-45
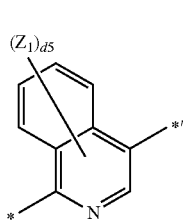
Formula 3-46
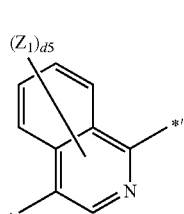
Formula 3-47
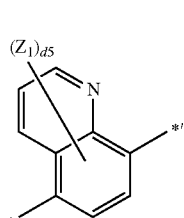
Formula 3-48
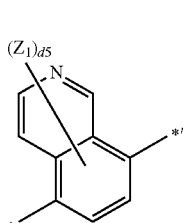
Formula 3-49
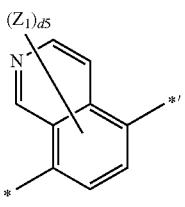
Formula 3-50
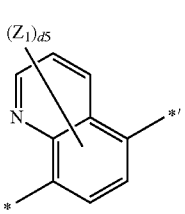
Formula 3-51
Formula 3-52
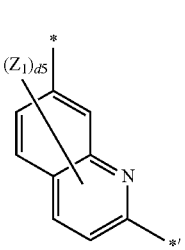
Formula 3-53
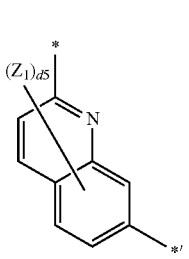
Formula 3-54
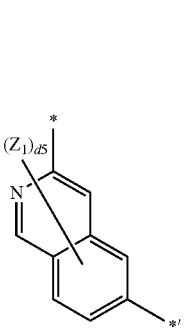
Formula 3-55

-continued
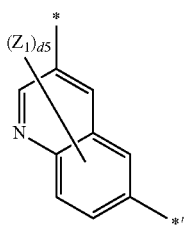
Formula 3-56
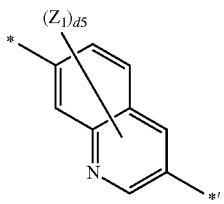
Formula 3-63
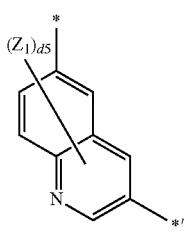
Formula 3-57
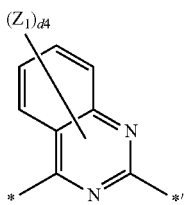
Formula 3-64
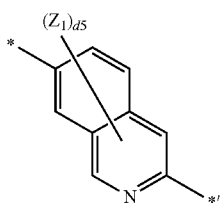
Formula 3-58
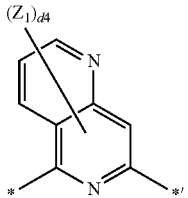
Formula 3-65
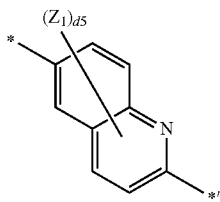
Formula 3-59
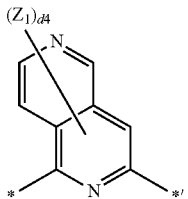
Formula 3-66
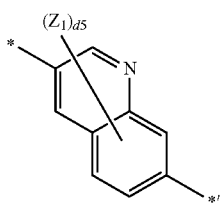
Formula 3-60
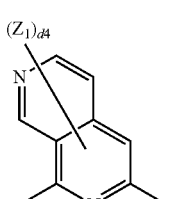
Formula 3-67
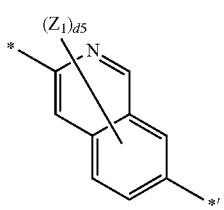
Formula 3-61
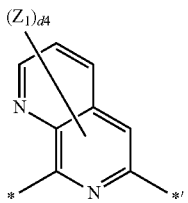
Formula 3-68
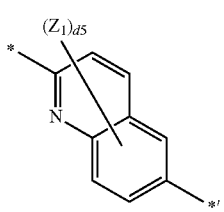
Formula 3-62
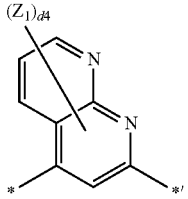
Formula 3-69

Formula 3-70
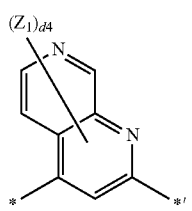
Formula 3-71
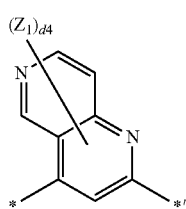
Formula 3-72
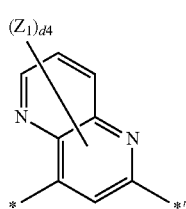
Formula 3-73
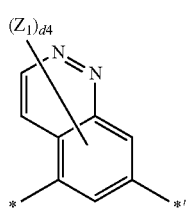
Formula 3-74
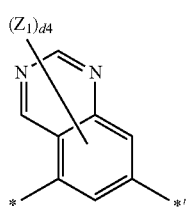
Formula 3-75
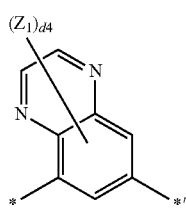
Formula 3-76
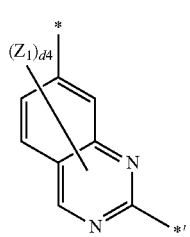
Formula 3-77
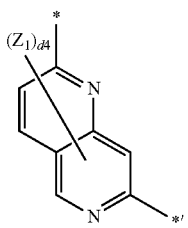
Formula 3-78
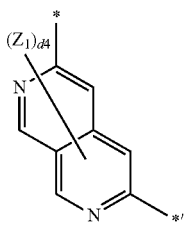
Formula 3-79
Formula 3-80
Formula 3-81
Formula 3-82

Formula 3-83
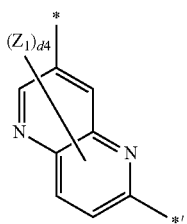
Formula 3-84
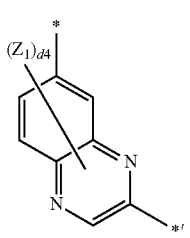
Formula 3-85
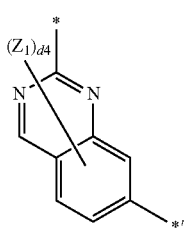
Formula 3-86
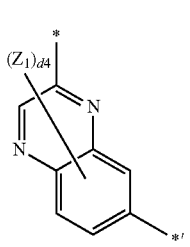
Formula 3-87
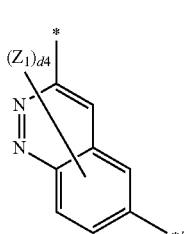
Formula 3-88
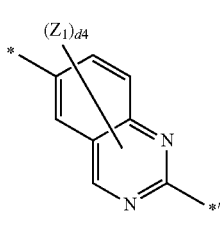
Formula 3-89
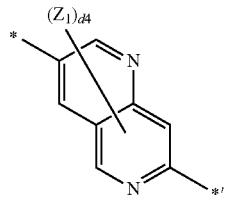
Formula 3-90
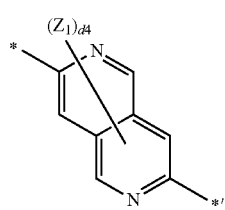
Formula 3-91
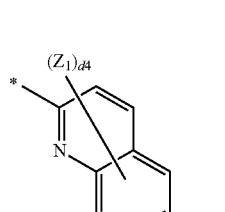
Formula 3-92
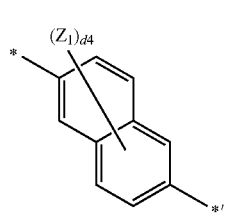
Formula 3-93
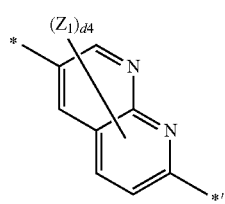
Formula 3-94
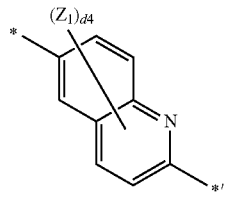
Formula 3-95
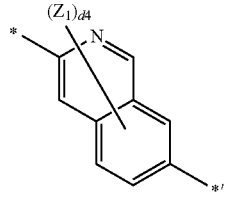

-continued

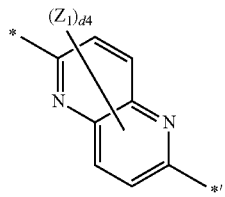

Formula 3-96

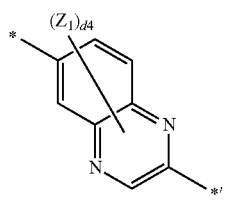

Formula 3-97

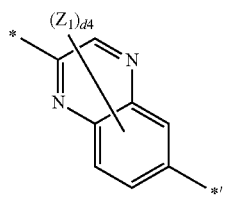

Formula 3-98

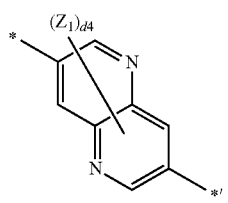

Formula 3-99

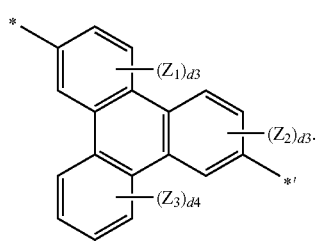

Formula 3-100

In Formulae 3-1 to 3-100, $Y_1$ may be O, S, $C(Z_4)(Z_5)$, or $Si(Z_6)(Z_7)$, $Z_1$ to $Z_7$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, a benzonaphthyridinyl group, an azafluorenyl group, an azadibenzofuranyl group, an azadibenzothiophenyl group, an azadibenzosilolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 may be an integer selected from 0 to 2, d3 may be an integer selected from 0 to 3, d4 may be an integer selected from 0 to 4, d5 may be an integer selected from 0 to 5, d6 may be an integer selected from 0 to 6, d8 may be an integer selected from 0 to 8, and

* and *' each indicate a binding site to a neighboring atom.

In various embodiments, $L_{41}$ to $L_{43}$ in Formula 2 may each independently be a group represented by one selected from Formulae 3-1 to 3-30 (where $Y_1$ in Formulae 3-17 to 3-20 may be O or S), and $Z_1$ and $Z_2$ in Formulae 3-1 to 3-30 may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an indolyl group, an isoindolyl group, a benzofuranyl group, a benzothiophenyl group, a benzosilolyl group, a dibenzofuranyl group, a dibenzothiophenyl group, a dibenzosilolyl group, and a pyridinyl group, but embodiments are not limited thereto.

In Formulae 1A to 1D and 2, a1 to a6, a11 to a24, a31 to a34 and a41 to a43 may each independently be an integer selected from 0 to 5. In Formulae 1A to 1D and 2, a1 indicates the number of $L_1$(s), wherein when a1 is 0, *-$(L_1)_{a1}$-*' may be a single bond, and when a1 is 2 or more, 2 or more $L_1$(s) may be identical to or different from each other. In Formulae 1A to 1D and 2, a2 to a6, a11 to a24, a31 to a34, and a41 to a43 may be understood by referring to the descriptions of a1 and Formulae 1A to 1D and 2 provided herein.

In an embodiment, a1 to a6, a11 to a24, a31 to a34, and a41 to a43 in Formulae 1A to 1D and 2 may each independently be 0, 1, 2, or 3 (or, 0, 1, or 2), but embodiments are not limited thereto.

In Formulae 1A to 1D and 2, $R_1$ to $R_6$, $R_{11}$ to $R_{24}$, $R_{31}$ to $R_{34}$, and $R_{51}$ to $R_{54}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), and $R_{41}$ and $R_{42}$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $R_1$ to $R_6$, $R_{11}$ to $R_{24}$, and $R_{31}$ to $R_{34}$ in Formulae 1A to 1D may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $R_{41}$ and $R_{42}$ in Formula 2 may each independently be selected from:

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, —Si($Q_{31}$)($Q_{32}$)($Q_{33}$), —N($Q_{31}$)($Q_{32}$), and —B($Q_{31}$)($Q_{32}$), and $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an embodiment, $R_1$ to $R_6$, $R_{11}$ to $R_{24}$, and $R_{31}$ to $R_{34}$ in Formulae 1A to 1D may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, groups represented by Formulae 5-1 to 5-38, groups represented by Formulae 6-1 to 6-123, Si($Q_1$)($Q_2$)($Q_3$), —S(=O)$_2$($Q_1$), and —P(=O)($Q_1$)($Q_2$), and $R_{41}$ and $R_{42}$ in Formula 2 may each independently be selected from groups represented by Formulae 5-1 to 5-38 (wherein $Y_{31}$ in Formulae 5-13 to 5-36 is O or S):

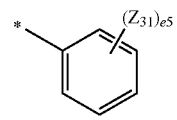

Formula 5-1

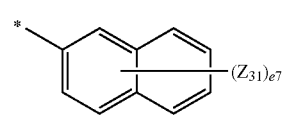

Formula 5-2

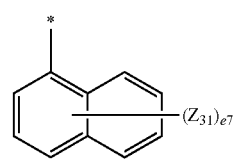

Formula 5-3

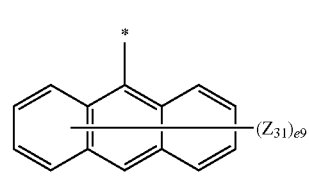

Formula 5-4

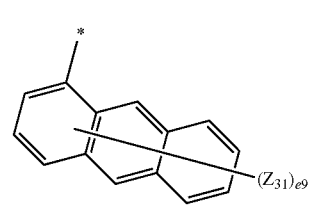

Formula 5-5

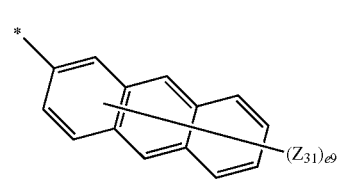

Formula 5-6

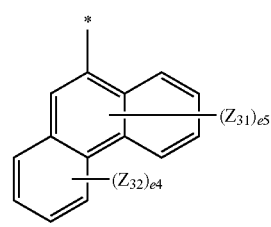

Formula 5-7

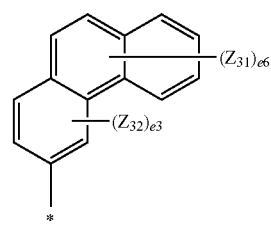

Formula 5-8

Formula 5-9
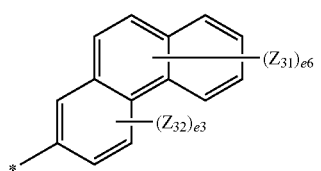
Formula 5-10
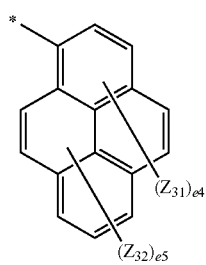
Formula 5-11
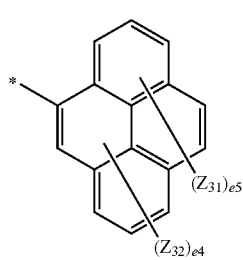
Formula 5-12
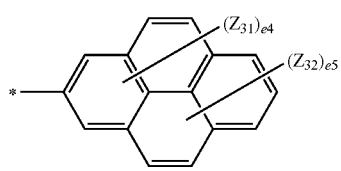
Formula 5-13
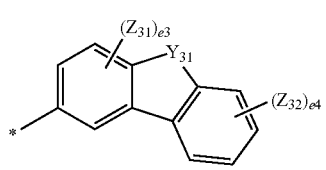
Formula 5-14
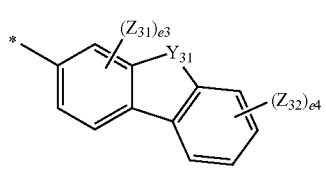
Formula 5-15
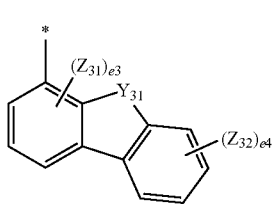
Formula 5-16
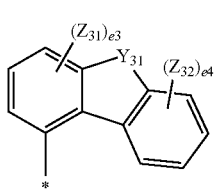
Formula 5-17
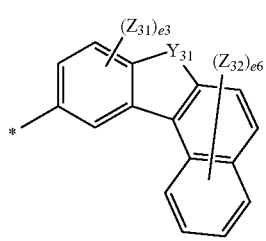
Formula 5-18
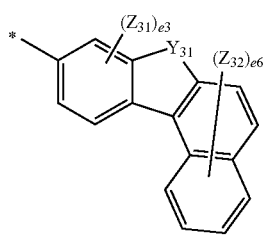
Formula 5-19
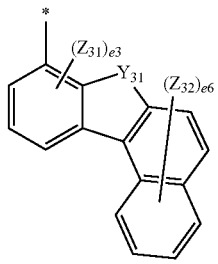
Formula 5-20
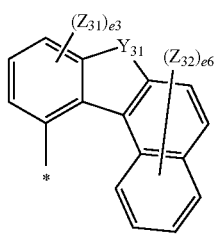
Formula 5-21
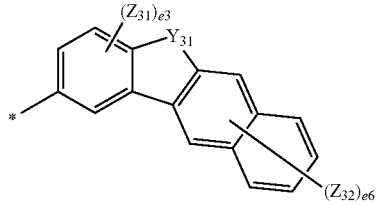
Formula 5-22
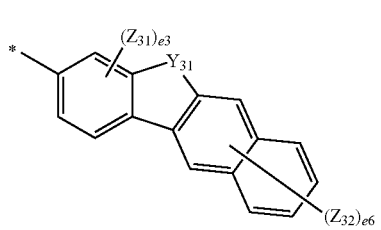

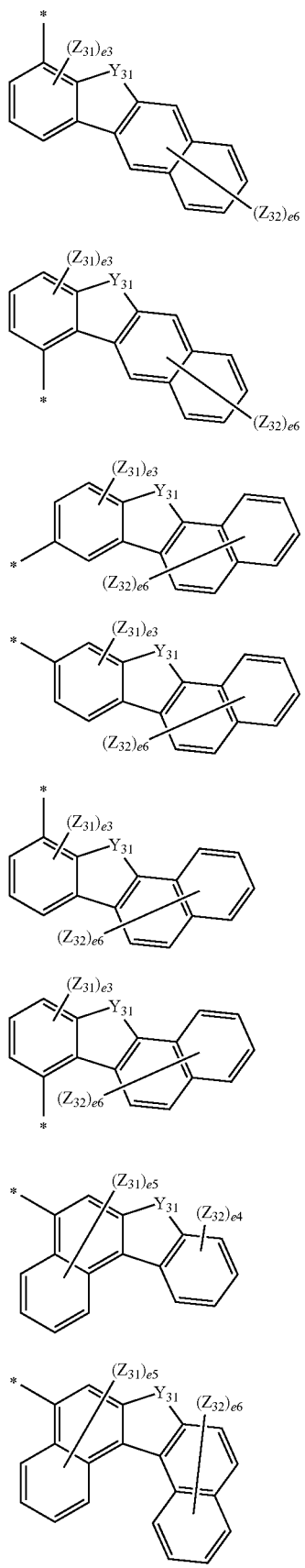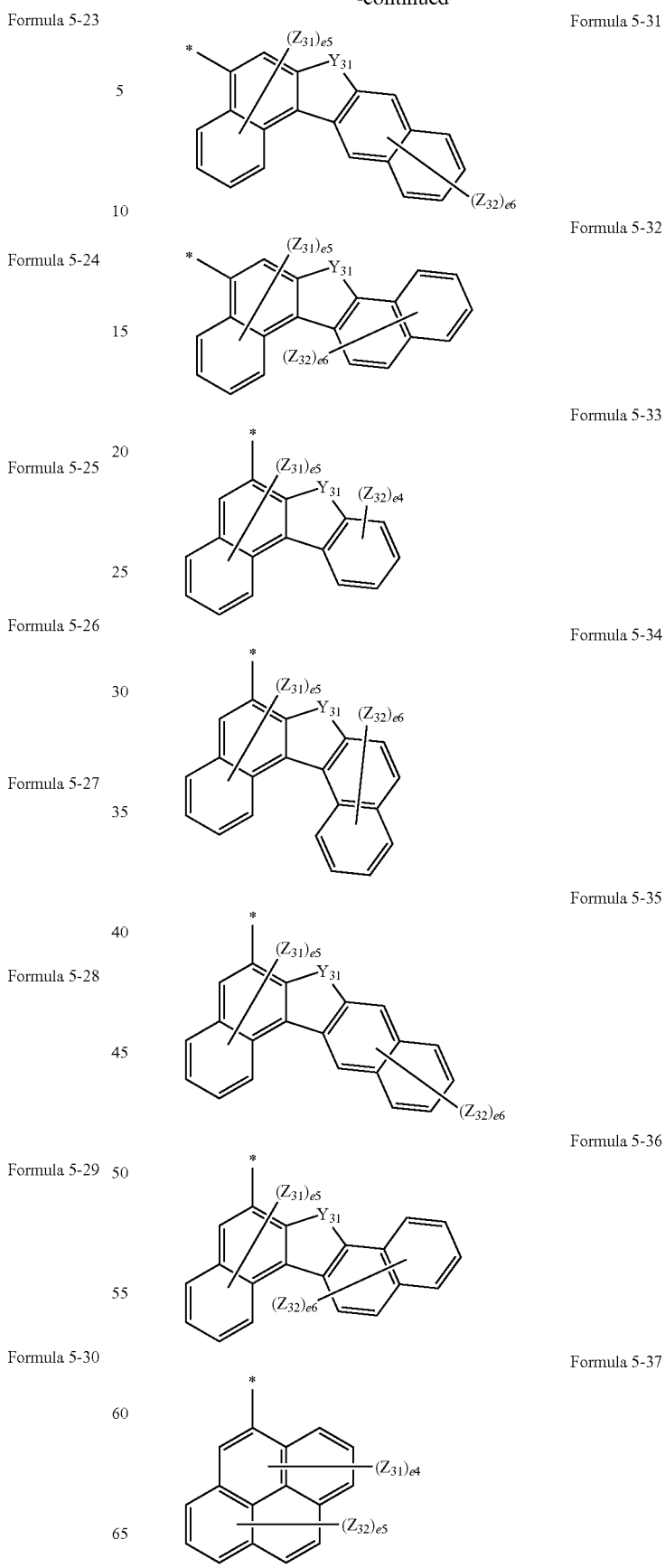

-continued
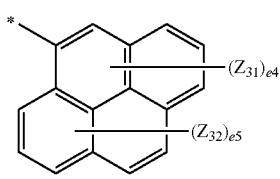
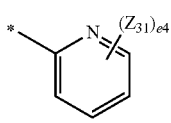
Formula 6-1
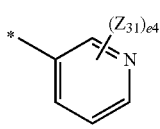
Formula 6-2
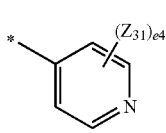
Formula 6-3
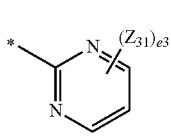
Formula 6-4
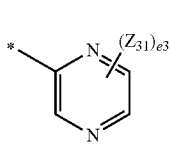
Formula 6-5
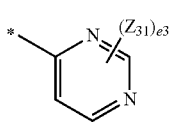
Formula 6-6
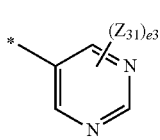
Formula 6-7
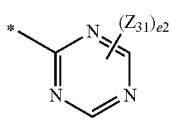
Formula 6-8
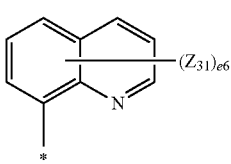
Formula 6-9
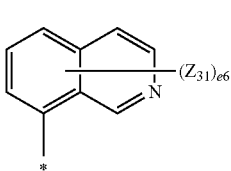
Formula 6-10
-continued
Formula 5-38
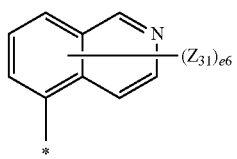
Formula 6-11
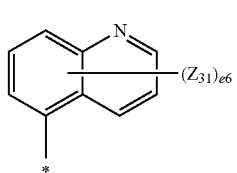
Formula 6-12
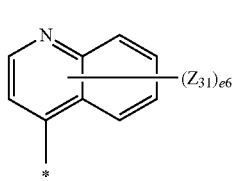
Formula 6-13
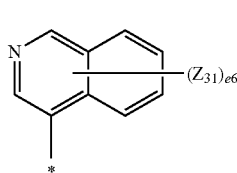
Formula 6-14
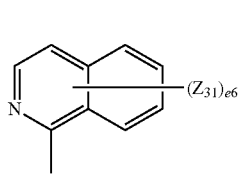
Formula 6-15
Formula 6-16
Formula 6-17
Formula 6-18
Formula 6-19
Formula 6-20

Formula 6-21
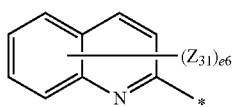
Formula 6-22
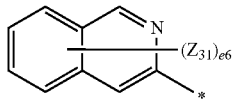
Formula 6-23
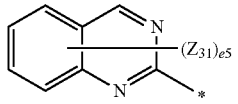
Formula 6-24
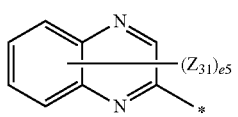
Formula 6-25
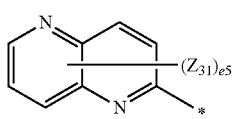
Formula 6-26
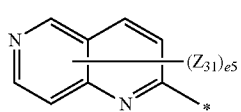
Formula 6-27
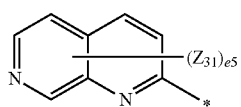
Formula 6-28
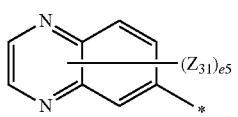
Formula 6-29
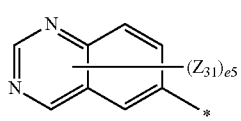
Formula 6-30
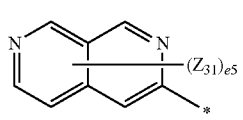
Formula 6-31
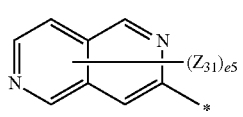
Formula 6-32
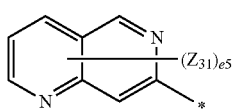
Formula 6-33
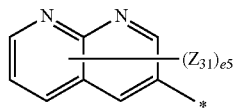
Formula 6-34
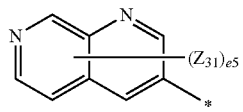
Formula 6-35
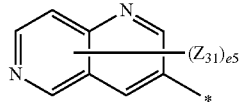
Formula 6-36
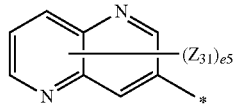
Formula 6-37
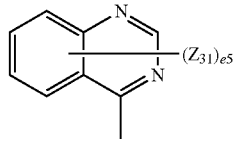
Formula 6-38
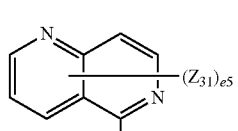
Formula 6-39
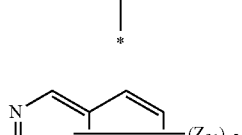
Formula 6-40
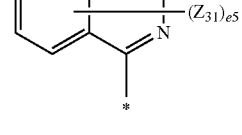
Formula 6-41
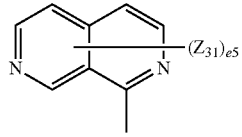
Formula 6-42
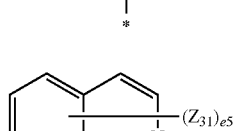

Formula 6-43
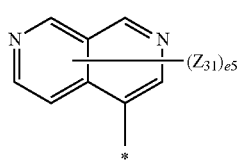
Formula 6-44
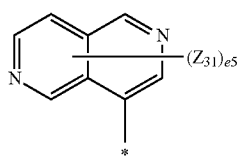
Formula 6-45
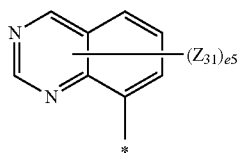
Formula 6-46
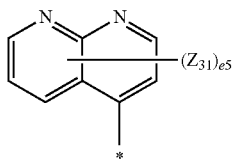
Formula 6-47
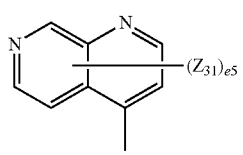
Formula 6-48
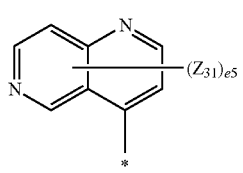
Formula 6-49
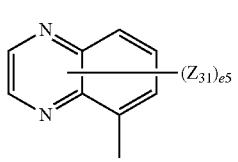
Formula 6-50
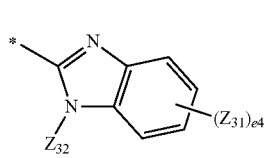
Formula 6-51
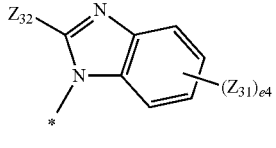
Formula 6-52
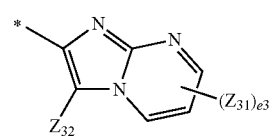
Formula 6-53
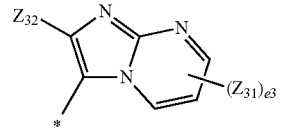
Formula 6-54
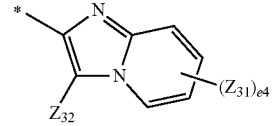
Formula 6-55
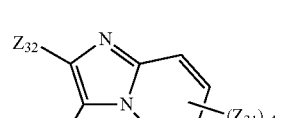
Formula 6-56
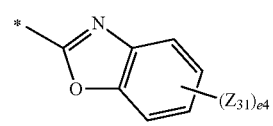
Formula 6-57
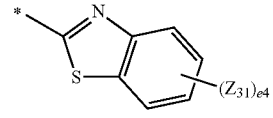
Formula 6-58
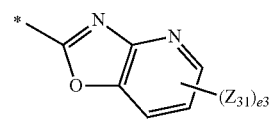
Formula 6-59
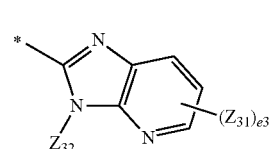
Formula 6-60
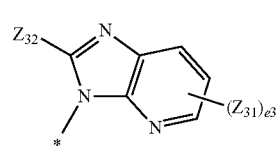
Formula 6-61
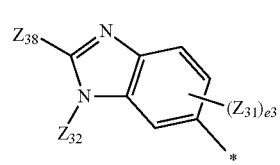
Formula 6-62

Formula 6-63
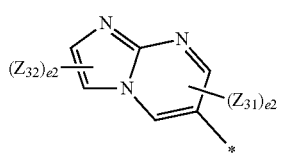
Formula 6-64
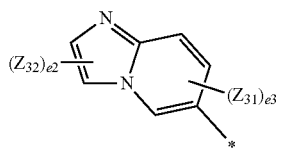
Formula 6-65
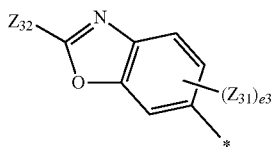
Formula 6-66
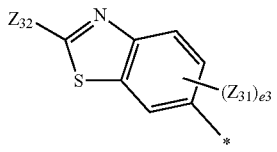
Formula 6-67
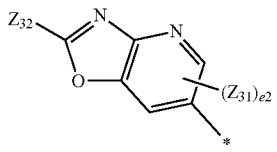
Formula 6-68
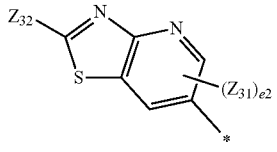
Formula 6-69
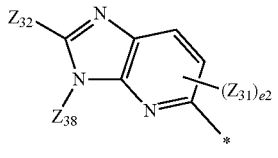
Formula 6-70
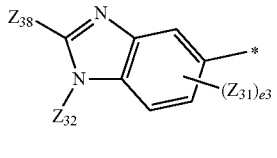
Formula 6-71
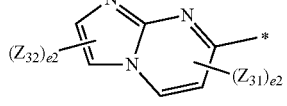
Formula 6-72
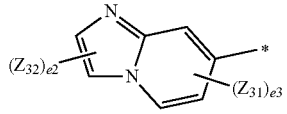
Formula 6-73
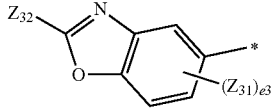
Formula 6-74
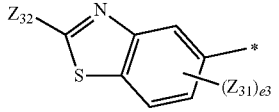
Formula 6-75
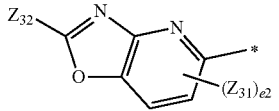
Formula 6-76
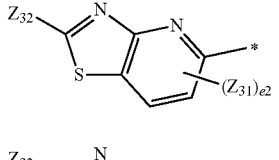
Formula 6-77
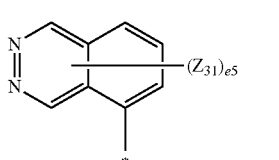
Formula 6-78
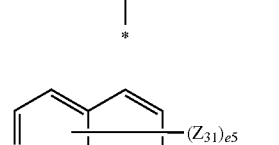
Formula 6-79
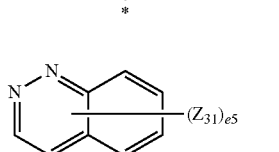
Formula 6-80
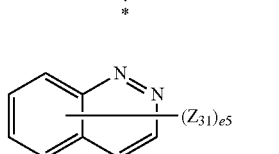
Formula 6-81
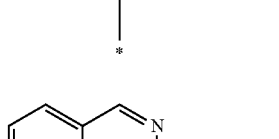
Formula 6-82
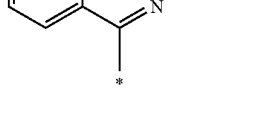

Formula 6-83
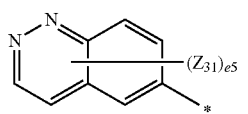
Formula 6-84
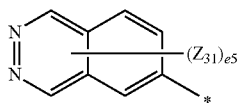
Formula 6-85
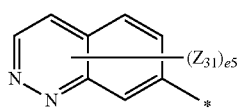
Formula 6-86
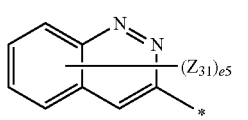
Formula 6-87
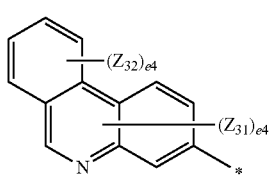
Formula 6-88
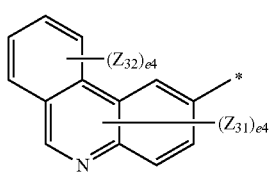
Formula 6-89
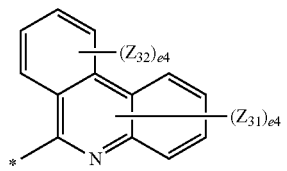
Formula 6-90
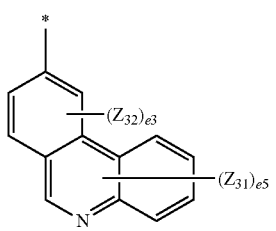
Formula 6-91
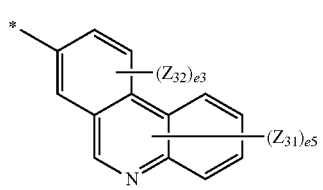
Formula 6-92
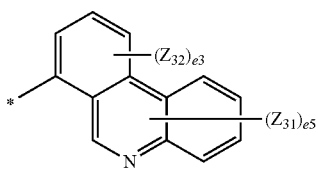
Formula 6-93
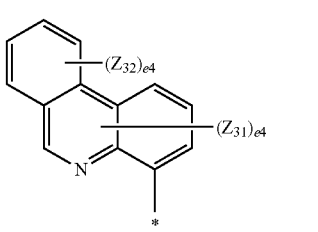
Formula 6-94
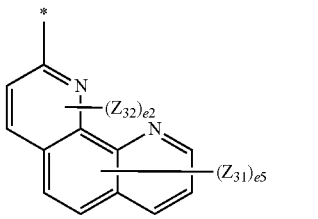
Formula 6-95
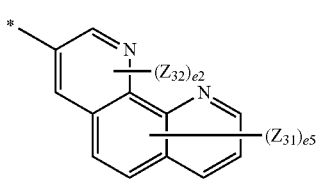
Formula 6-96
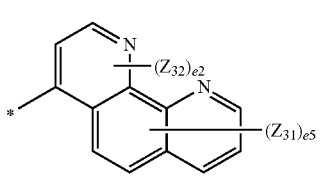
Formula 6-97
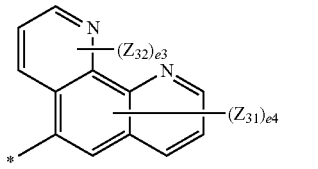
Formula 6-98
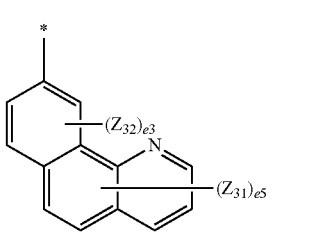
Formula 6-99
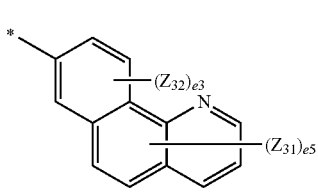

Formula 6-100
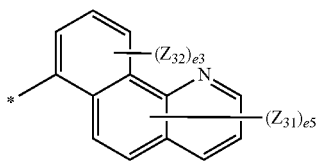
Formula 6-101
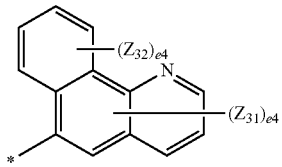
Formula 6-102
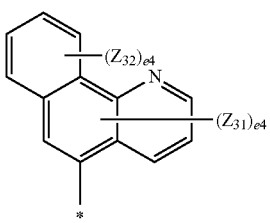
Formula 6-103
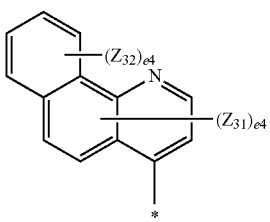
Formula 6-104
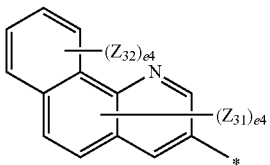
Formula 6-105
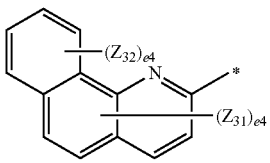
Formula 6-106
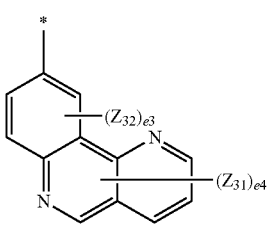
Formula 6-107
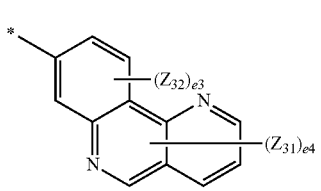
Formula 6-108
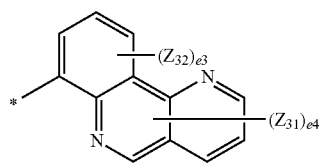
Formula 6-109
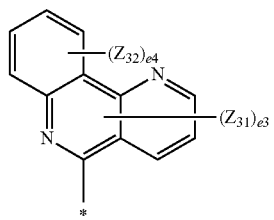
Formula 6-110
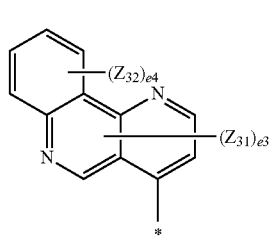
Formula 6-111
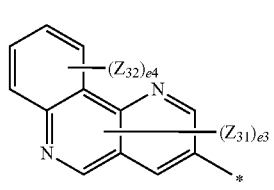
Formula 6-112
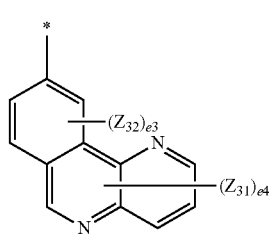
Formula 6-113
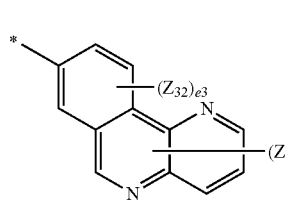
Formula 6-114
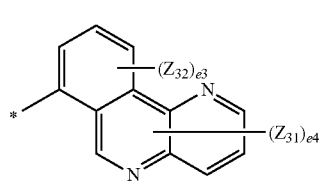
Formula 6-115
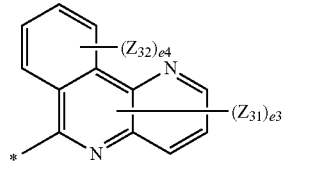

-continued

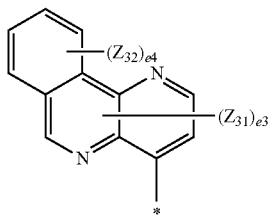
Formula 6-116

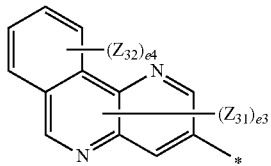
Formula 6-117

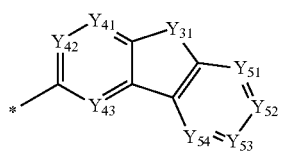
Formula 6-118

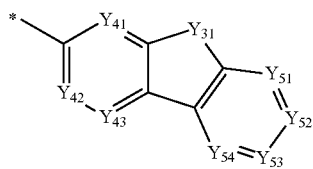
Formula 6-119

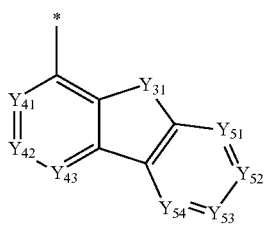
Formula 6-120

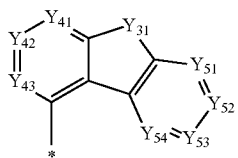
Formula 6-121

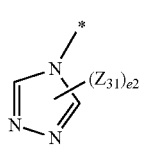
Formula 6-122

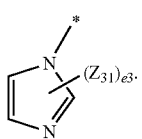
Formula 6-123

In Formulae 5-1 to 5-38 and 6-1 to 6-123, $Y_{31}$ and $Y_{32}$ may each independently be O, S, $C(Z_{33})(Z_{34})$, or $Si(Z_{35})(Z_{36})$, $Y_{41}$ may be N or $C(Z_{41})$, $Y_{42}$ may be N or $C(Z_{42})$, $Y_{43}$ may be N or $C(Z_{43})$, $Y_{51}$ may be N or $C(Z_{51})$, $Y_{52}$ may be N or $C(Z_{52})$, $Y_{53}$ may be N or $C(Z_{53})$, and $Y_{54}$ may be N or $C(Z_{54})$, $Z_{31}$ to $Z_{36}$, $Z_{41}$ to $Z_{43}$, and $Z_{51}$ to $Z_{54}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, a benzonaphthyridinyl group, an azafluorenyl group, an azadibenzofuranyl group, an azadibenzothiophenyl group, an azadibenzosilolyl group, and —Si$(Q_{31})(Q_{32})(Q_{33})$, $Q_1$ to $Q_3$ and $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, e3 may be an integer selected from 0 to 3,
e4 may be an integer selected from 0 to 4,
e5 may be an integer selected from 0 to 5,
e6 may be an integer selected from 0 to 6,
e7 may be an integer selected from 0 to 7,
e8 may be an integer selected from 0 to 8,
e9 may be an integer selected from 0 to 9, and
* indicates a binding site to a neighboring atom.

For example, $R_1$ to $R_6$, $R_{11}$ to $R_{24}$, and $R_{31}$ to $R_{34}$ in Formulae 1A to 1D may each independently be a group represented by one selected from Formulae 6-1 to 6-123, and $Z_{31}$ to $Z_{36}$ in Formulae 6-1 to 6-123 may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenylene group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an indolyl group, an isoindolyl group, a benzofuranyl group, a benzothiophenyl group, a benzosilolyl group, a dibenzofuranyl group, a dibenzothiophenyl group, a dibenzosilolyl group, and a pyridinyl group.

In various embodiments, $R_1$ to $R_6$, $R_{11}$ to $R_{24}$, and $R_{31}$ to $R_{34}$ in Formulae 1A to 1D may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, groups represented by Formulae 9-1 to 9-79, groups represented by Formulae 10-1 to 10-133, —Si($Q_1$)($Q_2$)($Q_3$), —S(=O)$_2$($Q_1$), and —P(=O)($Q_1$)($Q_2$) (wherein $Q_1$ to $Q_3$ may each independently be understood by referring to the descriptions thereof provided herein), and $R_{41}$ and $R_{42}$ in Formula 2 may each independently be selected from groups represented by Formulae 9-1 to 9-52 and 9-77 to 9-79, but embodiments are not limited thereto:

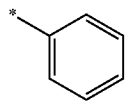

Formula 9-1

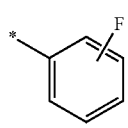

Formula 9-2

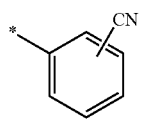

Formula 9-3

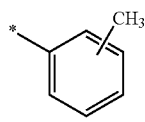

Formula 9-4

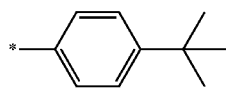

FOrmula 9-5

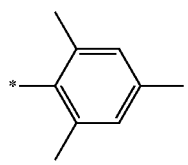

Formula 9-6

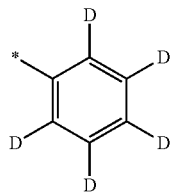

Formula 9-7

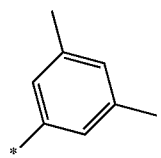

Formula 9-8

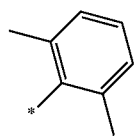

Formula 9-9

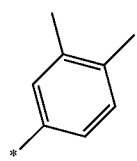

Formula 9-10

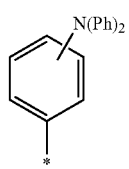

Formula 9-11

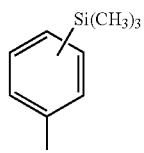

Formula 9-12

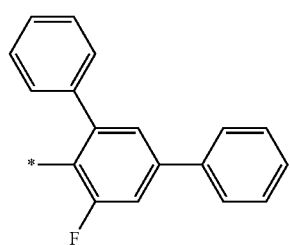

Formula 9-13

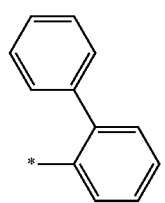

Formula 9-14

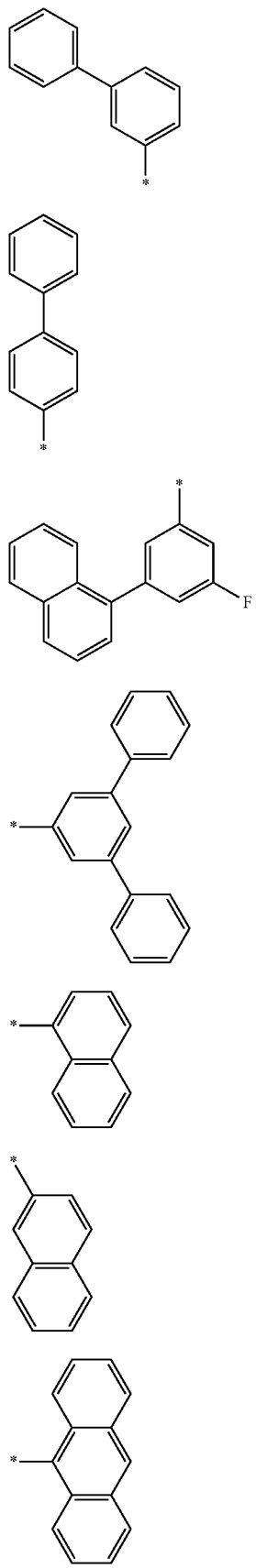
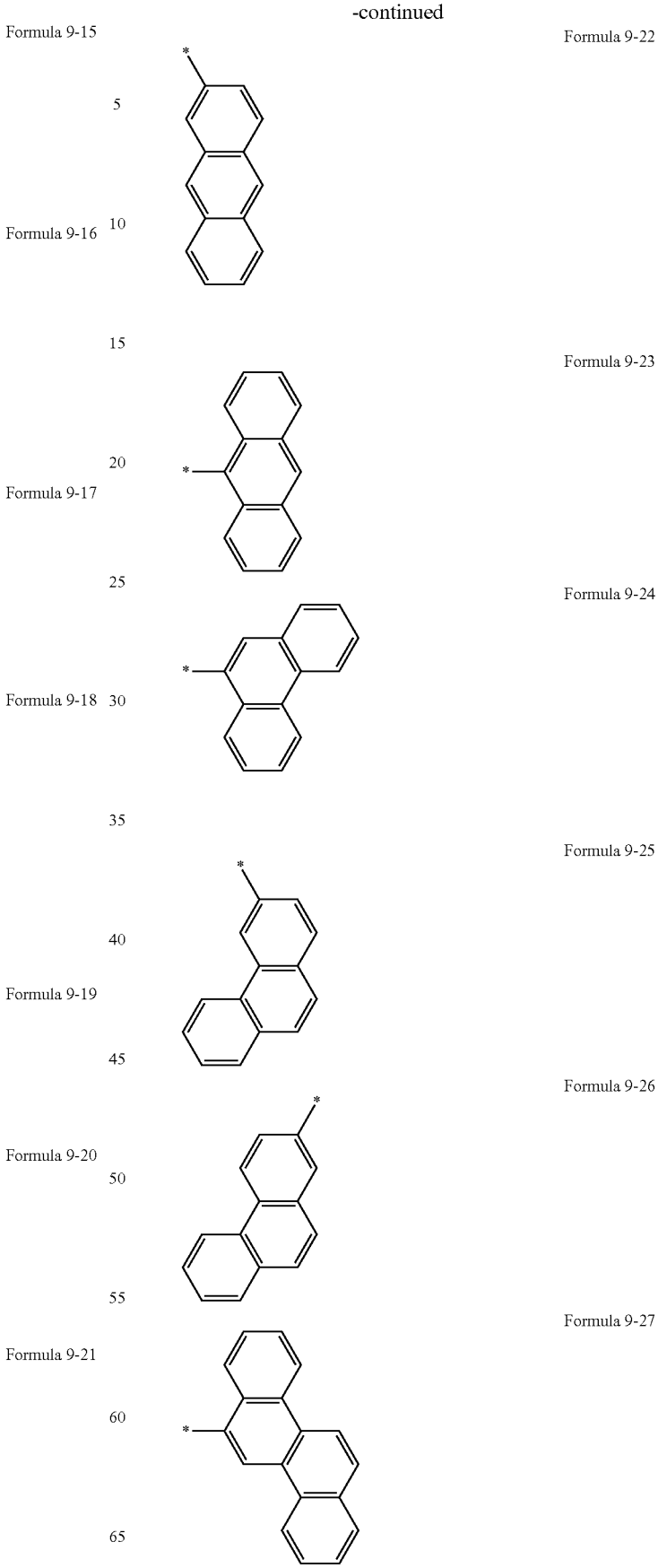

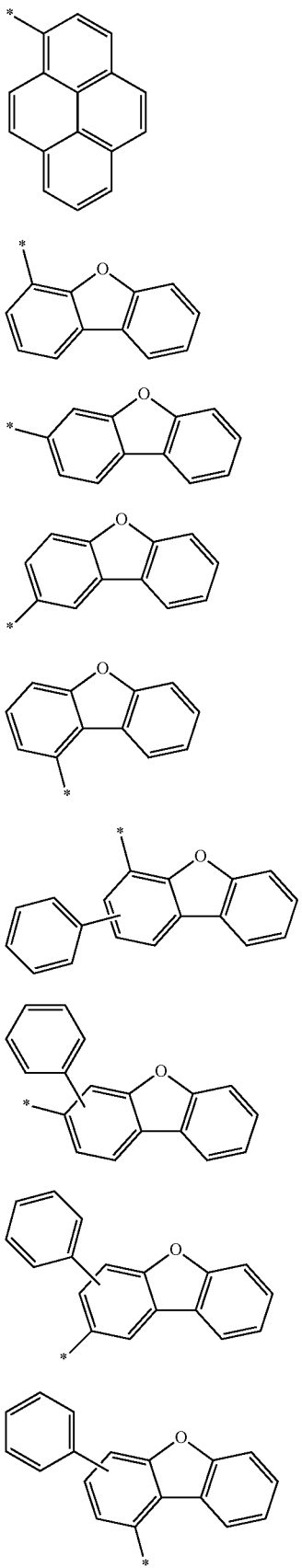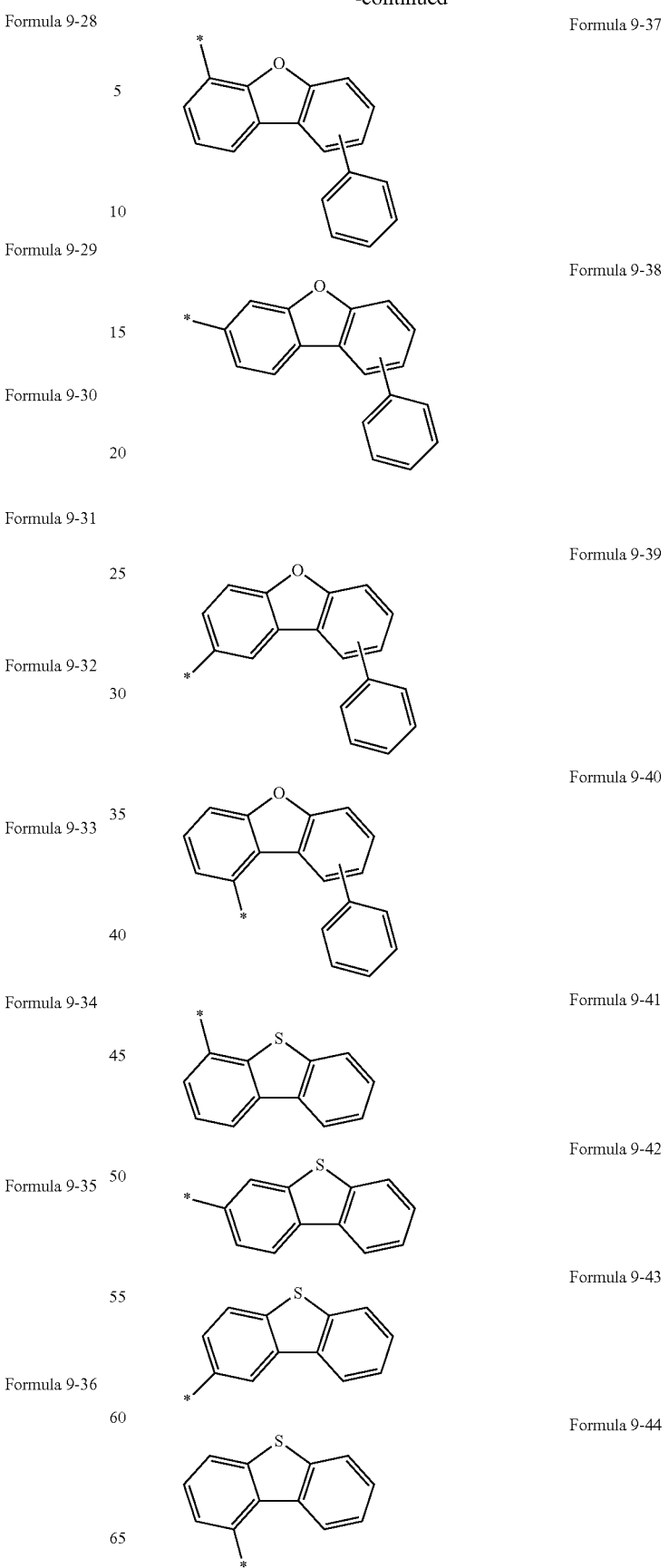

Formula 9-45
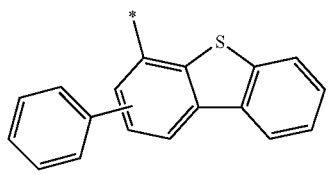
Formula 9-46
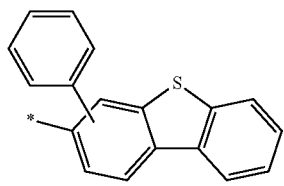
Formula 9-47
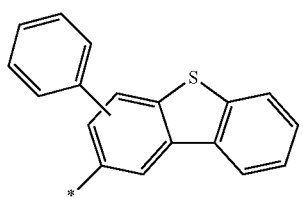
Formula 9-48
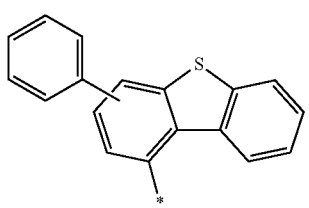
Formula 9-49
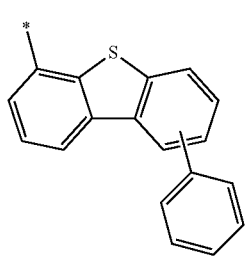
Formula 9-50
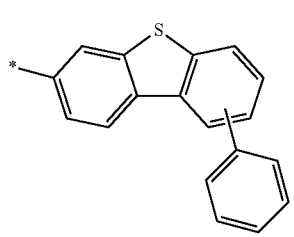
Formula 9-51
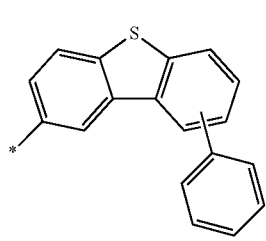
Formula 9-52
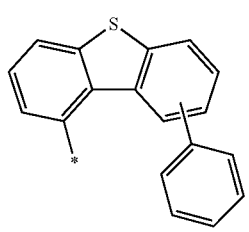
Formula 9-53
Formula 9-54
Formula 9-55
Formula 9-56
Formula 9-57
Formula 9-58
Formula 9-59

Formula 9-60
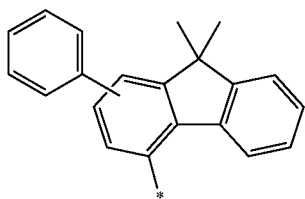
Formula 9-61
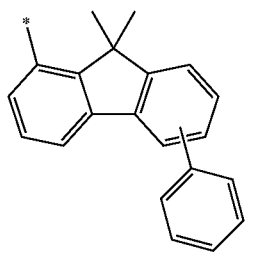
Formula 9-62
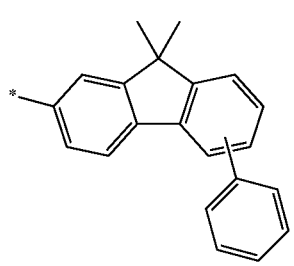
Formula 9-63
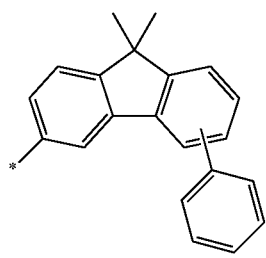
Formula 9-64
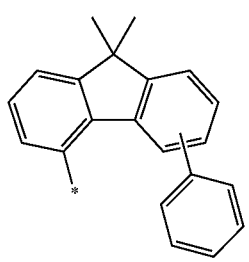
Formula 9-65
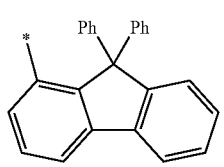
Formula 9-66
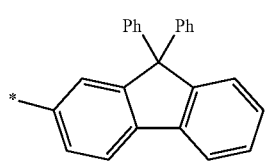
Formula 9-67
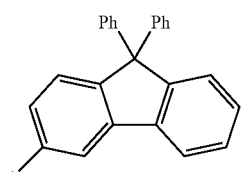
Formula 9-68
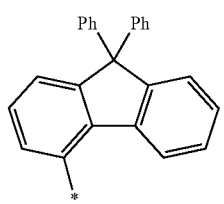
Formula 9-69
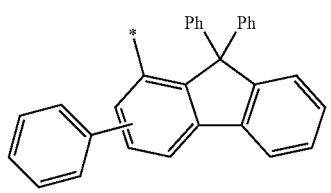
Formula 9-70
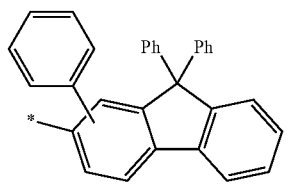
Formula 9-71
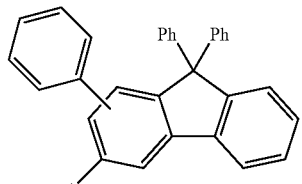
Formula 9-72
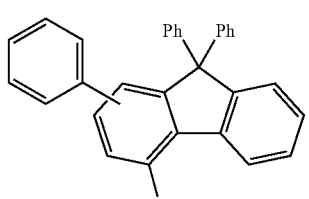
Formula 9-73
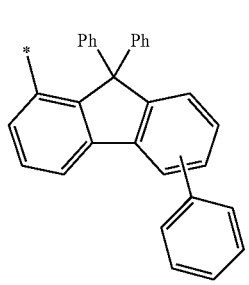

-continued
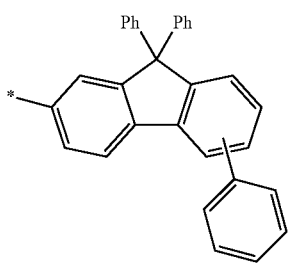
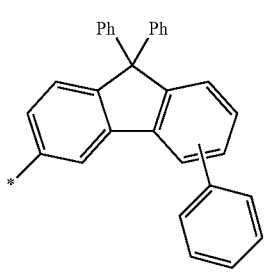
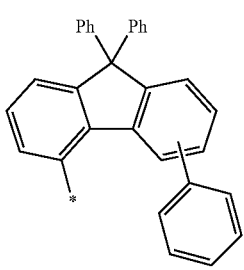
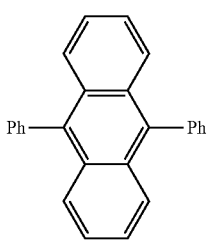
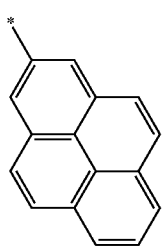
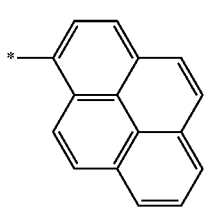
Formula 9-74
Formula 9-75
Formula 9-76
Formula 9-77
Formula 9-78
Formula 9-79
Formula 10-1
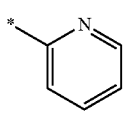
-continued
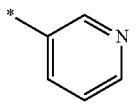 Formula 10-2
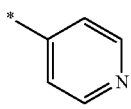 Formula 10-3
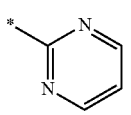 Formula 10-4
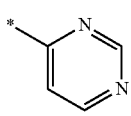 Formula 10-5
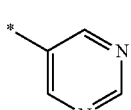 Formula 10-6
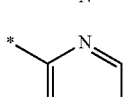 Formula 10-7
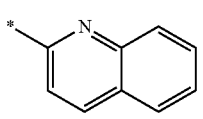 Formula 10-8
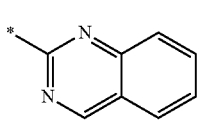 Formula 10-9
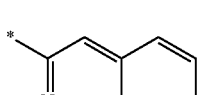 Formula 10-10
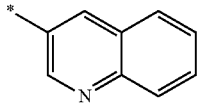 Formula 10-11
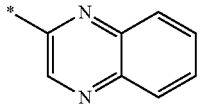 Formula 10-12
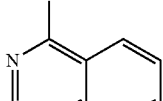 Formula 10-13
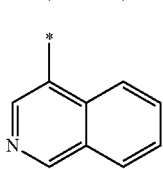 Formula 10-14

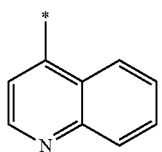
Formula 10-15
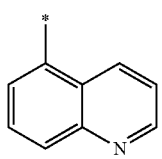
Formula 10-16
Formula 10-17
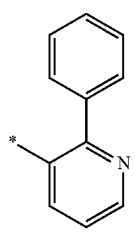
Formula 10-18
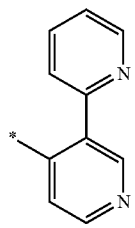
Formula 10-19
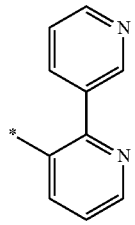
Formula 10-20
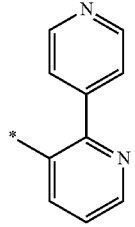
Formula 10-21
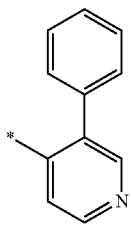
Formula 10-22
Formula 10-23
Formula 10-24
Formula 10-25
Formula 10-26
Formula 10-27

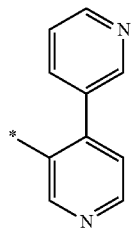
Formula 10-28
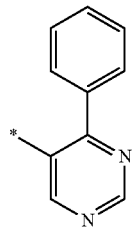
Formula 10-34
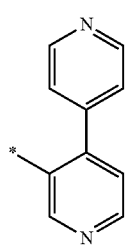
Formula 10-29
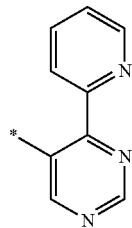
Formula 10-35
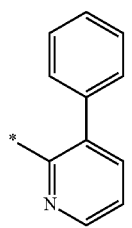
Formula 10-30
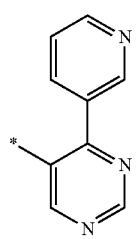
Formula 10-36
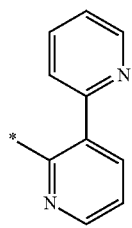
Formula 10-31
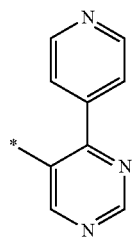
Formula 10-37
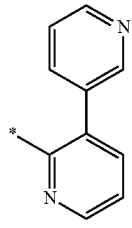
Formula 10-32
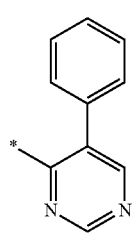
Formula 10-38
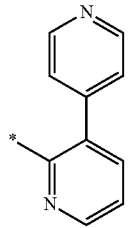
Formula 10-33
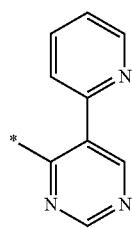
Formula 10-39

Formula 10-40
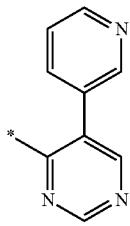
Formula 10-41
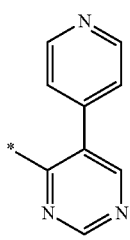
Formula 10-42
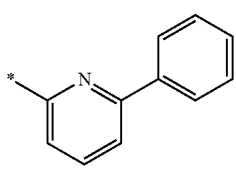
Formula 10-43
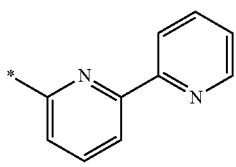
Formula 10-44
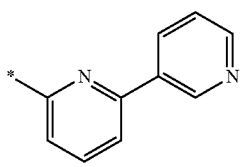
Formula 10-45
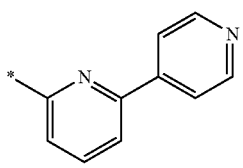
Formula 10-46
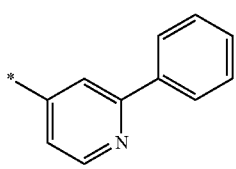
Formula 10-47
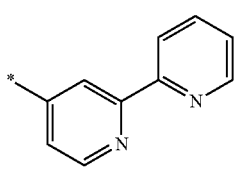
Formula 10-48
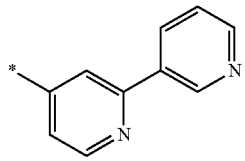
Formula 10-49
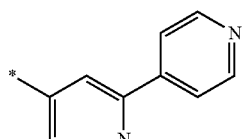
Formula 10-50
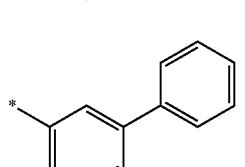
Formula 10-51
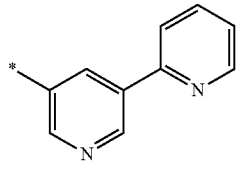
Formula 10-52
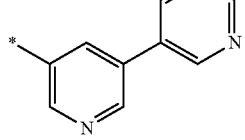
Formula 10-53
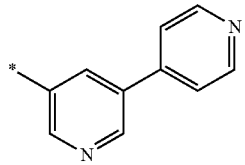
Formula 10-54
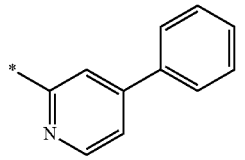
Formula 10-55
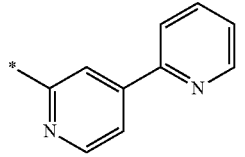
Formula 10-56
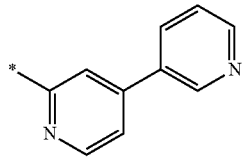

Formula 10-57 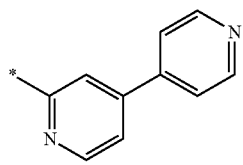
Formula 10-58 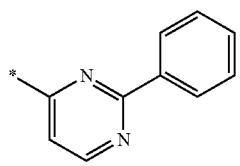
Formula 10-59 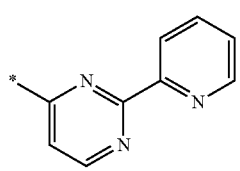
Formula 10-60 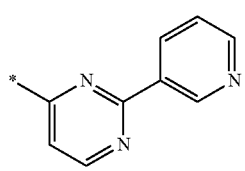
Formula 10-61 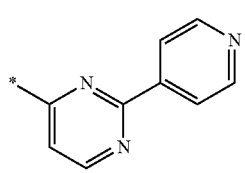
Formula 10-62 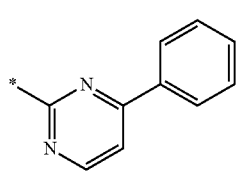
Formula 10-63 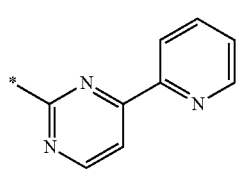
Formula 10-64 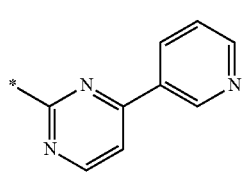
Formula 10-65 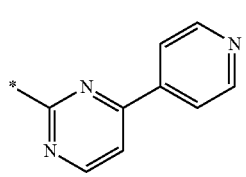
Formula 10-66 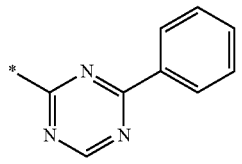
Formula 10-67 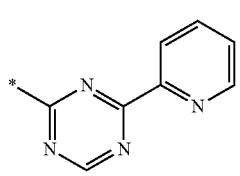
Formula 10-68 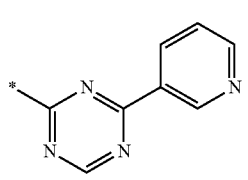
Formula 10-69 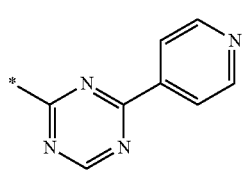
Formula 10-70 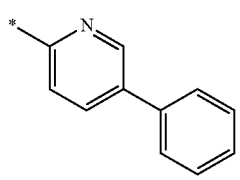
Formula 10-71 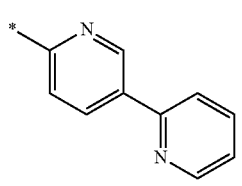
Formula 10-72 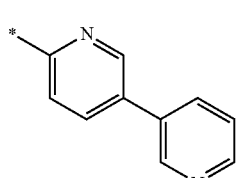
Formula 10-73 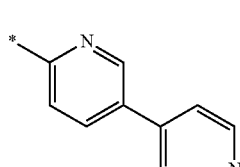
Formula 10-74 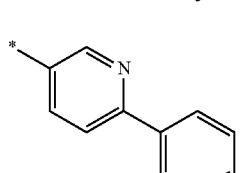

Formula 10-75
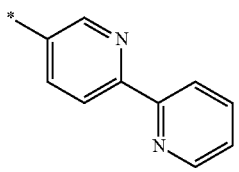
Formula 10-76
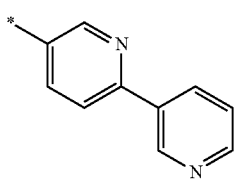
Formula 10-77
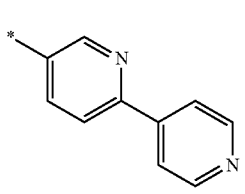
Formula 10-78
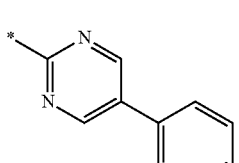
Formula 10-79
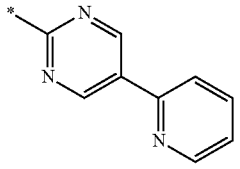
Formula 10-80
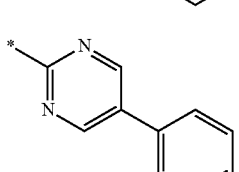
Formula 10-81
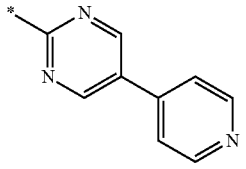
Formula 10-82
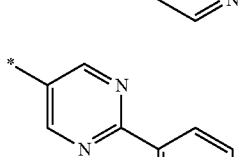
Formula 10-83
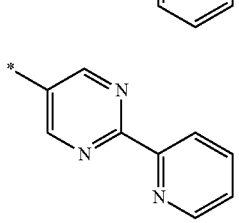
Formula 10-84
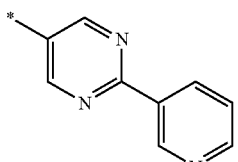
Formula 10-85
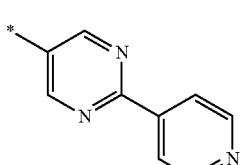
Formula 10-86
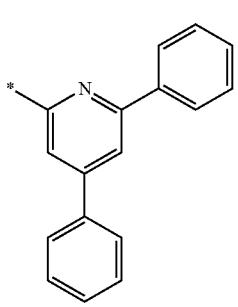
Formula 10-87
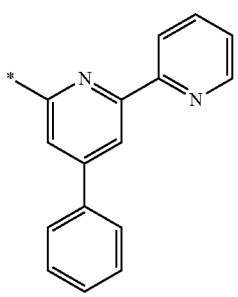
Formula 10-88
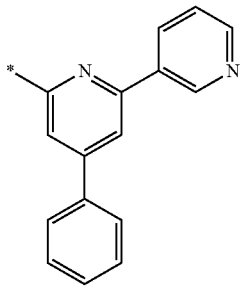
Formula 10-89
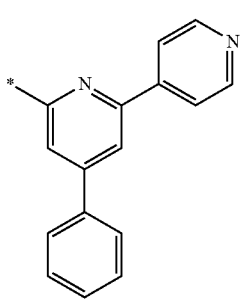

Formula 10-90

Formula 10-91

Formula 10-92

Formula 10-93

Formula 10-94

Formula 10-95

Formula 10-96

Formula 10-97

Formula 10-98

Formula 10-99

Formula 10-100
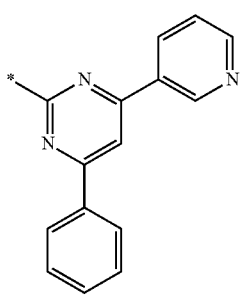
Formula 10-101
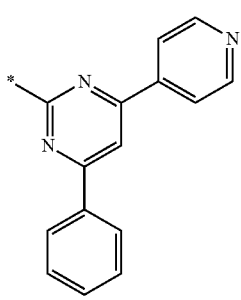
Formula 10-102
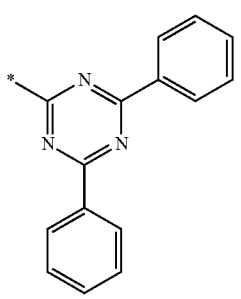
Formula 10-103
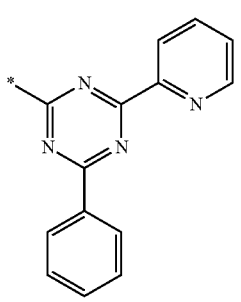
Formula 10-104
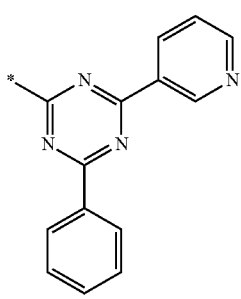
Formula 10-105
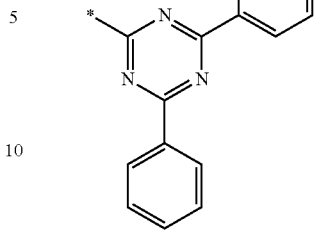
Formula 10-106
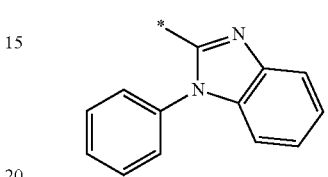
Formula 10-107
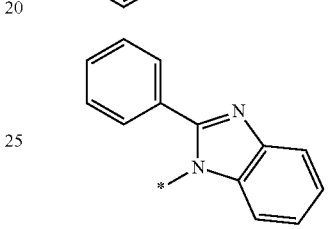
Formula 10-108
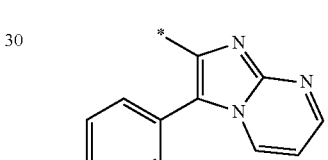
Formula 10-109
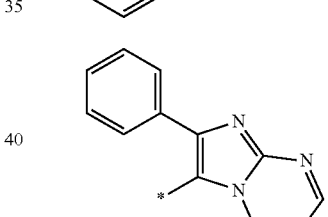
Formula 10-110
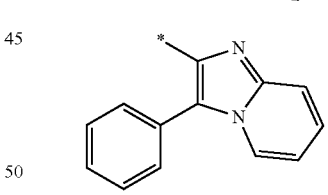
Formula 10-111
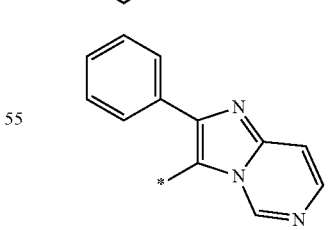
Formula 10-112
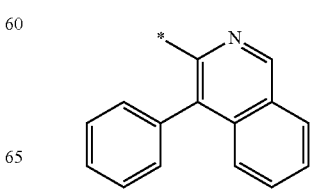

Formula 10-113
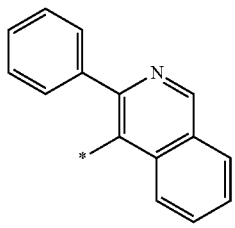
Formula 10-114
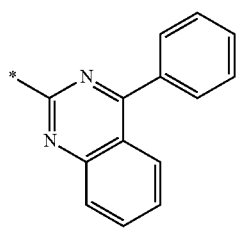
Formula 10-115
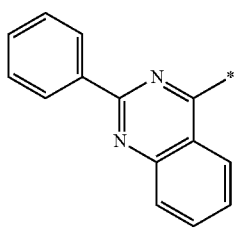
Formula 10-116
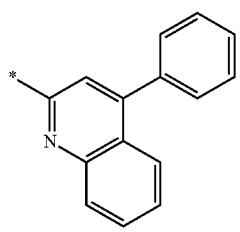
Formula 10-117
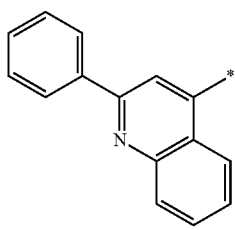
Formula 10-118
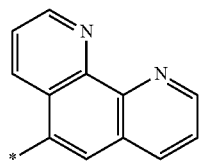
Formula 10-119
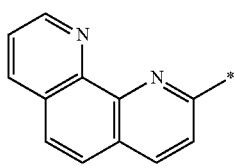
Formula 10-120
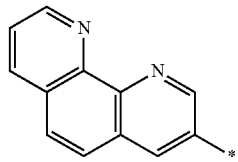
Formula 10-121
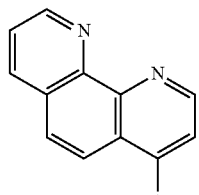
Formula 10-122
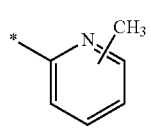
Formula 10-123
Formula 10-124
Formula 10-125
Formula 10-126
Formula 10-127
Formula 10-128
Formula 10-129
Formula 10-130

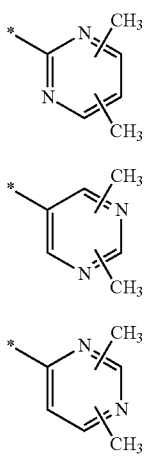

Formula 10-131

Formula 10-132

Formula 10-133

In Formulae 9-1 to 9-79 and 10-1 to 10-133, the term "Ph," as used herein, refers to a phenyl group, and * indicates a binding site to a neighboring atom.

In an embodiment, $R_1$ to $R_6$, $R_{11}$ to $R_{24}$, and $R_{31}$ to $R_{34}$ in Formulae 1A to 1D may each independently be hydrogen, deuterium, a cyano group, a $C_1$-$C_{10}$ alkyl group, a $C_1$-$C_{10}$ alkoxy group, a group represented by one selected from Formulae 9-1 to 9-79, or a group represented by one selected from Formulae 10-1 to 10-133.

In an embodiment, $R_{41}$ and $R_{42}$ in Formula 2 may each independently be a group represented by one selected from Formulae 9-1 to 9-52 and 9-77 to 9-79, but embodiments are not limited thereto.

In various embodiments, $R_{51}$ to $R_{54}$ in Formula 2 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, and a pyridinyl group; and a phenyl group, a biphenyl group, a terphenyl group, a naphthyl group, and a pyridinyl group, each substituted with at least one selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and a pyridinyl group.

The first compound represented by one selected from Formulae 1A to 1D does not include a carbazole ring and a spiro-bifluorene ring. That is, examples of the first compound do not include compounds represented by Formulae 1A to 1D in which $L_1$ to $L_6$, $L_{11}$ to $L_{24}$, $L_{31}$ to $L_{34}$, $R_1$ to $R_6$, $R_{11}$ to $R_{24}$, and $R_{31}$ to $R_{34}$ are each independently a carbazole ring or a spiro-bifluorene ring.

In addition, the second compound represented by Formula 2 does not include a carbazole ring and a fluorene ring. That is, examples of the second compound do not include compounds represented by Formula 2 in which $L_{41}$ to $L_{43}$, $R_{41}$, $R_{42}$, and $R_{51}$ to $R_{54}$ are each independently a carbazole ring or a fluorene ring.

For example, the carbazole ring may be selected from:

a carbazolylene group, a benzocarbazolylene group, a dibenzocarbazolylene group, an azacarbazolylene group, a carbazolyl group, a benzocarbazolyl group, a dibenzocarbazolyl group, and an azacarbazolyl group; and a carbazolylene group, a benzocarbazolylene group, a dibenzocarbazolylene group, an azacarbazolylene group, a carbazolyl group, a benzocarbazolyl group, a dibenzocarbazolyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), S(=O)$_2$($Q_{31}$), and —P(=O)($Q_{31}$)($Q_{32}$), the spiro-bifluorene ring may be selected from:

a spiro-bifluorenylene group, a spiro-benzofluorene-fluorenylene group, an azaspiro-bifluorenylene group, a spiro-bifluorenyl group, a spiro-benzofluorene-fluorenyl group, and an azaspiro-bifluorenyl group; and a spiro-bifluorenylene group, a spiro-benzofluorene-fluorenylene group, an azaspiro-bifluorenylene group, a spiro-bifluorenyl group, a spiro-benzofluorene-fluorenyl group, and an azaspiro-bifluorenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), S(=O)$_2$($Q_{31}$), and —P(=O)($Q_{31}$)($Q_{32}$), the fluorene ring may be selected from:

a fluorenylene group, a benzofluorenylene group, a dibenzofluorenylene group, a fluoranthenylene group, a spiro-bifluorenylene group, a spiro-benzofluorene-fluorenylene group, an azafluorenylene group, an azaspiro-bifluorenylene group, a fluorenyl group, a benzofluorenyl group, a dibenzofluorenyl group, a fluoranthenyl group, a spiro-bifluorenyl group, a spiro-benzofluorene-fluorenyl group, an azafluorenyl group, and an azaspiro-bifluorenyl group; and a fluorenylene group, a benzofluorenylene group, a dibenzofluorenylene group, a fluoranthenylene group, a spiro-bifluorenylene group, a spiro-benzofluorene-fluorenylene group, an azafluorenylene group, an azaspiro-bifluorenylene group, a fluorenyl group, a benzofluorenyl group, a dibenzofluorenyl group, a fluoranthenyl group, a spiro-bifluorenyl group, a spiro-benzofluorene-fluorenyl group, an azafluorenyl group, and an azaspiro-bifluorenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)

($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be understood by referring to the descriptions thereof provided herein.

In Formulae 1A to 1D and 2, b1 to b6, b11 to b24, b31 to b34, b53, and b54 may each independently be an integer selected from 0 to 5 (e.g., 0, 1, or 2), and b41 and b42 may each independently be an integer selected from 1 to 5 (e.g., 1 or 2).

In Formula 1A, b1 indicates the number of $R_1$(s), wherein when b1 is 2 or more, 2 or more $R_1$(s) may be identical to or different from each other. In Formula 1A, b2 to b6, b11 to b24, b31 to b34, b41, b42, b53, and b54 may be understood by referring to the descriptions of b1 and Formulae 1A to 1D and 2 provided herein.

In Formulae 1C and 1D, c1 to c4 may each independently be an integer selected from 0 to 10.

In Formula 1C, c1 indicates the number of [($L_{21}$)$_{a21}$-($R_{21}$)$_{b21}$](s), wherein when c1 is 2 or more, 2 or more [($L_{21}$)$_{a21}$-($R_{21}$)$_{b21}$](s) may be identical to or different from each other. In Formula 1C, c2 to c4 may be understood by referring to the descriptions of c1 and Formulae 1C and 1D provided herein.

In an embodiment, c1 to c4 in Formulae 1C and 1D may each independently be 0 or 1.

In an embodiment, the first compound may be represented by one selected from Formulae 1A(1) to 1A(3), 1B(1) to 1B(4), 1C(1) to 1C(3), and 1D(1) to 1D(4):

Formula 1A(1)
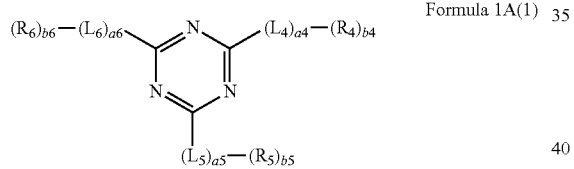

Formula 1A(2)
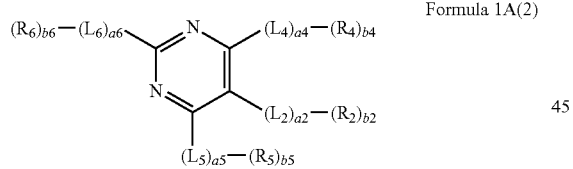

Formula 1A(3)
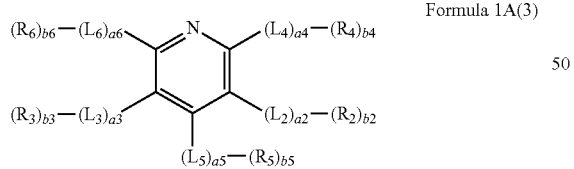

Formula 1B(1)
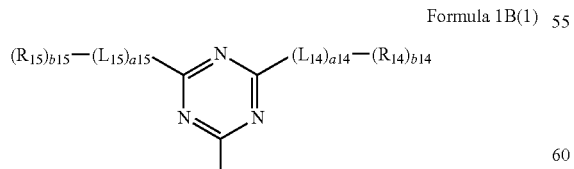

Formula 1B(2)
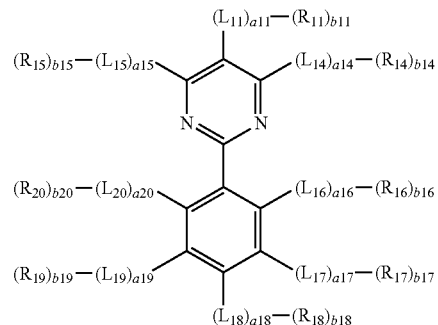

Formula 1B(3)
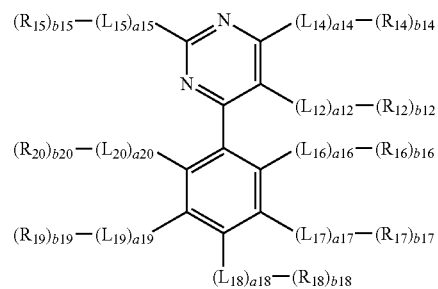

Formula 1B(4)
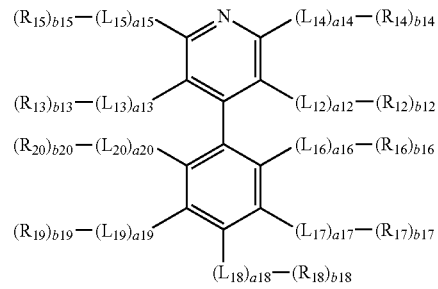

Formula 1C(1)
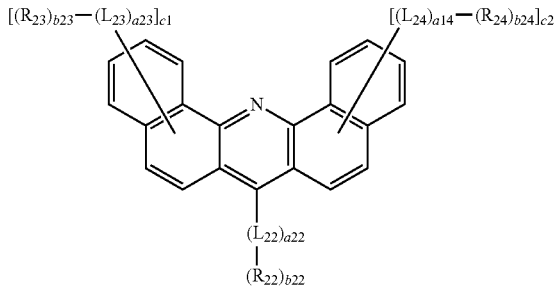

Formula 1C(2)
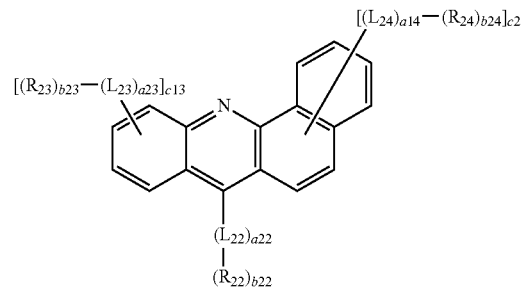

Formula 1C(3)

[Structure: acridine-type fused ring system with [(R₂₃)ᵦ₂₃—(L₂₃)ₐ₂₃]c13, (L₂₂)ₐ₂₂, (R₂₂)ᵦ₂₂, [(L₂₄)ₐ₁₄—(R₂₄)ᵦ₂₄]c2]

Formula 1D(1)

[Structure: phenanthroline-type with [(R₃₃)ᵦ₃₃—(L₃₃)ₐ₃₃]c3, (L₃₁)ₐ₃₁—(R₃₁)ᵦ₃₁, (L₃₂)ₐ₃₂—(R₃₂)ᵦ₃₂, (L₃₄)ₐ₃₄—(R₃₄)ᵦ₃₄]c4]

Formula 1D(2)

[Structure with substituents (R₃₃)ᵦ₃₃—(L₃₃)ₐ₃₃]c3, (L₃₁)ₐ₃₁—(R₃₁)ᵦ₃₁, (L₃₂)ₐ₃₂—(R₃₂)ᵦ₃₂, (L₃₄)ₐ₃₄—(R₃₄)ᵦ₃₄]c4]

Formula 1D(3)

[Structure with substituents (R₃₃)ᵦ₃₃—(L₃₃)ₐ₃₃]c3, (L₃₁)ₐ₃₁—(R₃₁)ᵦ₃₁, (L₃₂)ₐ₃₂—(R₃₂)ᵦ₃₂, (L₃₄)ₐ₃₄—(R₃₄)ᵦ₃₄]c4]

Formula 1D(4)

[Structure with substituents (R₃₃)ᵦ₃₃—(L₃₃)ₐ₃₃]c3, (L₃₁)ₐ₃₁—(R₃₁)ᵦ₃₁, (L₃₂)ₐ₃₂—(R₃₂)ᵦ₃₂, (L₃₄)ₐ₃₄—(R₃₄)ᵦ₃₄]c4]

In Formulae 1A(1) to 1A(3), 1B(1) to 1B(4), 1C(1) to 1C(3), and 1D(1) to 1D(4), $L_2$ to $L_6$, $L_{11}$ to $L_{20}$, $L_{22}$ to $L_{24}$, $L_{31}$ to $L_{34}$, a2 to a6, a11 to a20, a22 to a24, a31 to a34, $R_3$ to $R_6$, $R_{11}$ to $R_{20}$, $R_{22}$ to $R_{24}$, $R_{31}$ to $R_{34}$, b3 to b6, b11 to b20, b22 to b24, b31 to b34, and c1 to c4 may be understood by referring to the descriptions thereof provided herein.

For example, in Formulae 1A(1) to 1A(3), 1B(1) to 1B(4), 1C(1) to 1C(3), and 1D(1) to 1D(4), $L_2$ to $L_6$, $L_{11}$ to $L_{24}$, and $L_{31}$ to $L_{34}$ may each independently be a group represented by one selected from Formulae 3-1 to 3-100, a2 to a6, a11 to a24, and a31 to a34 may each independently be 0, 1, or 2, $R_3$ to $R_6$, $R_{11}$ to $R_{24}$, and $R_{31}$ to $R_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a group represented by one selected from Formulae 5-1 to 5-38 (e.g., a group represented one selected from Formulae 9-1 to 9-79), a group represented by Formulae 6-1 to 6-123 (e.g., a group represented by one selected from Formulae 10-1 to 10-133), $Si(Q_1)(Q_2)(Q_3)$, —S(=O)₂(Q₁), and —P(=O)(Q₁)(Q₂) (wherein $Q_1$ to $Q_3$ may each independently be understood by referring to the descriptions thereof provided herein), and b3 to b6, b11 to b24, and b31 to b34 may each independently be 0, 1, or 2.

In various embodiments, the second compound may be represented by one selected from Formulae 2A to 2D:

Formula 2A

[Structure: dibenzofuran/thiophene with (R₅₃)ᵦ₅₃, X₅₁, (R₅₄)ᵦ₅₄, (L₄₃)ₐ₄₃—N with (L₄₁)ₐ₄₁—(R₄₁)ᵦ₄₁ and (L₄₂)ₐ₄₂—(R₄₂)ᵦ₄₂]

Formula 2B

[Structure with X₅₁, (R₅₃)ᵦ₅₃, (R₅₄)ᵦ₅₄, (L₄₃)ₐ₄₃—N with (L₄₁)ₐ₄₁—(R₄₁)ᵦ₄₁ and (L₄₂)ₐ₄₂—(R₄₂)ᵦ₄₂]

Formula 2C

[Structure with X₅₁, (R₅₃)ᵦ₅₃, (R₅₄)ᵦ₅₄, (L₄₃)ₐ₄₃—N with (L₄₁)ₐ₄₁—(R₄₁)ᵦ₄₁ and (L₄₂)ₐ₄₂—(R₄₂)ᵦ₄₂]

Formula 2D

[Structure with (R₅₄)ᵦ₅₄, X₅₁, (R₅₃)ᵦ₅₃, (L₄₃)ₐ₄₃—N with (L₄₁)ₐ₄₁—(R₄₁)ᵦ₄₁ and (L₄₂)ₐ₄₂—(R₄₂)ᵦ₄₂]

In Formulae 2A to 2D, $X_{51}$, $L_{41}$ to $L_{43}$, a41 to a43, $R_{41}$, $R_{42}$, $R_{53}$, $R_{54}$, b41, b42, b53, and b54 may each independently be understood by referring to descriptions thereof provided herein.

For example, in Formulae 2A to 2D, $X_{51}$ may be O or S, $L_{41}$ to $L_{43}$ may each independently be a group represented by one selected from Formulae 3-1 to 3-30, a41 to a43 may each independently be 0, 1, or 2, $R_{41}$ and $R_{42}$ may each independently be selected from groups represented by Formulae 9-1 to 9-52 and 9-77 to 9-79, $R_{53}$ and $R_{54}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, and a pyridinyl group; and a phenyl group, a biphenyl group, a terphenyl group, a naphthyl group, and a pyridinyl group, each substituted with at least one selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and a pyridinyl group, b41 and b42 may each independently be 1 or 2, and b53 and b54 may each independently be 0, 1, or 2.

In an embodiment, the first compound may be selected from Compounds 1-1 to 1-261:

1-1

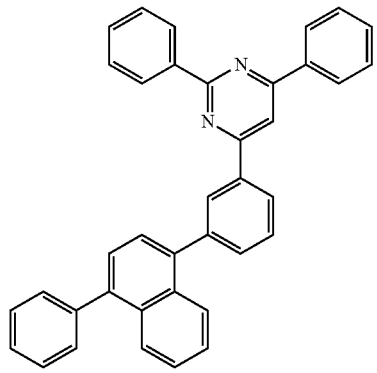

1-2

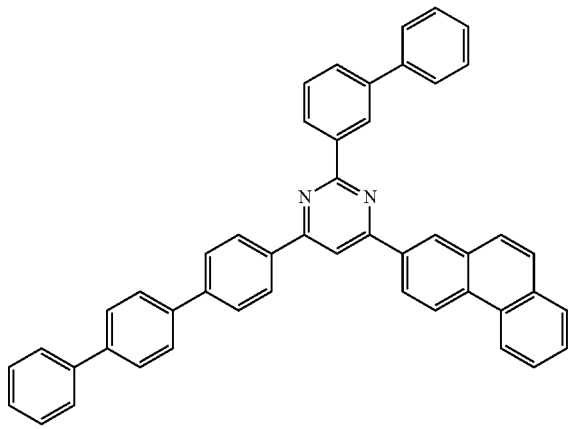

1-3

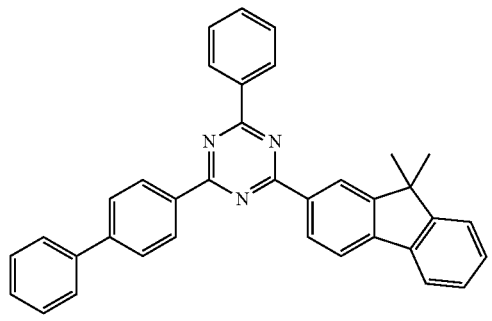

1-4

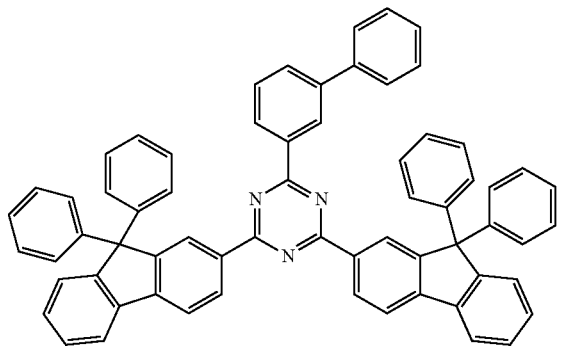

1-5

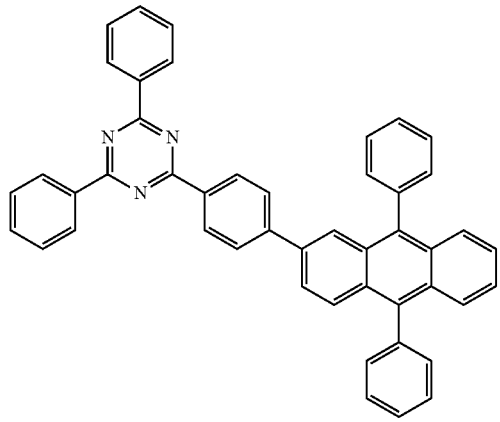

1-6

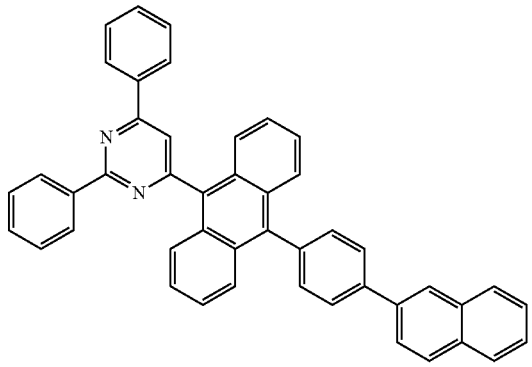

-continued
1-7
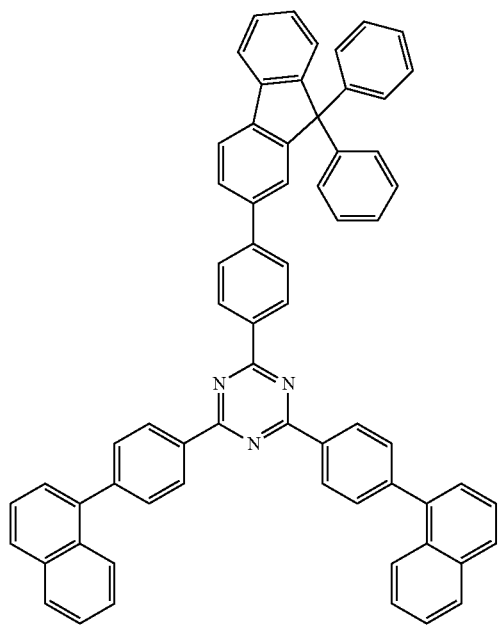
1-8
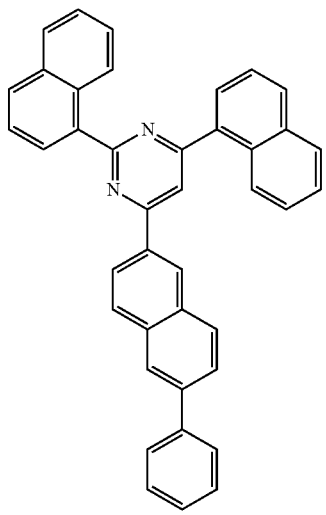
1-9
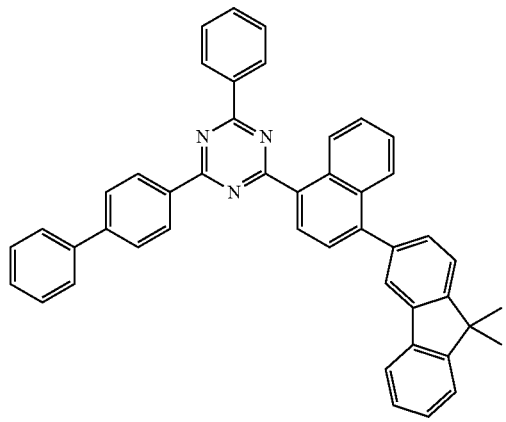
1-10
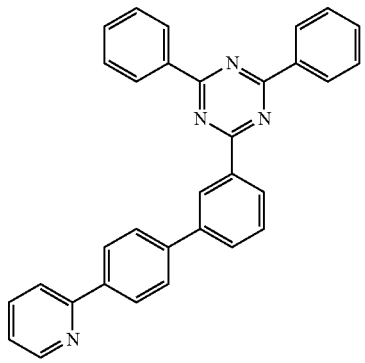
1-11
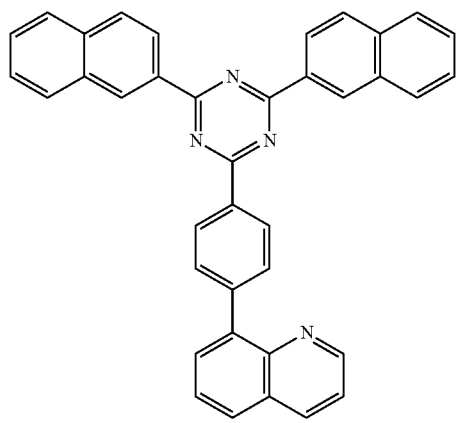
1-12
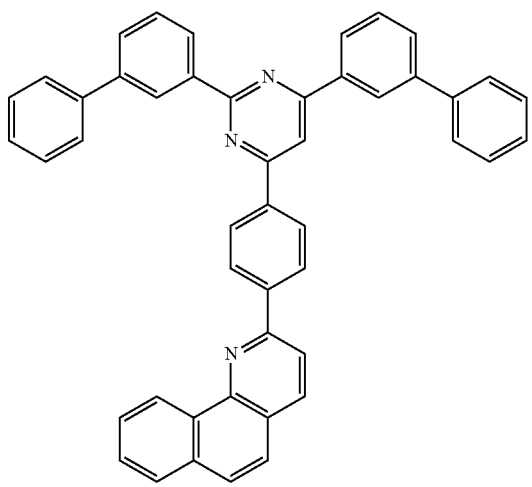

1-13
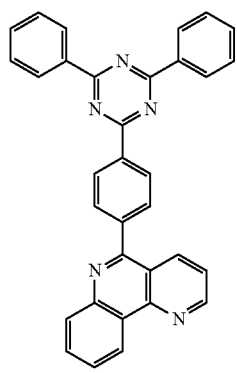
1-14
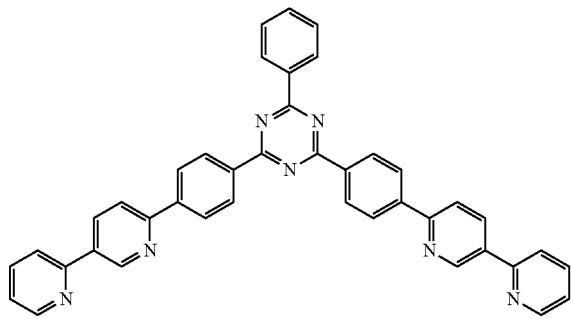
1-15
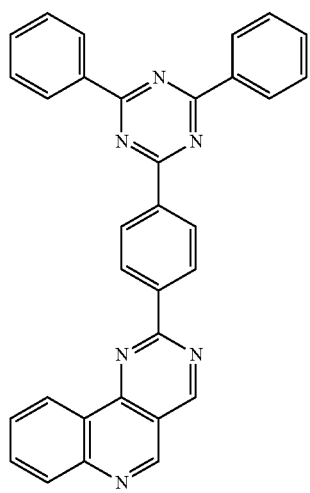
1-16
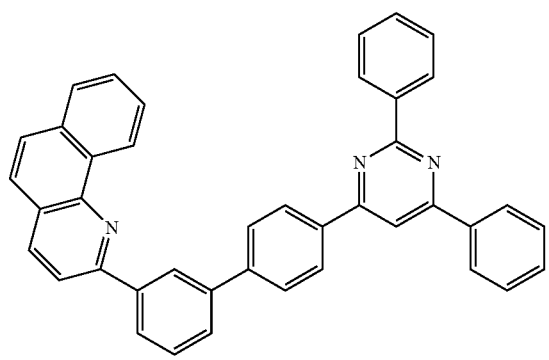
1-17
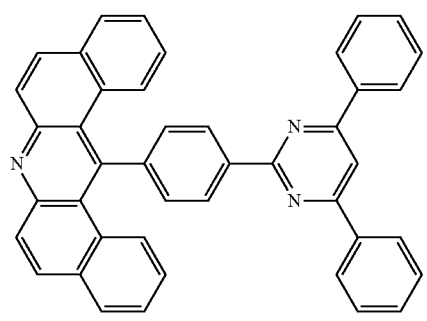
1-18
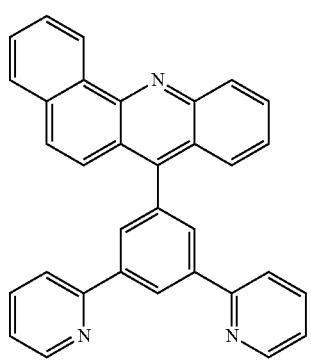

-continued
1-19
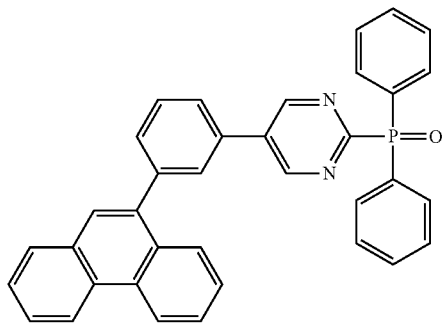
1-20
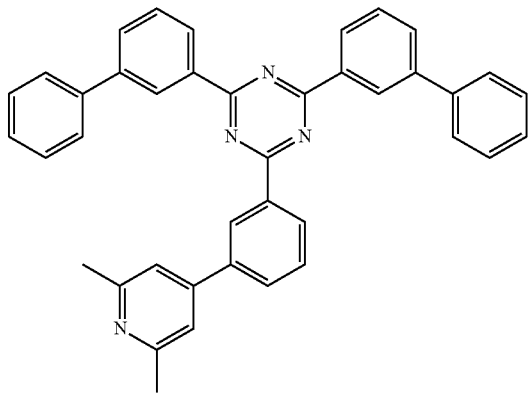
1-21
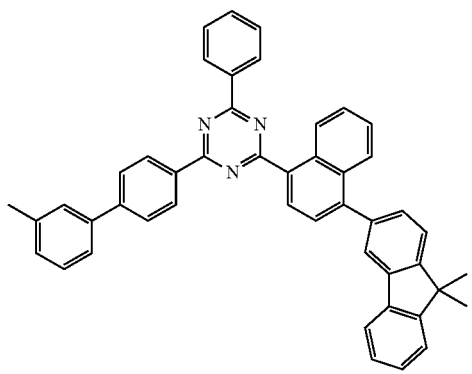
1-22
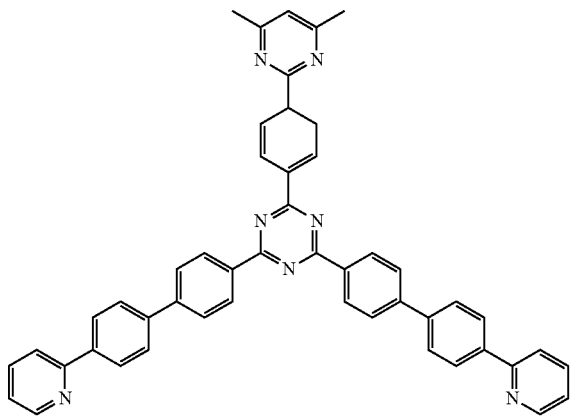
1-23
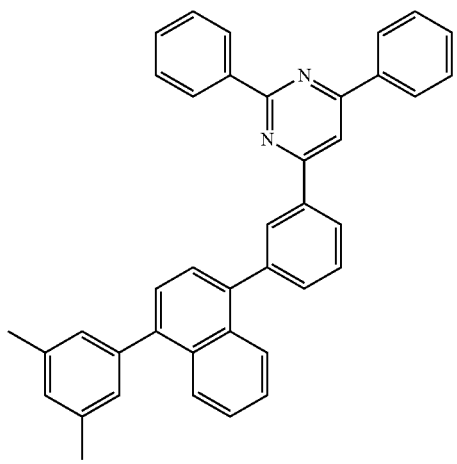
1-24
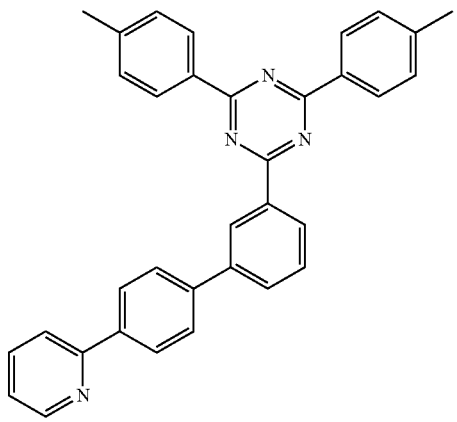

1-25
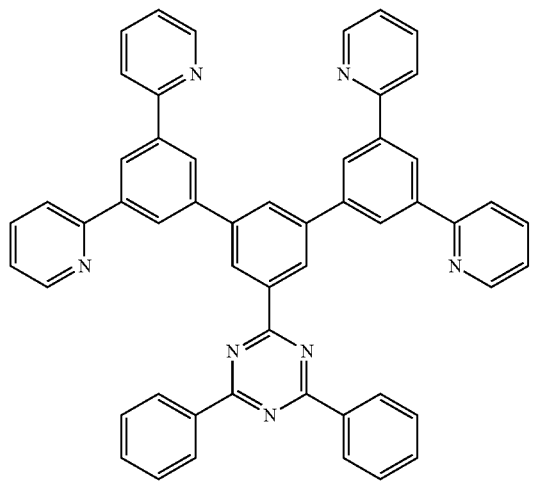
1-26
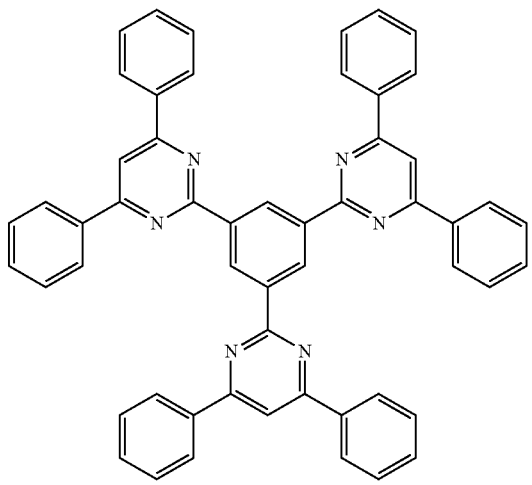
1-27
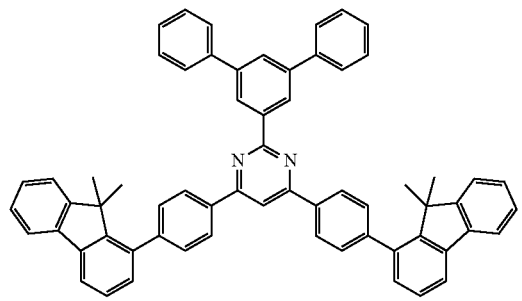
1-28
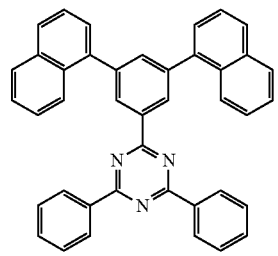
1-29
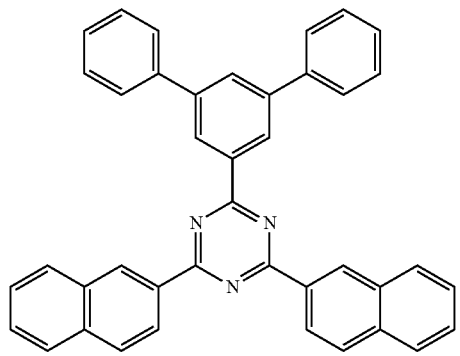
1-30
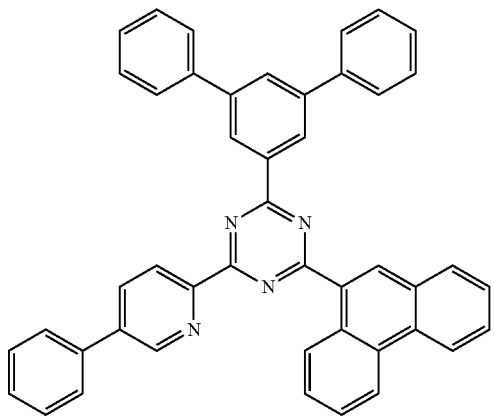

-continued
1-31
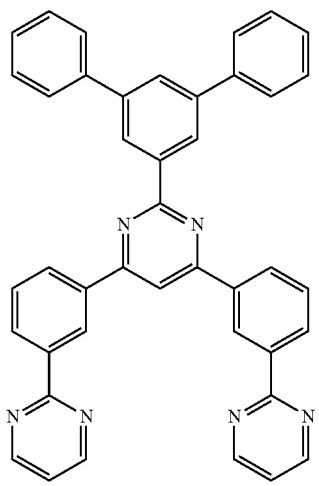
1-32
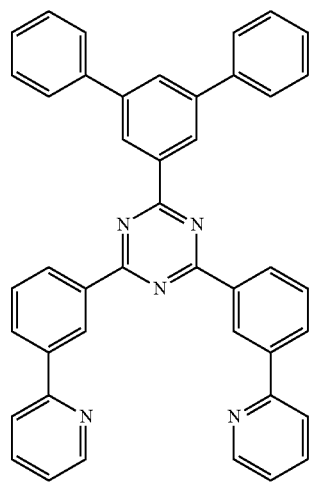
1-33
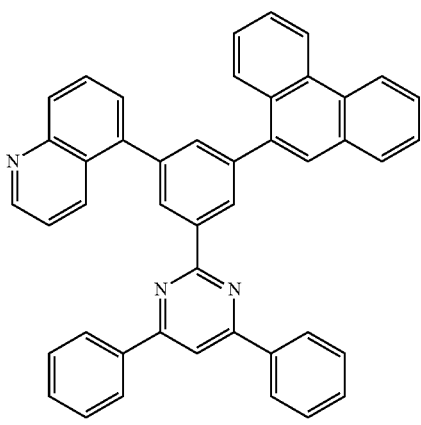
1-34
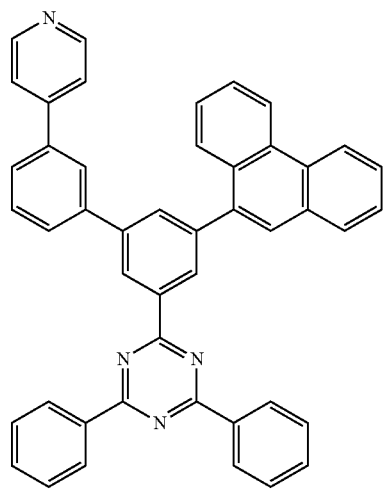
1-35
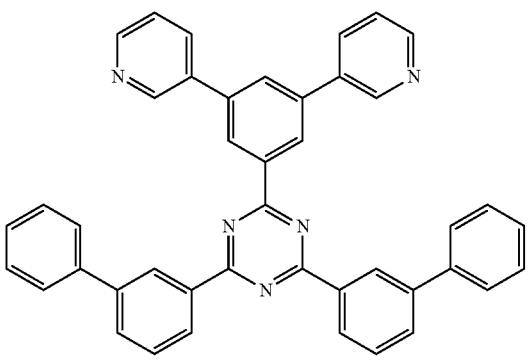
1-36
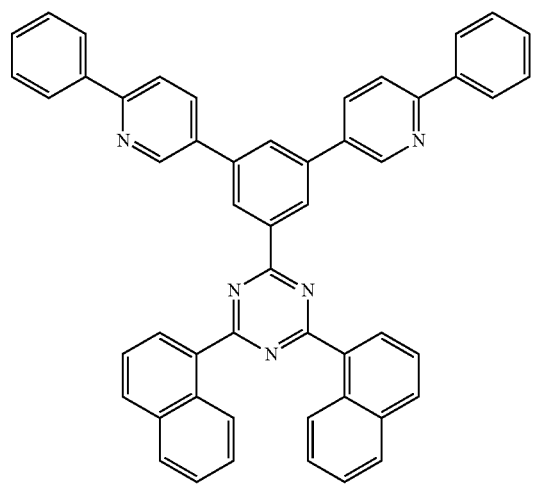

-continued
1-37
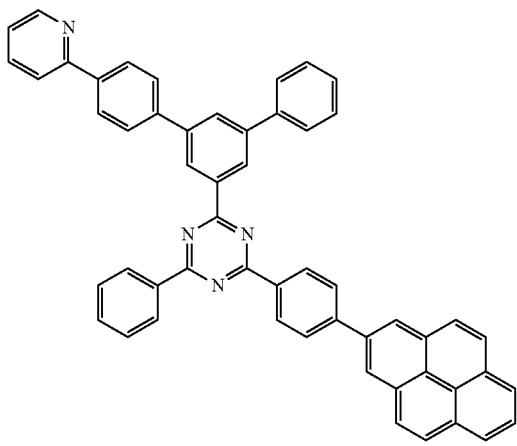
1-38
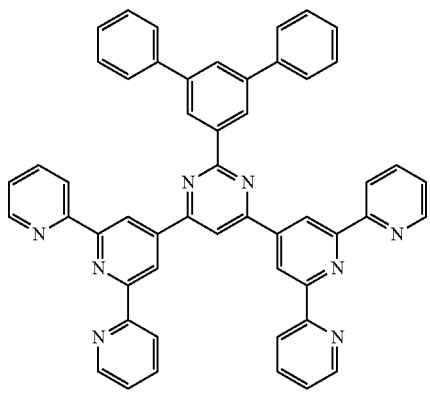
1-39
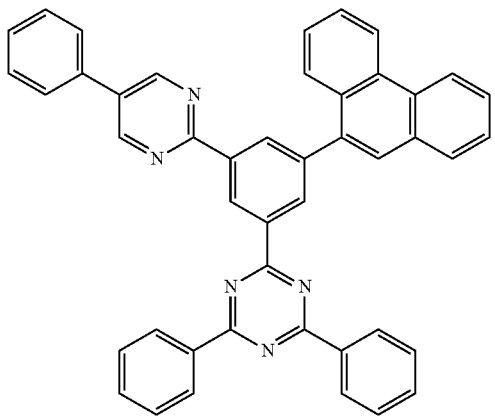
1-40
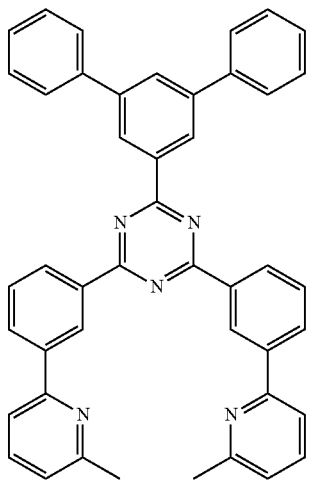
1-41
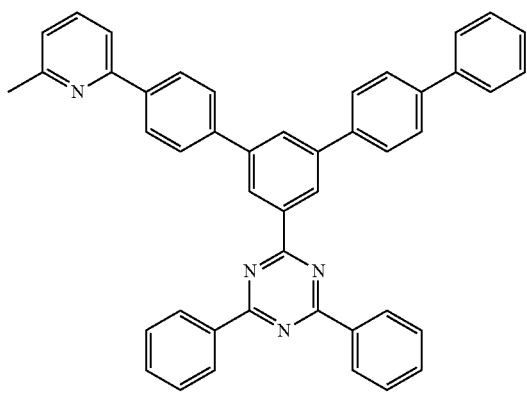
1-42
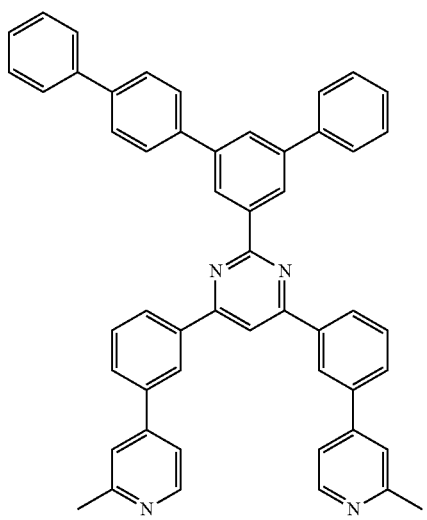

-continued
1-43
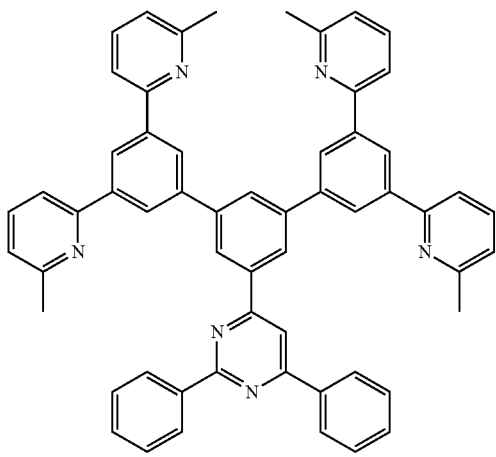
1-44
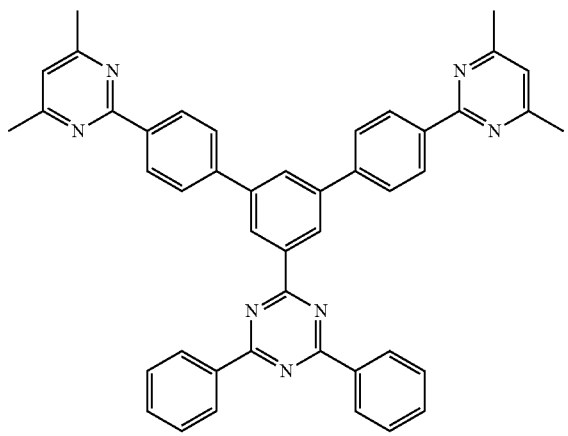
1-45
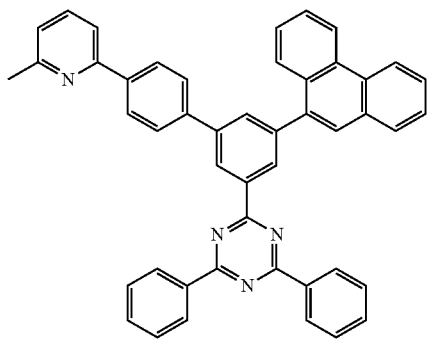
1-46
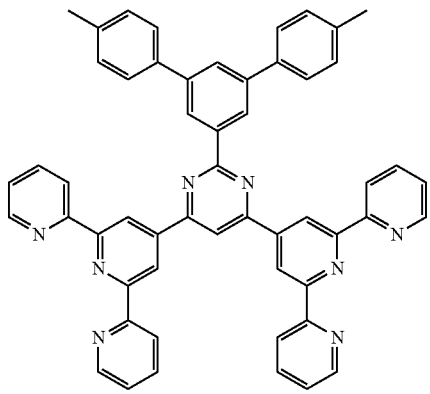
1-47
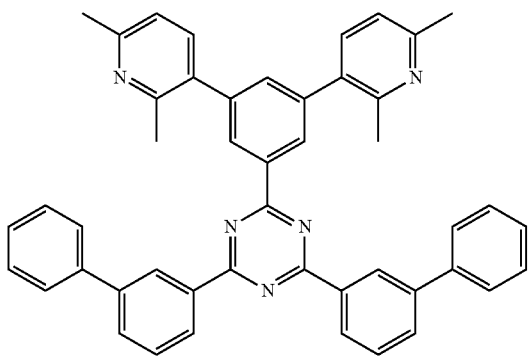
1-48
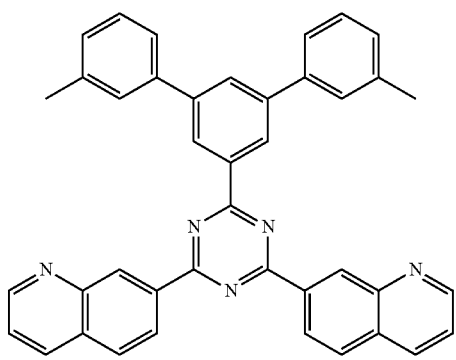

-continued
1-49
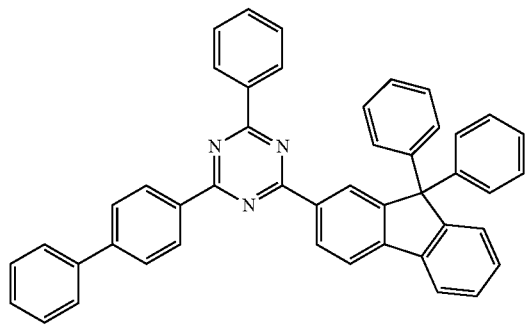
1-50
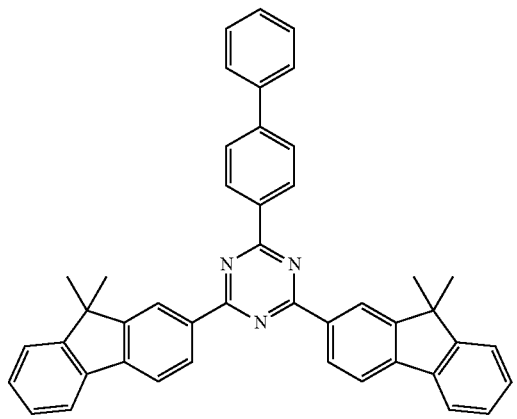
1-51
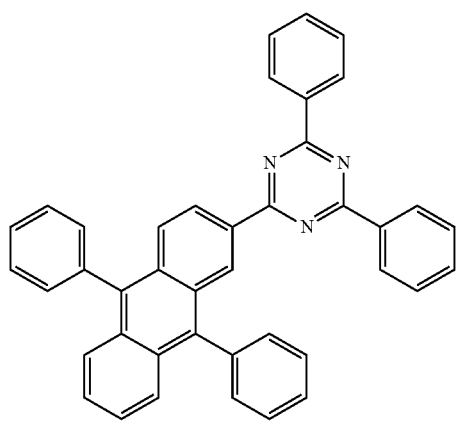
1-52
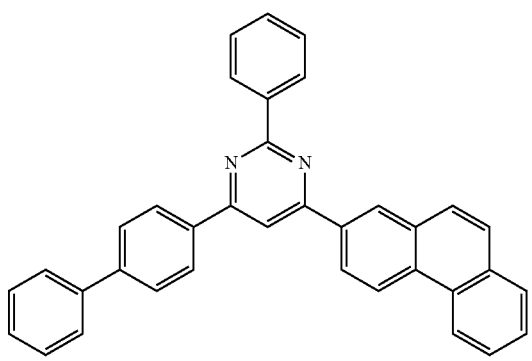
1-53
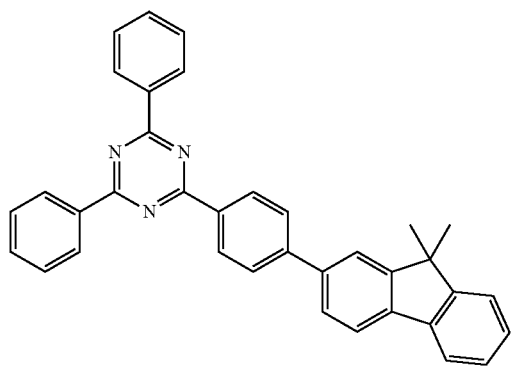
1-54
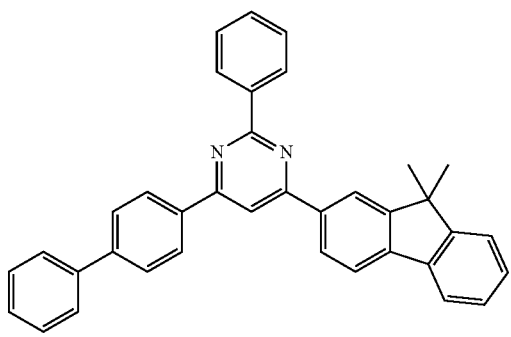

1-55
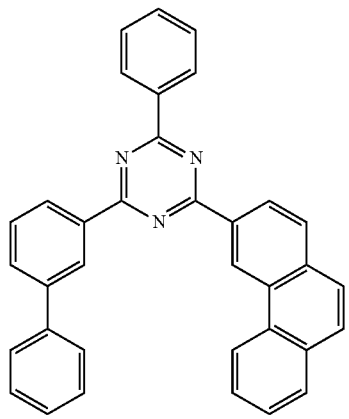
1-56
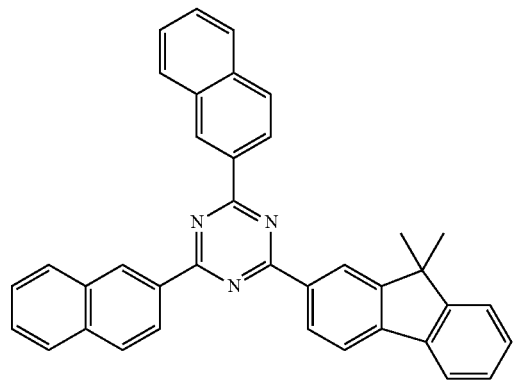
1-57
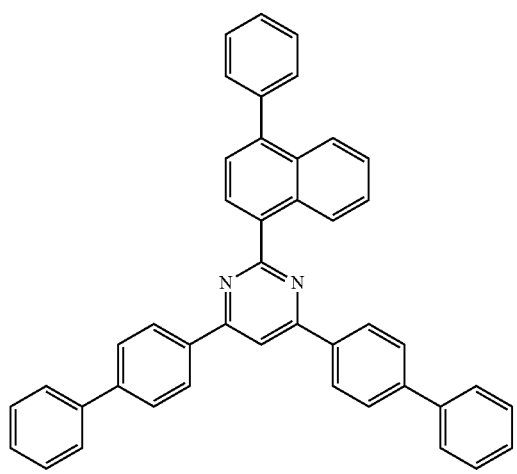
1-58
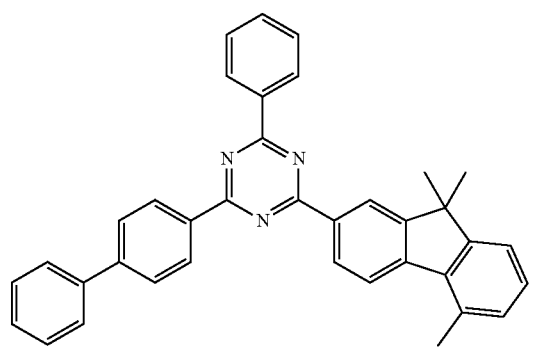
1-59
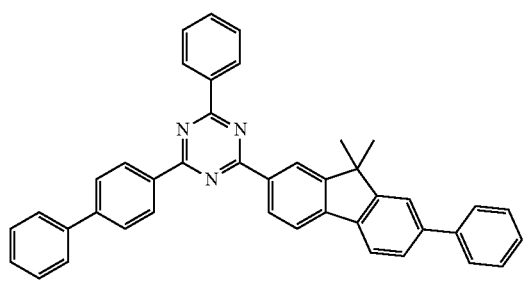
1-60
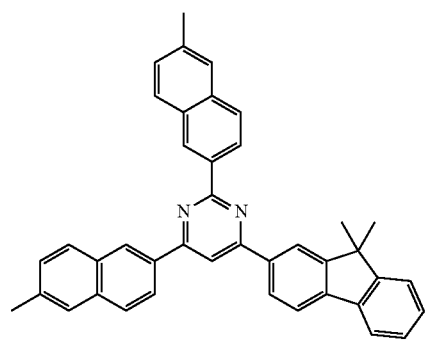

-continued
1-61
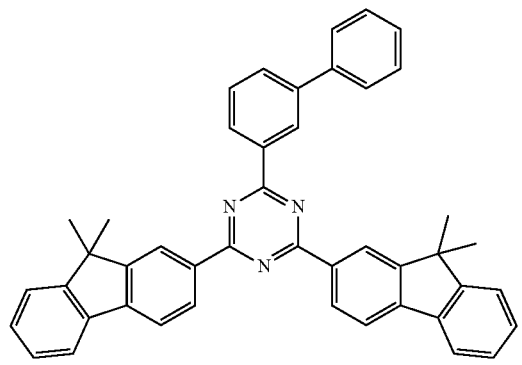
1-62
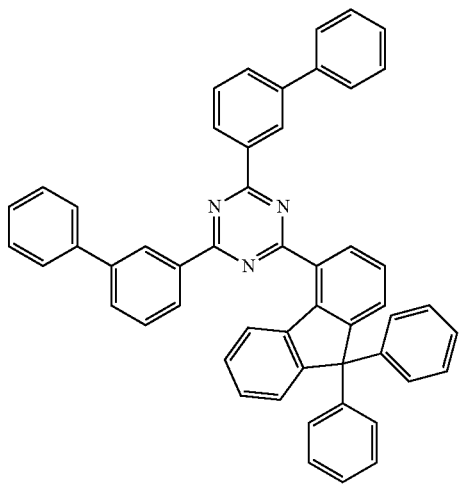
1-63
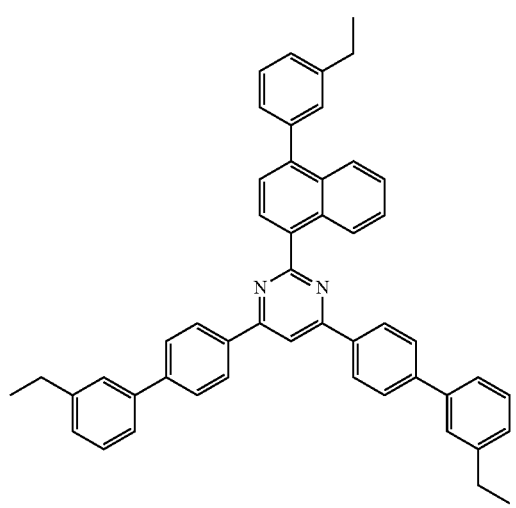
1-64
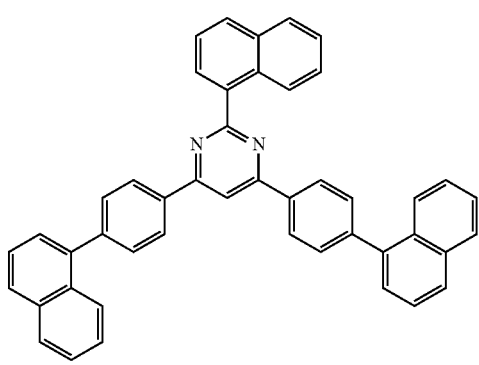
1-65
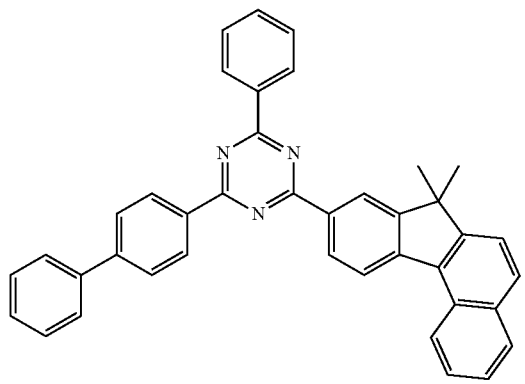
1-66
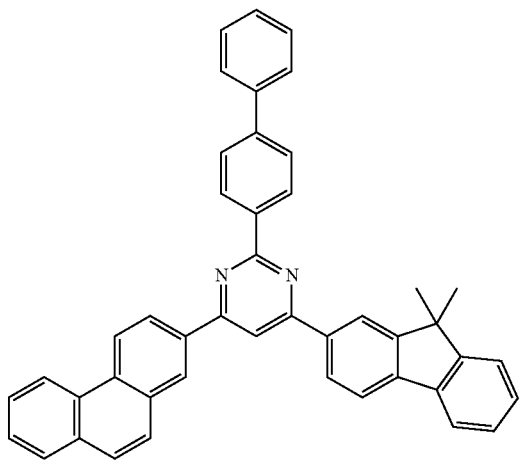

-continued
1-67
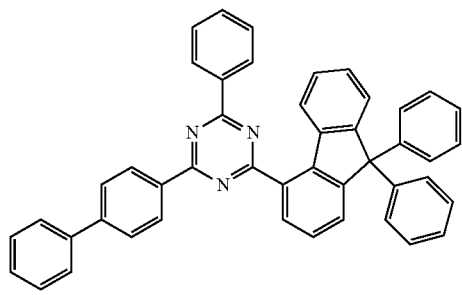
1-68
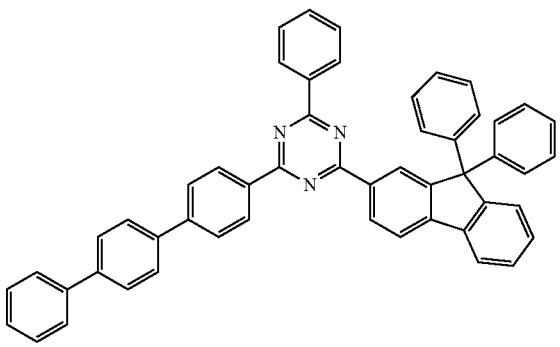
1-69
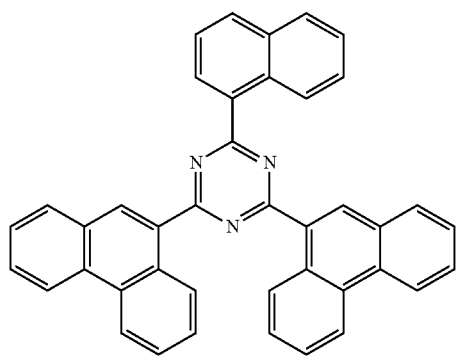
1-70
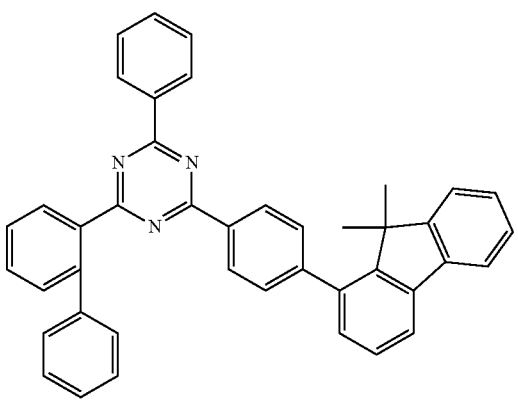
1-71
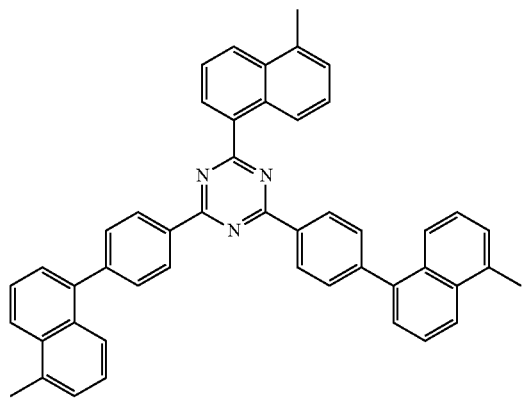
1-72
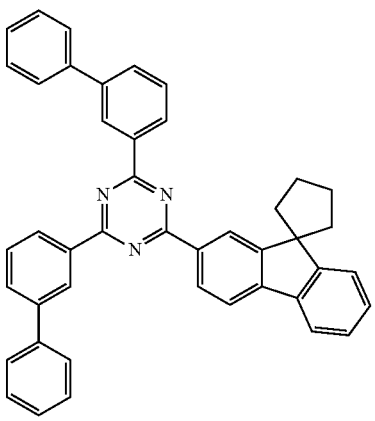
1-73
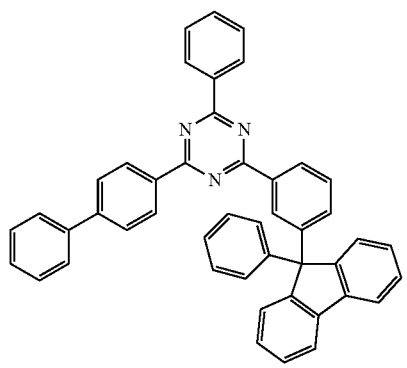
1-74
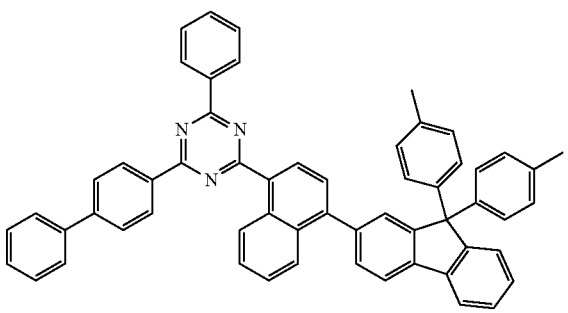

-continued
1-75
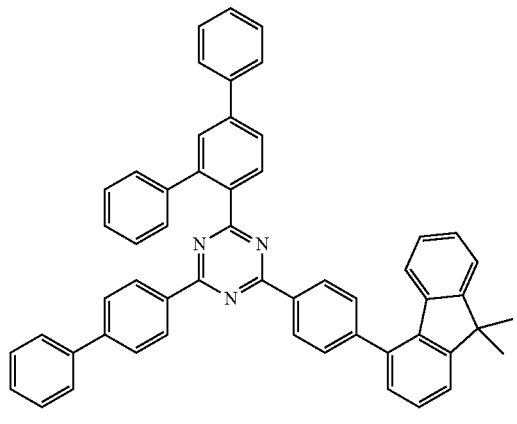
1-76
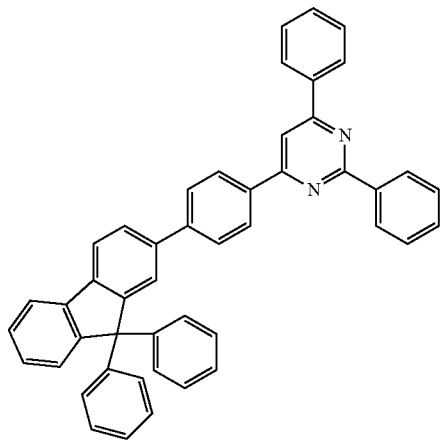
1-77
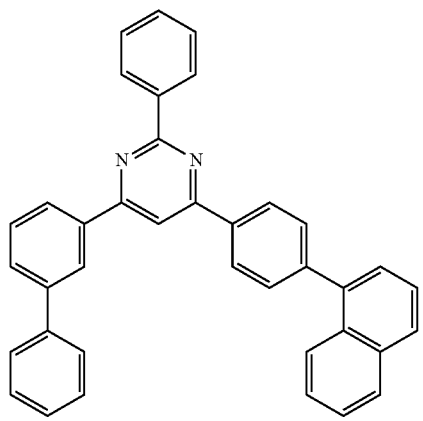
1-78
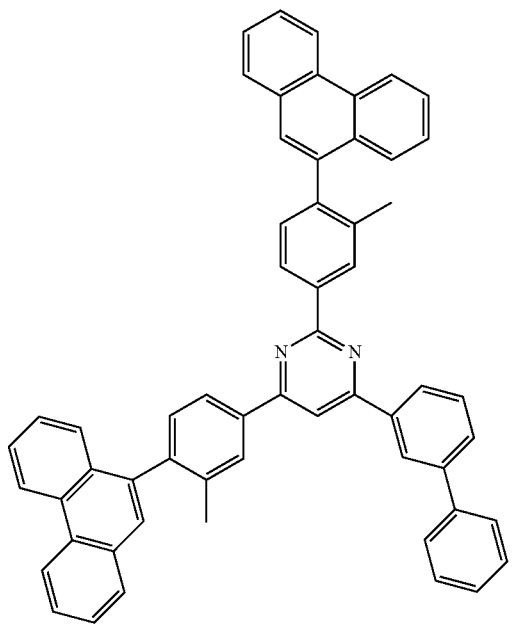
1-79
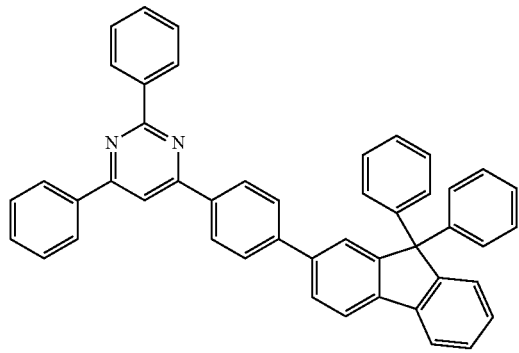
1-80
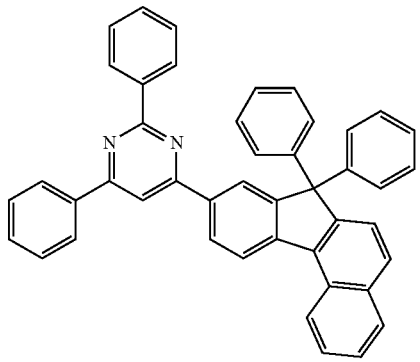

-continued
1-81
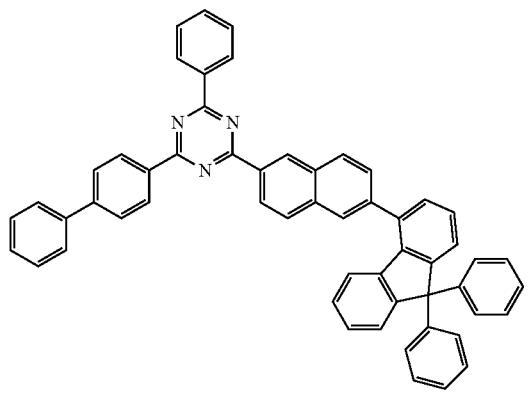
1-82
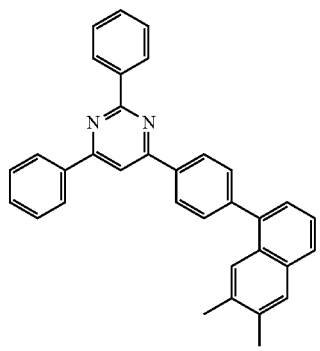
1-83
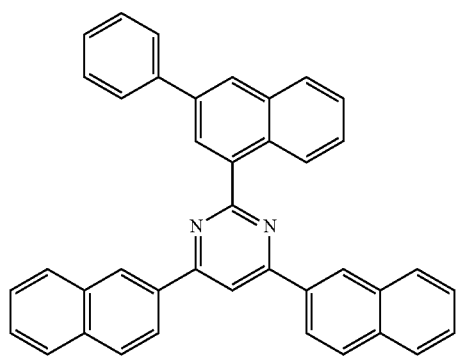
1-84
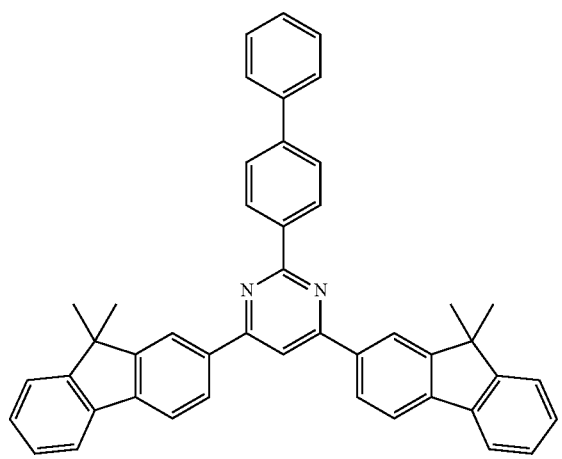
1-85
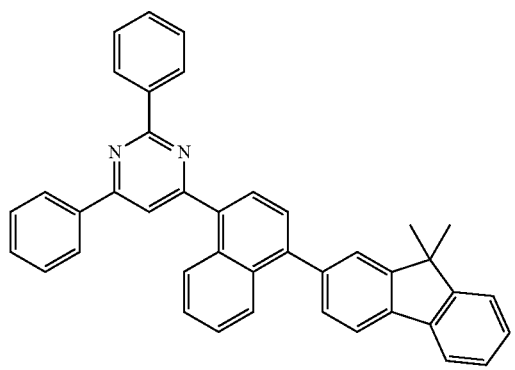
1-86
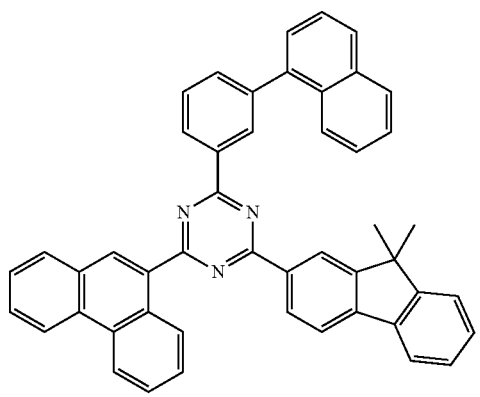

-continued
1-87
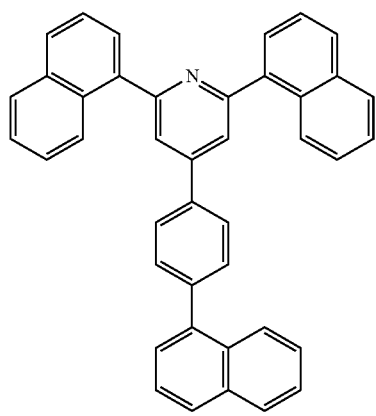
1-88
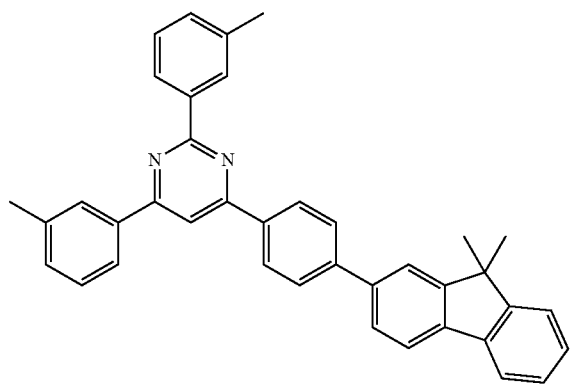
1-89
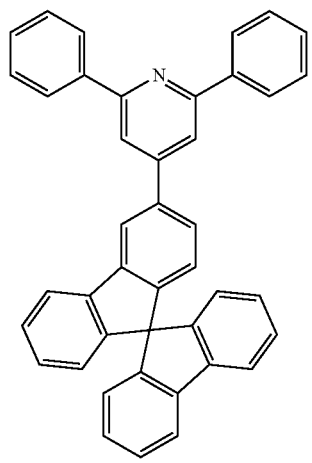
1-90
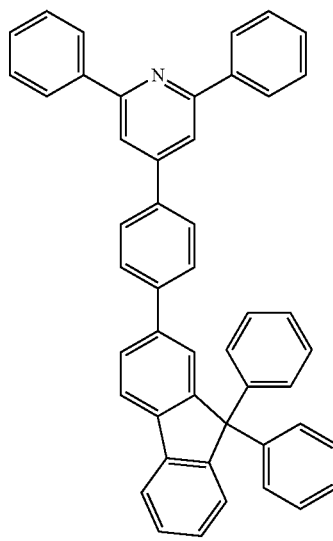
1-91
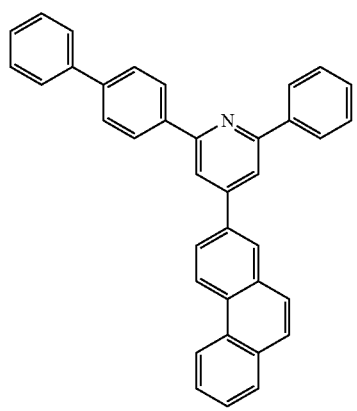
1-92
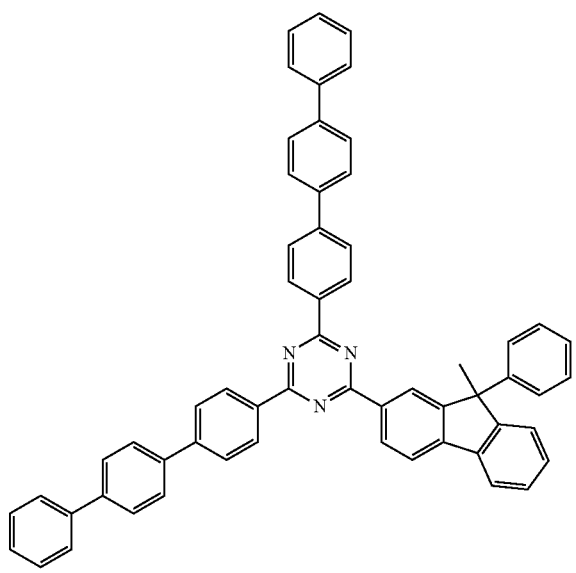

-continued
1-93
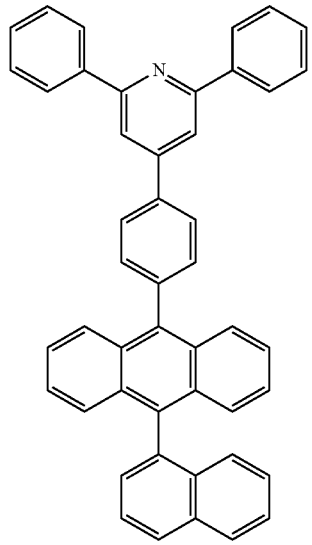
1-94
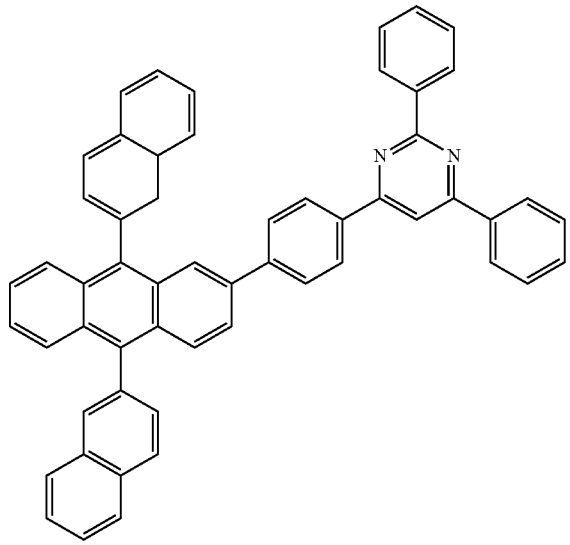
1-95
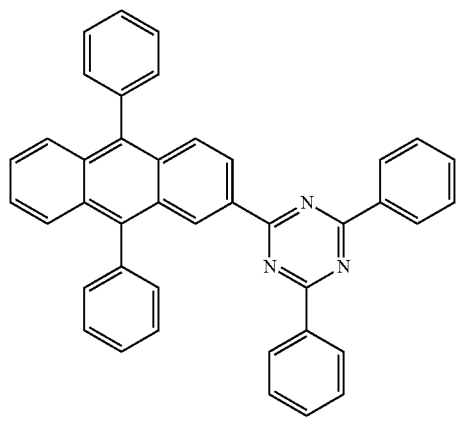
1-96
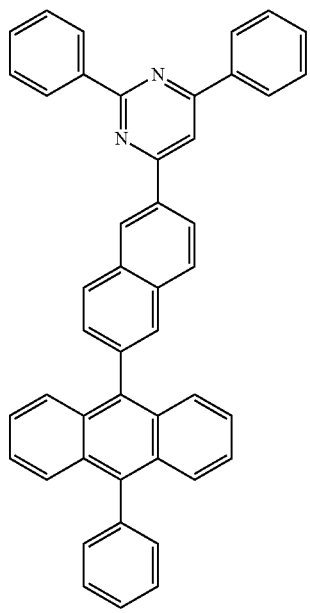

113                                        114
-continued
1-97                                        1-98
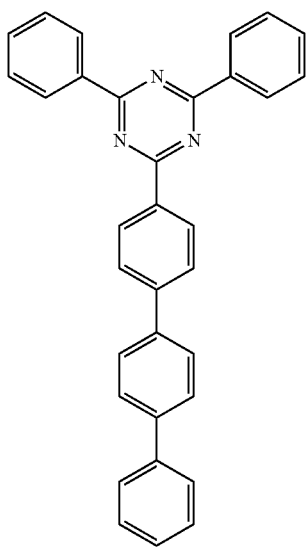
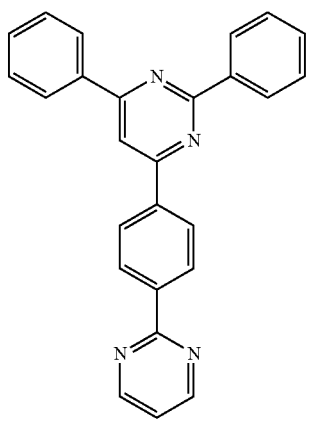
1-99                                        1-100
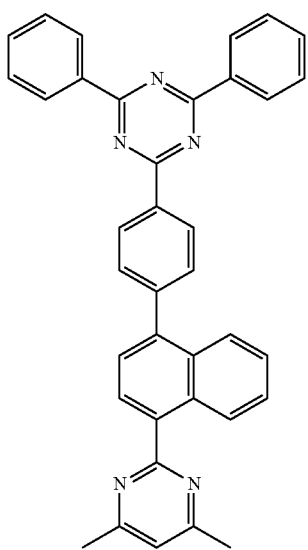
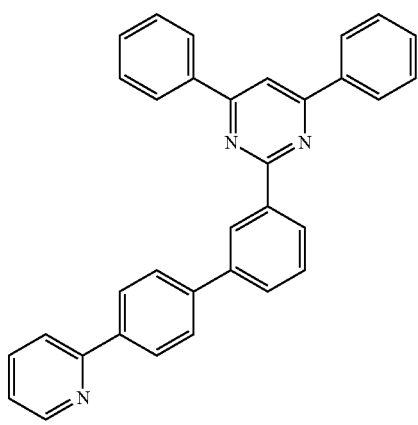
1-101                                       1-102
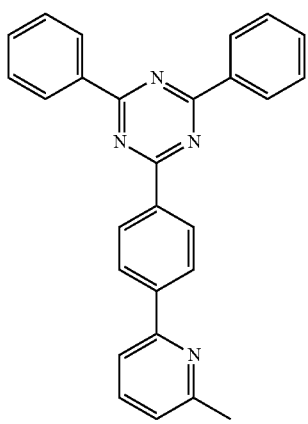
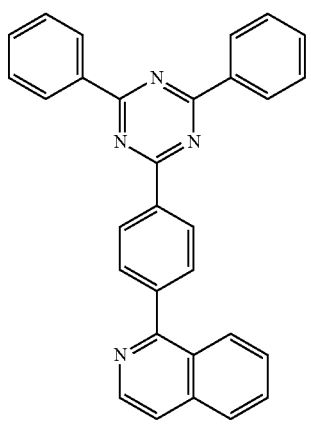

-continued
1-103
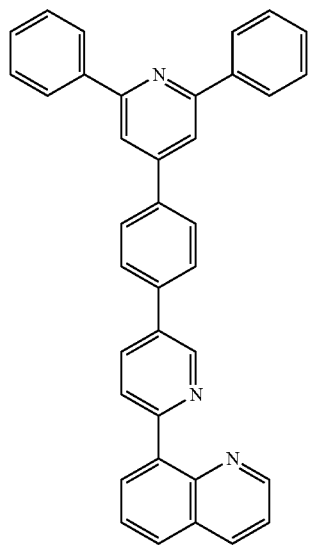
1-104
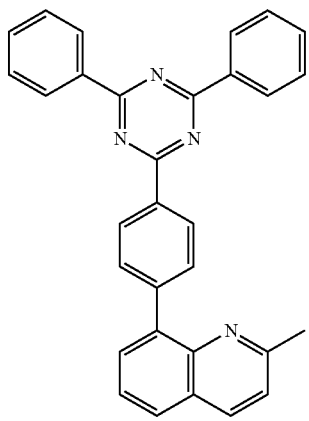
1-105
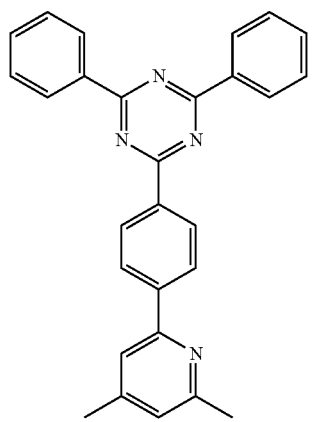
1-106
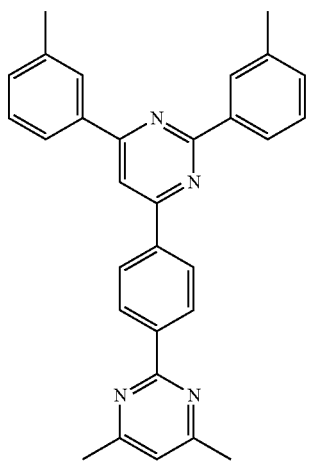
1-107
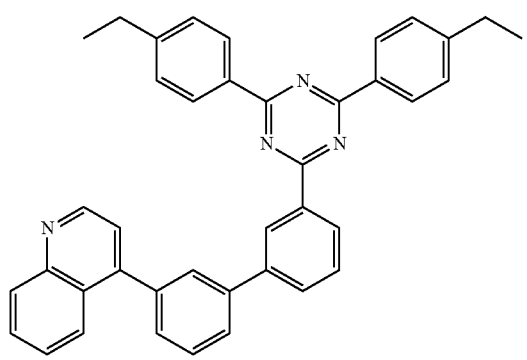
1-108
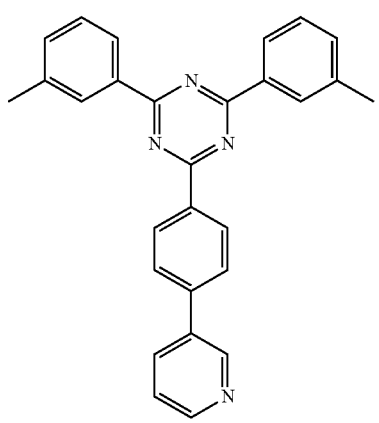

-continued
1-109
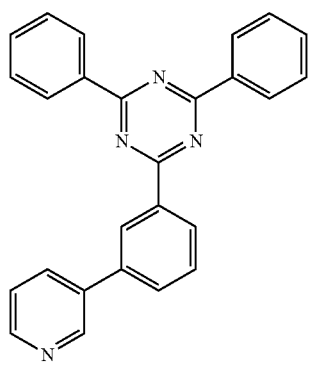
1-110
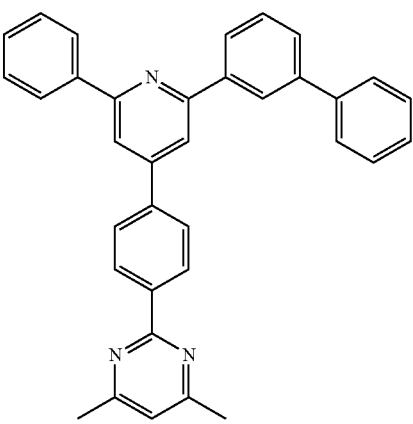
1-111
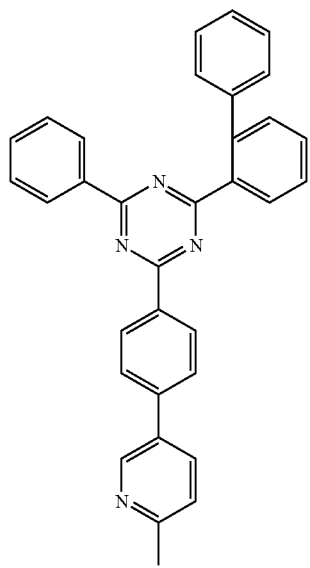
1-112
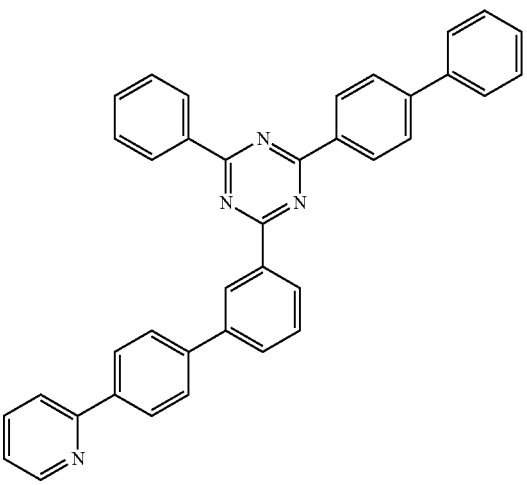
1-113
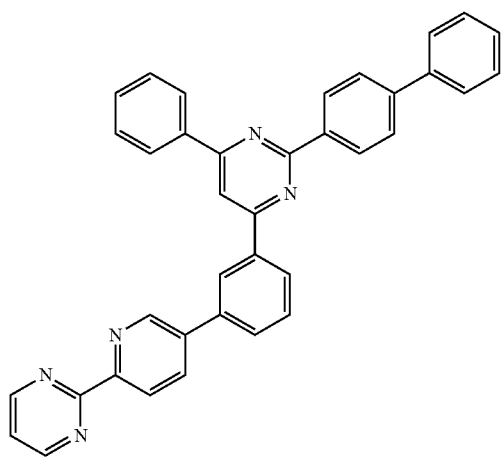
1-114
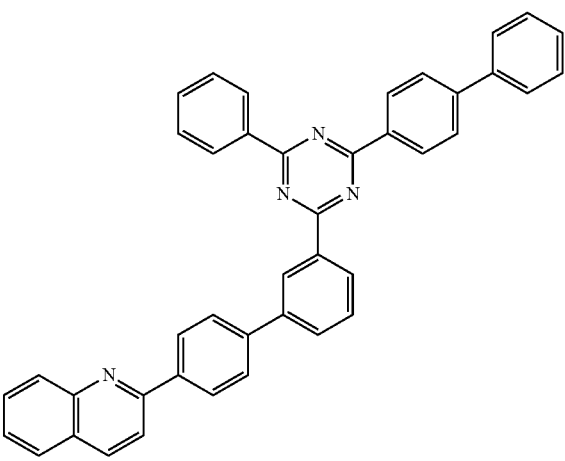

-continued
1-115
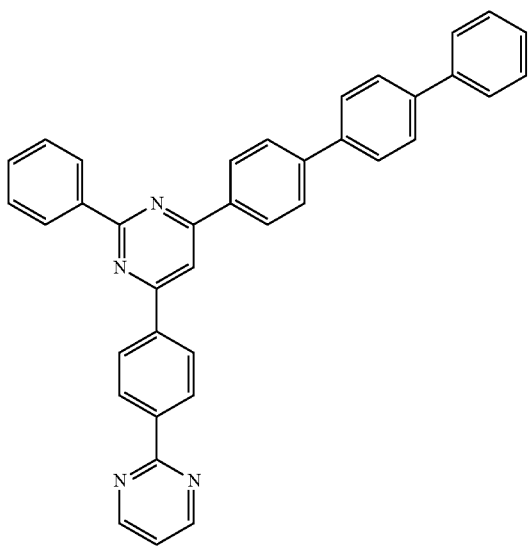
1-116
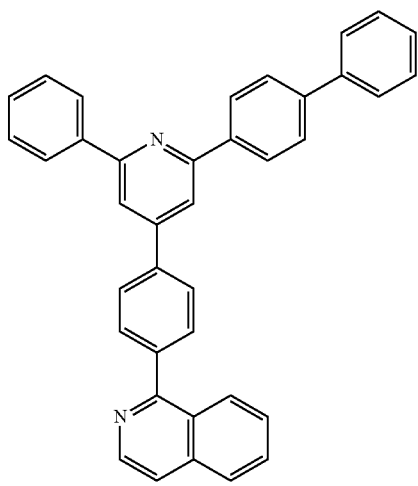
1-117
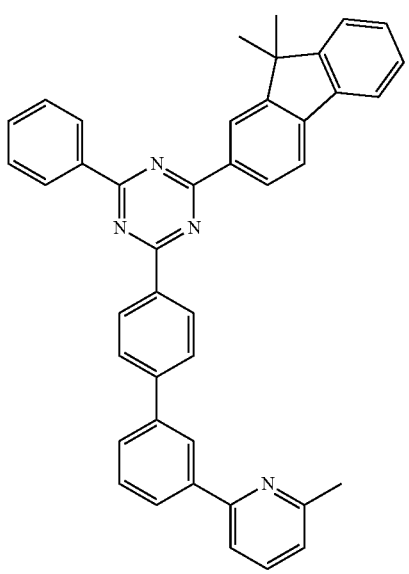
1-118
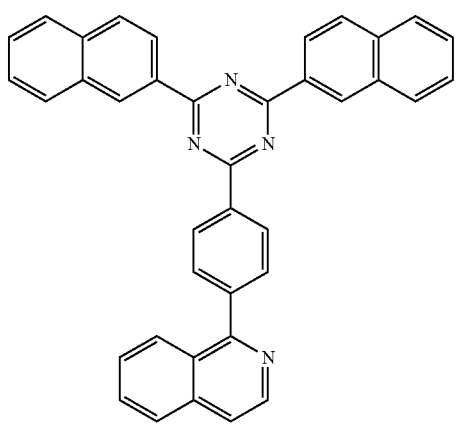
1-119
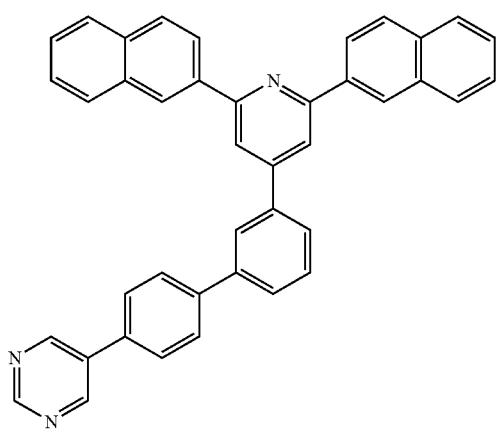
1-120
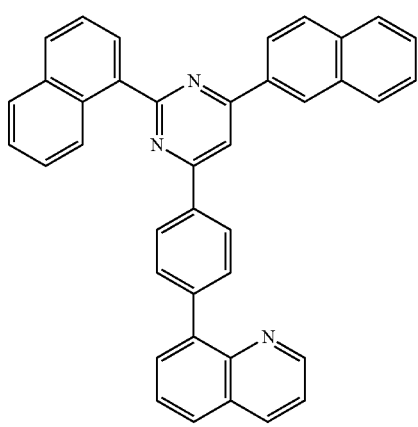

-continued
1-121
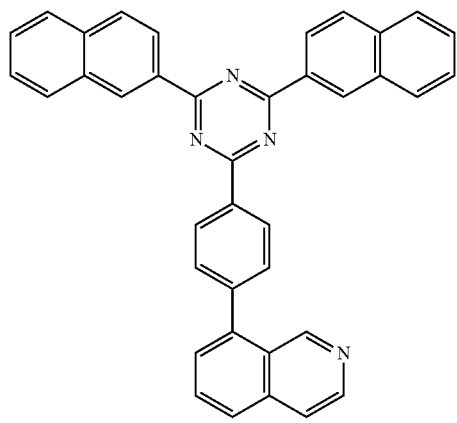
1-122
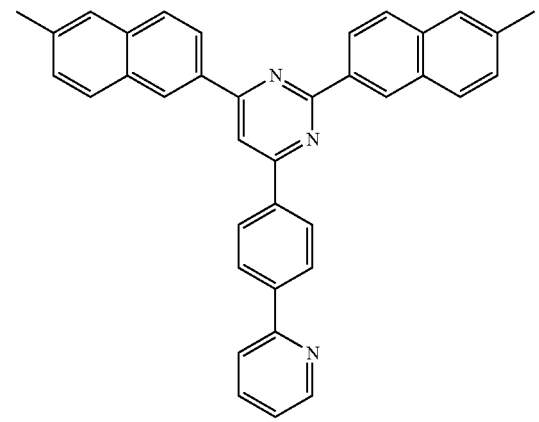
1-123
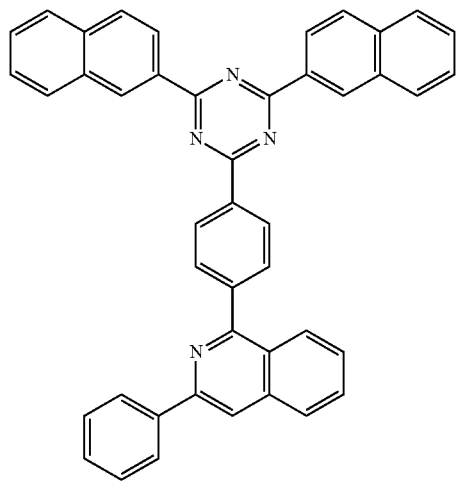
1-124
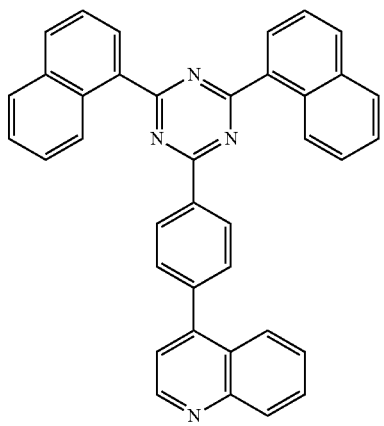
1-125
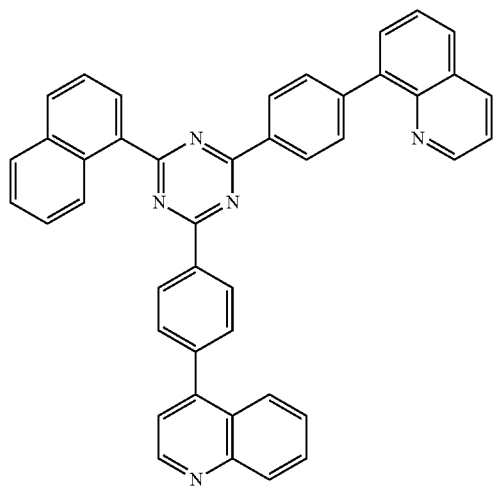
1-126
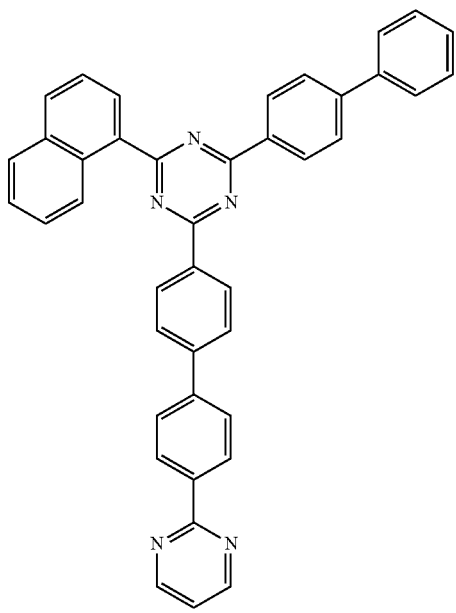

1-127
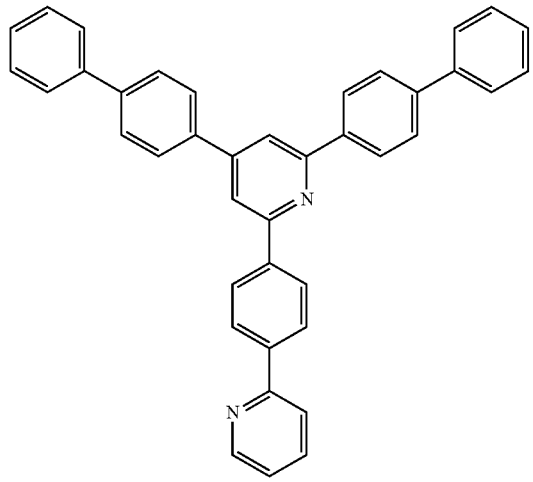
1-128
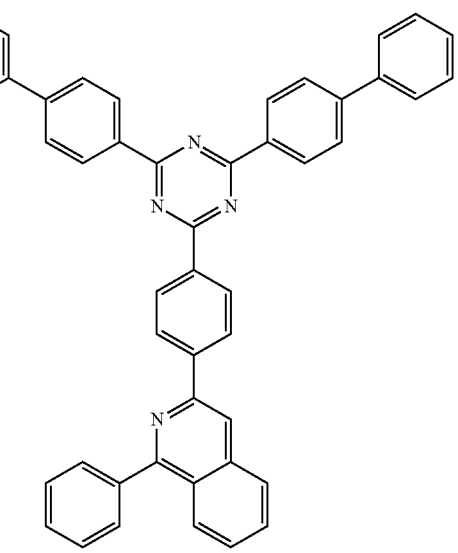
1-129
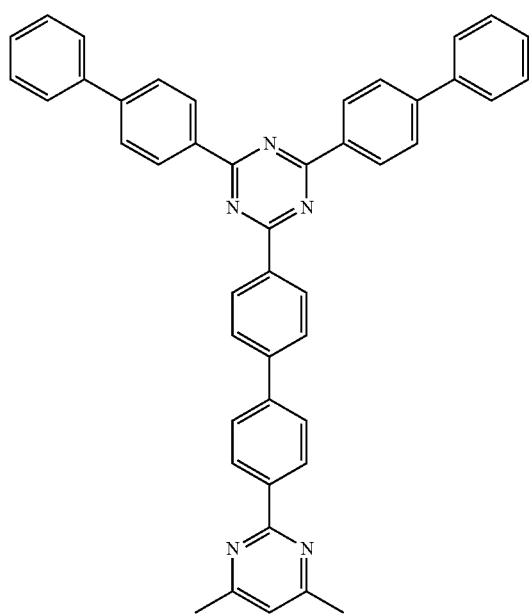
1-130
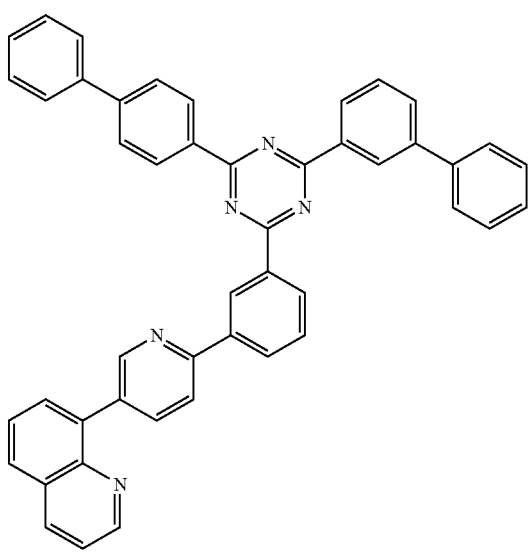

-continued
1-131
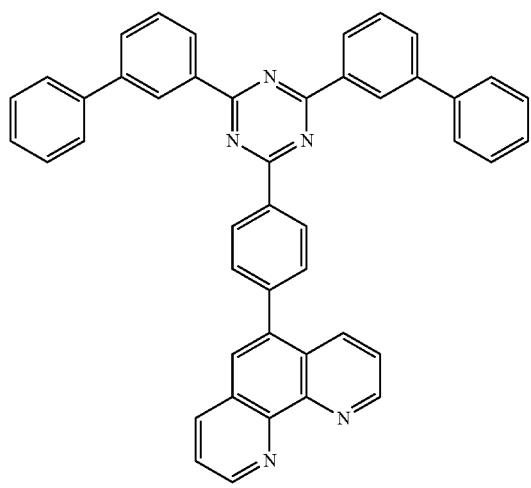
1-132
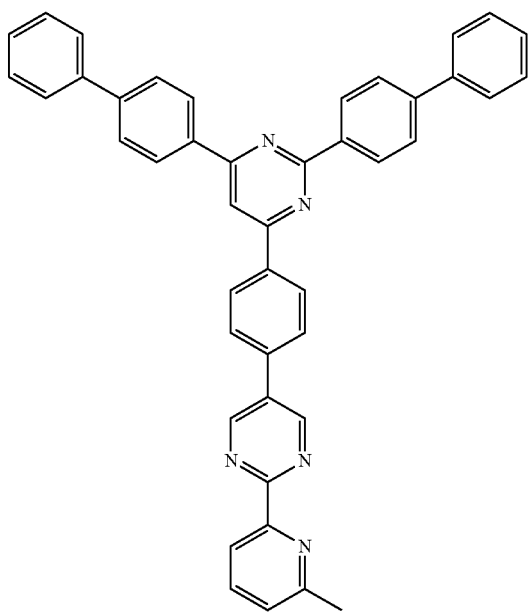
1-133
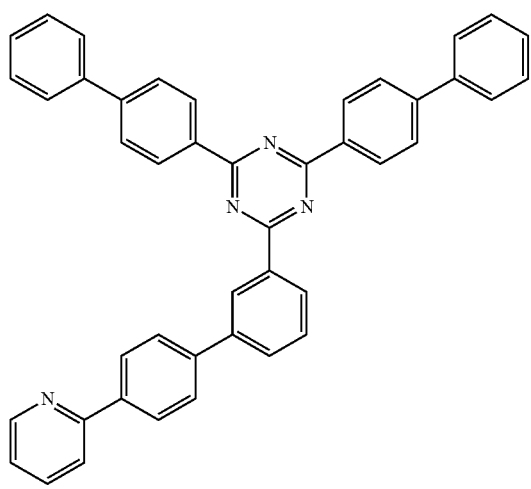
1-134
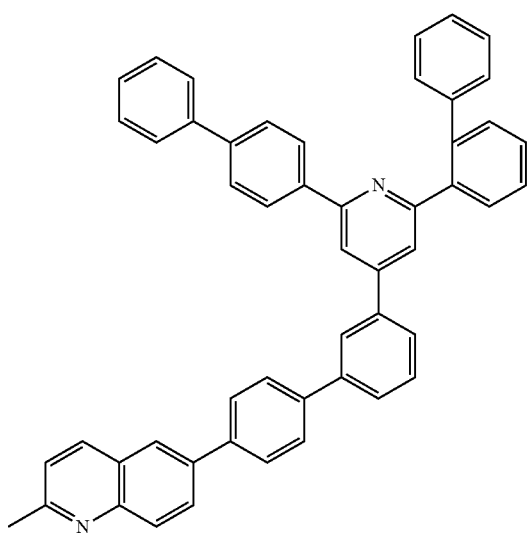
1-135
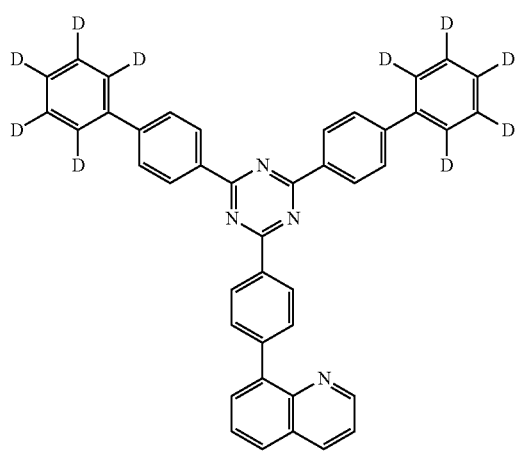
1-136
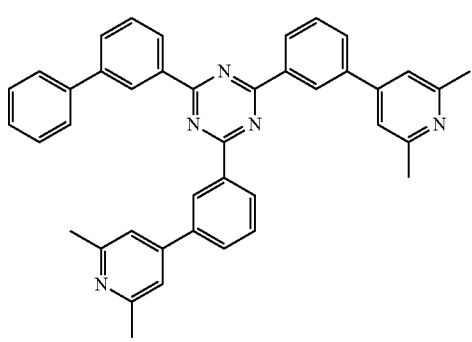

1-137 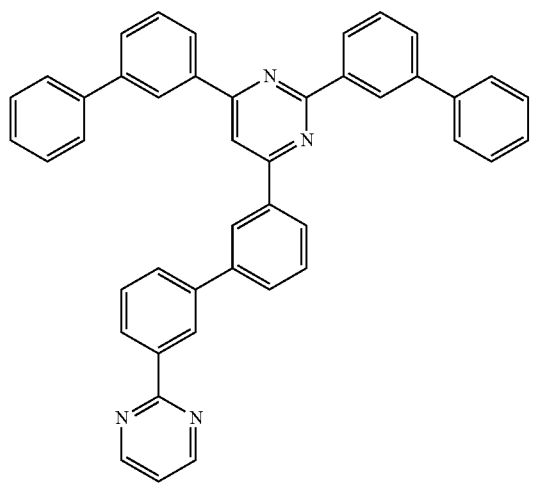
1-138 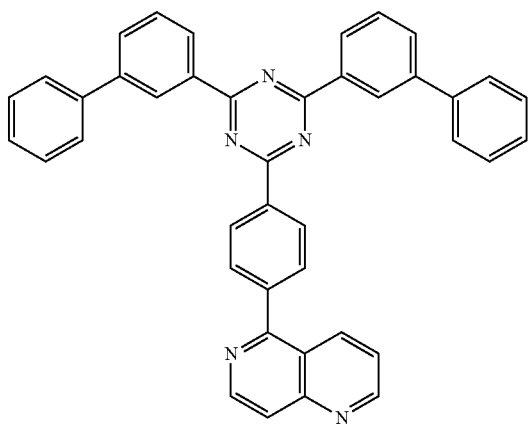
1-139 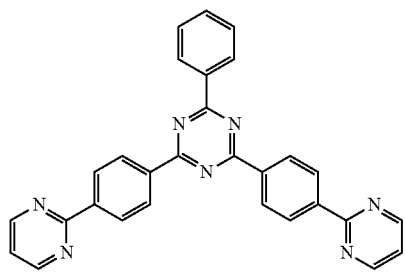
1-140 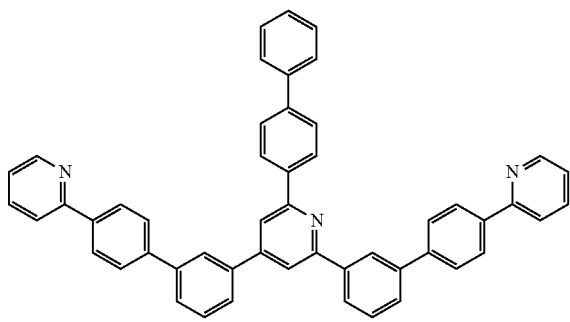
1-141 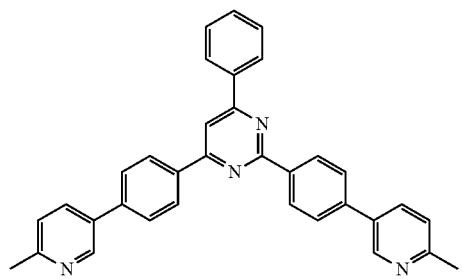
1-142 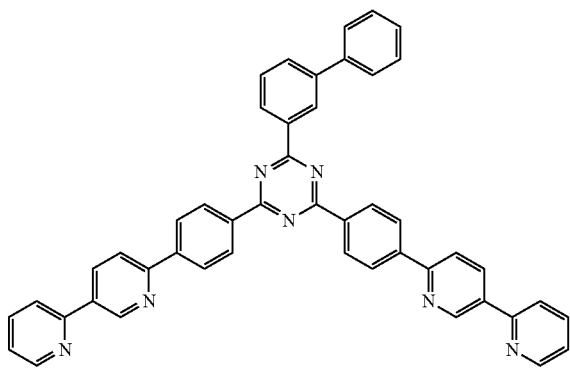

-continued
1-143
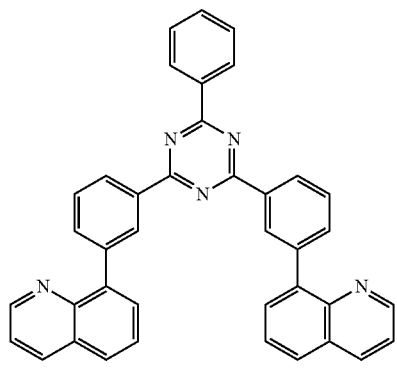
1-144
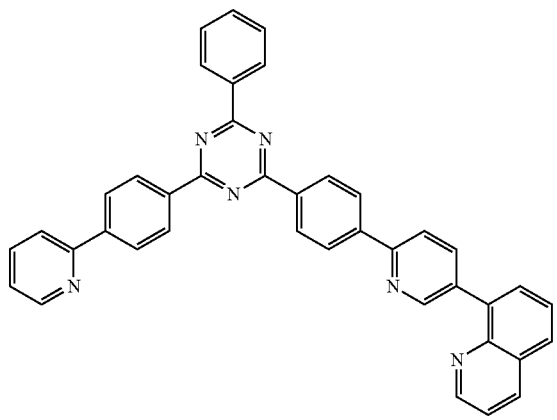
1-145
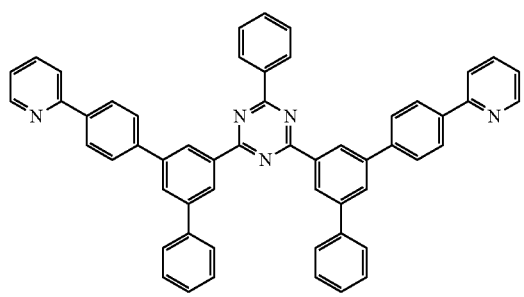
1-146
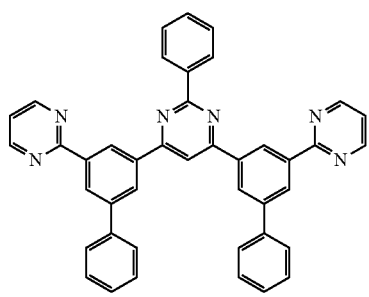
1-147
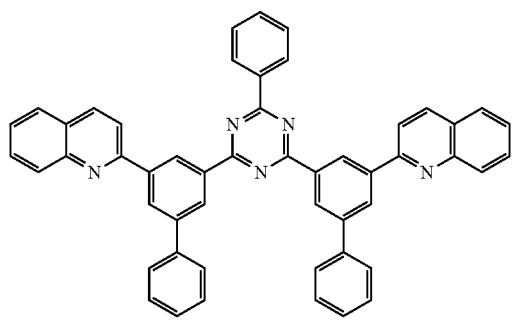
1-148
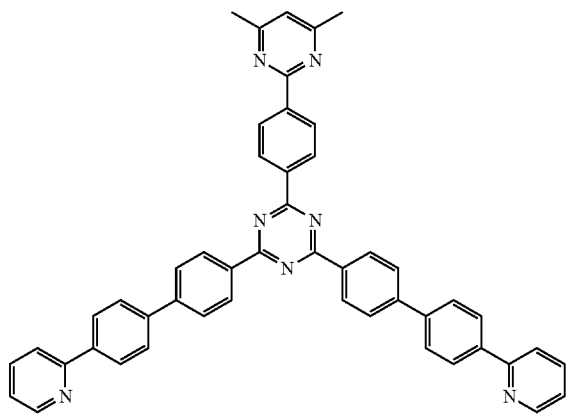

-continued
1-149
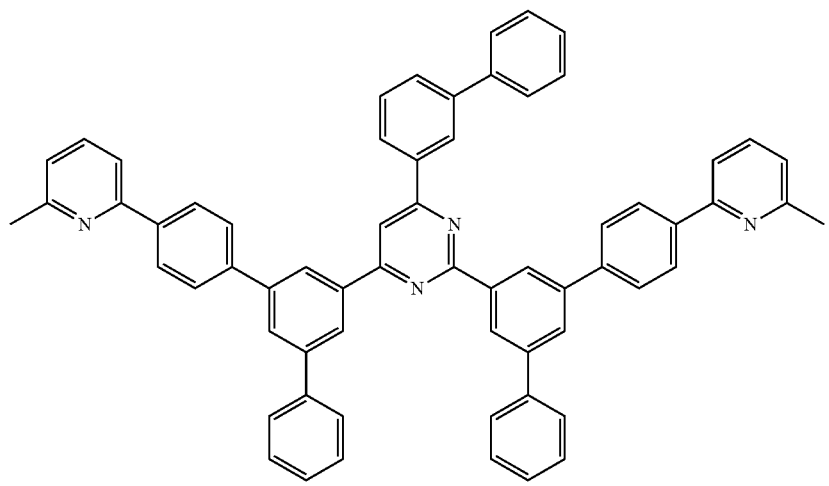
1-150
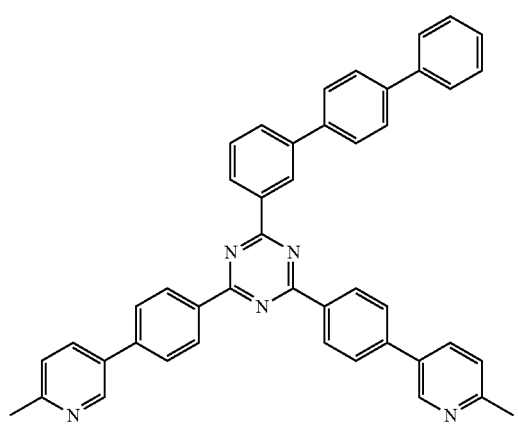
1-151
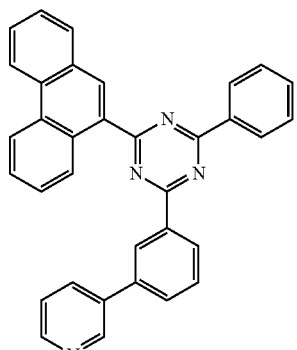
1-152
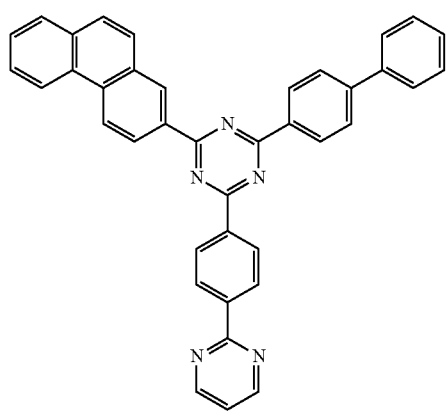
1-153
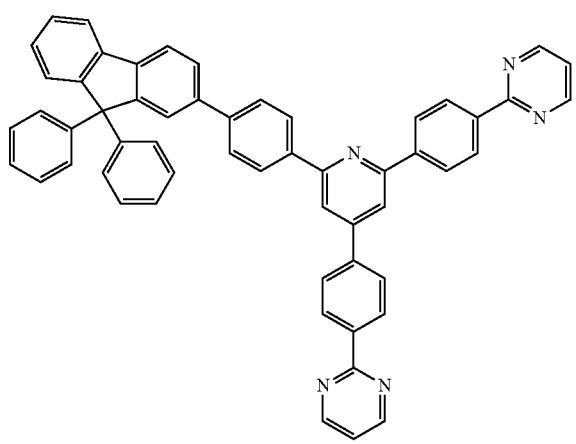

-continued
1-154
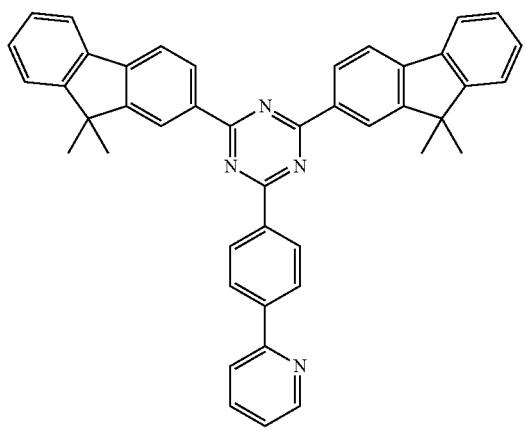
1-155
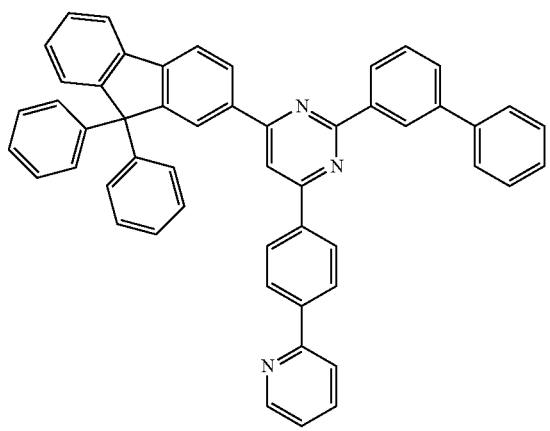
1-156
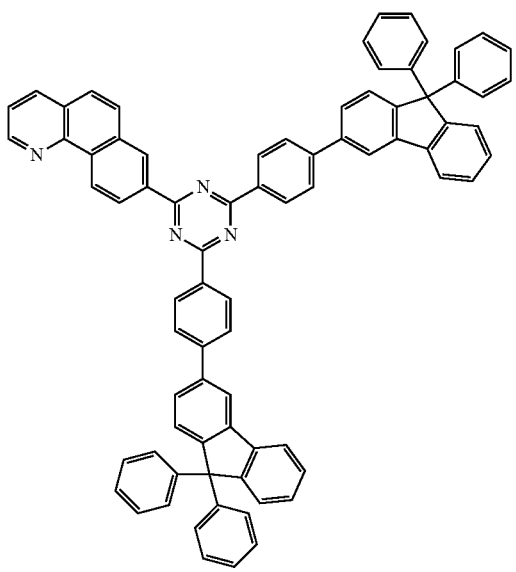
1-157
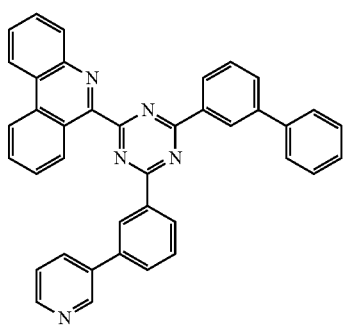
1-158
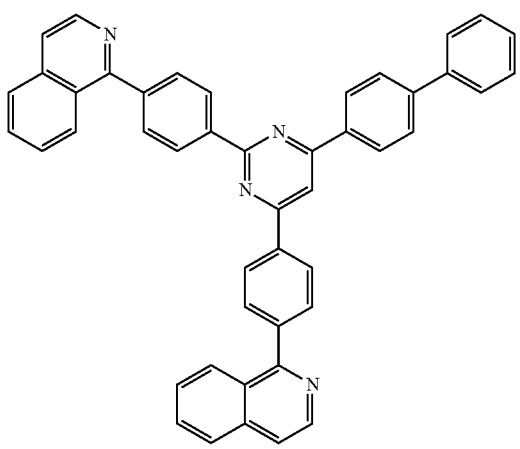
1-159
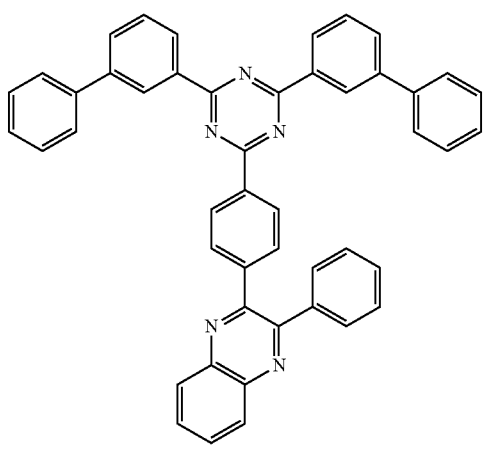

1-160
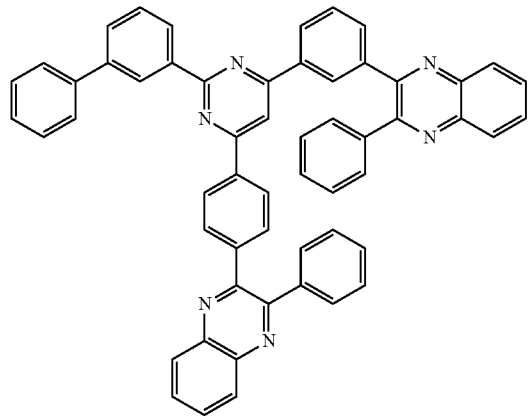
1-161
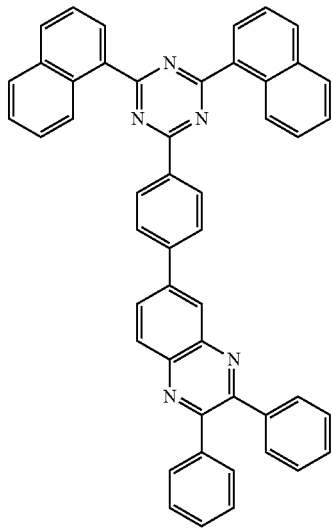
1-162
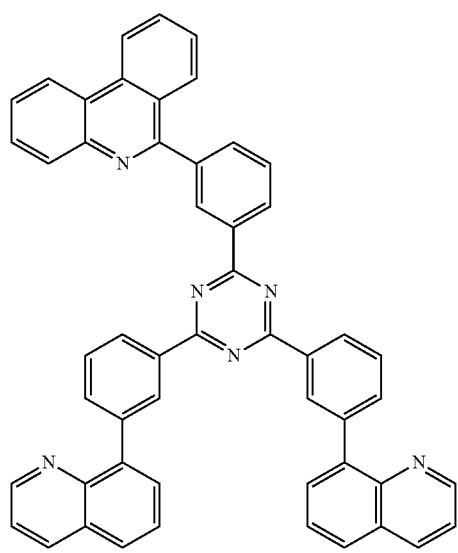
1-163
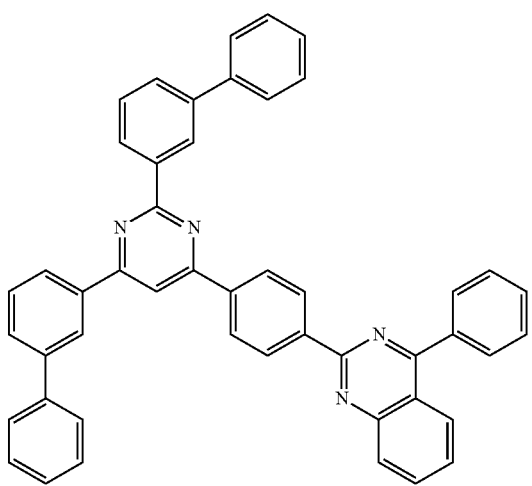

1-164
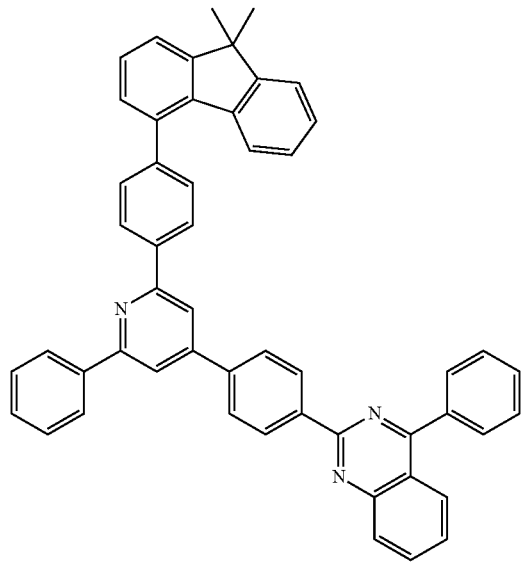
1-165
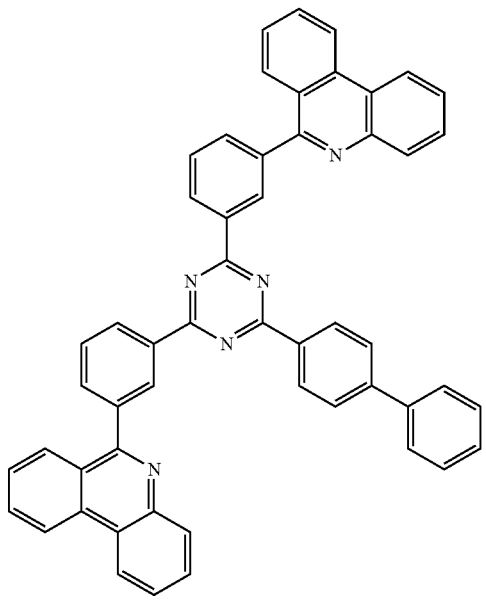
1-166
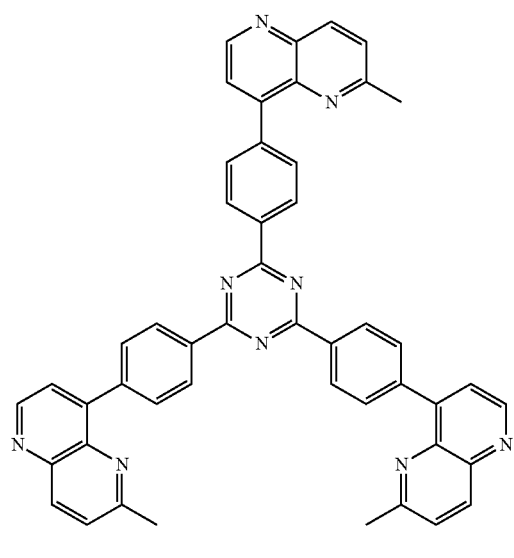
1-167
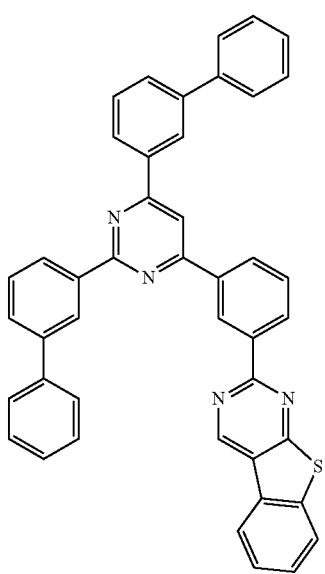

1-168
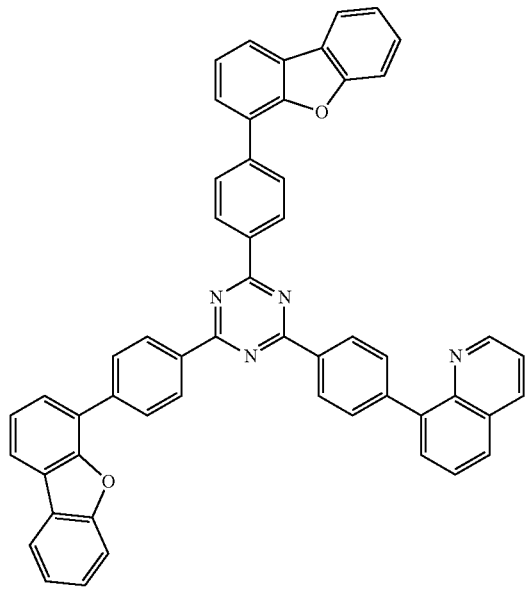
1-169
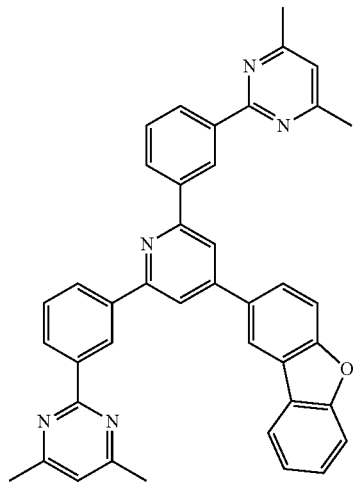
1-170
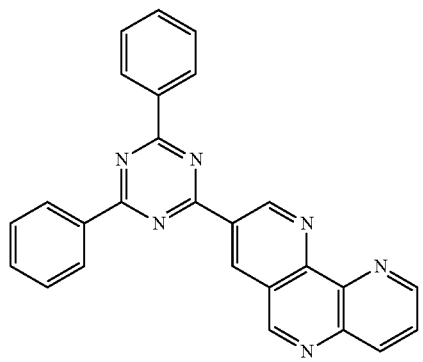
1-171
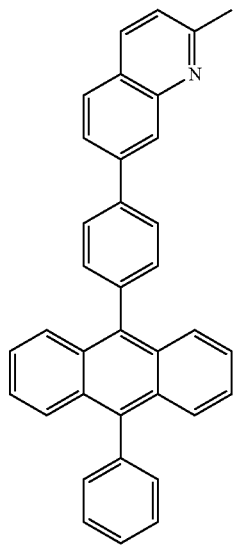

-continued
1-172
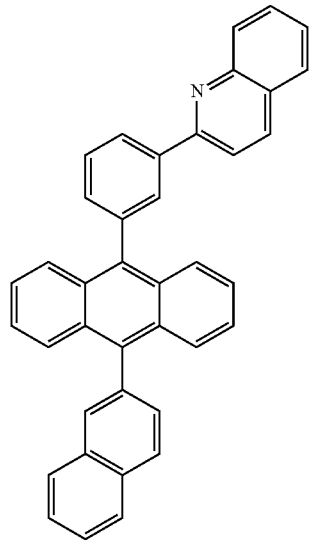
1-173
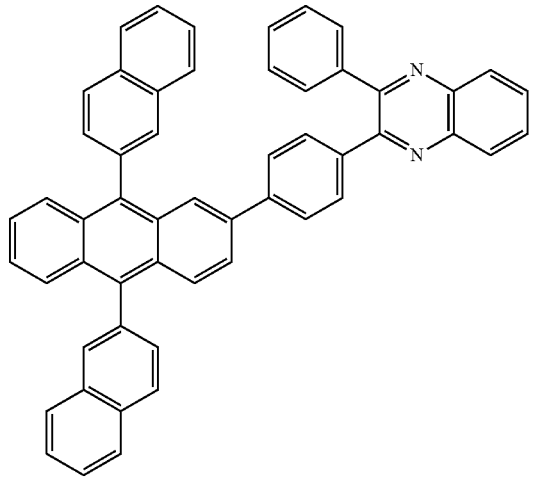
1-174
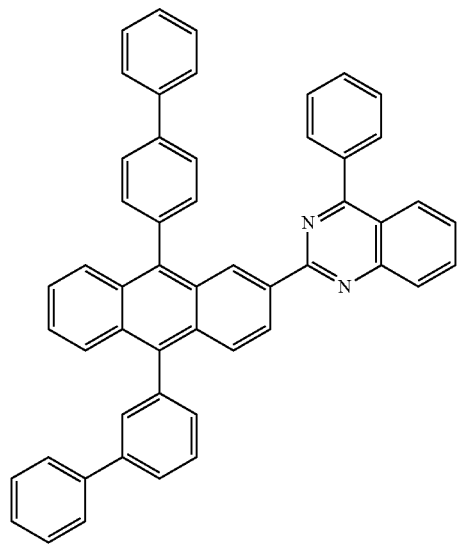
1-175
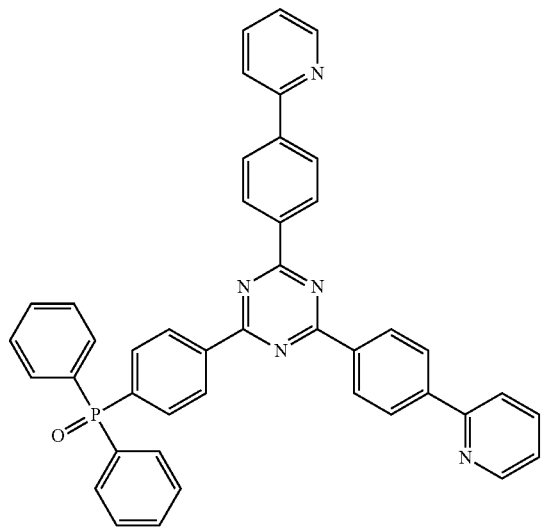

-continued
1-176
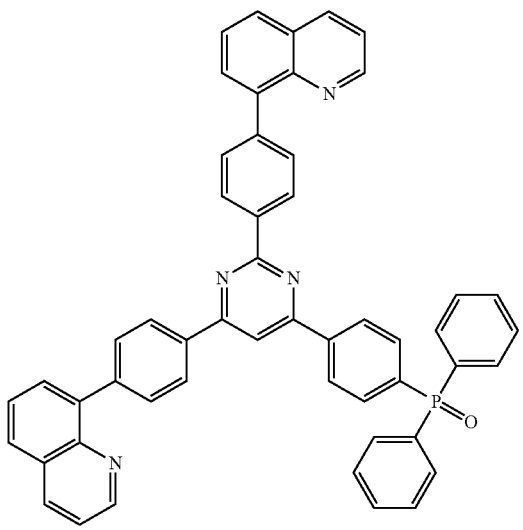
1-177
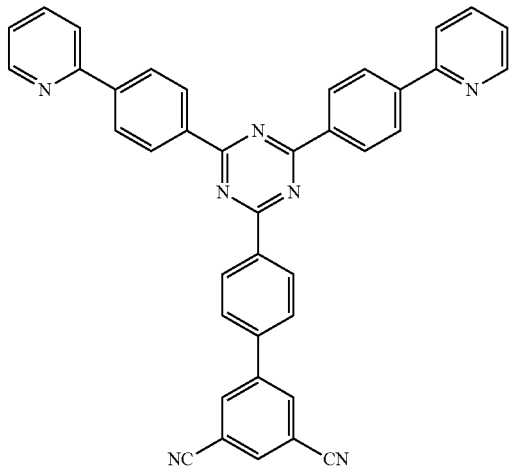
1-178
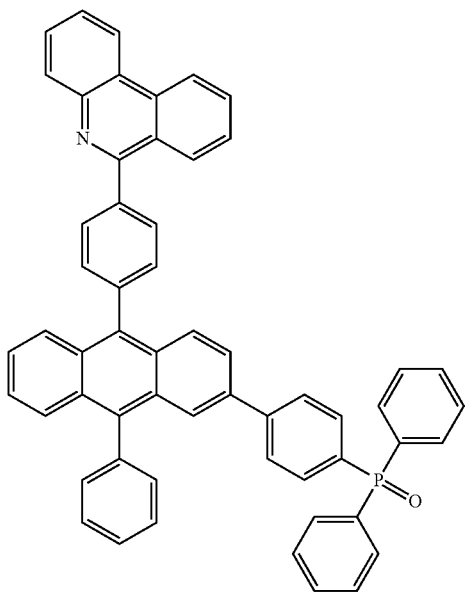
1-179
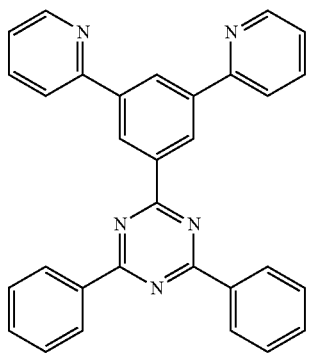
1-180
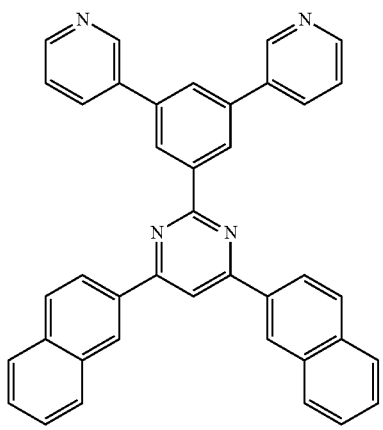
1-181
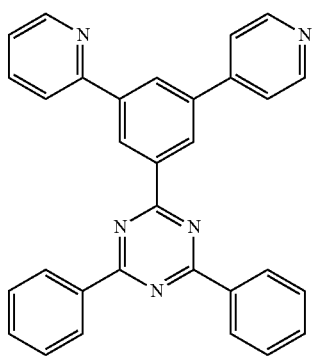

-continued
1-182
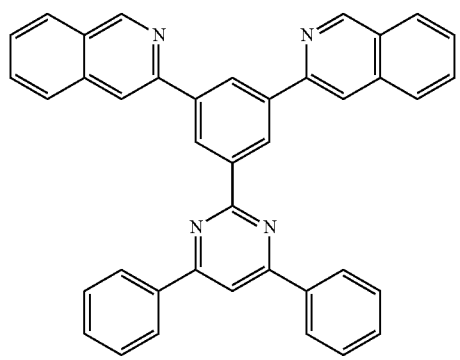
1-183
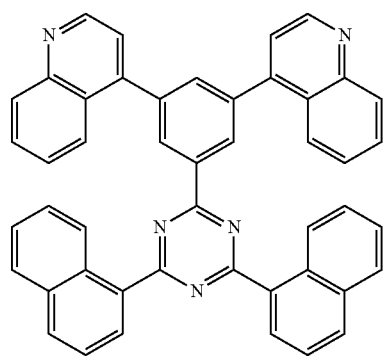
1-184
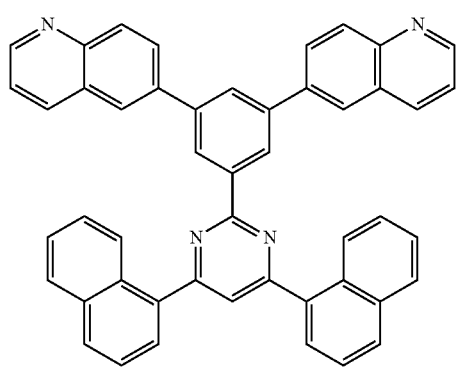
1-185
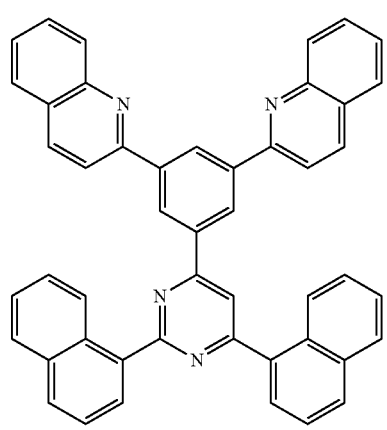
1-186
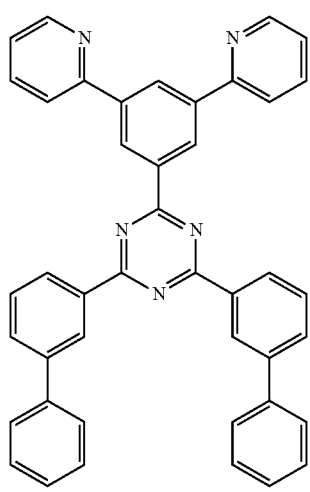
1-187
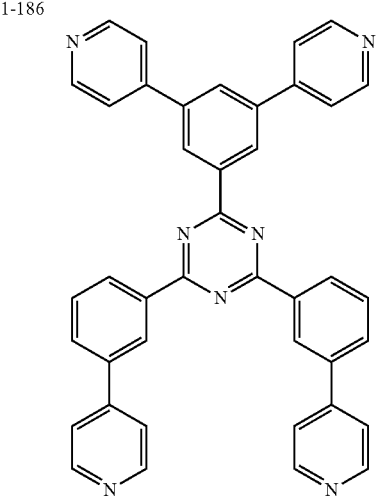

-continued
1-188
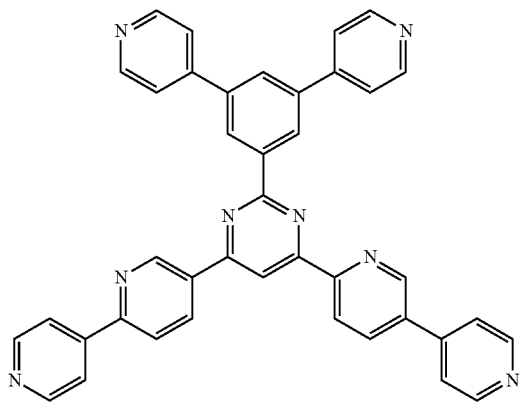
1-189
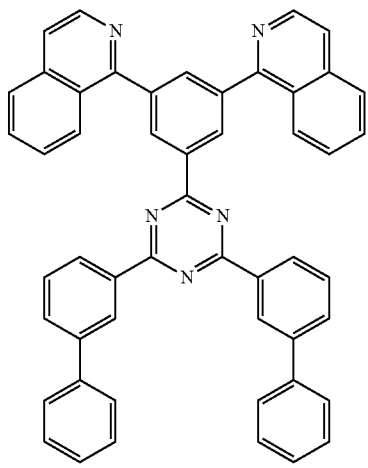
1-190
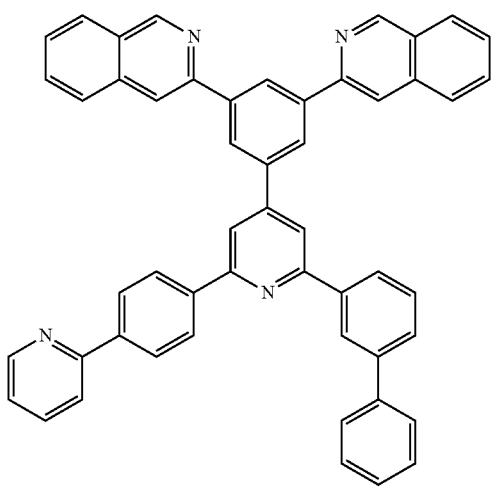
1-191
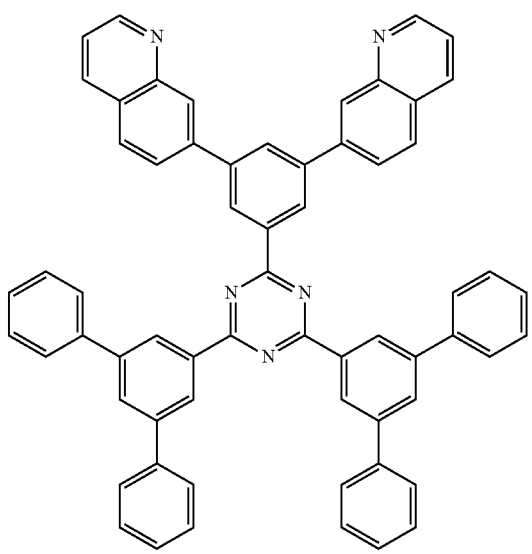
1-192
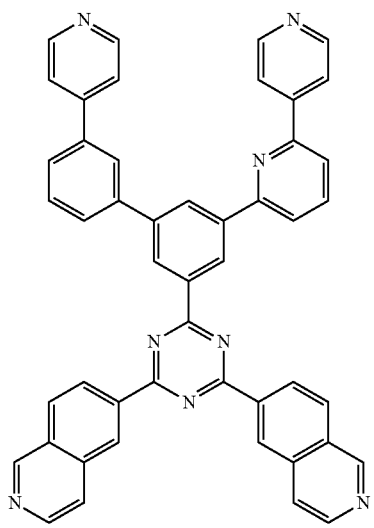
1-193
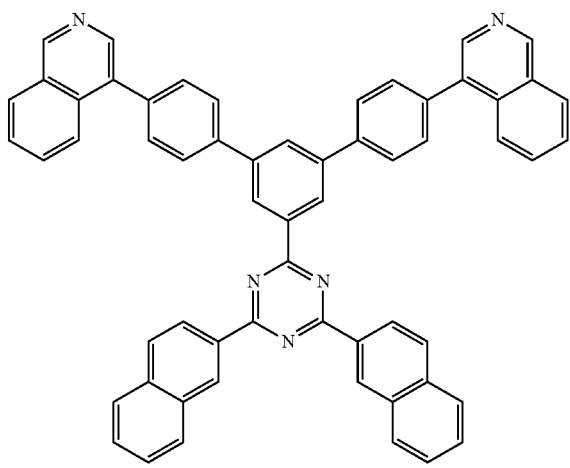

-continued
1-194
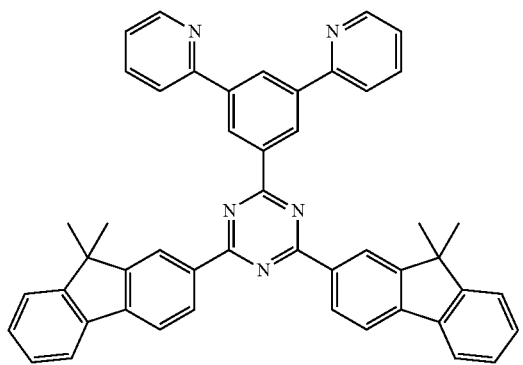
1-195
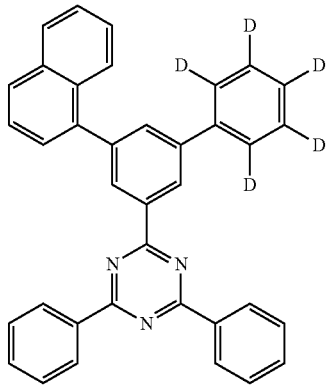
1-196
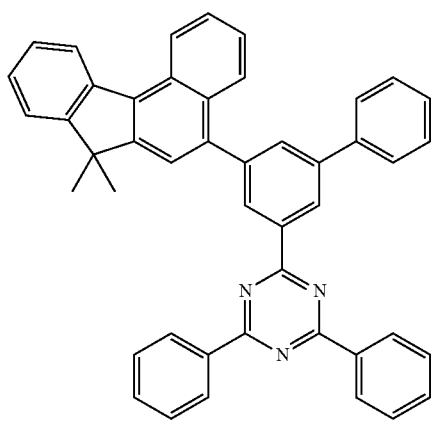
1-197
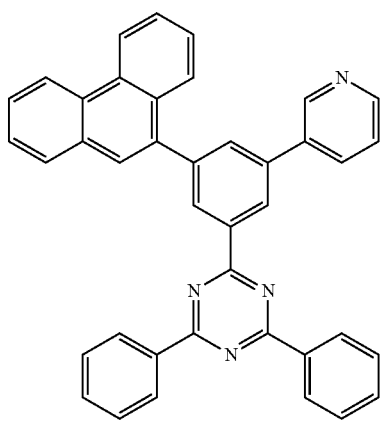
1-198
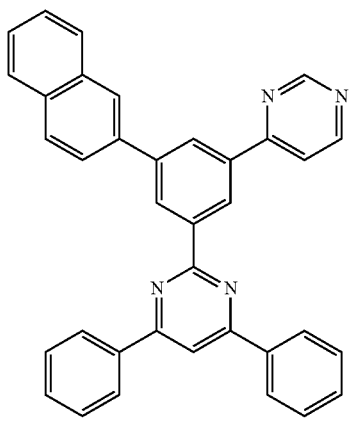
1-199
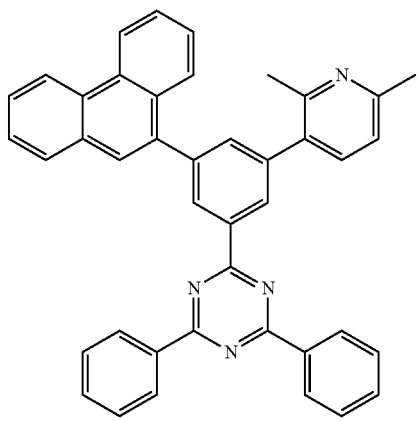

151
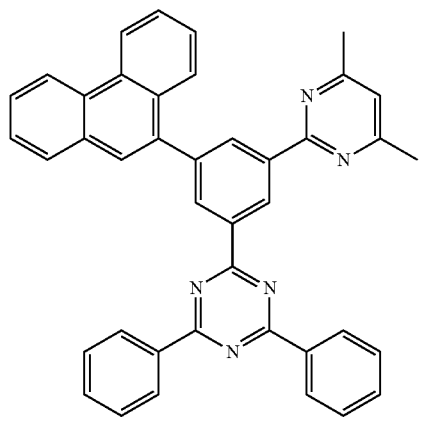
152
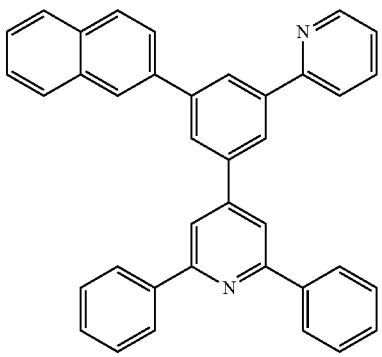
-continued
1-200
1-201
1-202
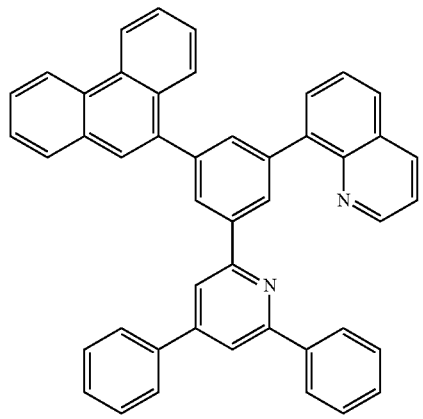
1-203
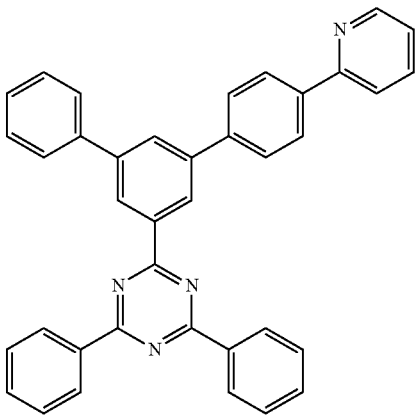
1-204
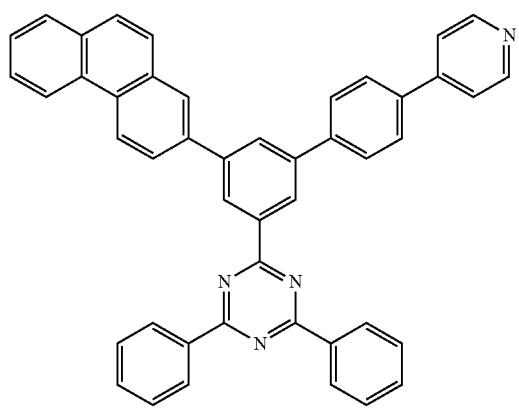
1-205
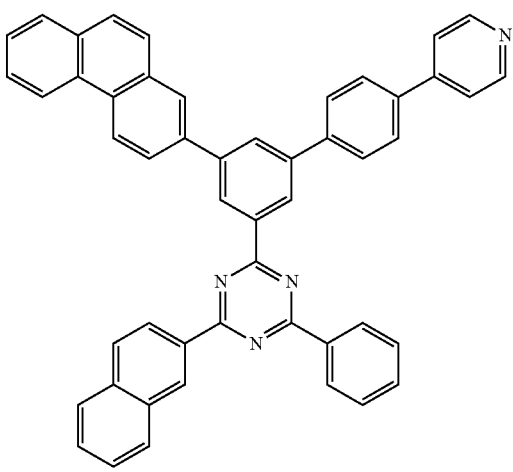

-continued
1-206
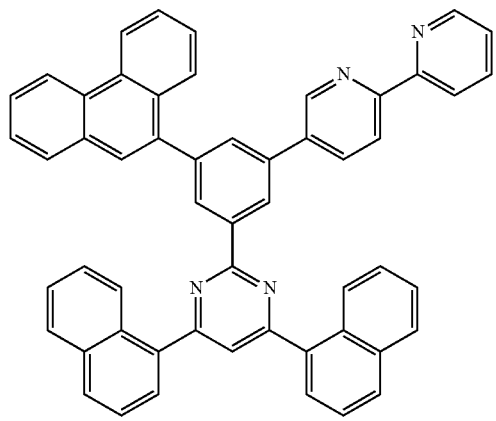
1-207
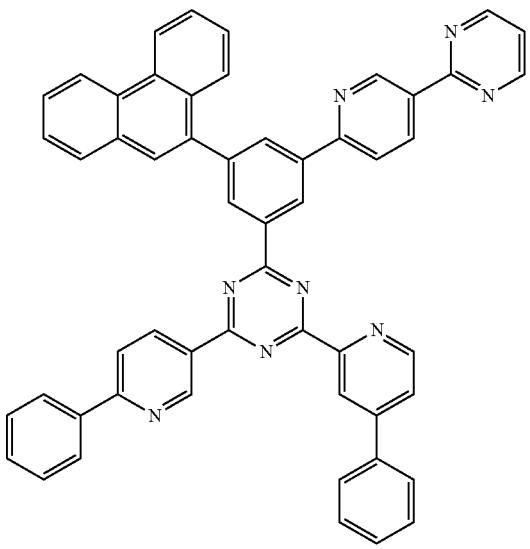
1-208
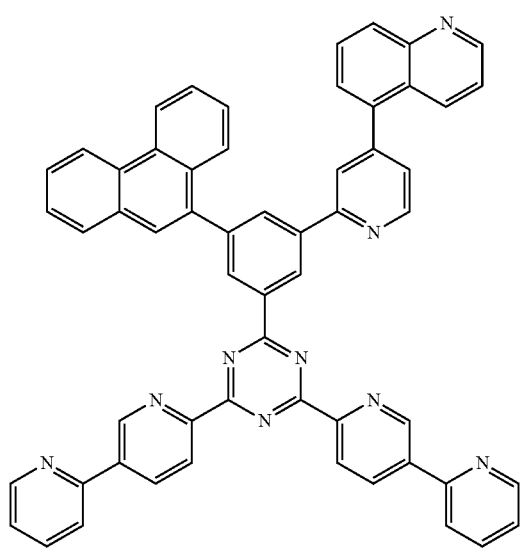
1-209
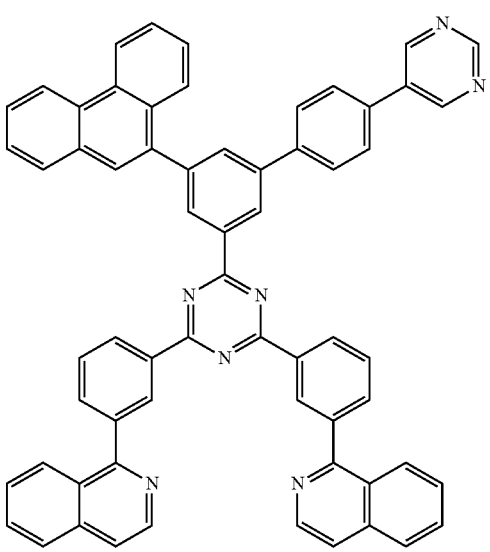
1-210
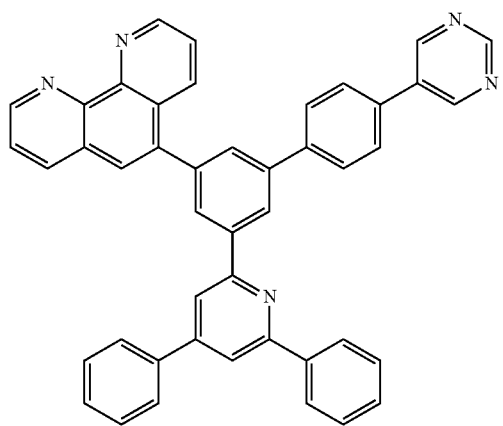
1-211
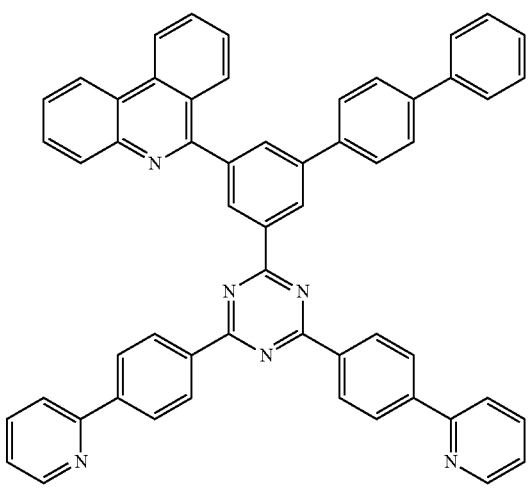

-continued
1-212
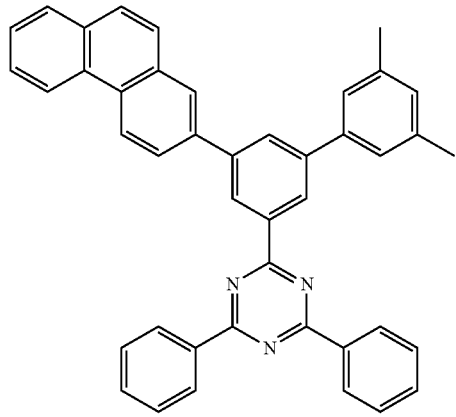
1-213
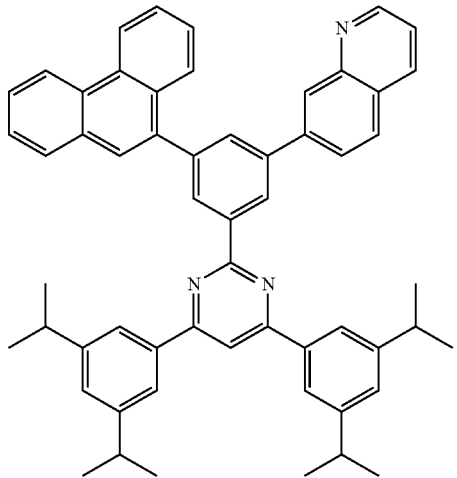
1-214
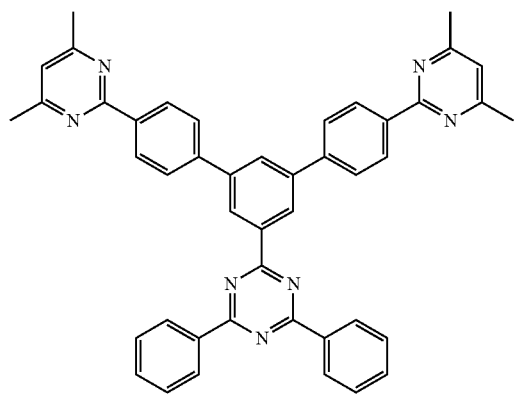
1-215
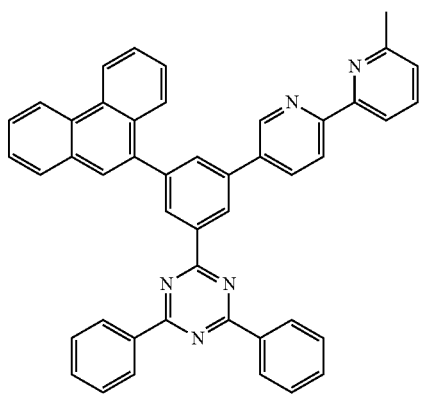
1-216
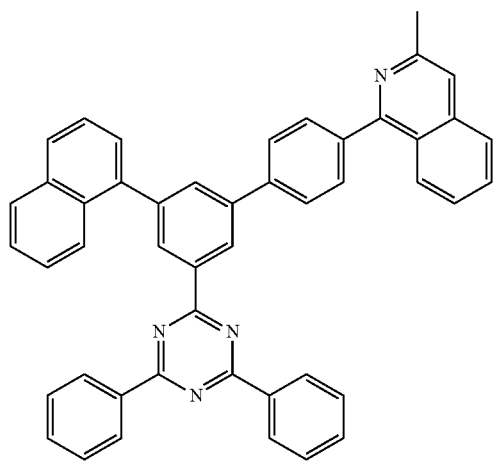
1-217
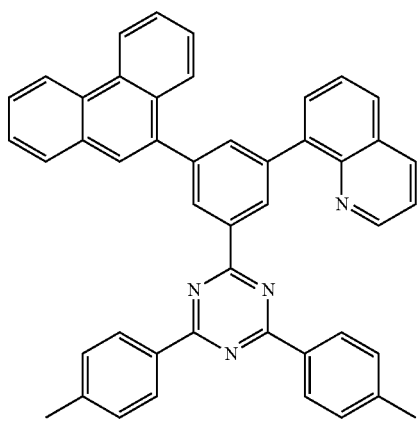

1-218
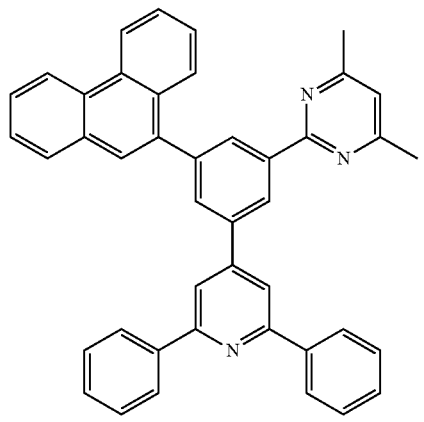
1-219
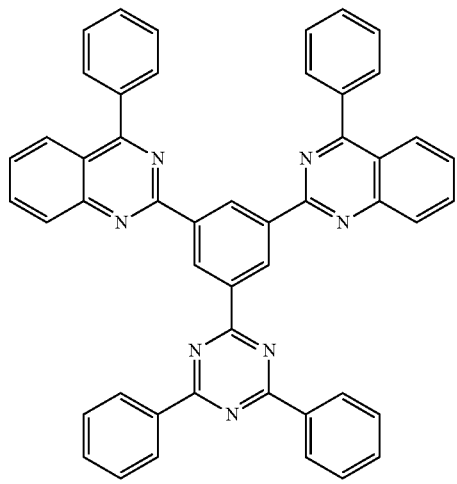
1-220
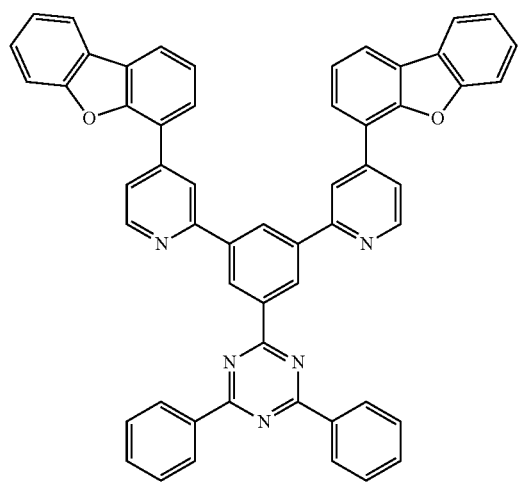
1-221
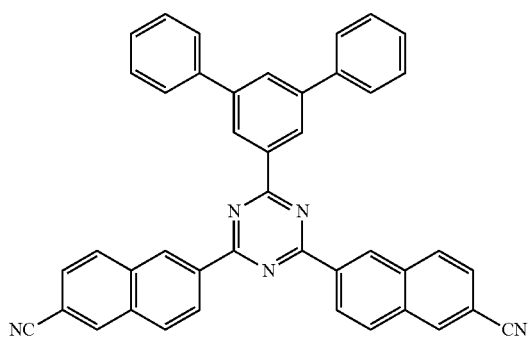
1-222
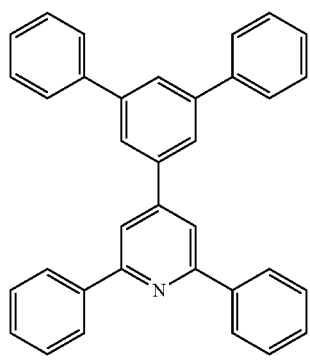
1-223
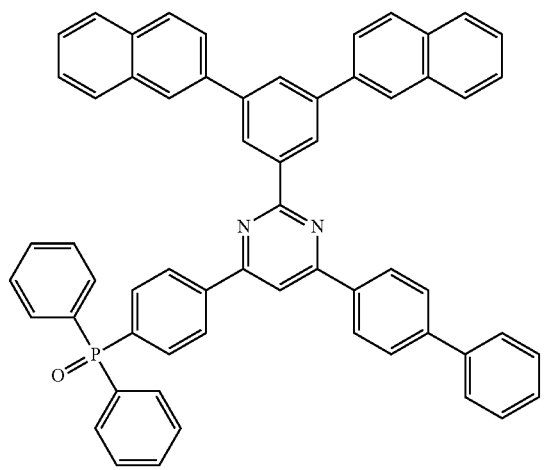

-continued
1-224
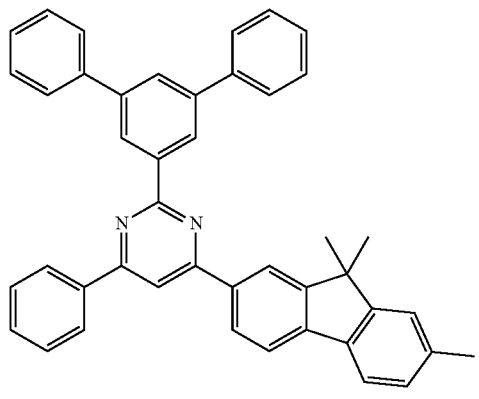
1-225
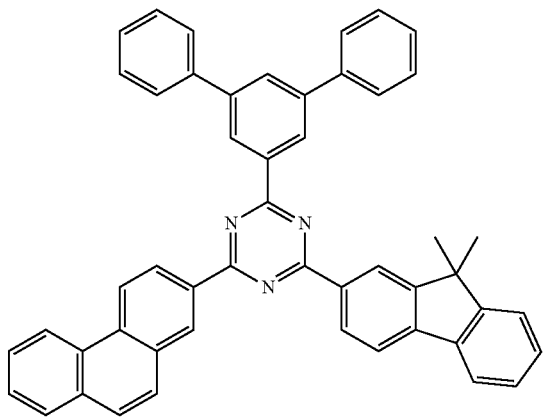
1-226
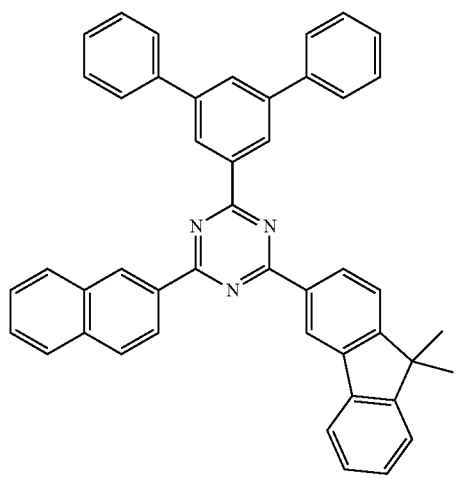
1-227
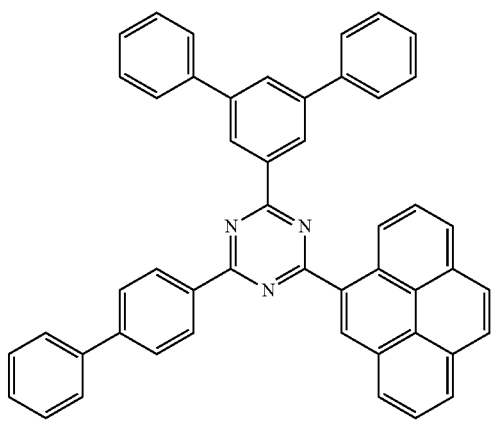
1-228
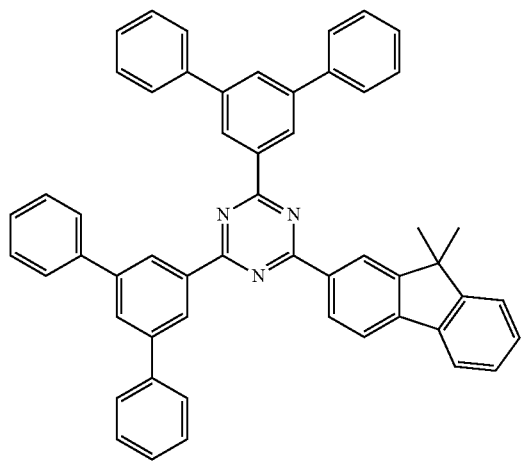
1-229
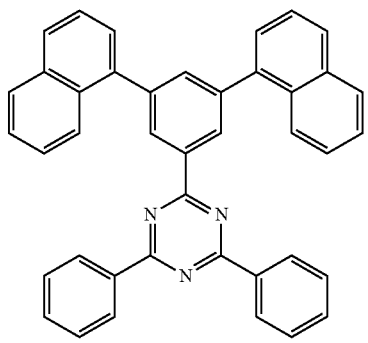

-continued
1-230
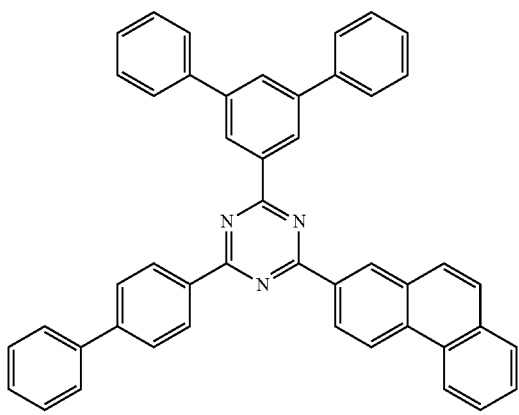
1-231
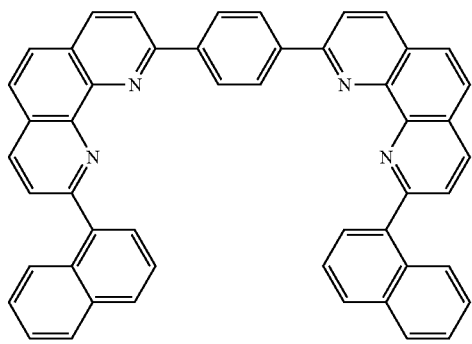
1-232
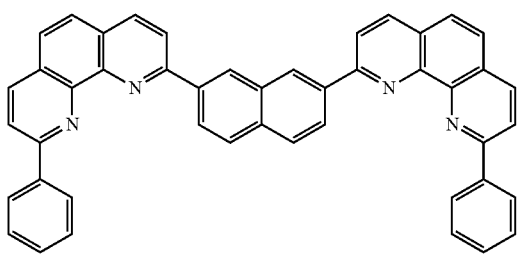
1-233
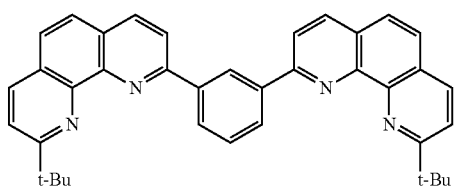
1-234
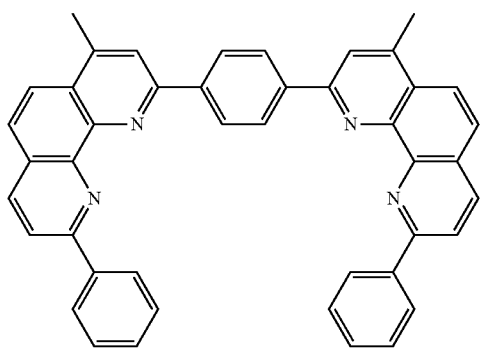
1-235
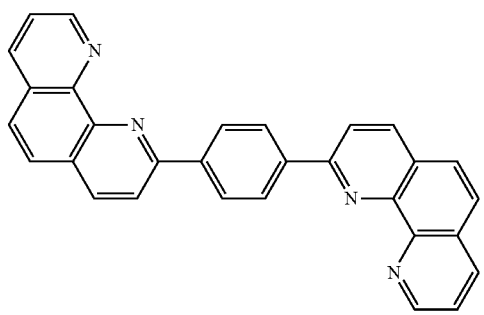
1-236
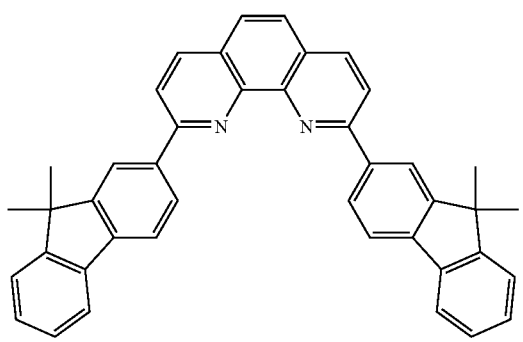
1-237
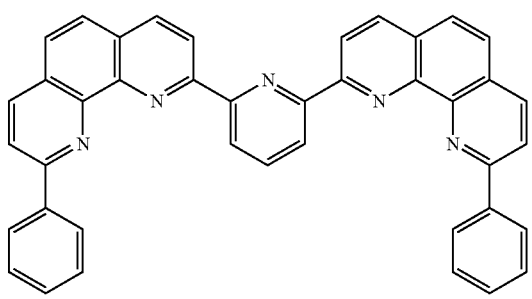

1-238
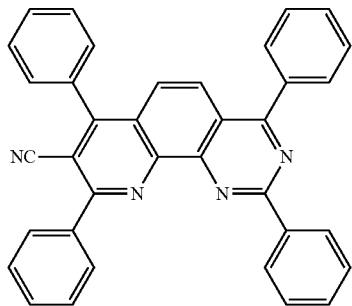
1-239
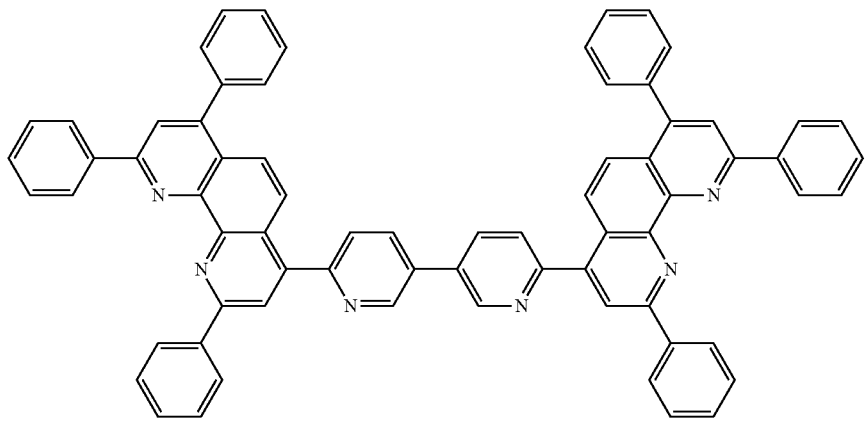
1-240
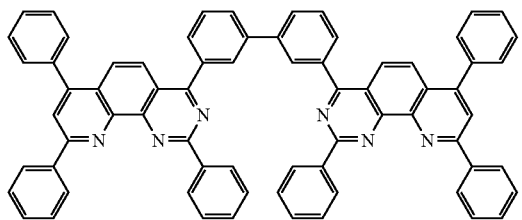
1-241
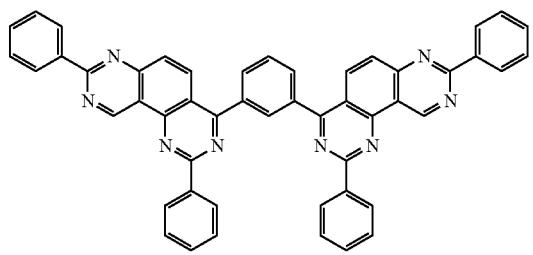
1-242
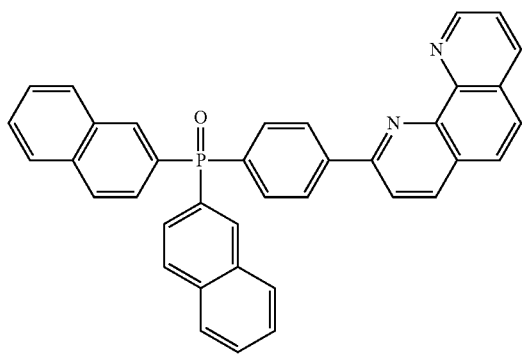
1-243
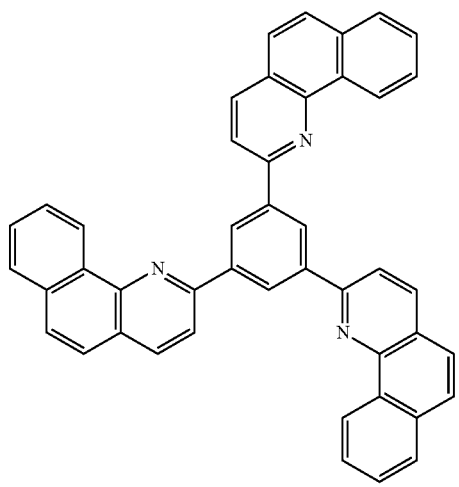

-continued
1-244
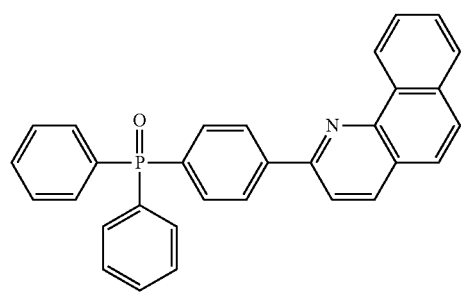
1-245
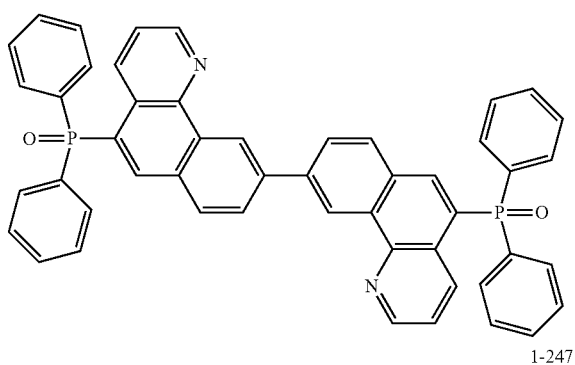
1-246
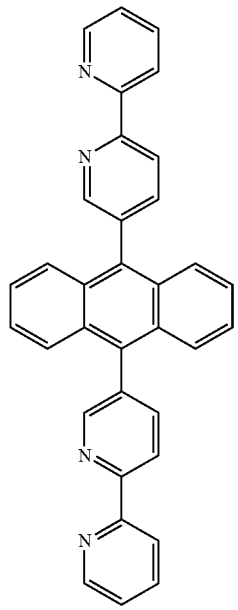
1-247
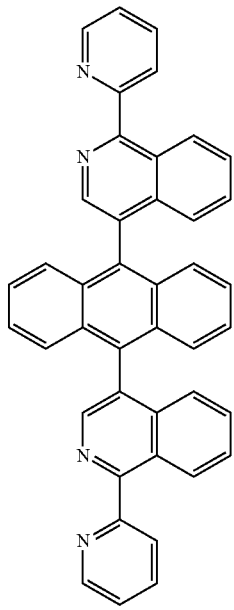
1-248
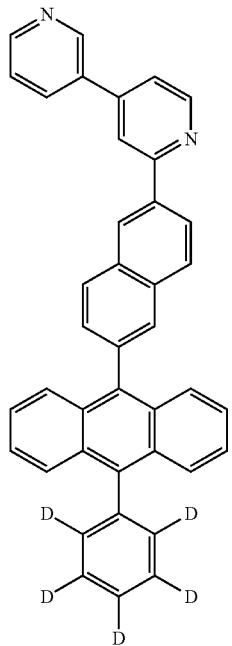
1-249
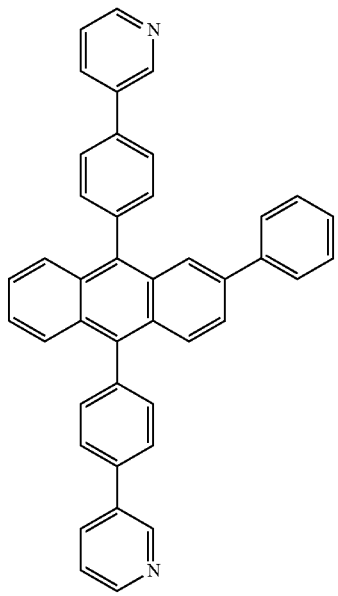

-continued
1-250
1-251
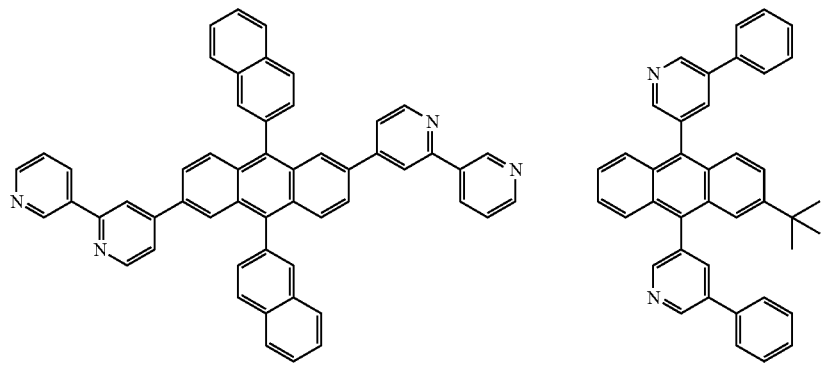
1-252
1-253
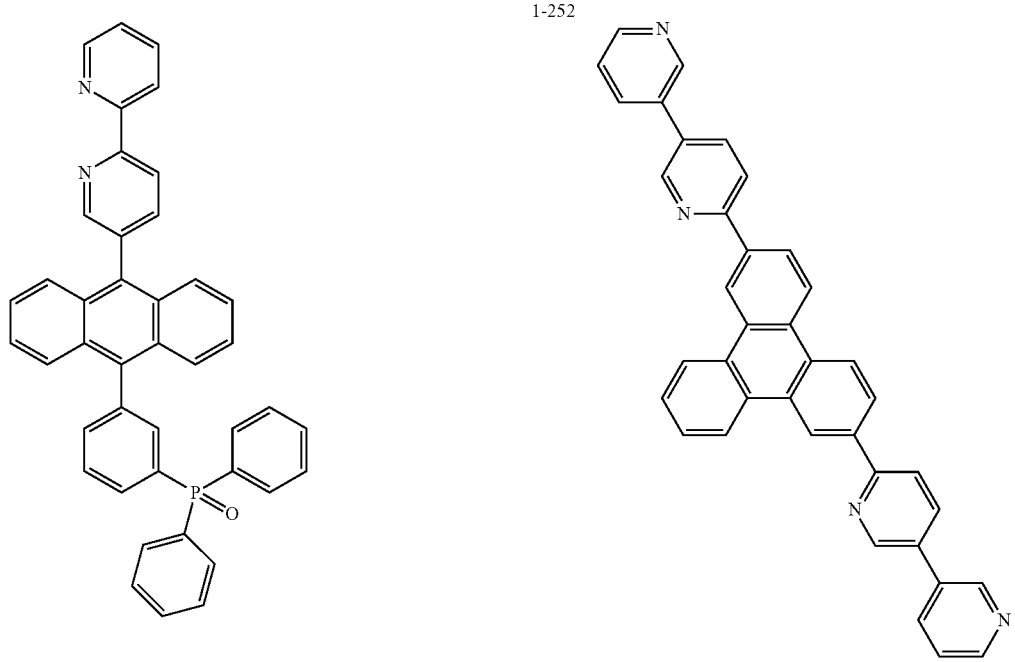
1-254
1-255
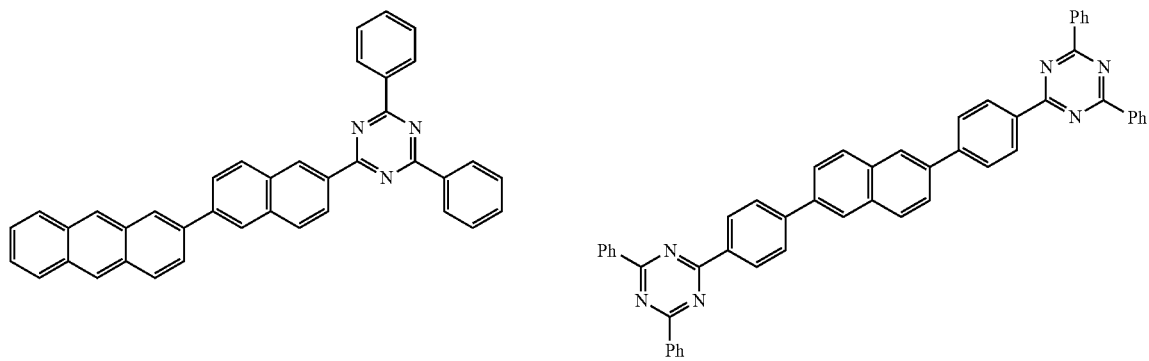

-continued
1-256
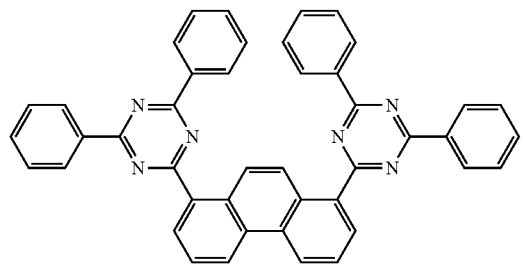
1-257
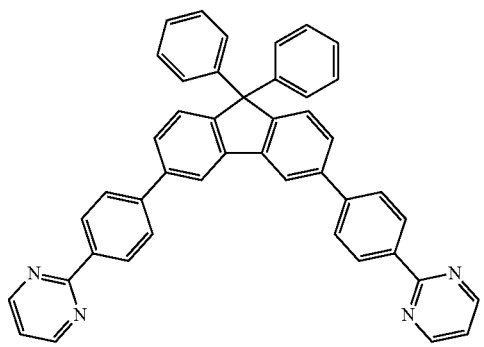
1-258
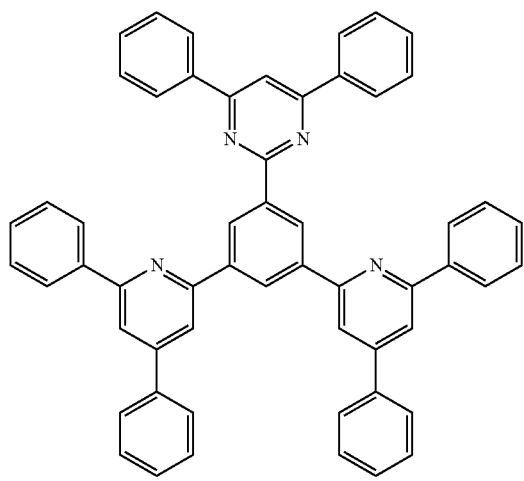
1-259
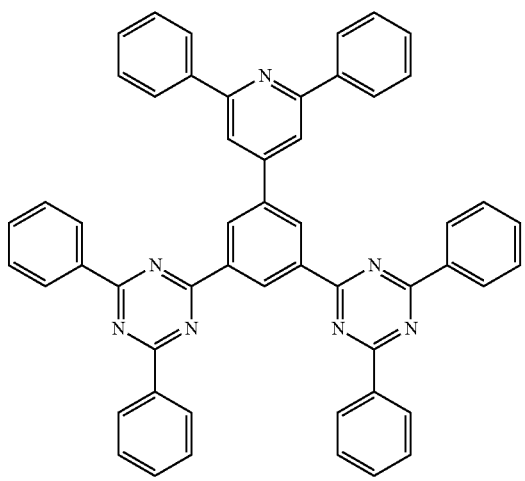
1-260
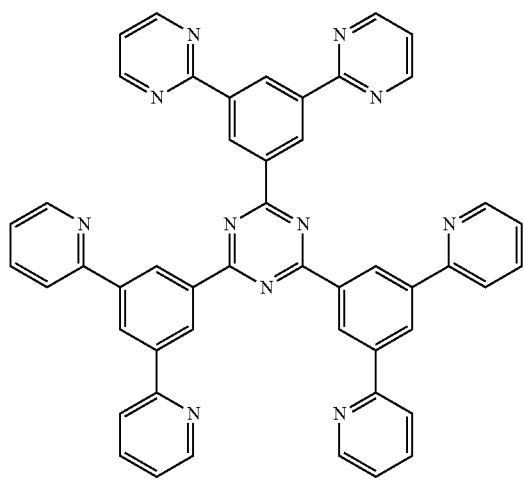
1-261
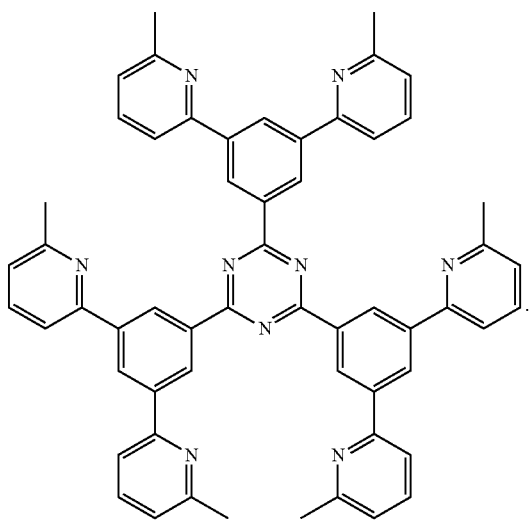

In various embodiments, the second compound may be selected from Compounds 2-1 to 2-110:
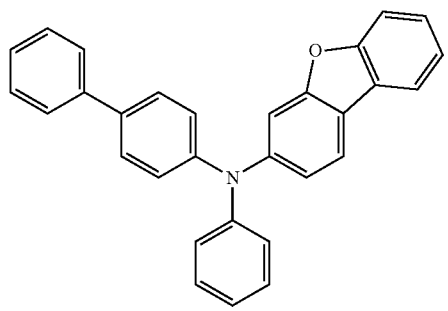
2-1
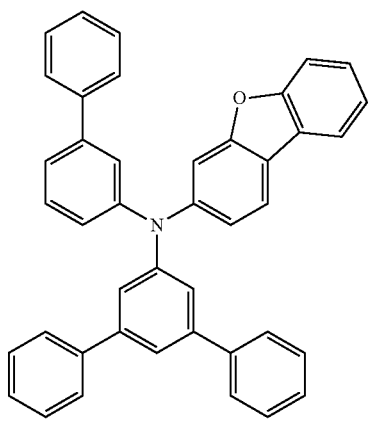
2-2
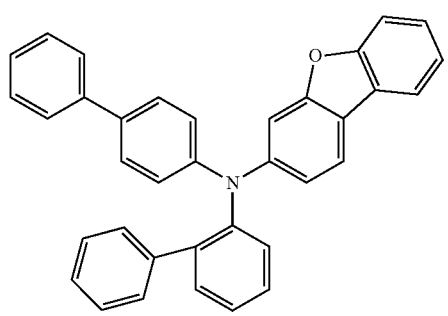
2-3
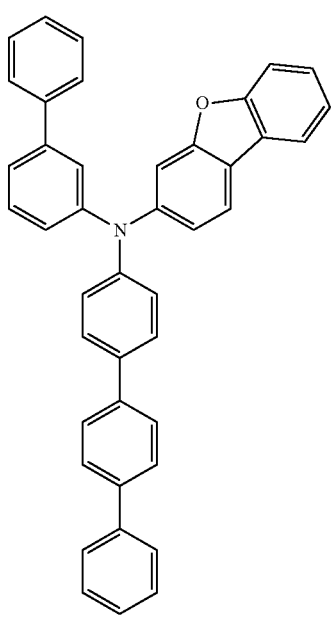
2-4
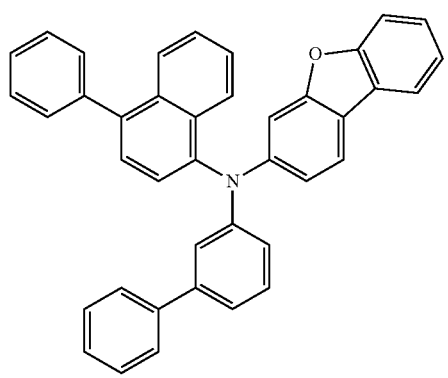
2-5
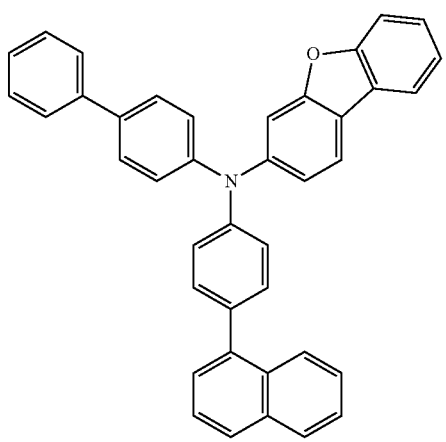
2-6

-continued
2-7
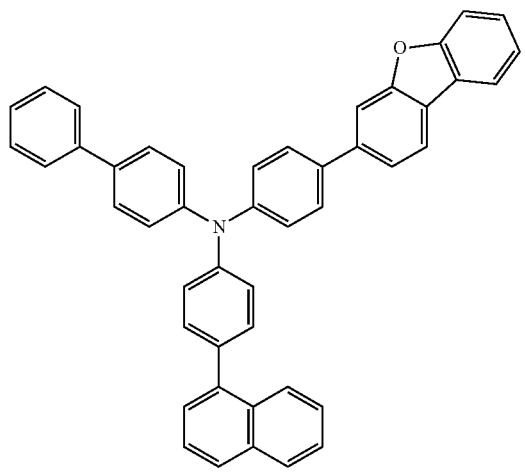
2-8
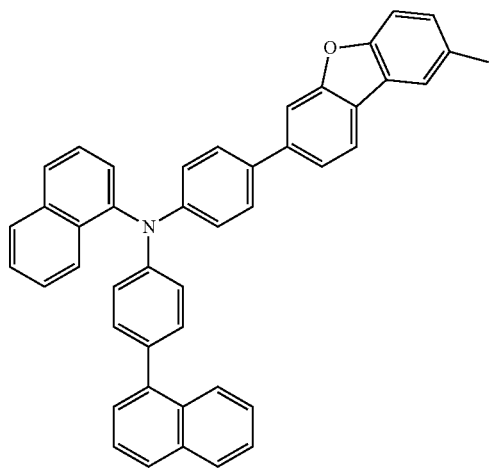
2-9
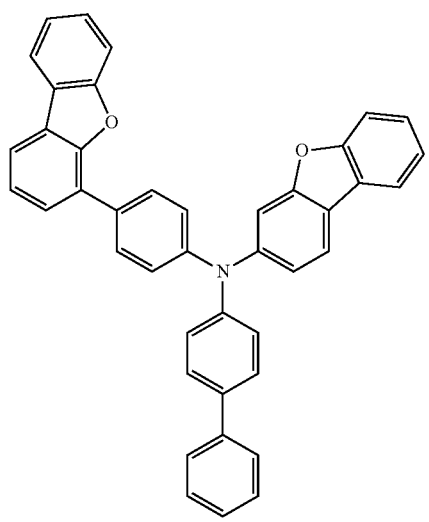
2-10
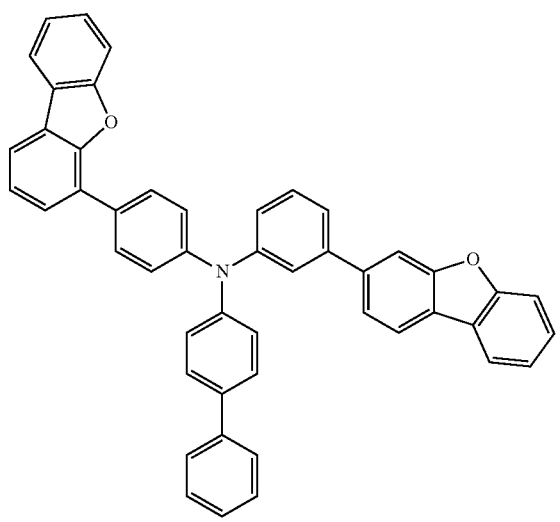
2-11
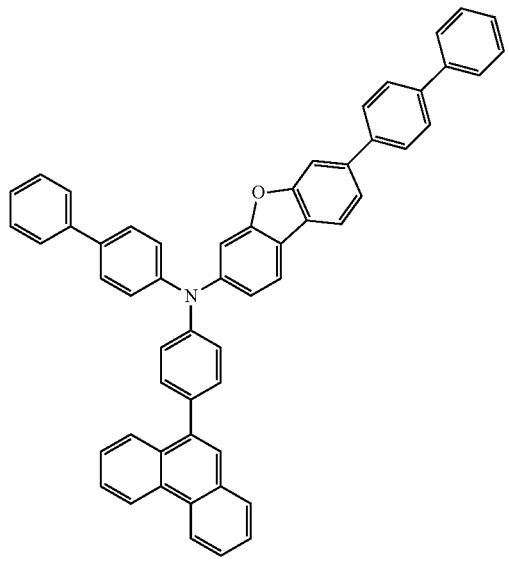
2-12
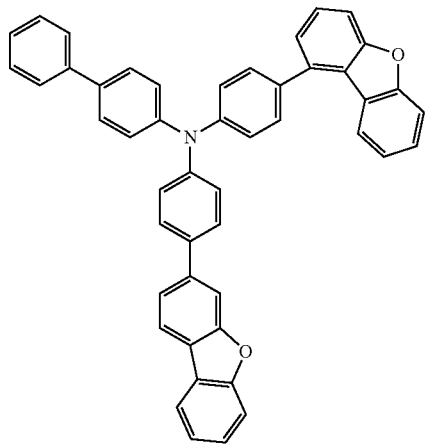

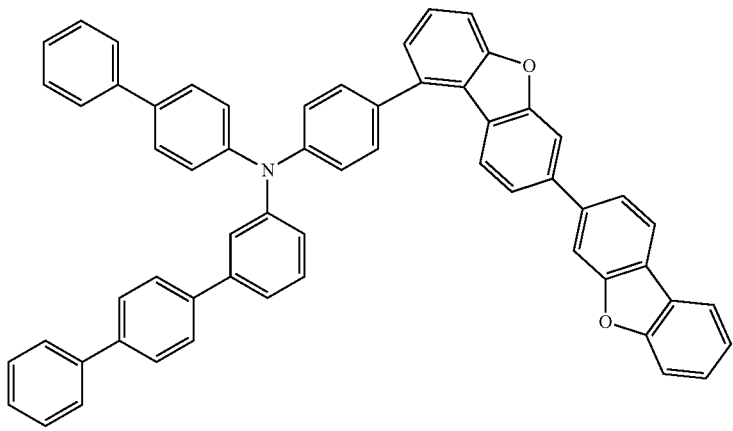
2-13
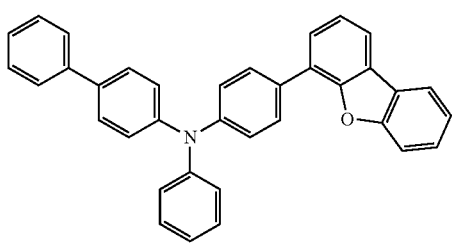
2-14
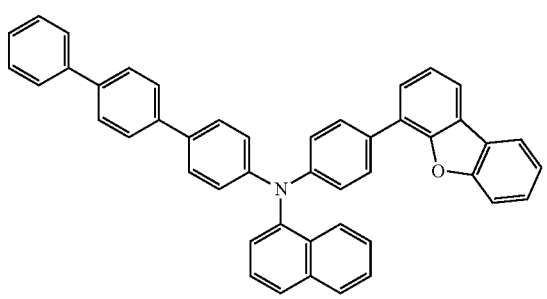
2-15
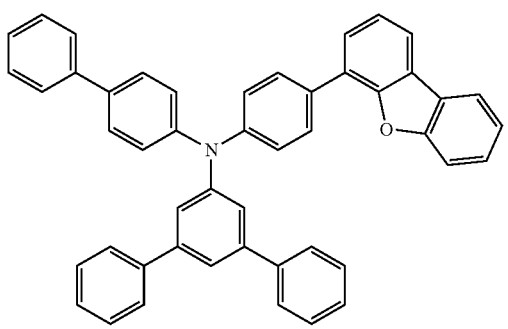
2-16
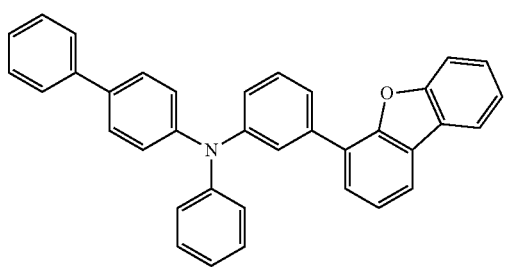
2-17
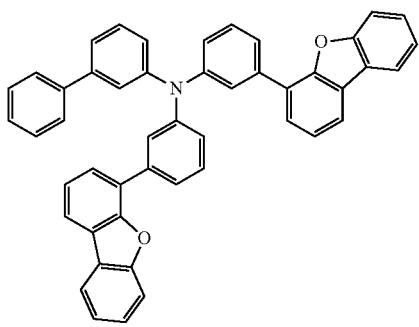
2-18
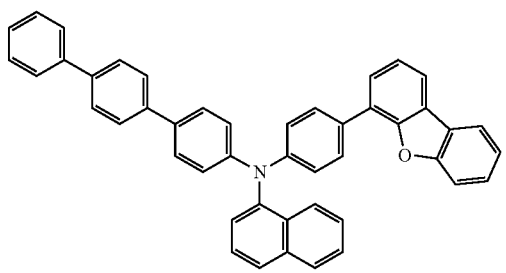
2-19

-continued
2-20
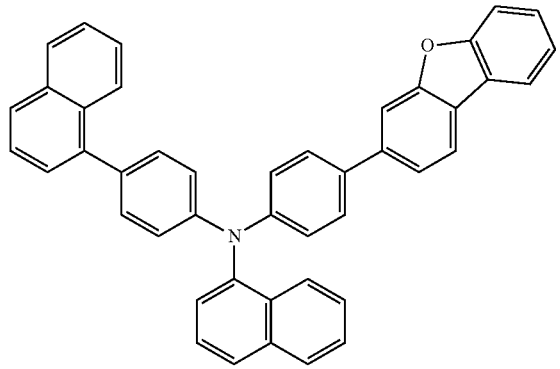
2-21
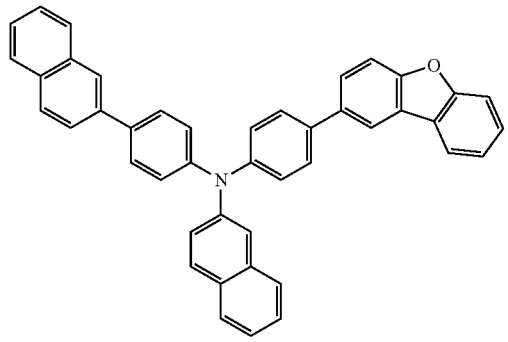
2-22
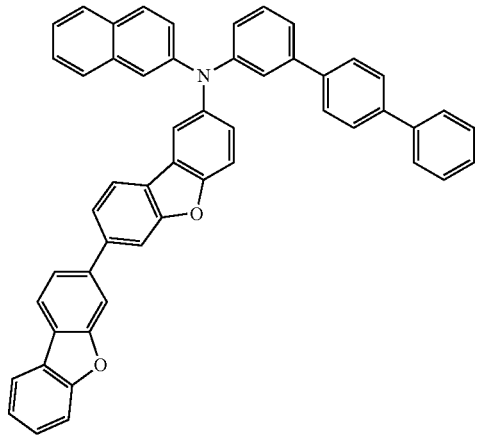
2-23
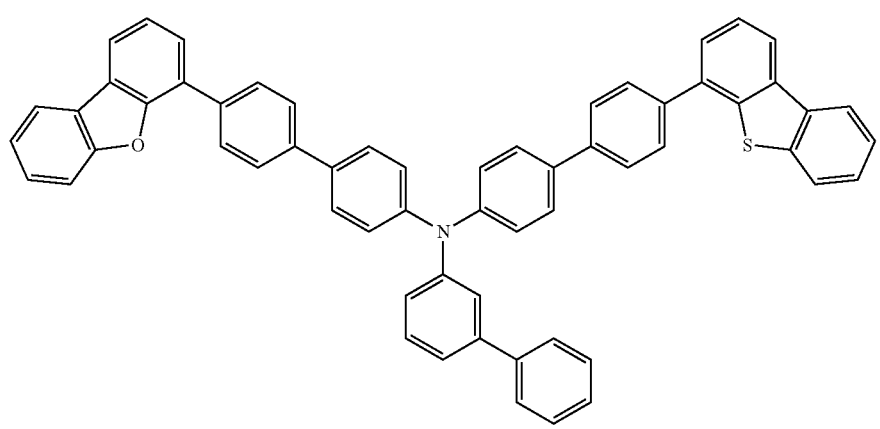
2-24
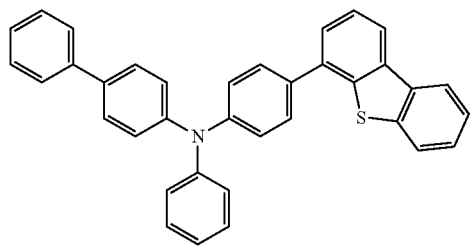
2-25
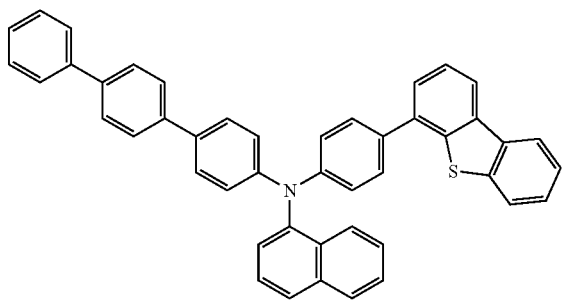

-continued
2-26
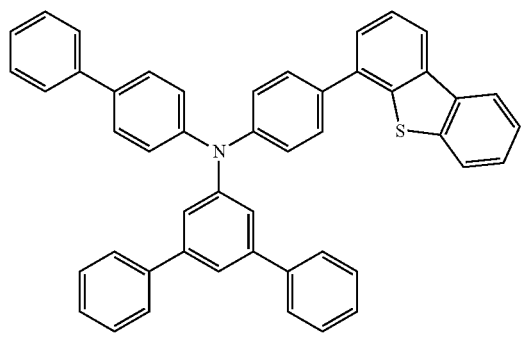
2-27
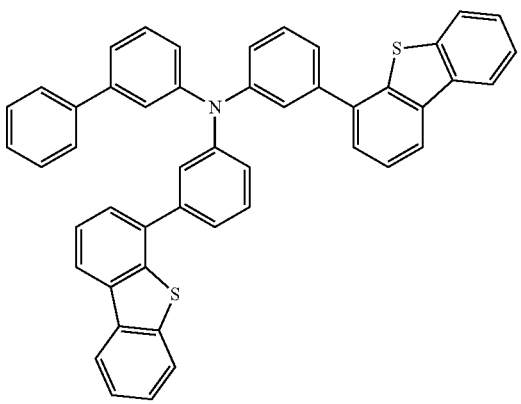
2-28
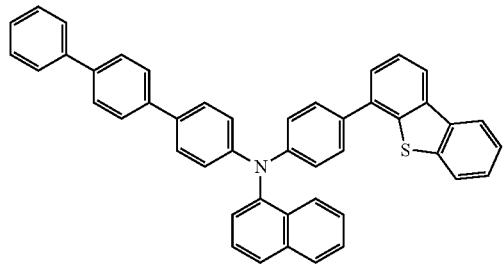
2-29
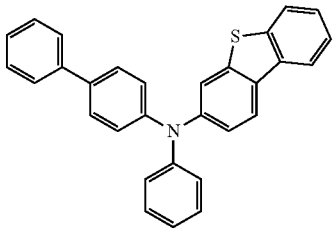
2-30
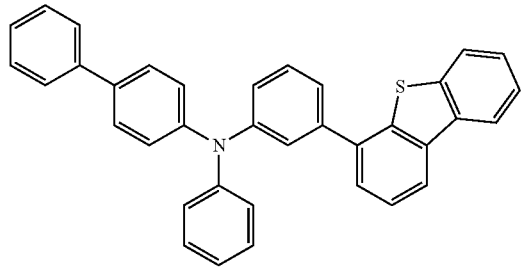
2-31
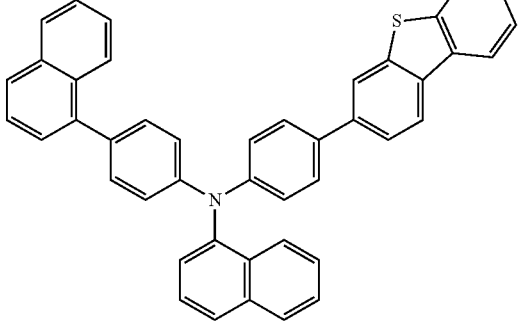
2-32
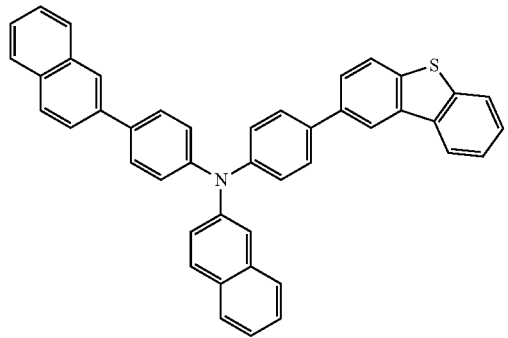
2-33
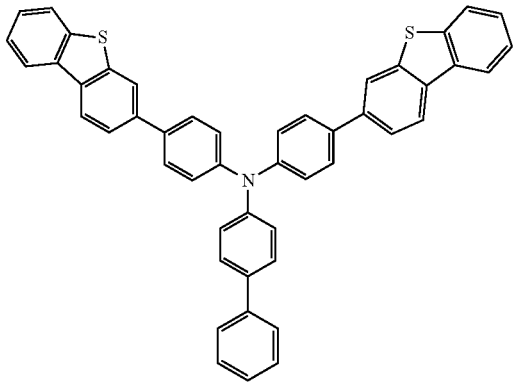

-continued
2-34
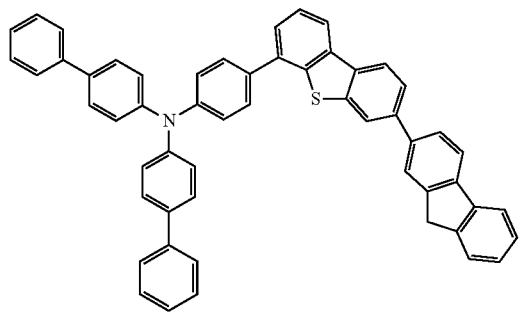
2-35
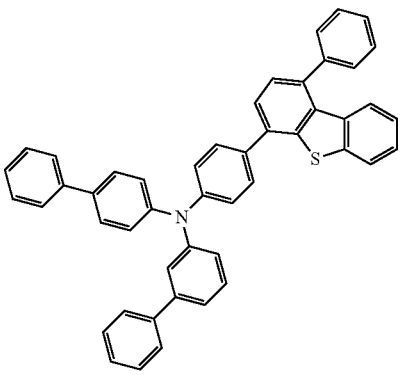
2-36
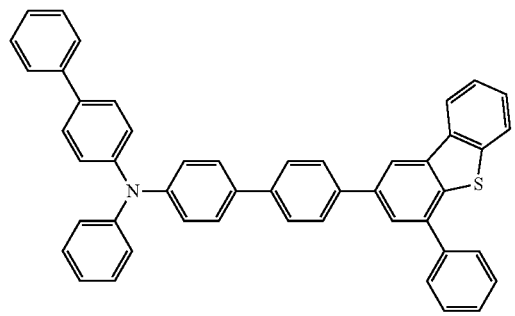
2-37
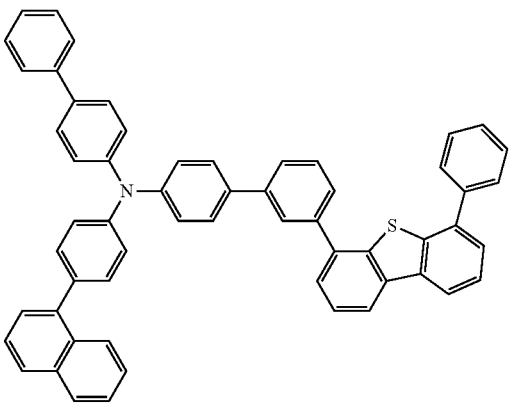
2-38
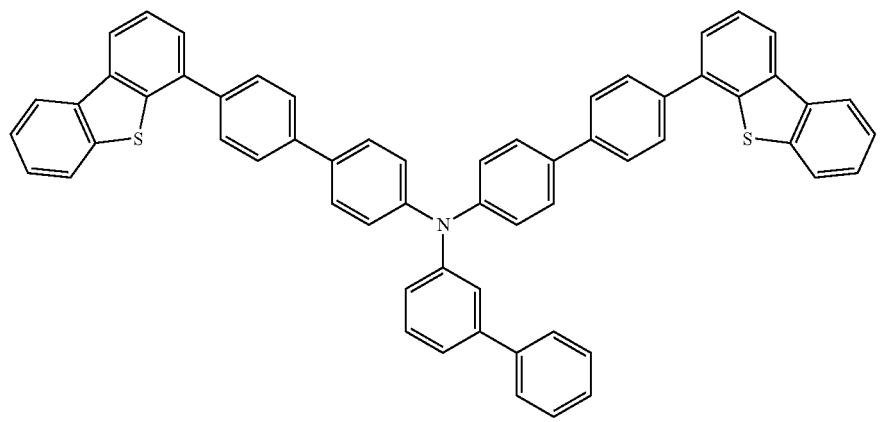

2-39
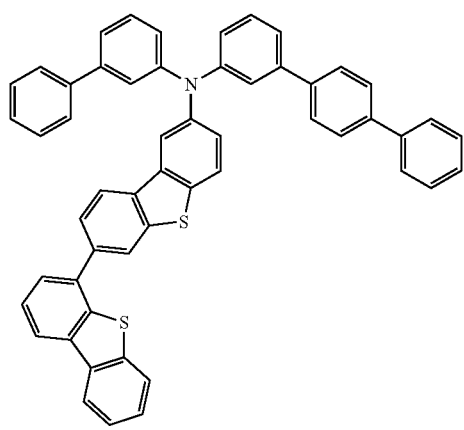
2-40
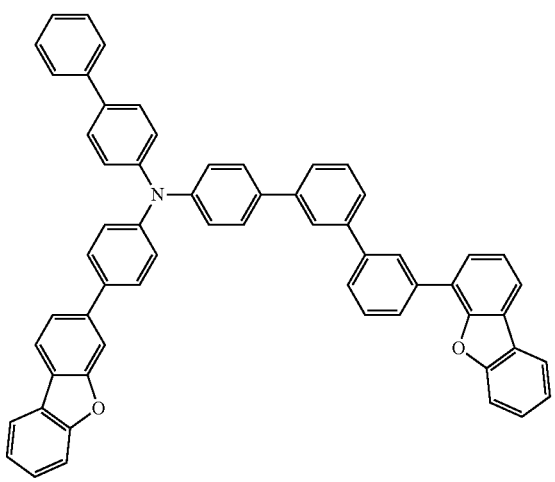
2-41
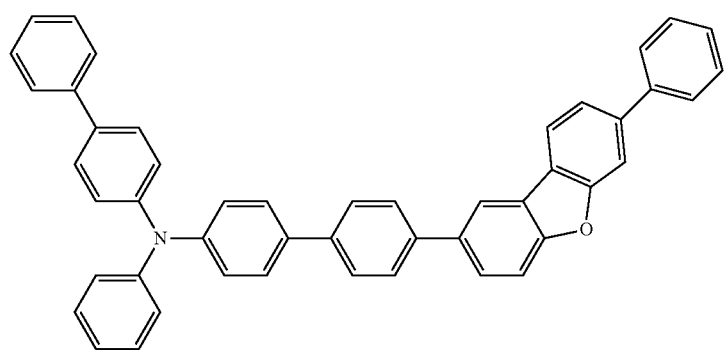
2-42
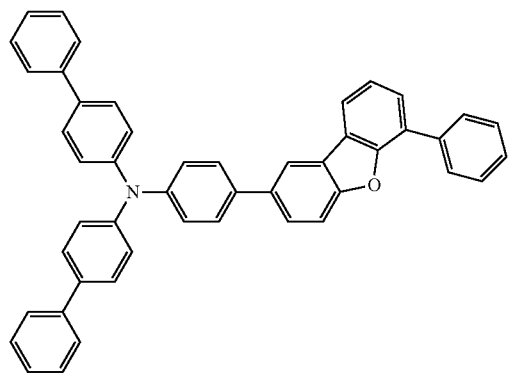
2-43
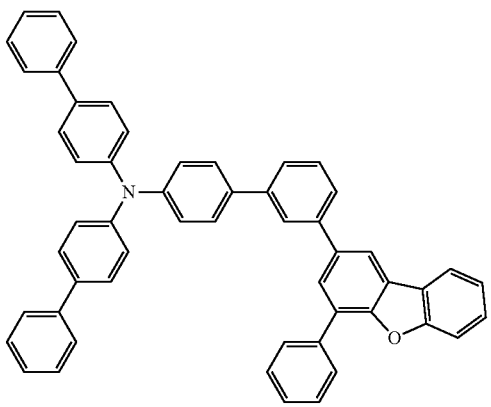
2-44
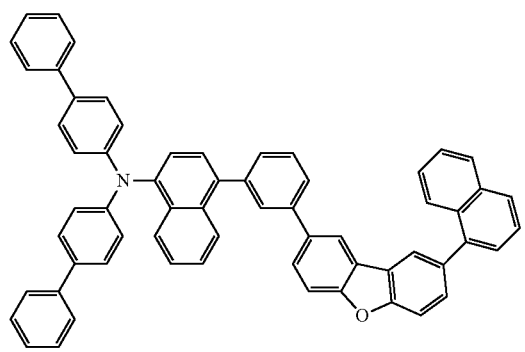
2-45
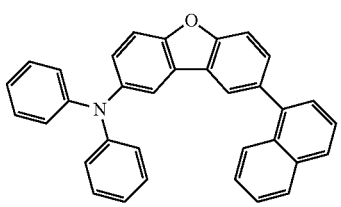

-continued
2-46
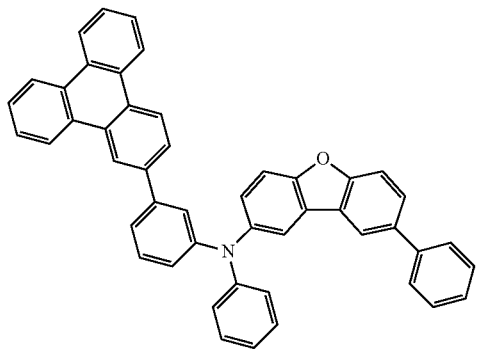
2-47
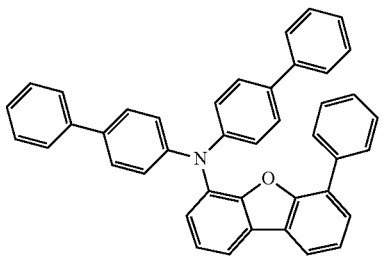
2-48
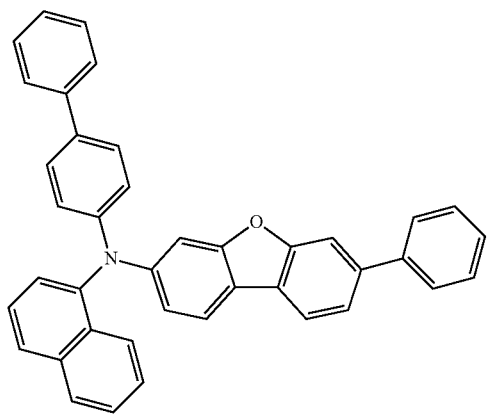
2-49
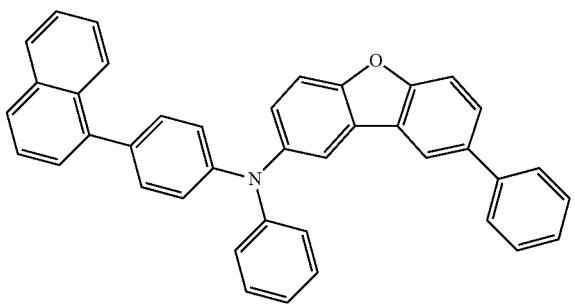
2-50
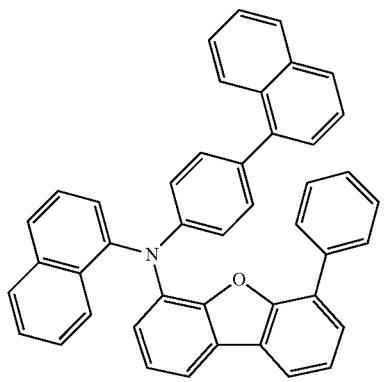
2-51
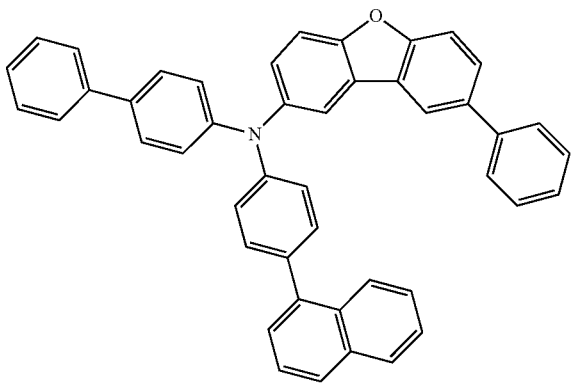
2-52
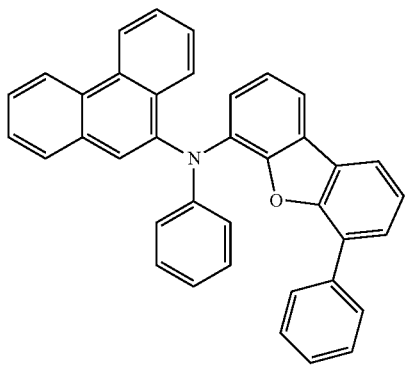
2-53
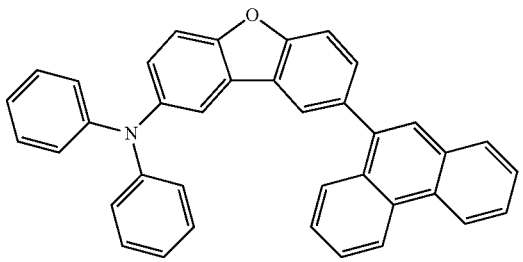

-continued
2-54
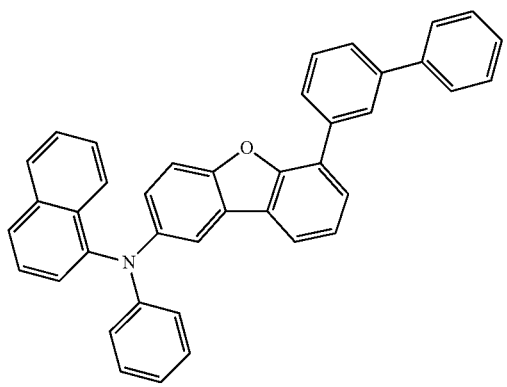
2-55
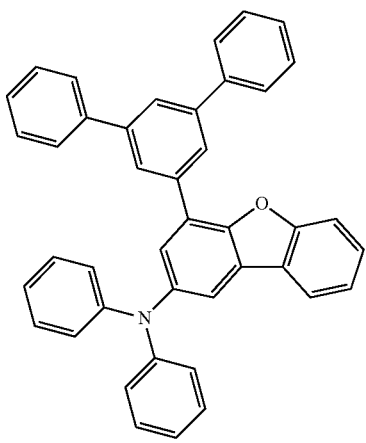
2-56
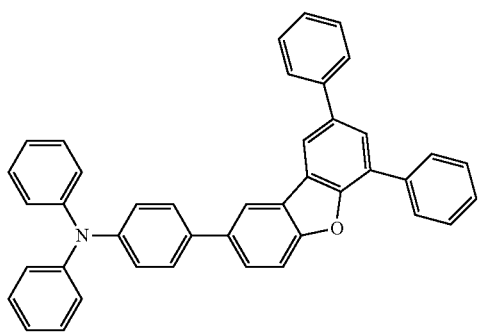
2-57
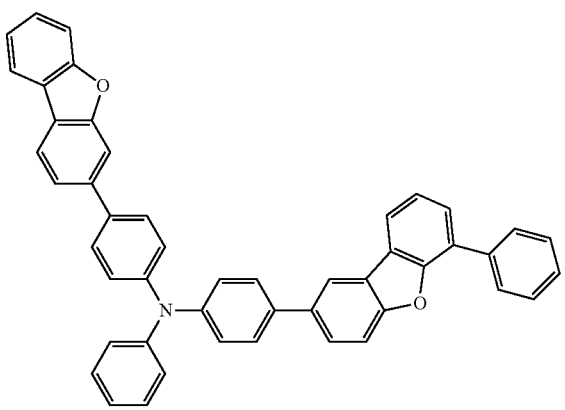
2-58
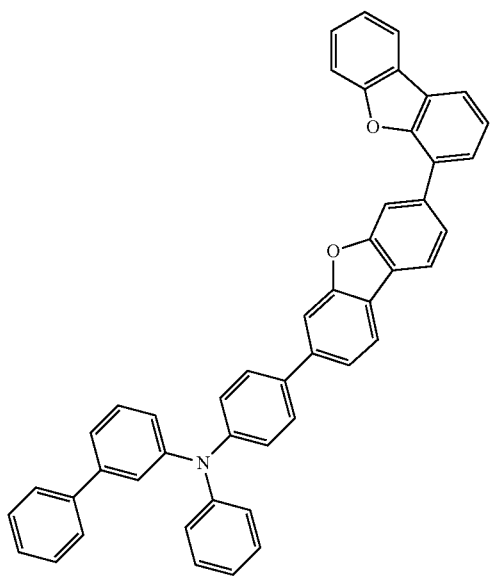
2-59
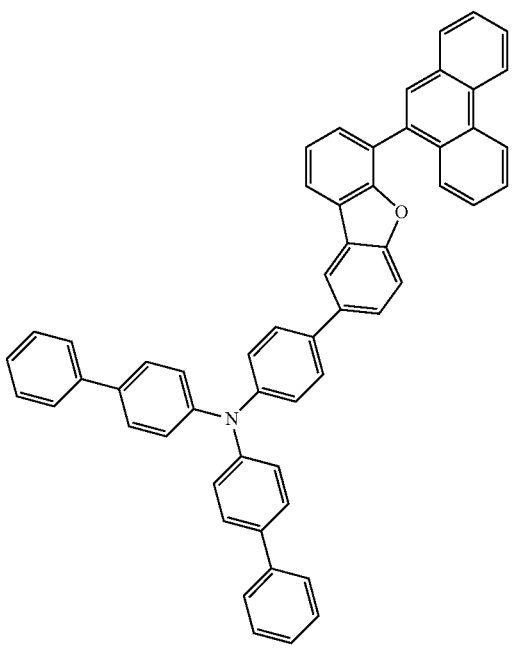

-continued
2-60
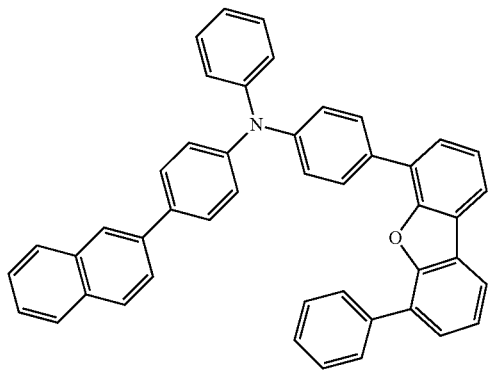
2-61
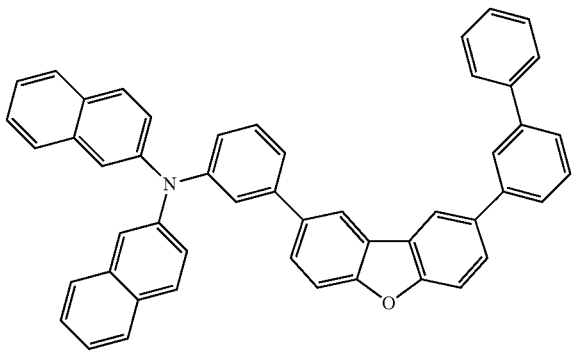
2-62
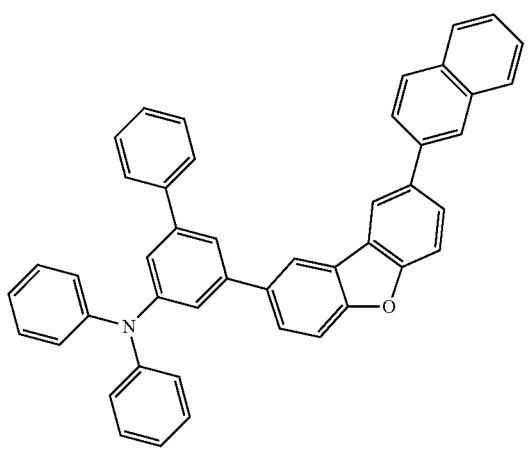
2-63
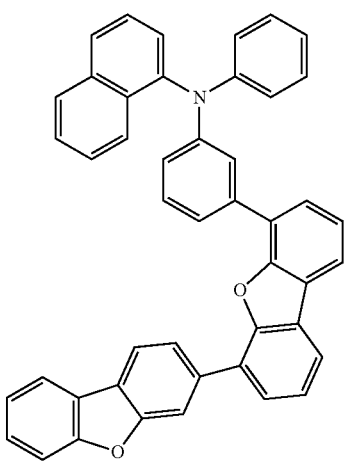
2-64
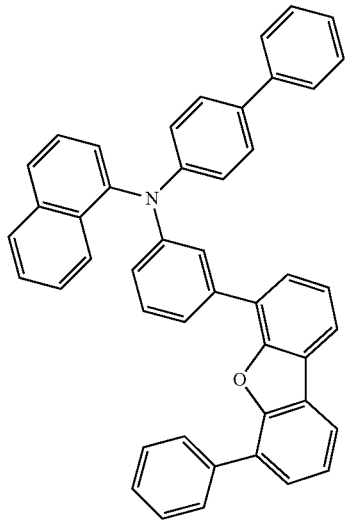
2-65
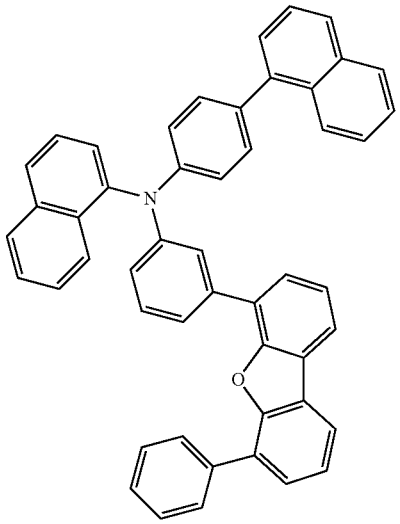

-continued
2-66
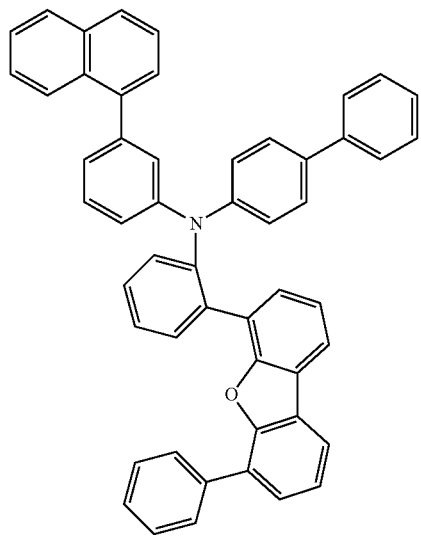
2-67
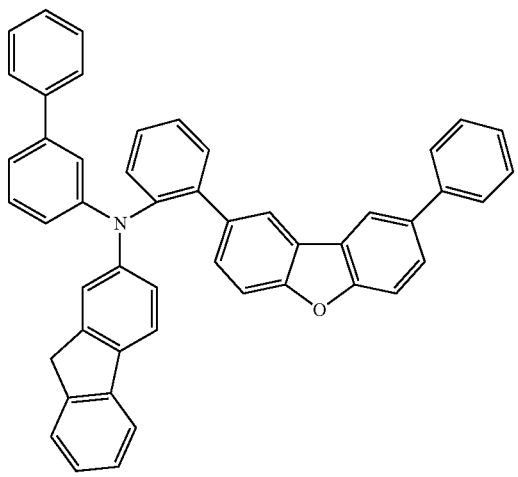
2-68
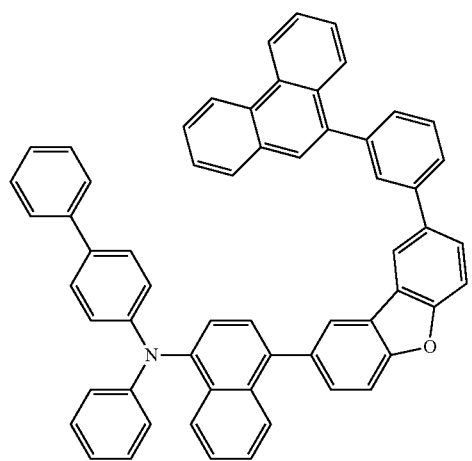
2-69
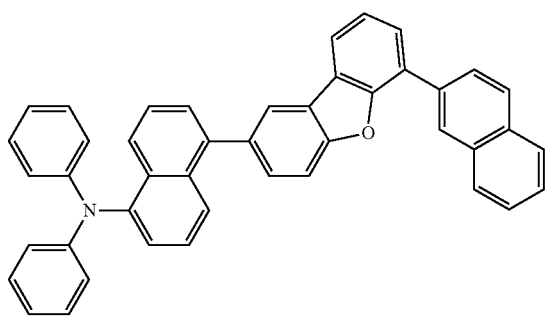
2-70
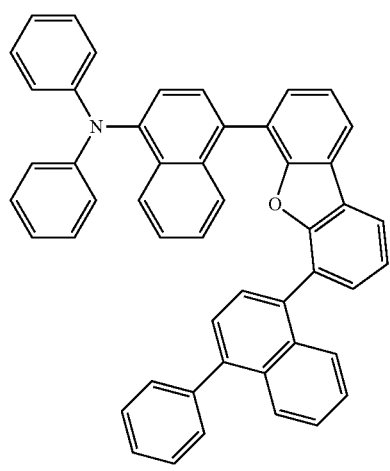
2-71
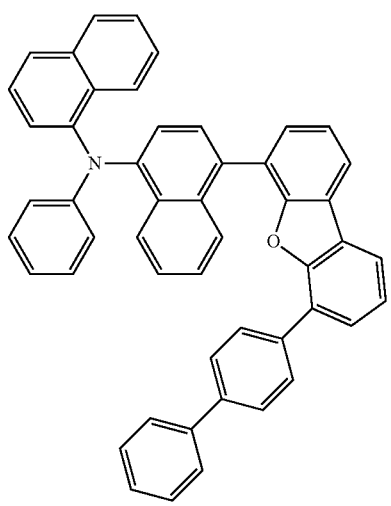

-continued
2-72
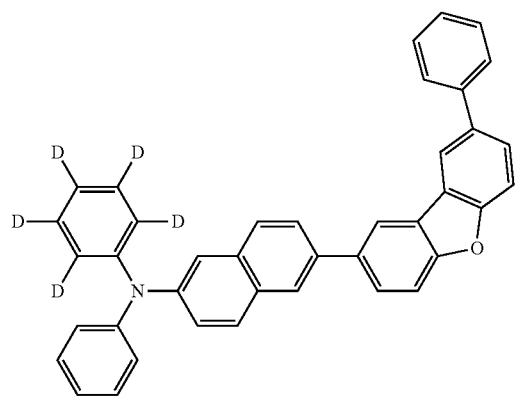
2-73
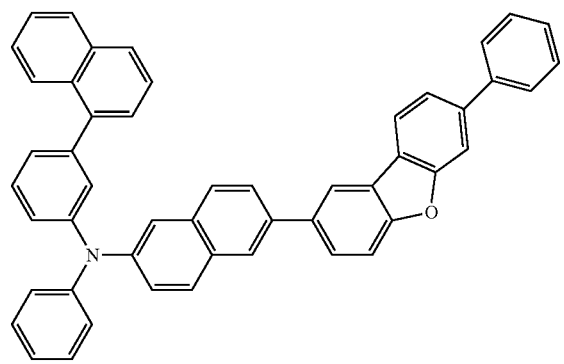
2-74
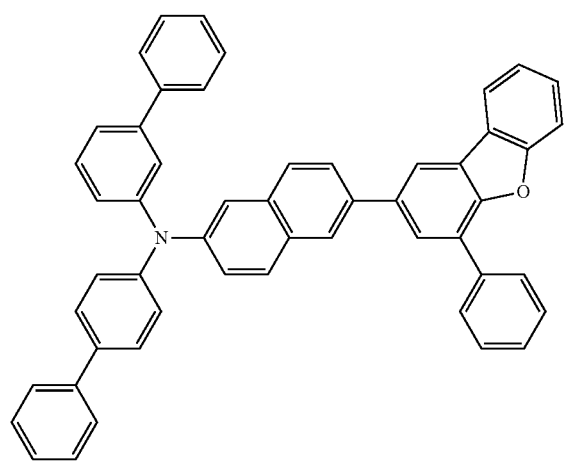
2-75
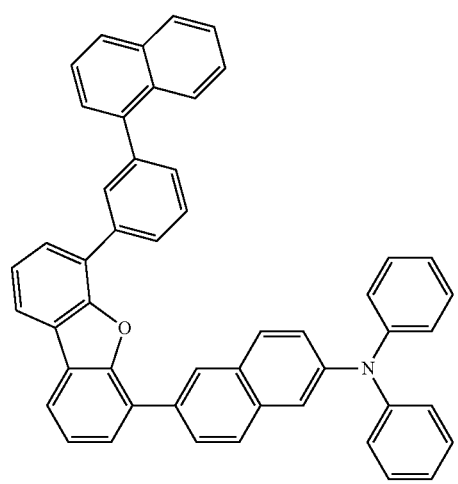
2-76
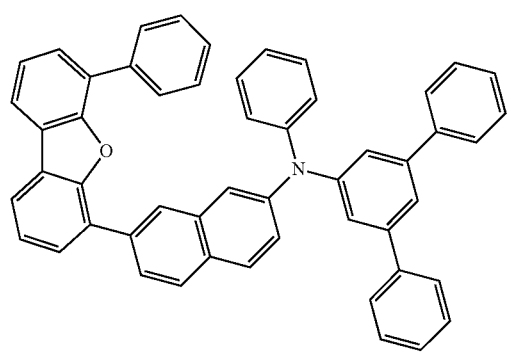
2-77
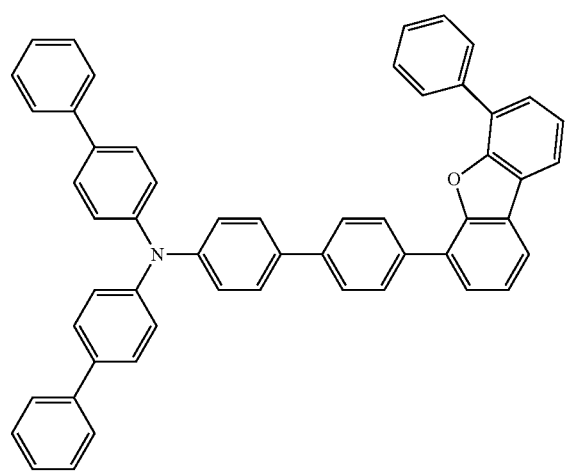

-continued
2-78
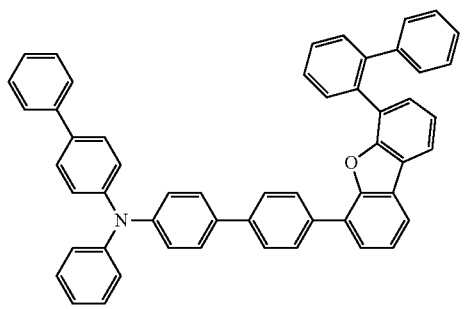
2-79
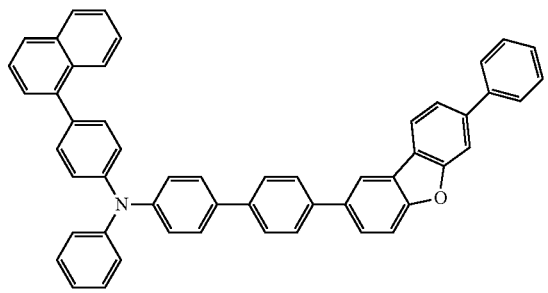
2-80
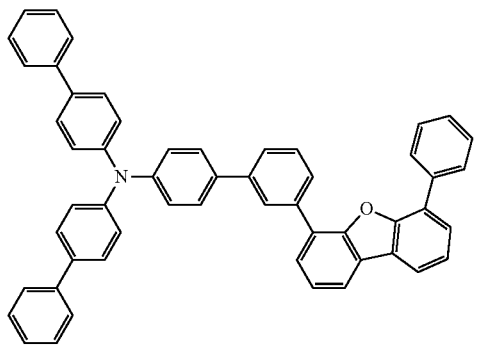
2-81
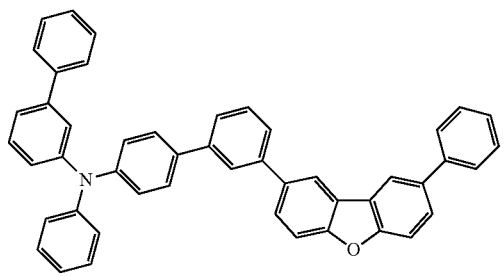
2-82
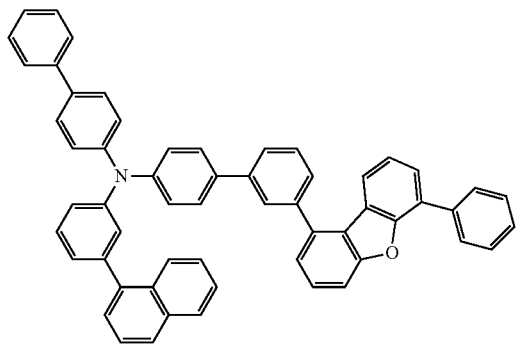
2-83
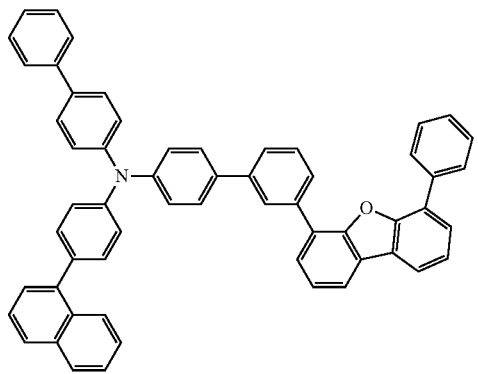
2-84
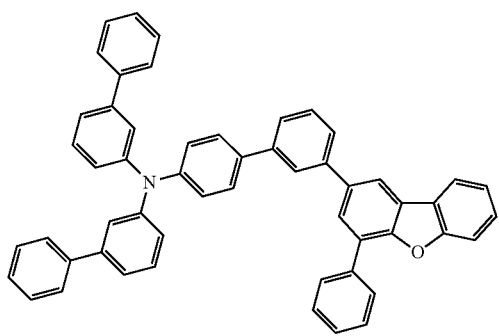
2-85
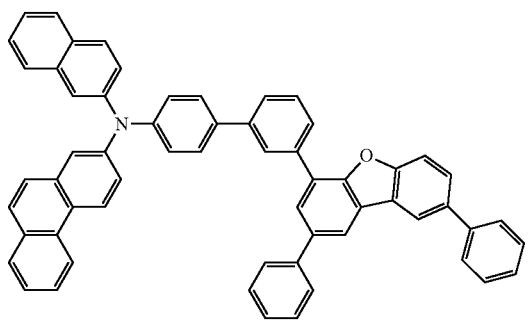

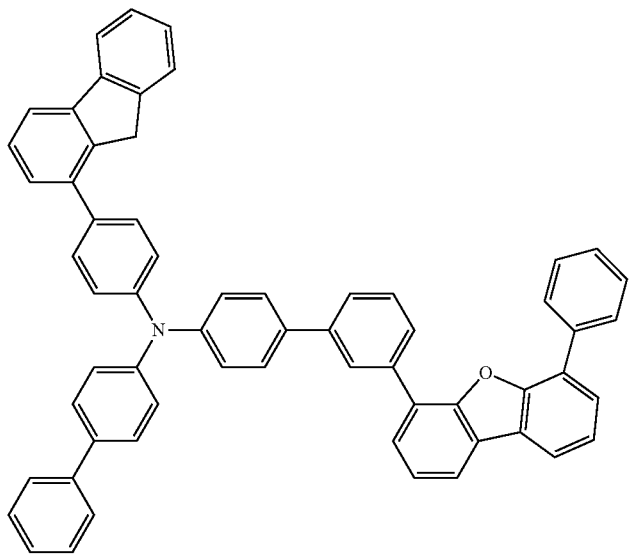
2-86
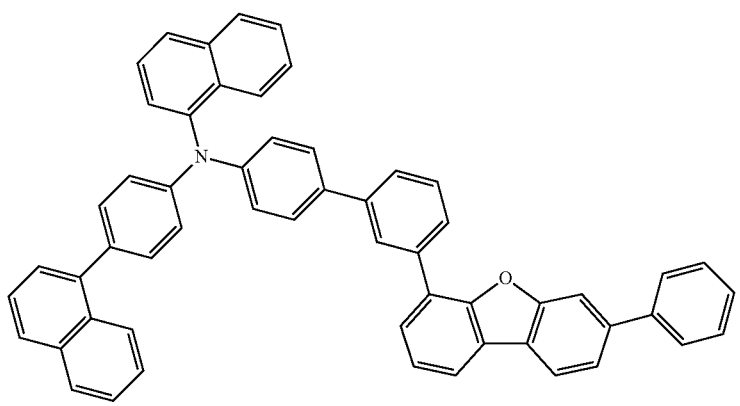
2-87
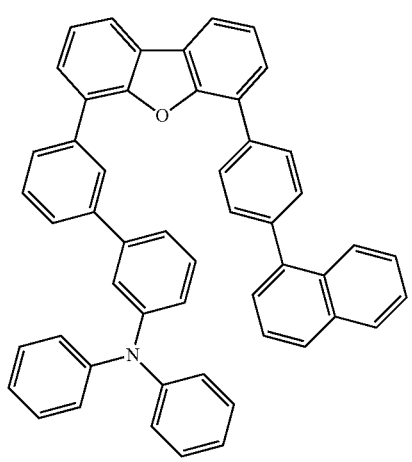
2-88

2-89
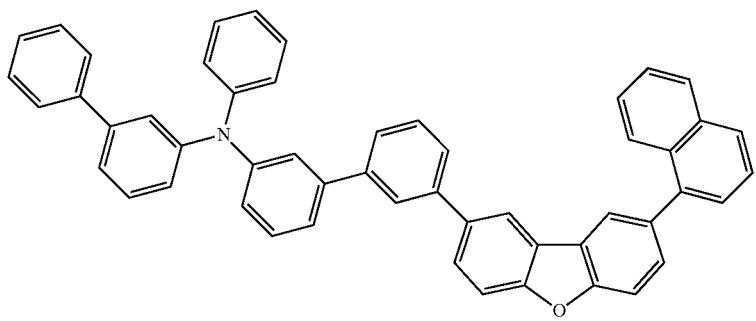
2-90
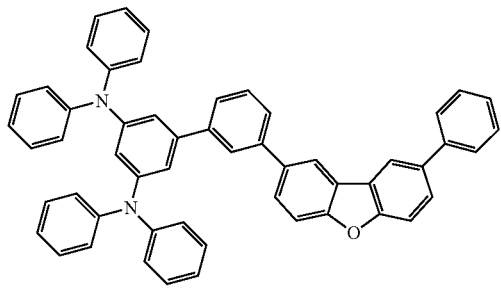
2-91
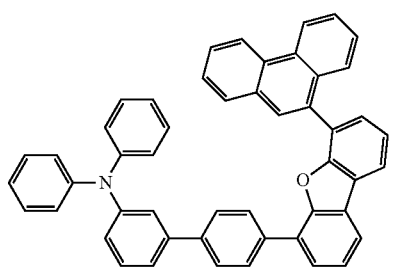
2-92
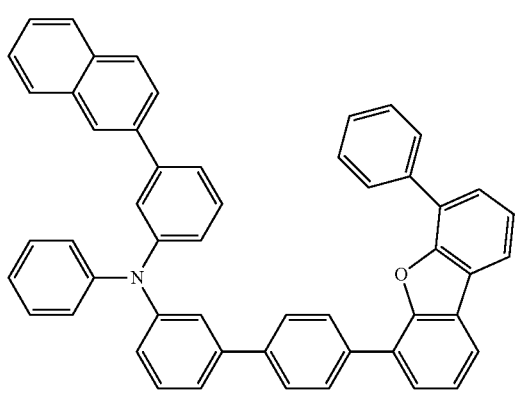
2-93
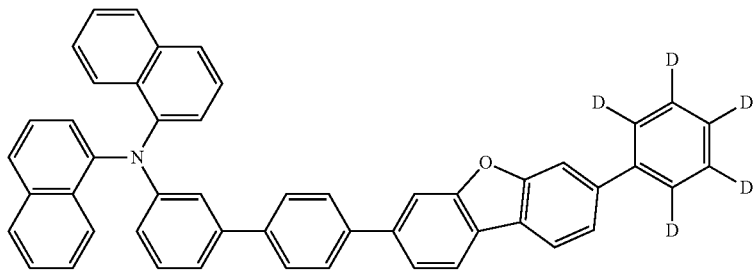

-continued
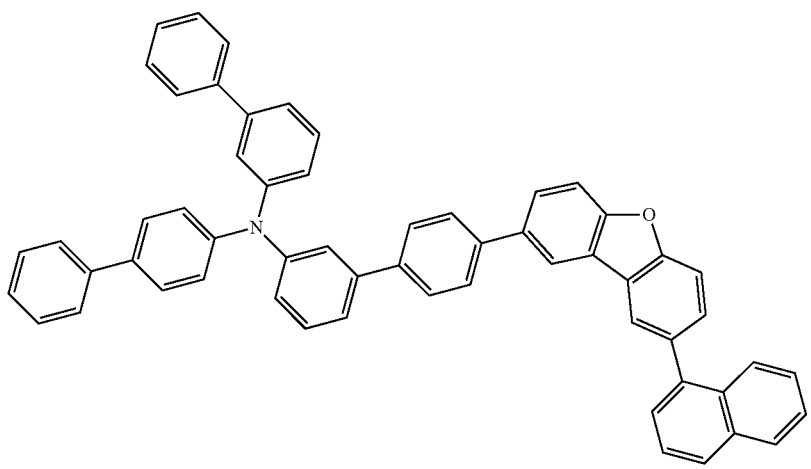
2-94
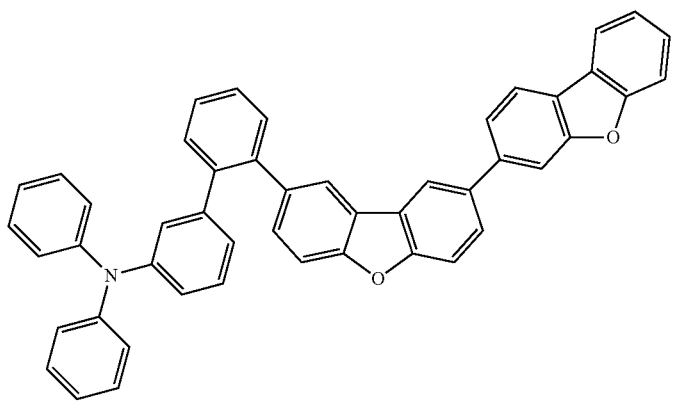
2-95
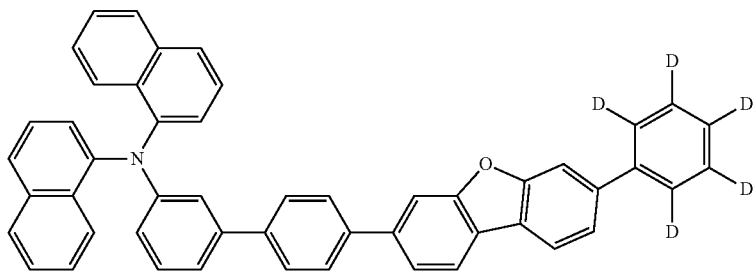
2-96
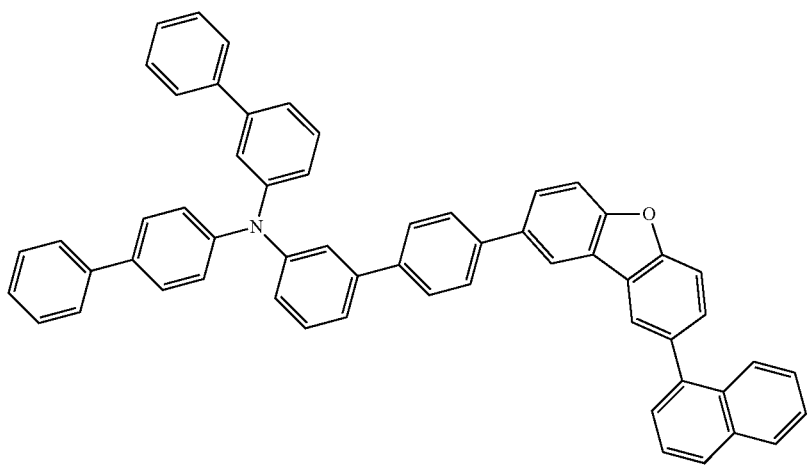
2-97

-continued
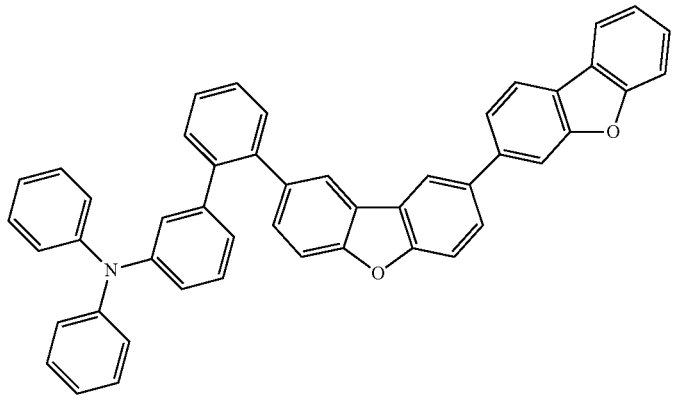
2-98
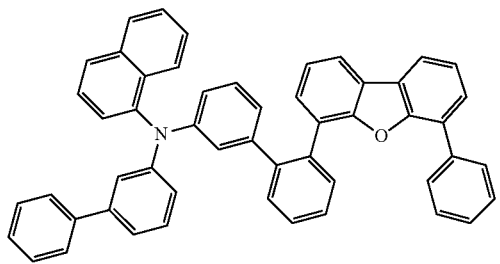
2-99
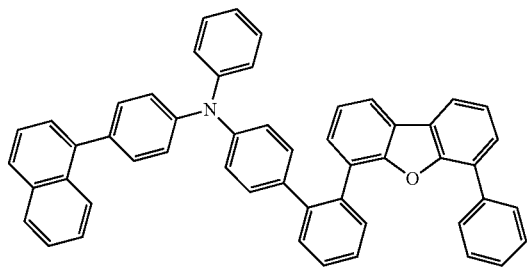
2-100
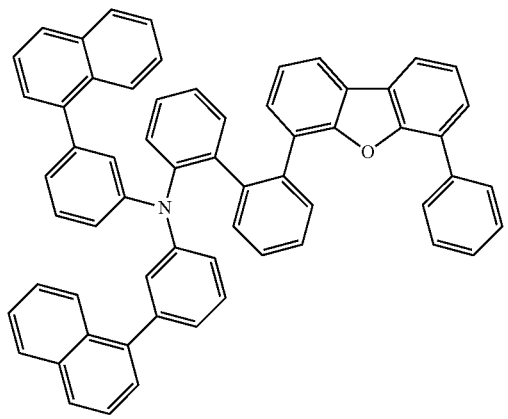
2-101
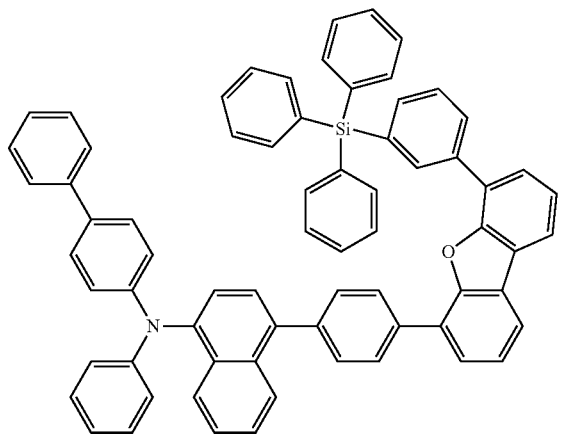
2-102
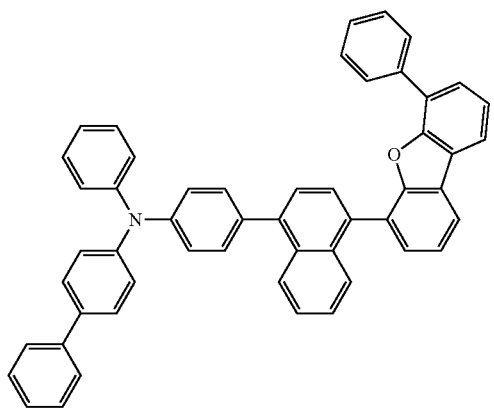
2-103
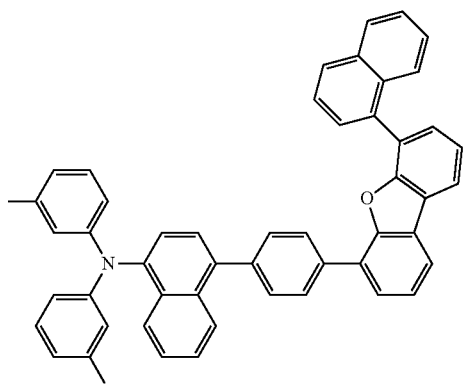
2-104

2-105
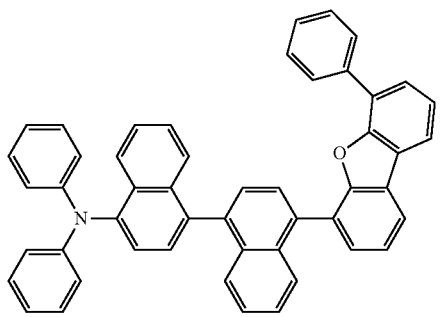

2-106
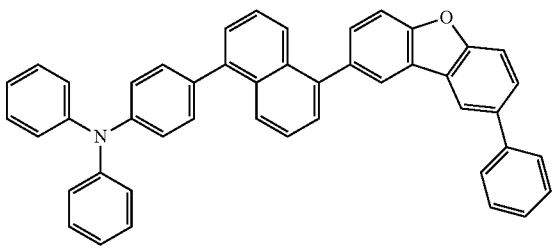

2-107
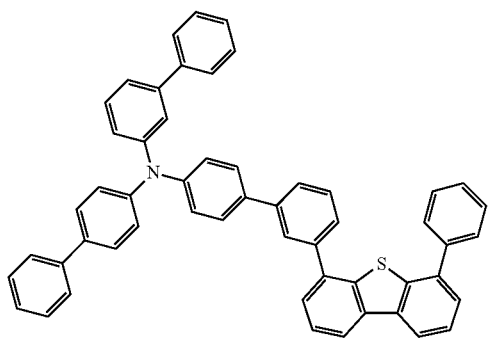

2-108
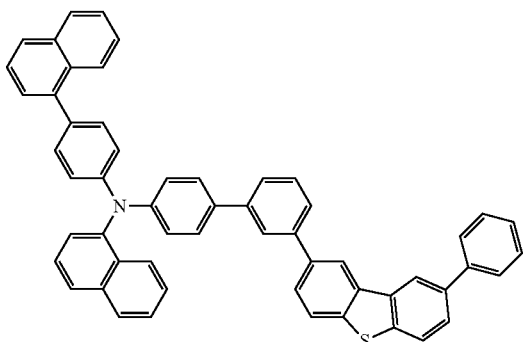

2-109
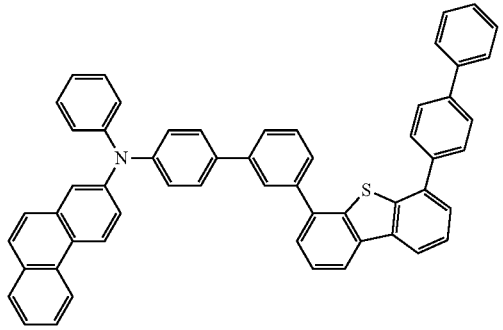

2-110
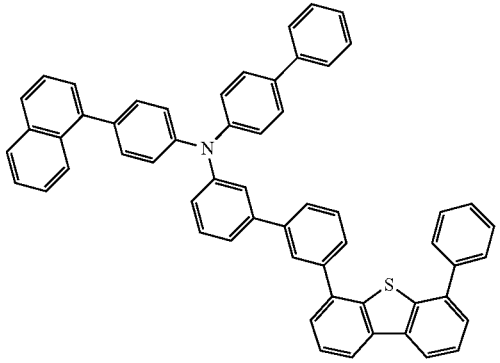

The organic light-emitting device including the first compound and the second compound may accordingly have low driving voltage and high efficiency.

In an embodiment, the electron transport region may include the first compound.

For example, the electron transport region may include an electron transport layer and an electron injection layer, wherein the electron transport layer may be disposed between the emission layer and the electron injection layer and may include the first compound.

In various embodiments, the hole transport region may include the second compound.

For example, the hole transport region may include a hole injection layer, a hole transport layer, and an emission auxiliary layer, wherein the emission auxiliary layer may directly contact the emission layer and may include the second compound, but embodiments are not limited thereto.

[Description of FIG. 1]

Figure 1:
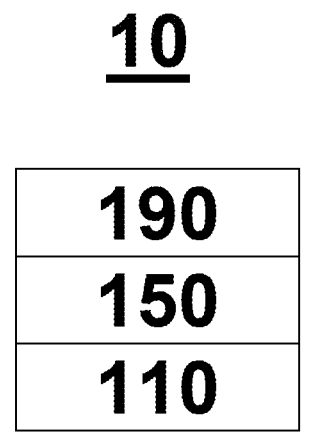

FIG. 1 is a diagram schematically illustrating a cross-section of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 according to an embodiment will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water-resistance.

The first electrode 110 may be formed by, for example, depositing or sputtering a material for forming the first electrode 110 on the substrate.

When the first electrode 110 is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, the material for forming the first electrode 110 may be selected from indium oxide (ITO), indium zinc oxide (IZO), tin oxide (SnO$_2$), zinc oxide (ZnO), and combinations thereof, but embodiments are not limited thereto. In various embodiments, when the first electrode 110 is a semi-transmissive electrode or a reflective electrode, the material for forming the first electrode 110 may be selected from magnesium (Mg), silver Ag), aluminum (Al), aluminum-lithium (Al—Li), calcium (Ca), magnesium-indium (Mg—In), magnesium-silver (Mg—Ag), and combinations thereof, but embodiments are not limited thereto.

The first electrode 110 may have a single-layered structure, or a multi-layered structure including two or more layers. For example, the first electrode 110 may have a three-layered structure of ITO/Ag/ITO, but embodiments are not limited thereto.

[Organic Layer 150]

The organic layer 150 may be disposed on the first electrode 110. The organic layer 150 may include an emission layer.

The organic layer 150 may include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer, a structure of hole injection layer/hole transport layer/emission auxiliary layer, a structure of hole injection layer/emission auxiliary layer, a structure of hole transport layer/emission auxiliary layer, or a structure of hole injection layer/hole transport layer/electron blocking layer, wherein for each structure, constituting layers are sequentially stacked from the first electrode 10 in this stated order, but embodiments are not limited thereto.

In an embodiment, the hole transport region may include an emission auxiliary layer, the emission auxiliary layer may directly contact the emission layer, and the emission auxiliary layer may include the second compound.

The hole transport region may further include, in addition to the second compound, at least one elected from m-MTDATA, TDATA, 2-TNATA, NPB(NPD), β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202, but embodiments are not limited thereto:

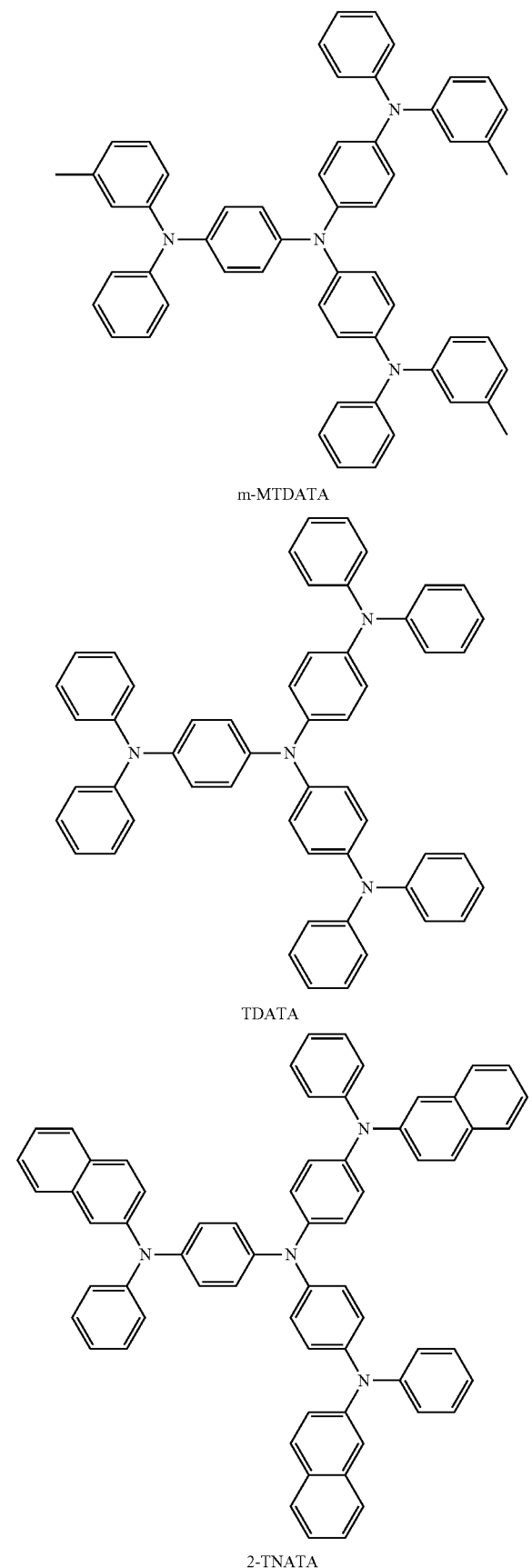

-continued
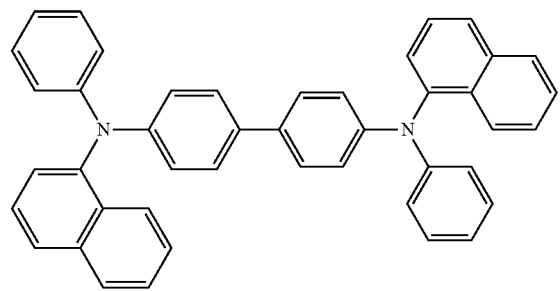
NPB
β-NPB
TPD
Spiro-TPD
Spiro-NPB
-continued
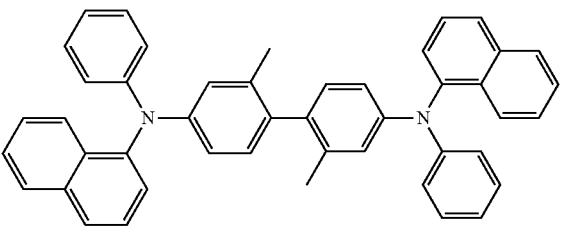
methylated NPB
TAPC
HMTPD
TCTA
<Formula 201>
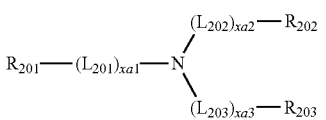

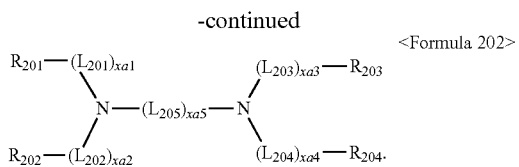

<Formula 202>

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer selected from 0 to 3, xa5 may be an integer selected from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may be optionally linked to each other via a single bond, a dimethyl-methylene group, or a diphenyl-methylene group, and $R_{203}$ and $R_{204}$ may be optionally linked to each other via a single bond, a dimethyl-methylene group, or a diphenyl-methylene group.

In an embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xa1 to xa4 may each independently be 0, 1, or 2.

In various embodiments, xa5 may be 1, 2, 3, or 4.

In various embodiments, $R_{102}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be understood by referring to the descriptions thereof provided herein.

In various embodiments, in Formula 201, at least one selected from $R_{201}$ to $R_{203}$ may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In various embodiments, in Formula 202, i) $R_{201}$ and $R_{202}$ may be linked to each other via a single bond, and/or ii) $R_{203}$ and $R_{204}$ may be linked to each other via a single bond.

In various embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201A:

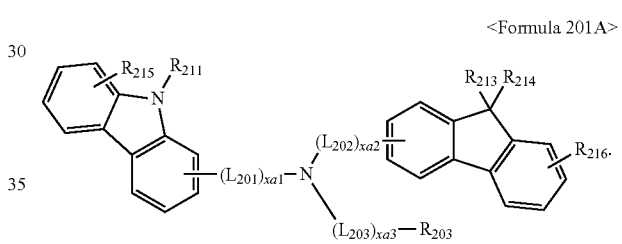

<Formula 201A>

For example, the compound represented by Formula 201 may be represented by Formula 201A(1), but embodiments are not limited thereto:

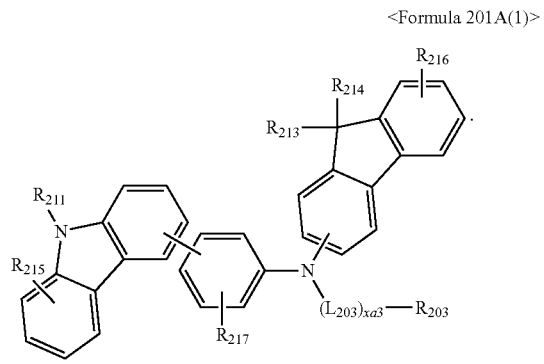

<Formula 201A(1)>

In various embodiments, the compound represented by Formula 201 may be represented by Formula 201A-1, but embodiments are not limited thereto:

<Formula 201A-1>

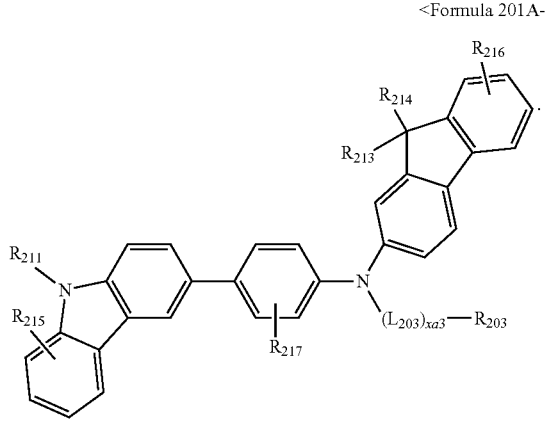

The compound represented by Formula 202 may be represented by Formula 202A:

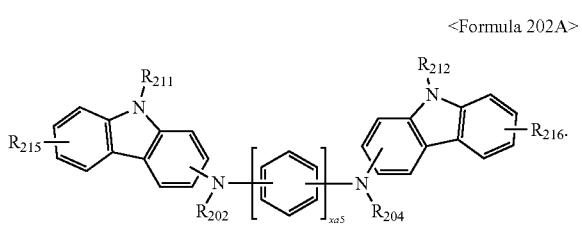

<Formula 202A>

In various embodiments, the compound represented by Formula 202 may be represented by Formula 202A-1:

<Formula 202A-1>

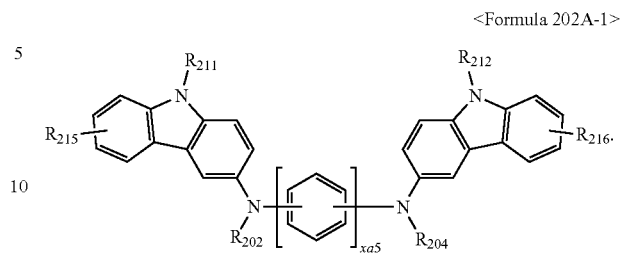

In Formulae 201A, 201A(1), 201A-1, 202A, and 202A-1, $L_{201}$ to $L_{203}$, xa1 to xa3, and $R_{202}$ to $R_{204}$ may each independently be understood by referring to the descriptions thereof provided herein, $R_{211}$ and $R_{212}$ may each independently be understood by referring to the description of $R_{203}$ provided herein, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one selected from Compounds HT1 to HT39, but embodiments are not limited thereto:

HT1

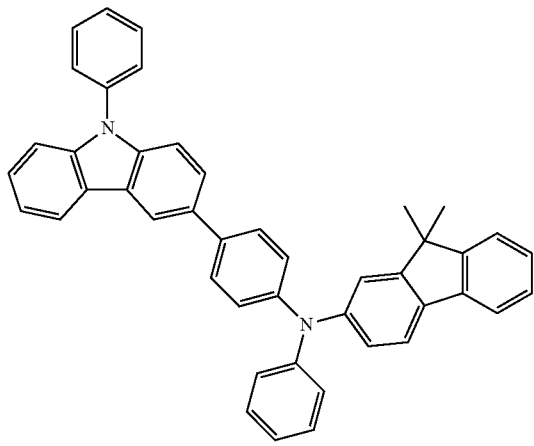

HT2

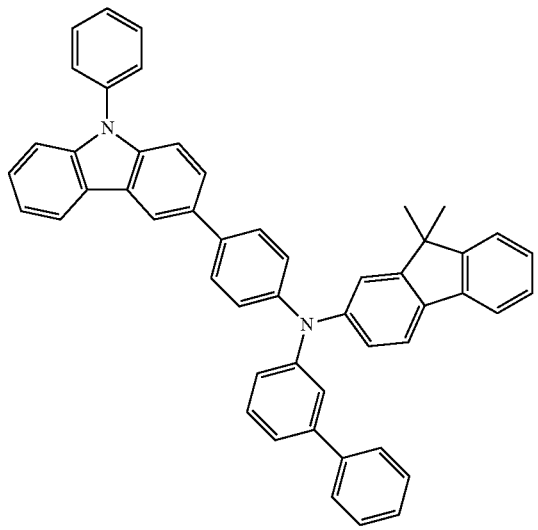

HT3
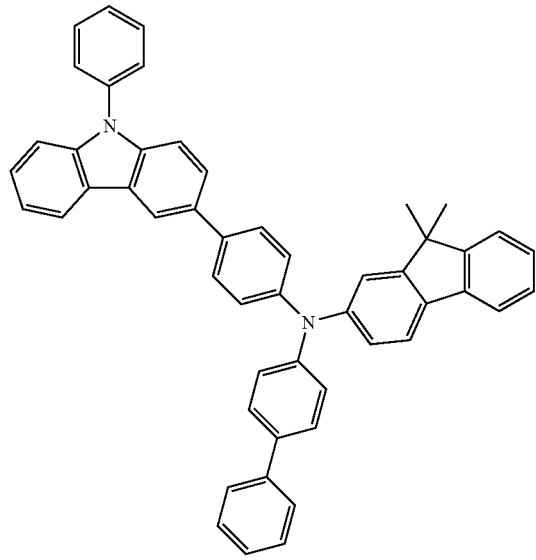
HT4
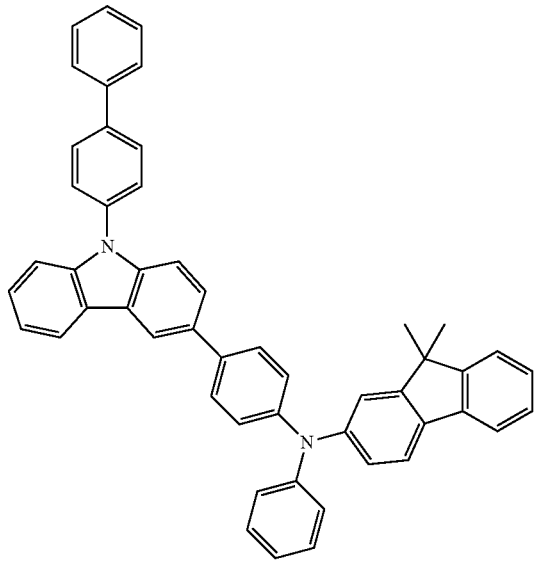
HT5
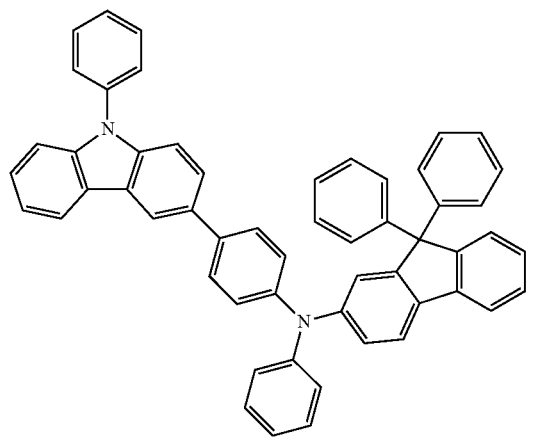
HT6
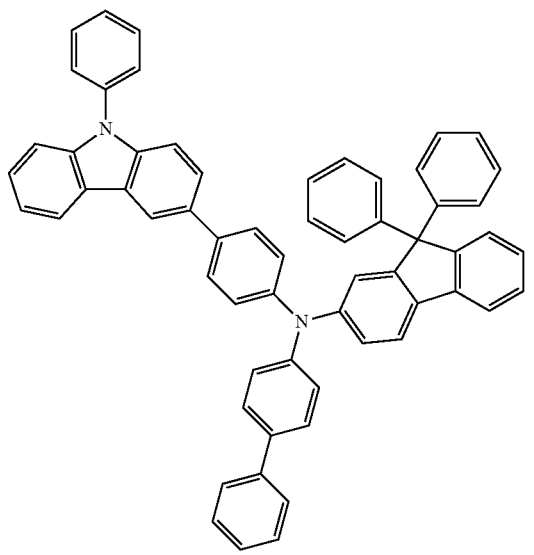

-continued
HT7
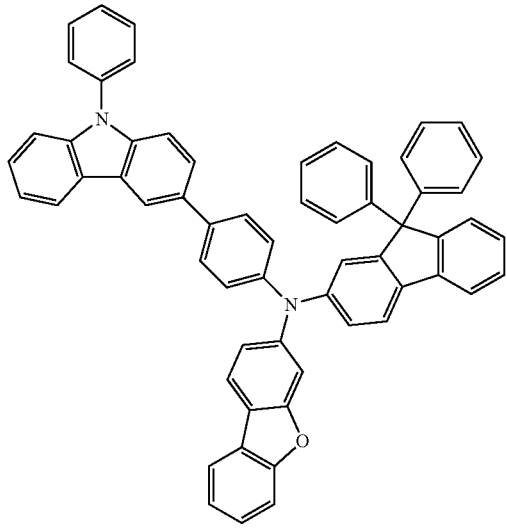
HT8
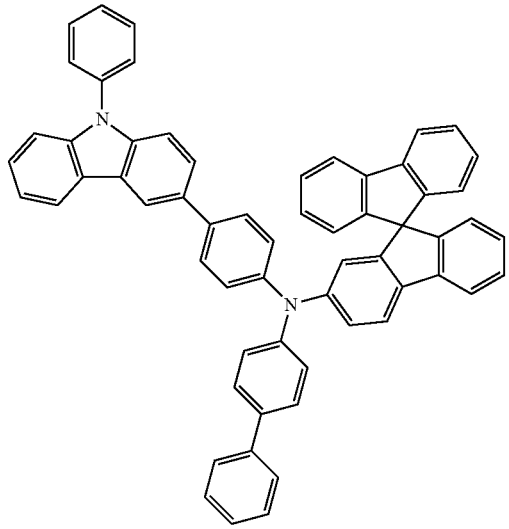
HT9
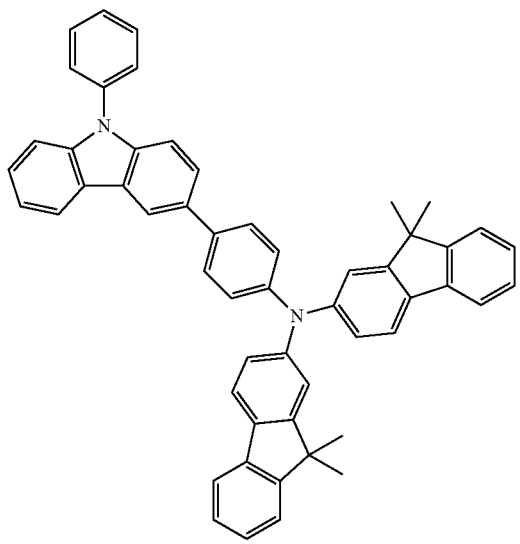
HT10
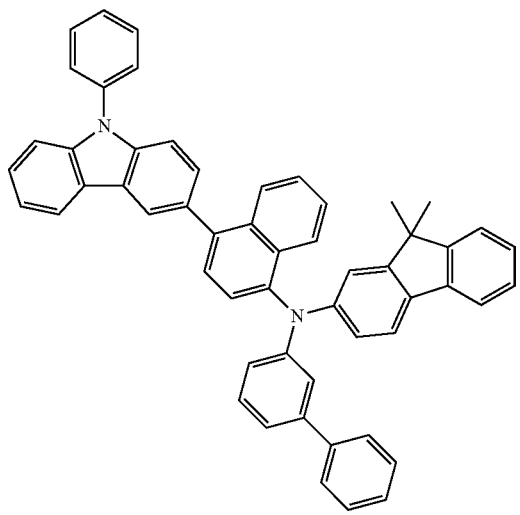
HT11
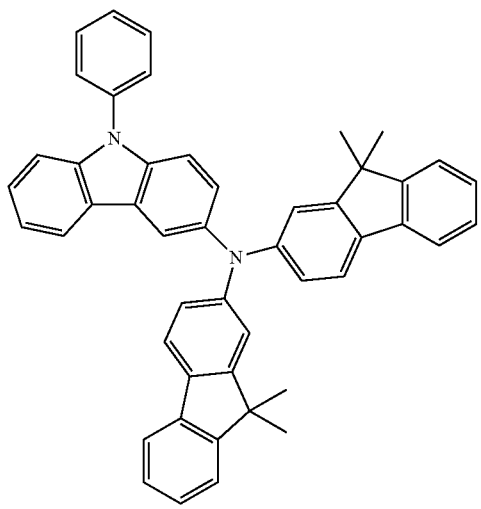
HT12
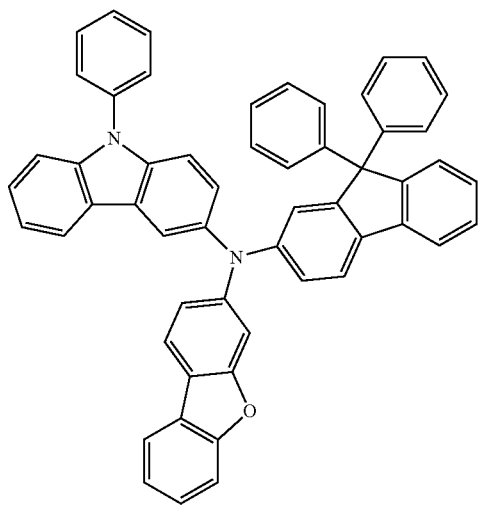

-continued
HT13
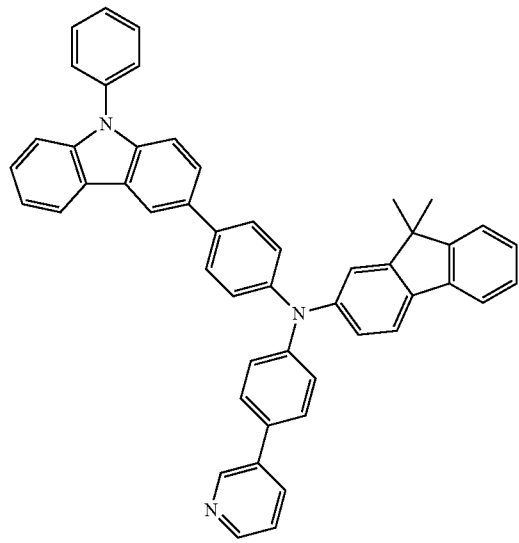
HT14
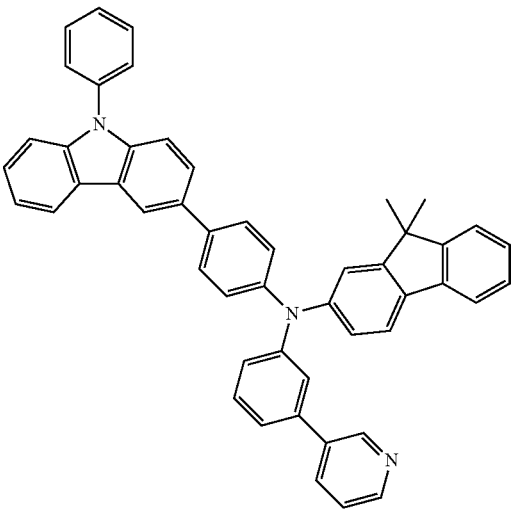
HT15
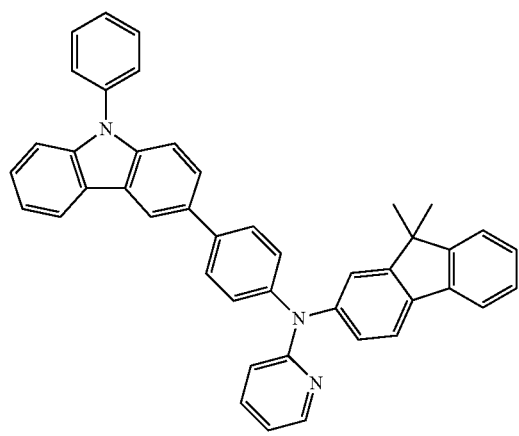
HT16
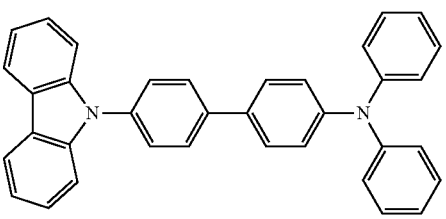
HT17
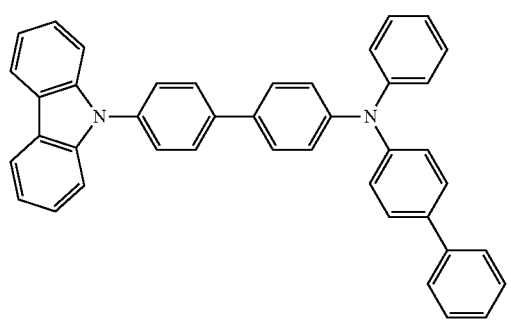
HT18
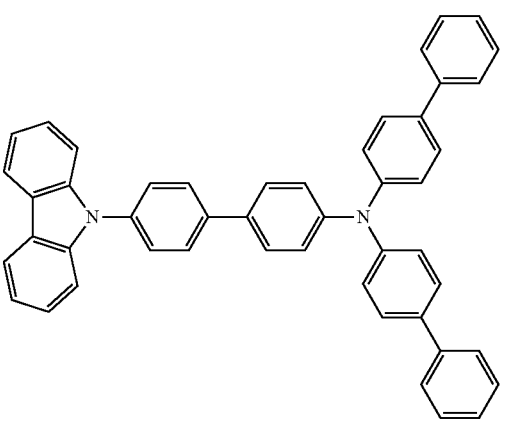

-continued
HT19
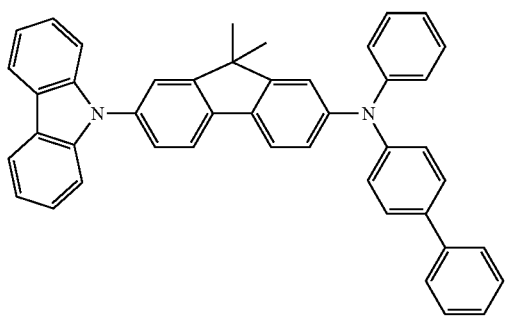
HT20
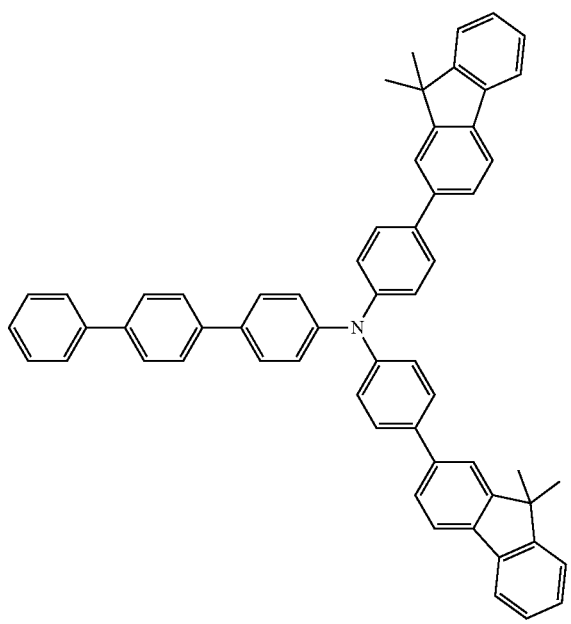
HT21
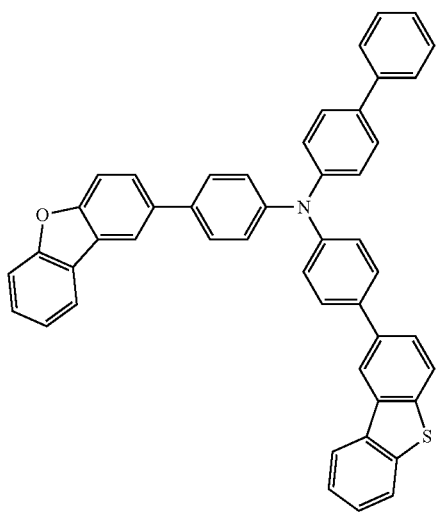
HT22
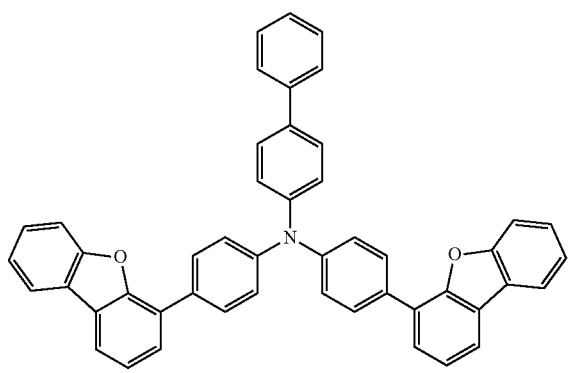
HT23
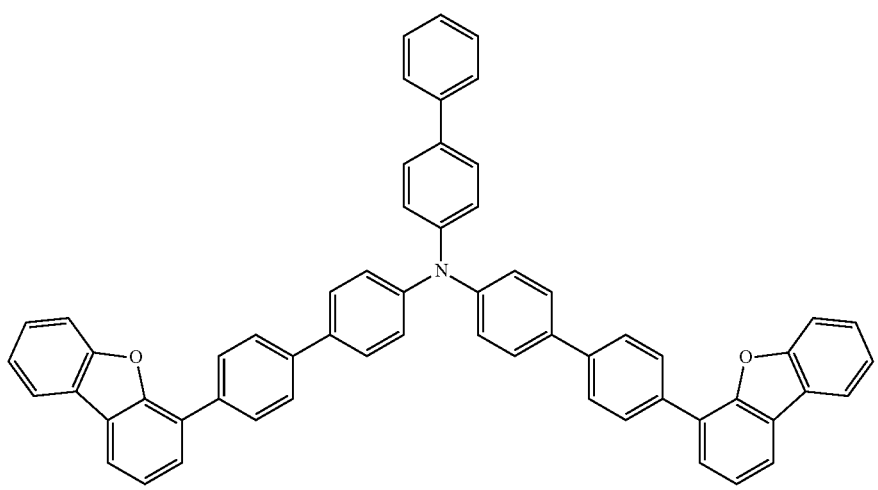

HT24
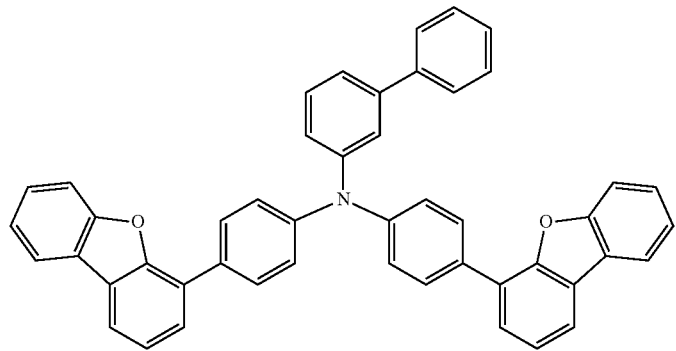
HT25
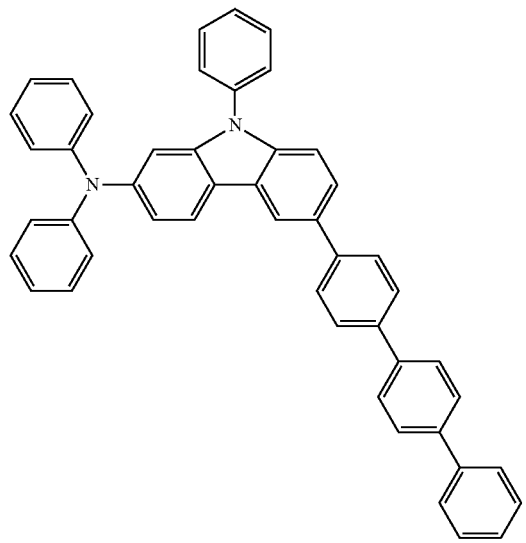
HT26
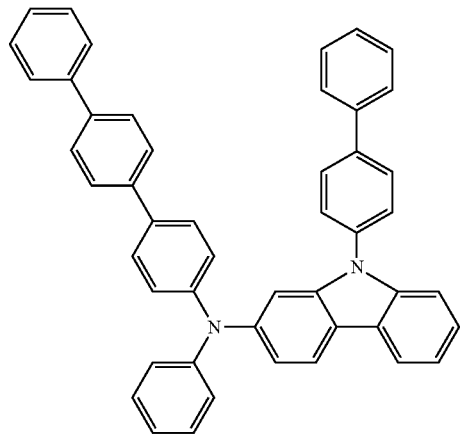
HT27
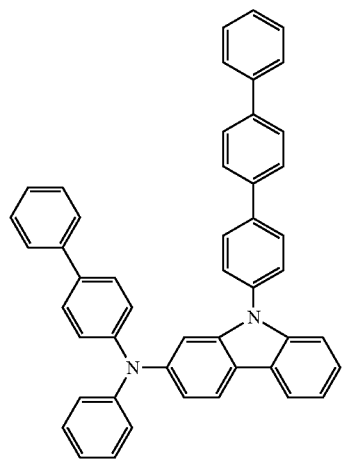
HT28
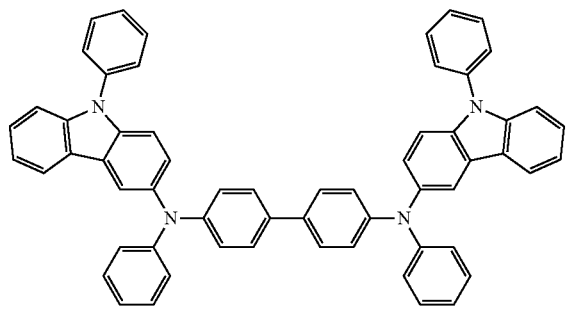

-continued
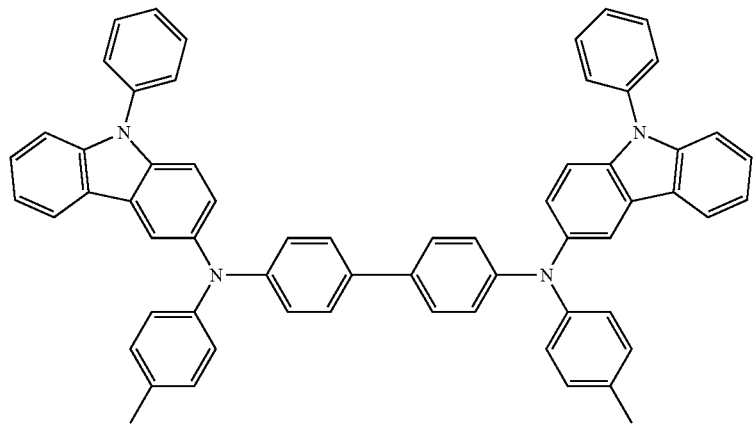
HT29
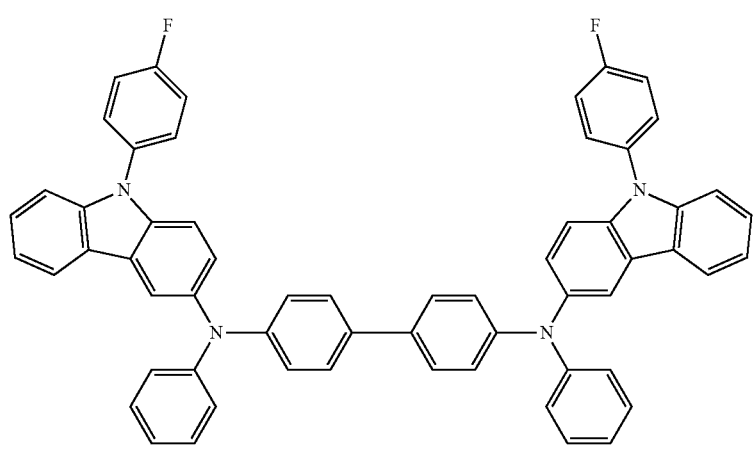
HT30
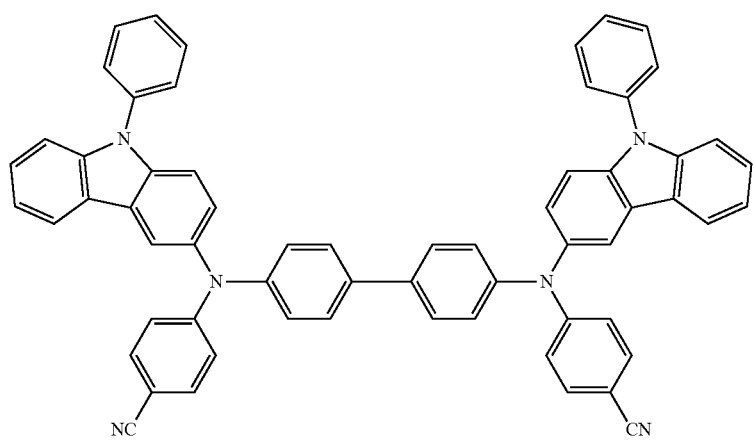
HT31

-continued
HT32
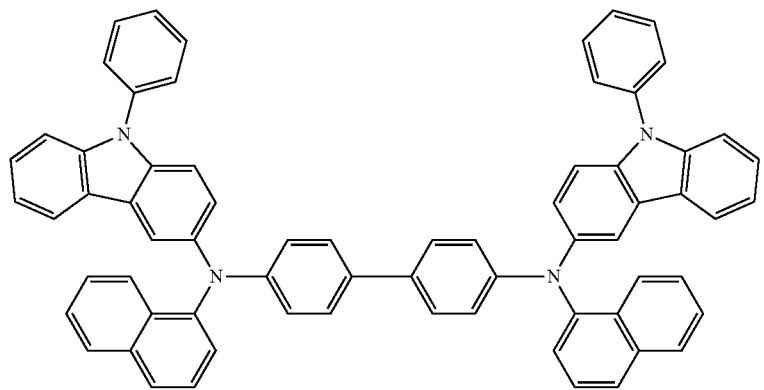
HT33
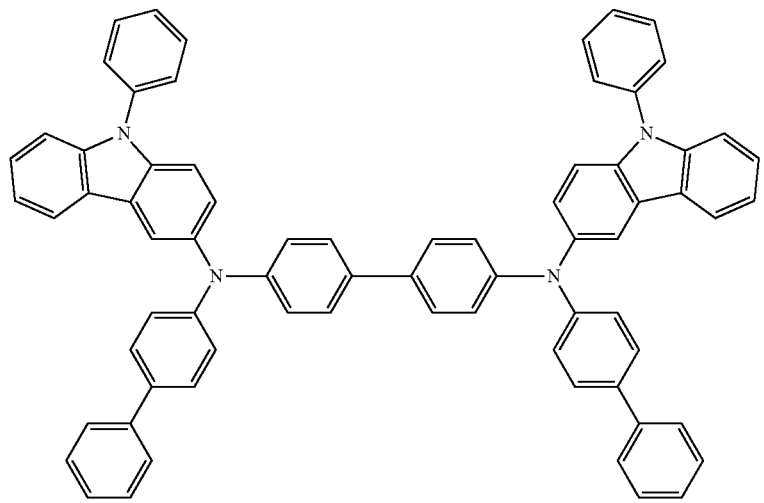
HT34
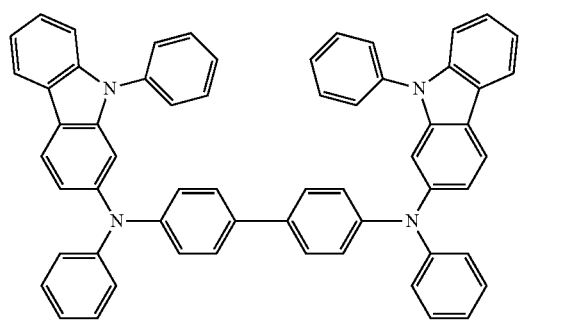
HT35
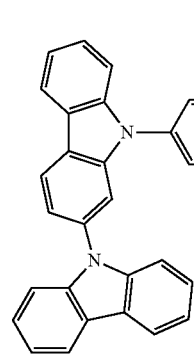

HT36

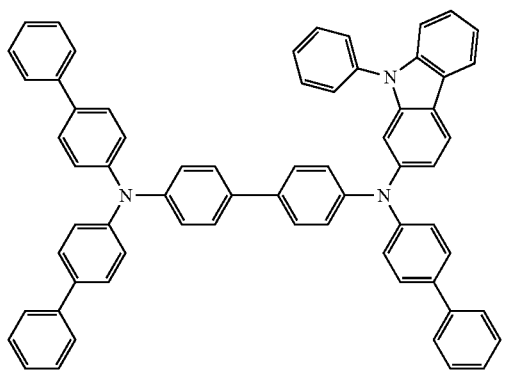

HT37

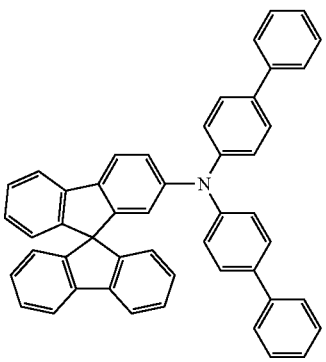

HT38

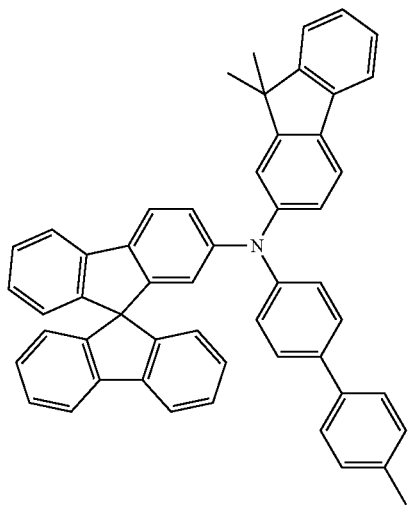

HT39

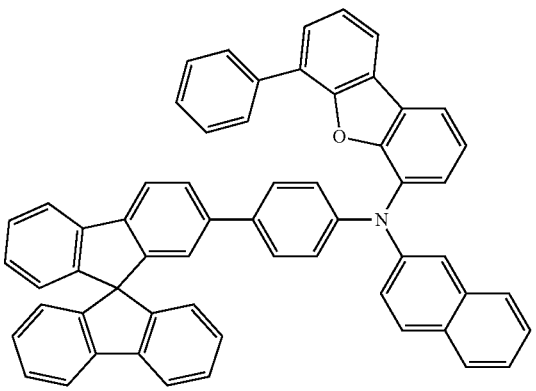

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to a wavelength of light emitted from the emission layer, and the electron blocking layer may block the flow of electrons from the electron transport region. The emission auxiliary layer and the electron blocking layer may include the materials as described above.

[P-Dopant]

The hole transport region may further include, in addition to the materials described above, a charge-generation material to improve conductive properties. The charge-generation material may be homogeneously or non-homogeneously dispersed in the hole transport region.

The charge-generation material may be, for example, a p-dopant.

In an embodiment, a lowest unoccupied molecular orbital (LUMO) level of the p-dopant may be about −3.5 eV or less.

The p-dopant may include at least one selected from a quinone derivative, a metal oxide, and a cyano group-containing compound, but embodiments are not limited thereto.

For example, the p-dopant may include at least one selected from:

quinone derivatives, such as tetracyanoquinodimethane (TCNQ) and 2,3,5,6-tetrafluoro-7,7,8,8-tetracyanoquinodimethane (F4-TCNQ);

metal oxides, such as a tungsten oxide and a molybdenum oxide;

1,4,5,8,9,11-hexaazatriphenylene-hexacarbonitrile (HAT-CN); and a compound represented by Formula 221, but embodiments are not limited thereto:

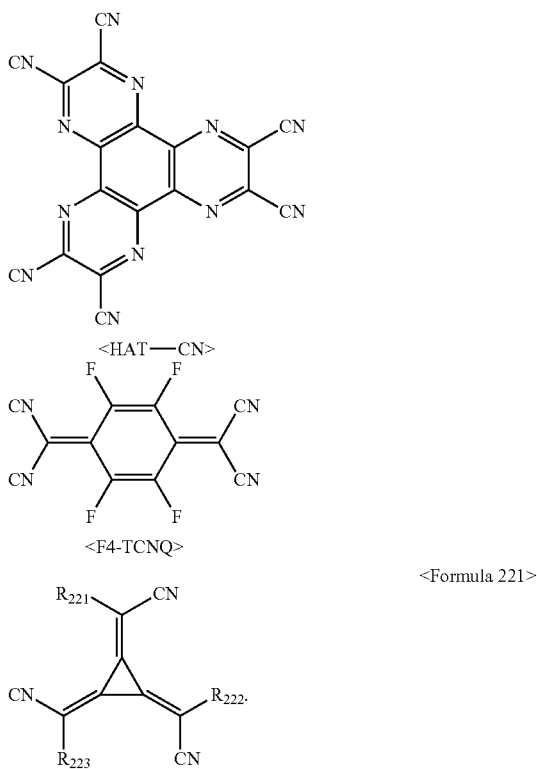

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full color organic light-emitting device, the emission layer may be patterned into a red emission layer, a green emission layer, or a blue emission layer, according to an individual subpixel. In various embodiments, the emission layer may have a stacked structure of two or more layers selected from a red emission layer, a green emission layer, and a blue emission layer, in which the two or more layers contact each other or are separated from each other. In various embodiments, the emission layer may include two or more materials selected from a red-light emission material, a green-light emission material, and a blue-light emission material, in which the two or more materials are mixed with each other in a single layer to emit white light.

In an embodiment, the emission layer of the organic light-emitting device 10 may be a first-color-light emission layer, and the organic light-emitting device 10 may further include, between the first electrode 110 and the second electrode 190, i) at least one second-color-light emission layer or ii) at least one second-color-light emission layer and at least one third-color-light emission layer, wherein a maximum emission wavelength of the first-color-light emission layer, a maximum emission wavelength of the second-color-light emission layer, and a maximum emission wavelength of the third-color-light emission may be identical to or different from each other, and the organic light-emitting device 10 may emit mixed light including first-color-light and second-color-light, or mixed light including first-color-light, second-color-light, and third-color-light, but embodiments are not limited thereto.

For example, the maximum emission wavelength of the first-color-light emission layer may be different from the maximum emission wavelength of the second-color-light emission layer, and the mixed light including first-color-light and second-color-light may be white light, but embodiments are not limited thereto.

In various embodiments, the maximum emission wavelength of the first-color-light emission layer, the maximum emission wavelength of the second-color-light emission layer, and the maximum emission wavelength of the third-color-light emission layer may be different from one another, and the mixed light including first-color-light, second-color-light, and third-color-light may be white light. However, embodiments are not limited thereto.

The emission layer may include a host and a dopant. The dopant may include at least one selected from a phosphorescent dopant and a fluorescent dopant.

An amount of the dopant in the emission layer may be, in general, in a range of about 0.01 to about 15 parts by weight based on 100 parts by weight of the host, but embodiments are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

The host may include a compound represented by Formula 301:

$$[Ar_{301}]_{xb11}\text{-}[(L_{301})_{xb1}\text{-}R_{301}]_{xb21}. \quad \text{<Formula 301>}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer selected from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In Formula 301, when xb11 is 2 or more, 2 or more $Ar_{301}$(s) may be linked to each other via a single bond.

In various embodiments, the compound represented by Formula 301 may be represented by Formula 301-1 or 301-2:

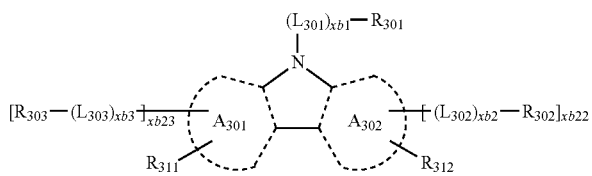

<Formula 301-1>

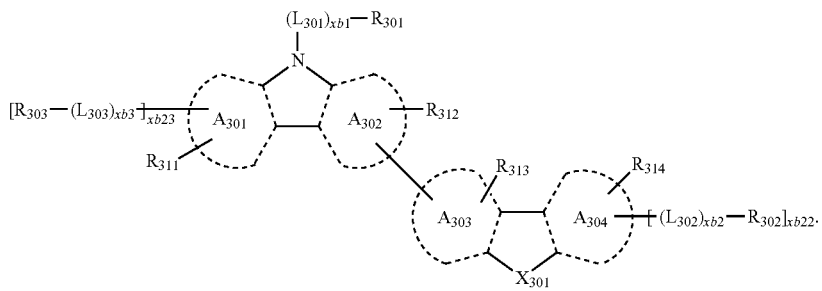

<Formula 301-2> non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer selected from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In an embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be understood by referring to the descriptions thereof provided herein, $L_{302}$ to $L_{304}$ may each independently be understood by referring to the description of $L_{301}$ provided herein, xb2 to xb4 may each independently be understood by referring to the description of xb1 provided herein, and $R_{302}$ to $R_{304}$ may each independently be understood by referring to the description $R_{301}$ provided herein.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be understood by referring to the descriptions thereof provided herein.

In various embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be understood by referring to the descriptions thereof provided herein.

In various embodiments, the host may include an alkaline earth-metal complex. For example, the host may be selected from a Be complex (for example, Compound H55), a Mg complex, and a Zn complex.

In various embodiments, the host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl) (CBP), 1,3-di-9-carbazolylbenzene (mCP), 1,3,5-tri(carbazol-9-yl)benzene (TCP), and Compounds H1 to H55, but embodiments are not limited thereto:

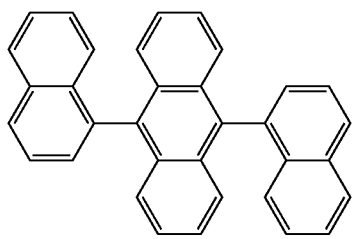

H1

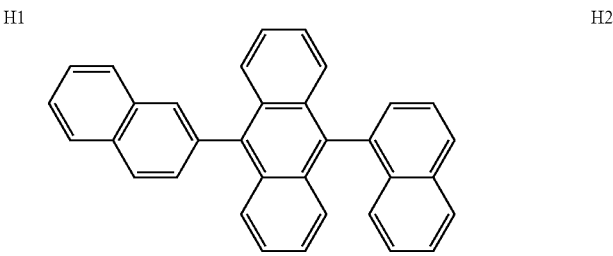

H2

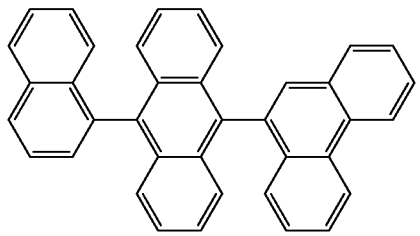

H3

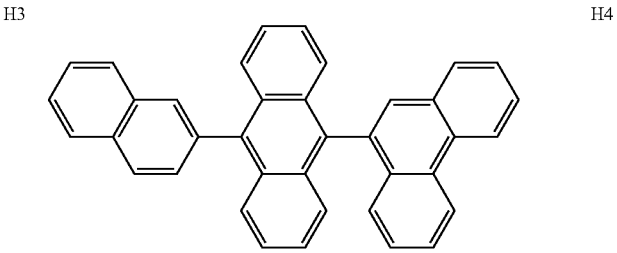

H4

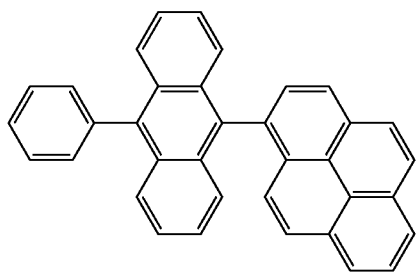

H5

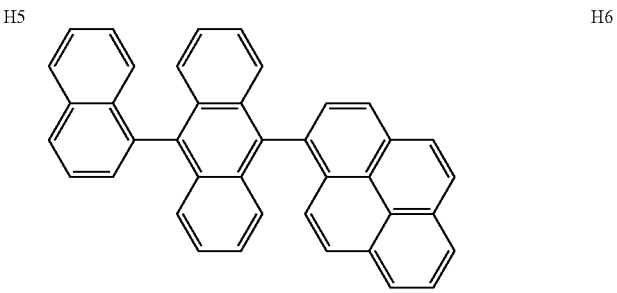

H6

-continued
H7
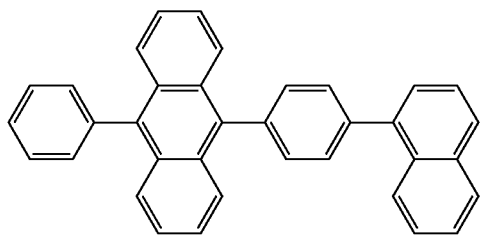
H8
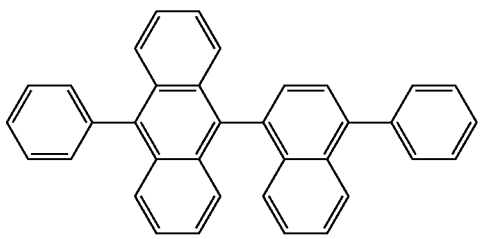
H9
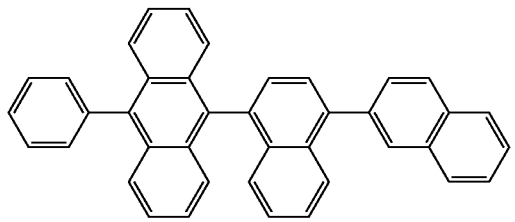
H10
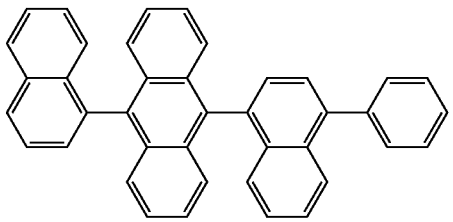
H11
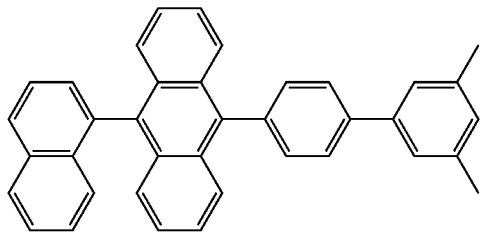
H12
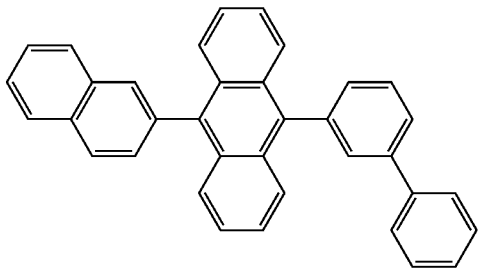
H13
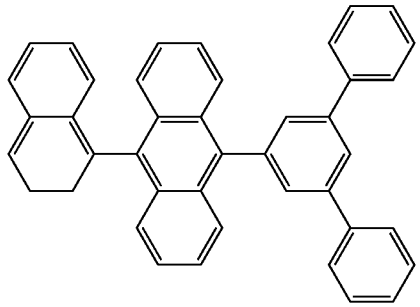
H14
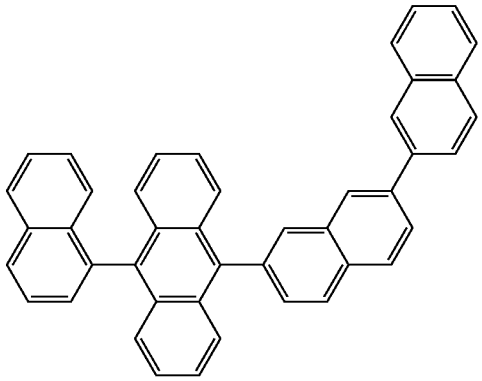
H15
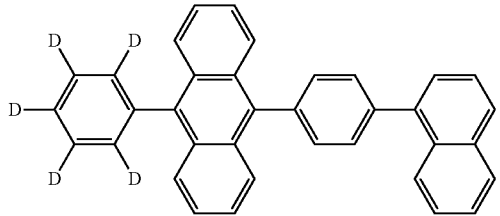
H16
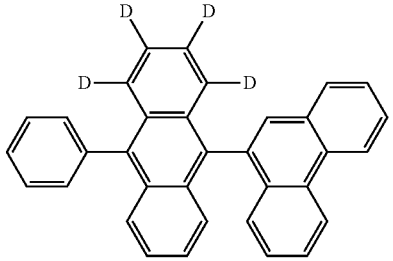

-continued
H17
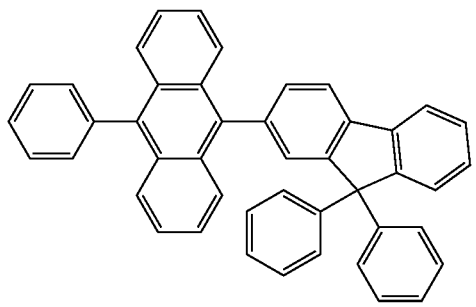
H18
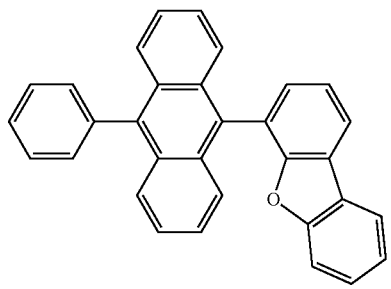
H19
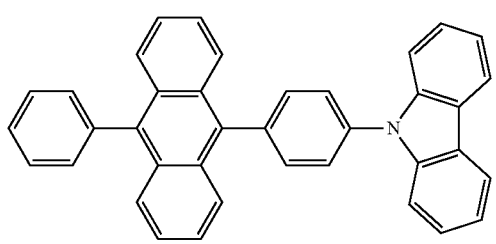
H20
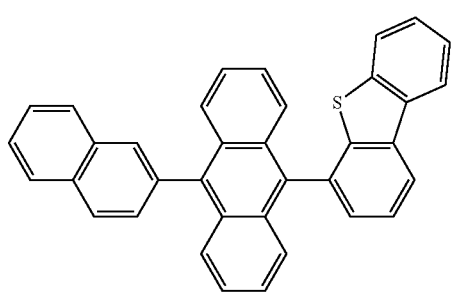
H21
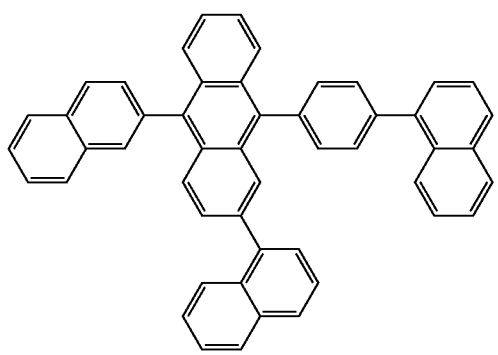
H22
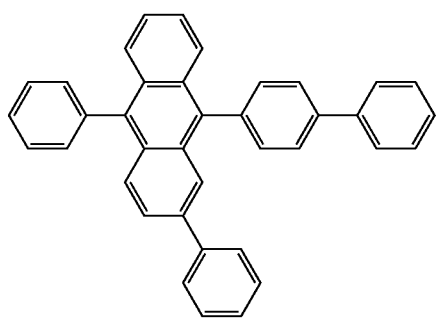
H23
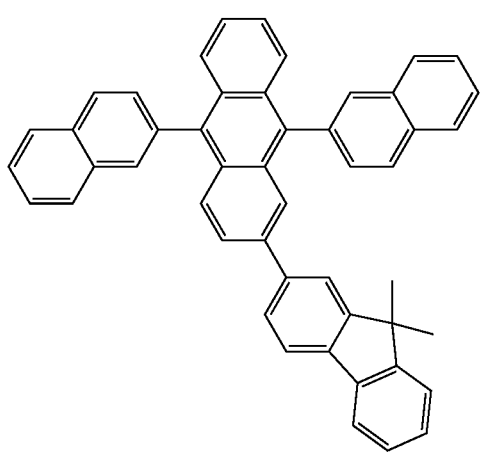
H24
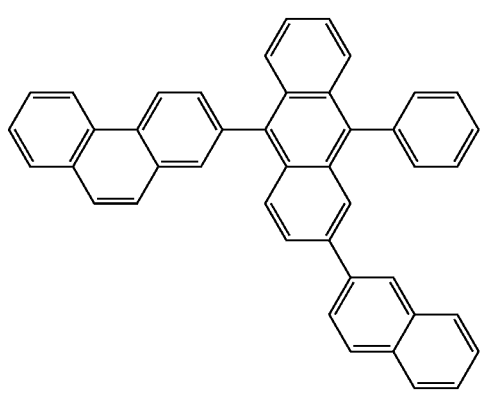

-continued
245
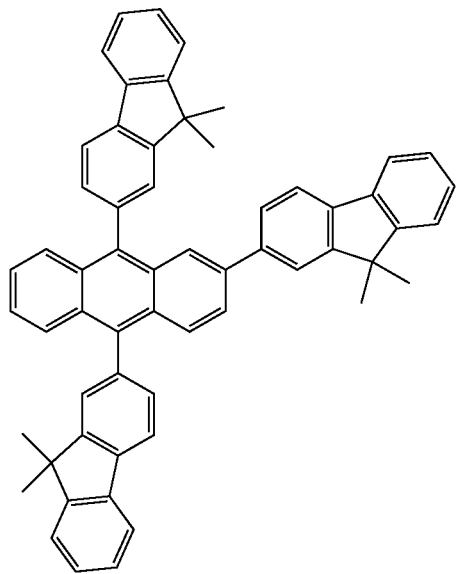
H25
246
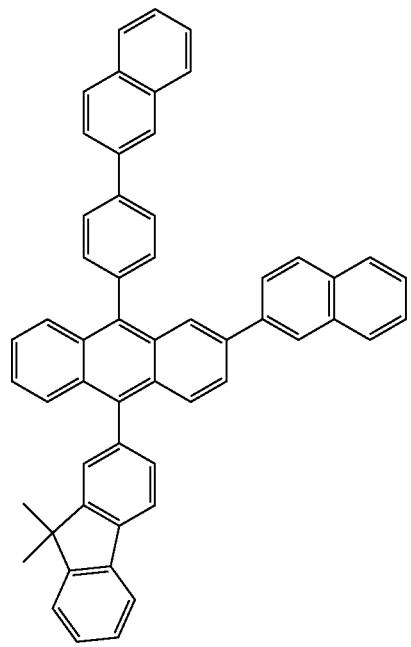
H26
H27
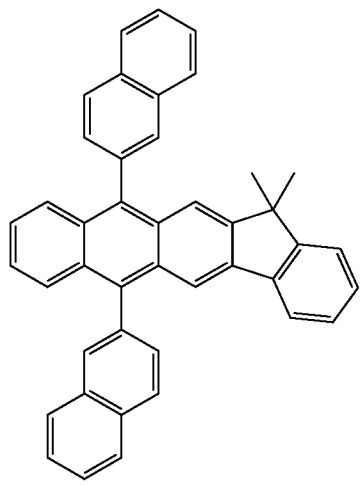
H28
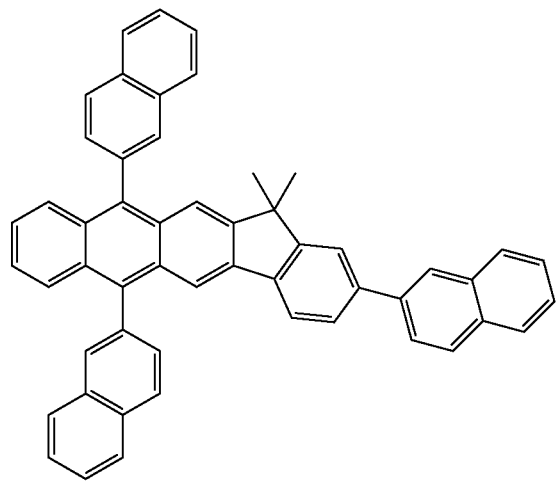
H29
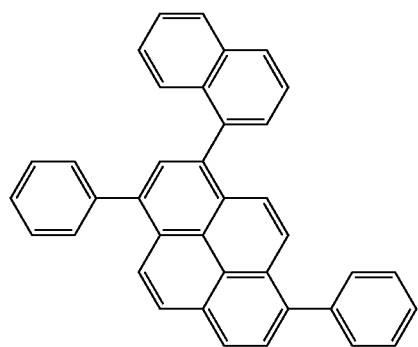
H30
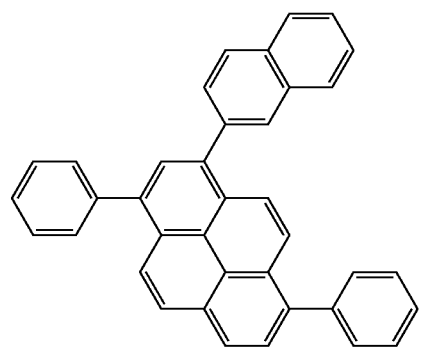

-continued
H31
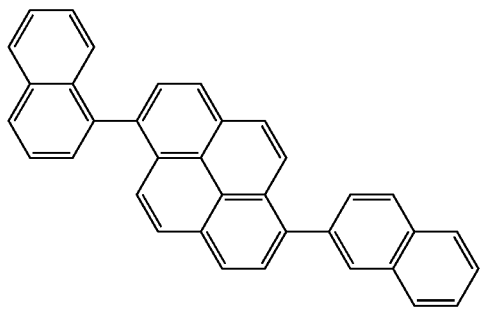
H32
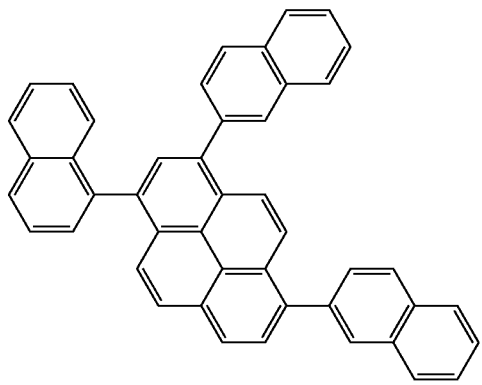
H33
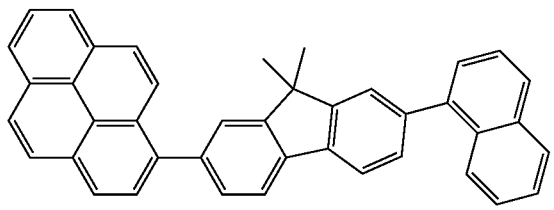
H34
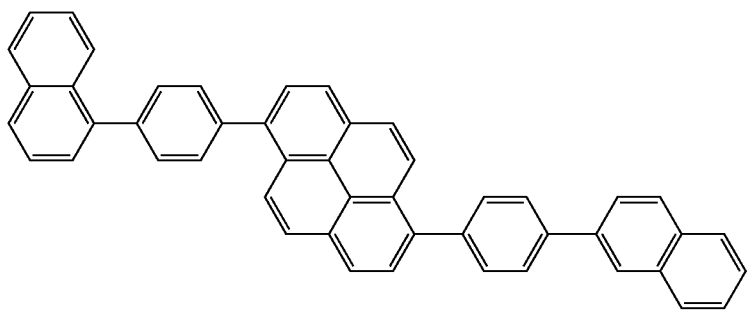
H35
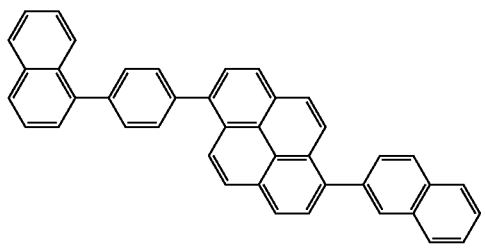
H36
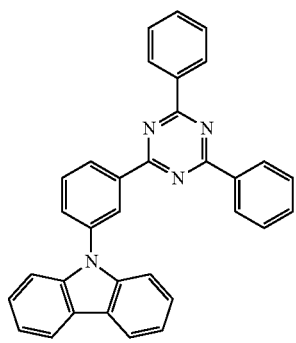
H37
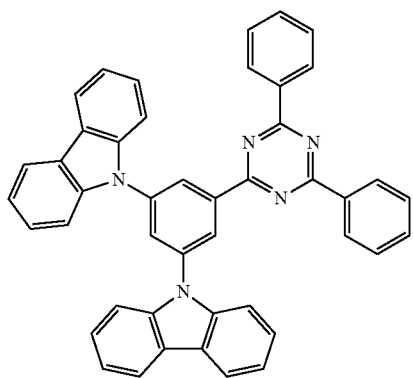
H38
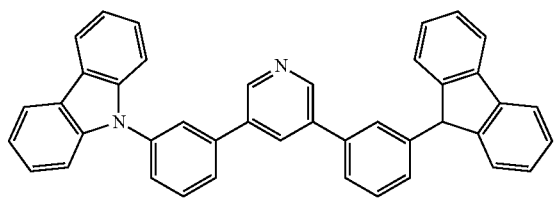

-continued
H39
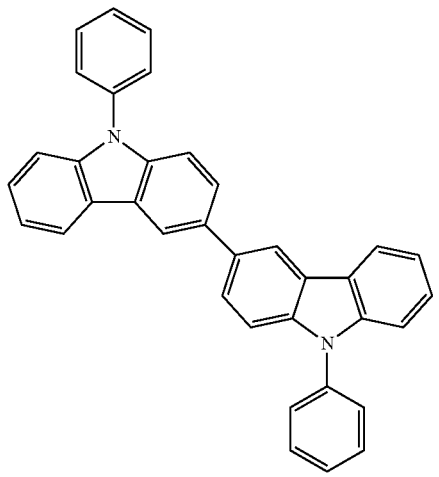
H40
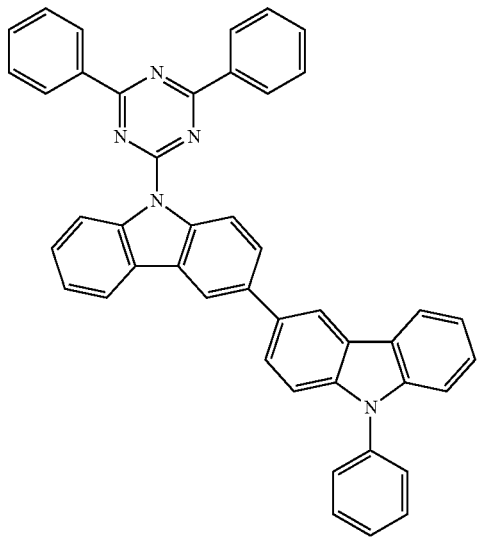
H41
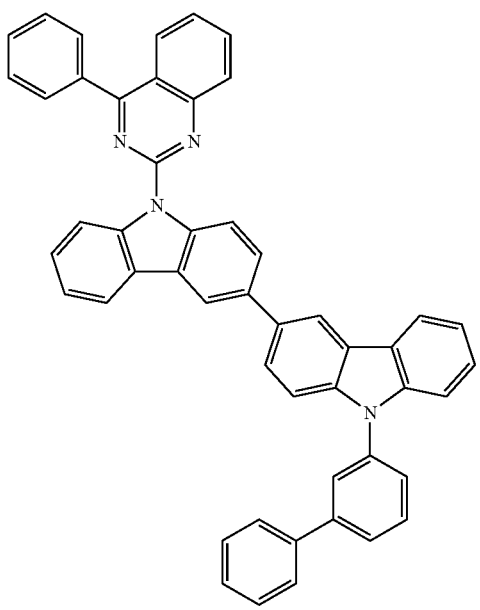
H42
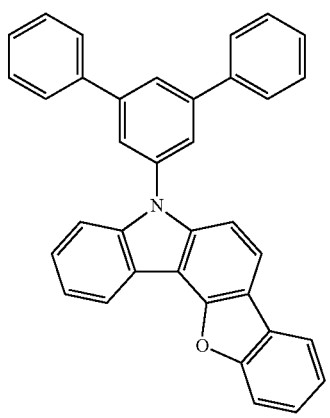
H43
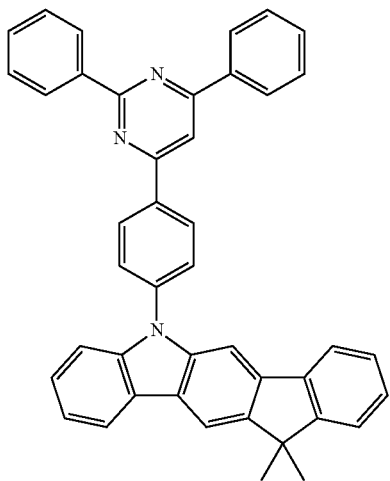
H44
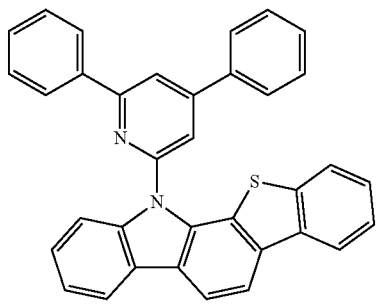

-continued
H45
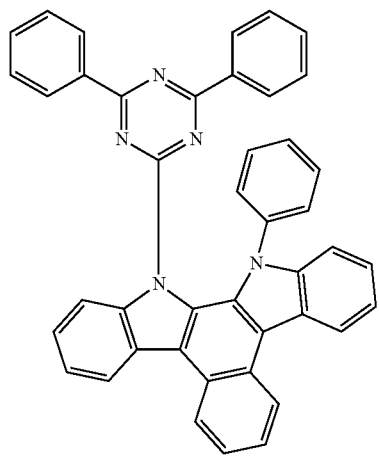
H46
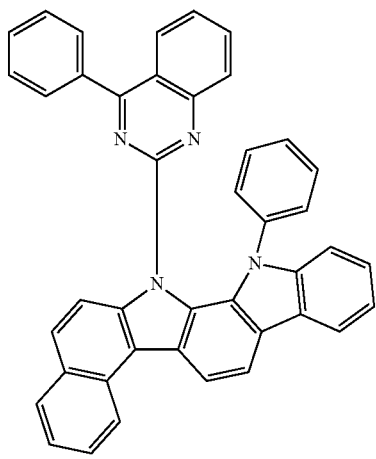
H47
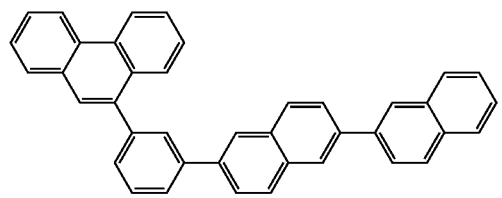
H48
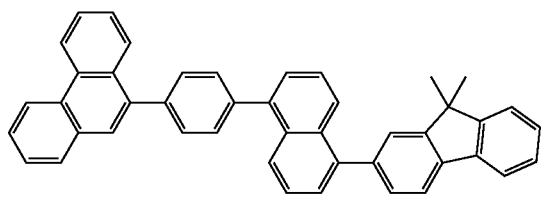
H49
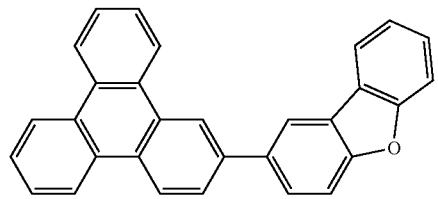
H50
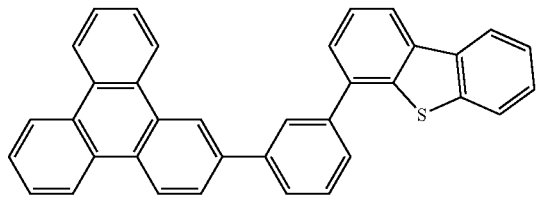
H51
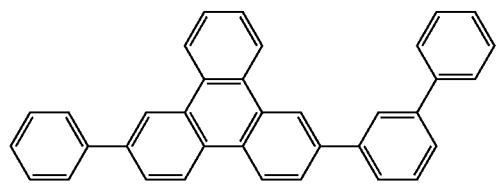
H52
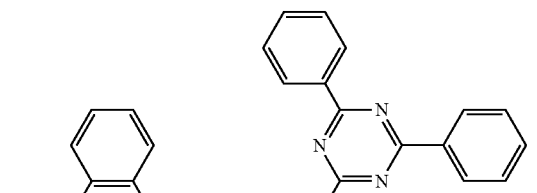
H53
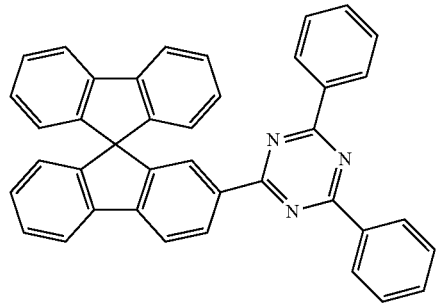
H54
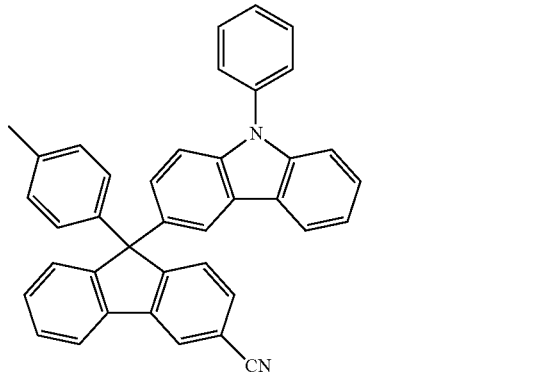

H55

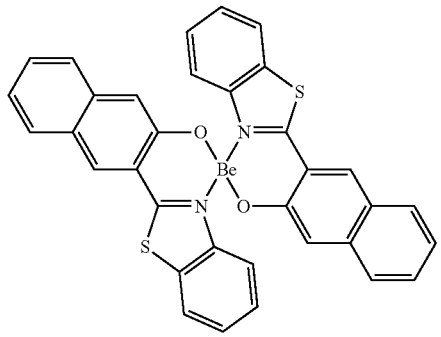

[Phosphorescent Dopant included in Emission Layer in Organic Layer 150]

The phosphorescent dopant may include an organometallic compound including iridium (Ir), platinum (Pt), palladium (Pd), osmium (Os), titanium (Ti), zirconium (Zr), hafnium (Hf), europium (Eu), terbium (Tb), rhodium (Rh), or thulium (Tm).

In an embodiment, the phosphorescent dopant may include an organometallic compound represented by Formula 401:

<Formula 401>  $M(L_{401})_{xc1}(L_{402})_{xc2}$

<Formula 402>

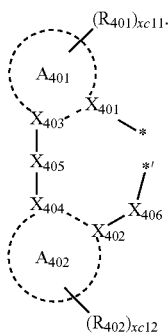

In Formulae 401 and 402,

M may be selected from Ir, Pt, Pd, Os, Ti, Zr, Hf, Eu, Tb, Rh, and Tm, $L_{401}$ may be a ligand represented by Formula 402, xc1 may be 1, 2, or 3, wherein when xc1 is 2 or more, 2 or more $L_{401}$(s) may be identical to or different from each other, $L_{402}$ may be an organic ligand, xc2 may be an integer selected from 0 to 4, wherein when xc2 is 2 or more, 2 or more $L_{402}$(s) may be identical to or different from each other, $X_{401}$ to $X_{404}$ may each independently be nitrogen or carbon, $X_{401}$ and $X_{403}$ may each independently be linked to each other via a single bond or a double bond, and $X_{402}$ and $X_{404}$ may each independently be linked to each other via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer selected from 1 to 10, and

* and *' in Formula 402 each indicate a binding site to M of Formula 401.

In an embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In various embodiments, in Formula 402, i) $X_{401}$ may be nitrogen, and $X_{402}$ may be carbon, or ii) $X_{401}$ and $X_{402}$ may both be nitrogen.

In various embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments are not limited thereto.

In various embodiments, when xc1 in Formula 401 is 2 or more, 2 $L_{401}$(s) in 2 or more $A_{401}$ (s) may be optionally linked to each other via $X_{407}$, which is a linking group, or 2 $A_{402}$(s) in 2 or more $A_{401}$ (s) may be optionally linked to each other via $X_{408}$, which is a linking group (see Compounds PD1 to PD4 and PD7). In various embodiments, $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments are not limited thereto.

In Formula 401, $L_{402}$ may be a monovalent, divalent, or trivalent organic ligand. For example, in Formula 401, $L_{402}$ may be selected from a halogen ligand, a diketone ligand (for example, acetylacetonate), a carboxylic acid ligand (for example, picolinate), —C(=O), an isontrile ligand, —CN, and phosphorus (for example, phosphine and phosphite), but embodiments are not limited thereto.

In various embodiments, the phosphorescent dopant may be, for example, selected from Compounds PD1 to PD26, but embodiments are not limited thereto:

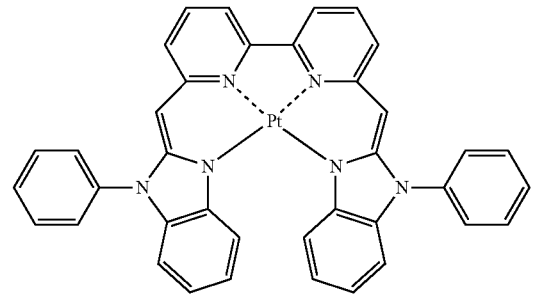

PD1

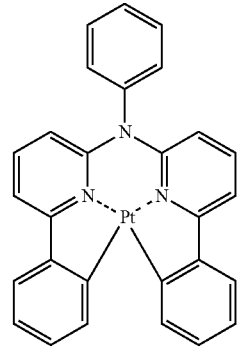

PD2

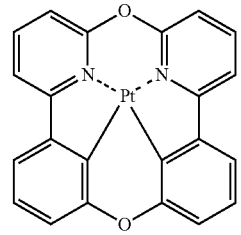

PD3

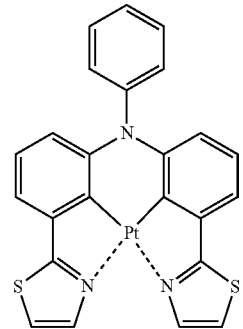

PD4

-continued
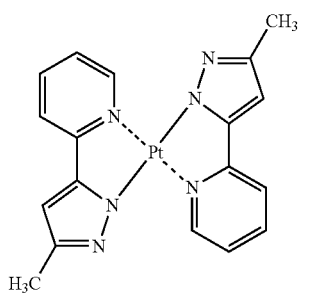
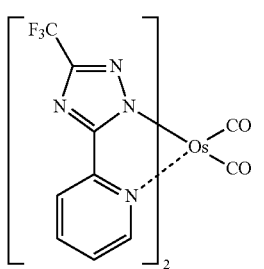
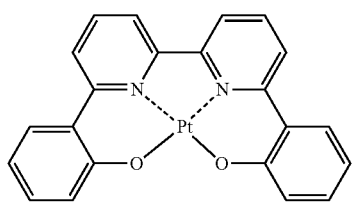
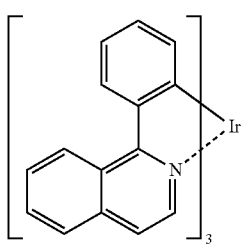
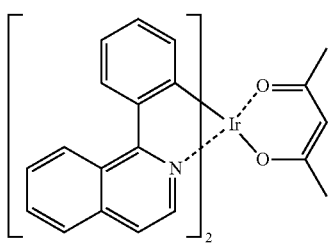
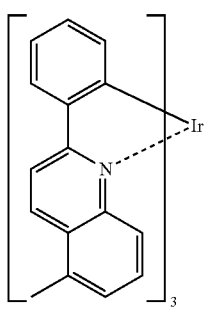
-continued
PD5 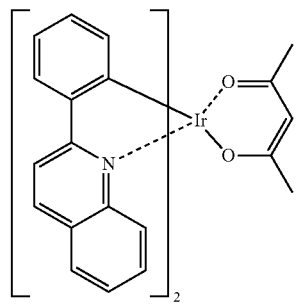
PD6
PD7 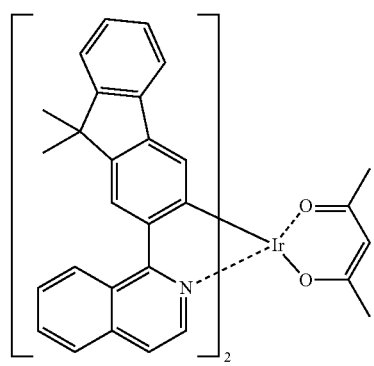
PD8
PD9
PD10
PD11
PD12
PD13 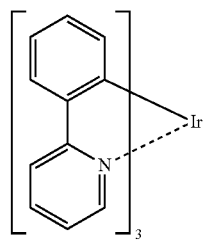
PD14 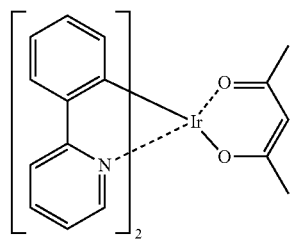
PD15 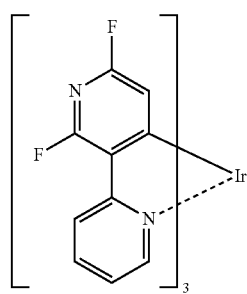

PD16
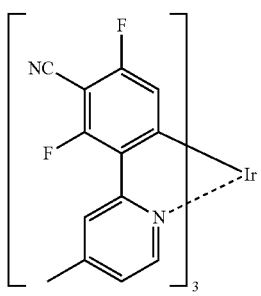
PD17
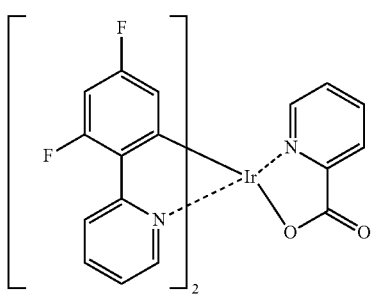
PD18
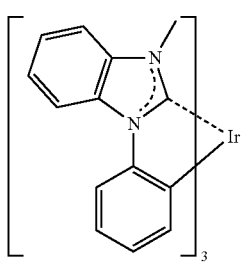
PD19
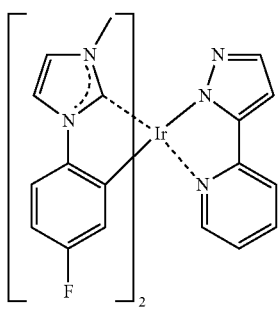
PD20
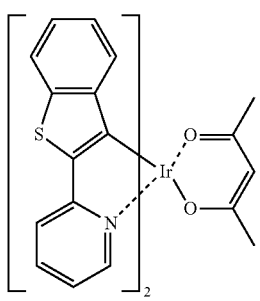
PD21
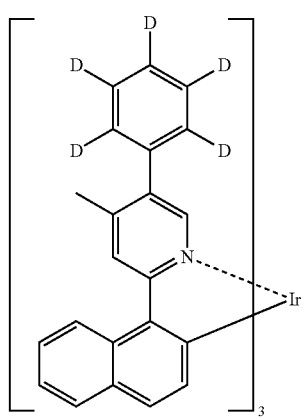
PD22
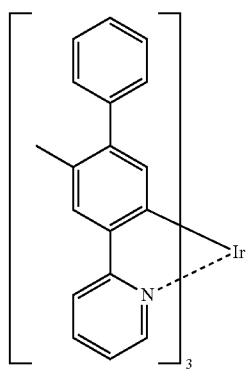
PD23
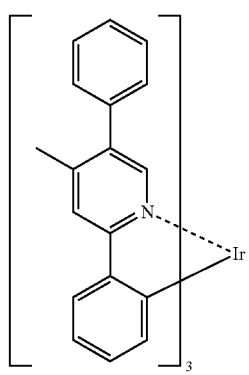
PD24
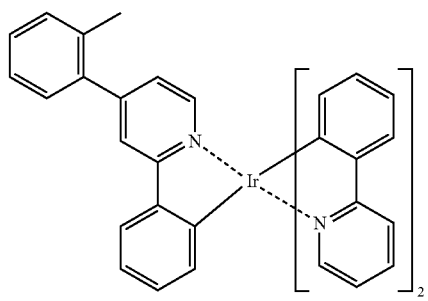

PD25

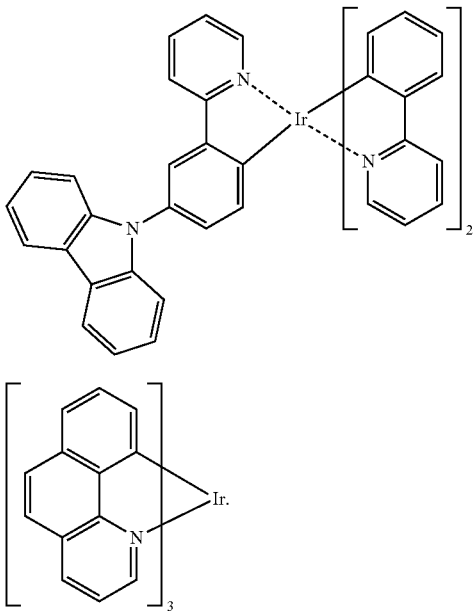

PD26

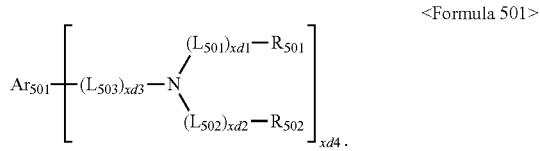

[Fluorescent Dopant in Emission Layer]

The fluorescent dopant may include an arylamine compound or a styrylamine compound.

In an embodiment, the fluorescent dopant may include a compound represented by Formula 501:

<Formula 501>

$$Ar_{501}{-}{\left[{(L_{503})_{xd3}}{-}N{\diagdown \atop \diagup}{(L_{501})_{xd1}{-}R_{501} \atop (L_{502})_{xd2}{-}R_{502}}\right]}_{xd4}.$$

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer selected from 0 to 3, $R_{501}$ and $R_{502}$ may each independently be selected from a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer selected from 1 to 6.

In an embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In various embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In various embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xd4 in Formula 501 may be 2, but embodiments are not limited thereto.

For example, the fluorescent dopant may be selected from Compounds FD1 to FD22:

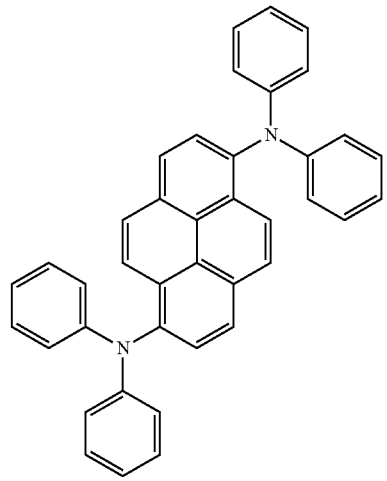

FD1

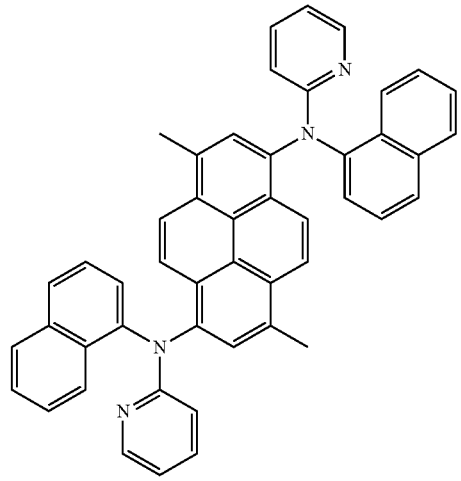

FD2

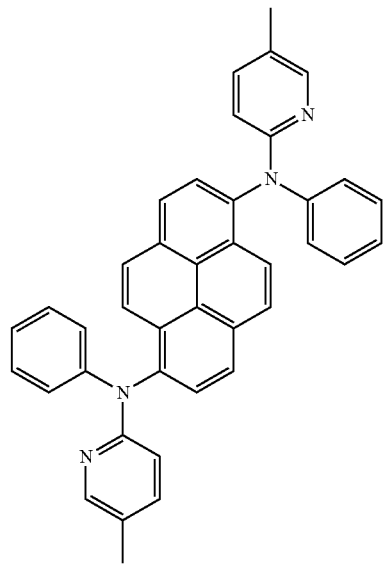

FD3

-continued
FD4
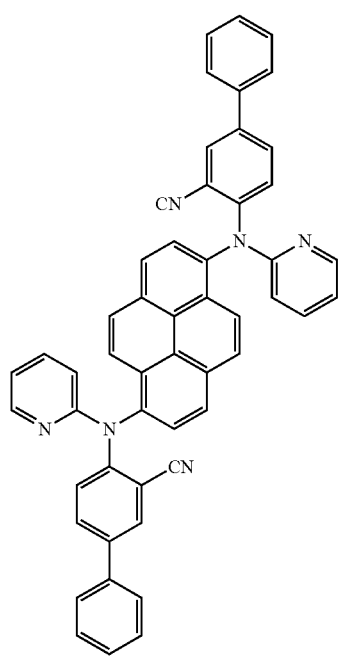
FD5
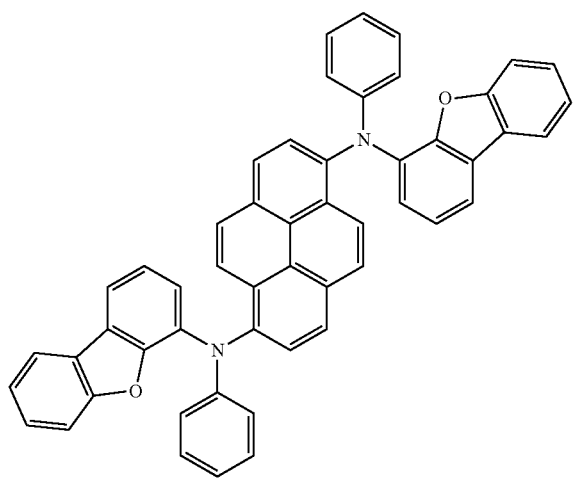
FD6
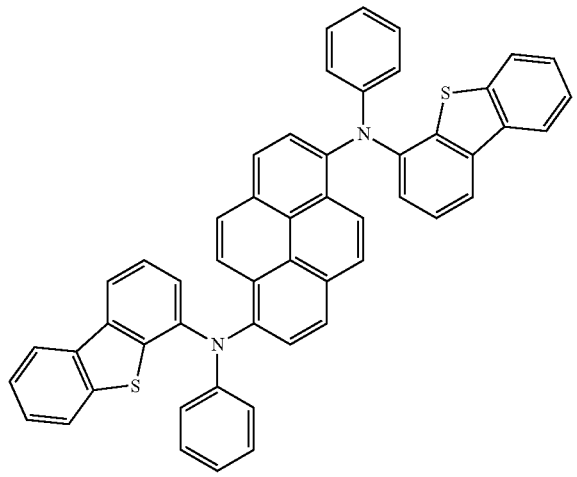
-continued
FD7
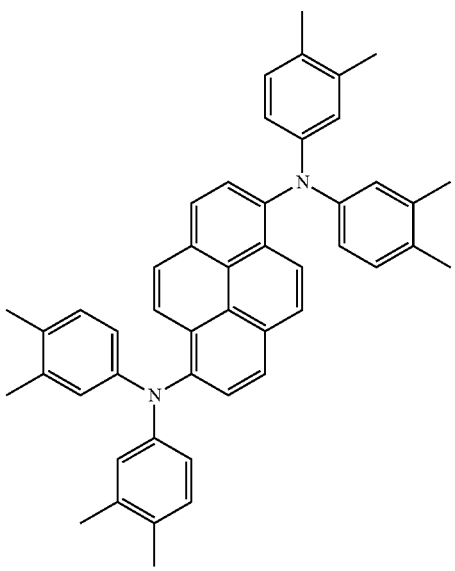
FD8
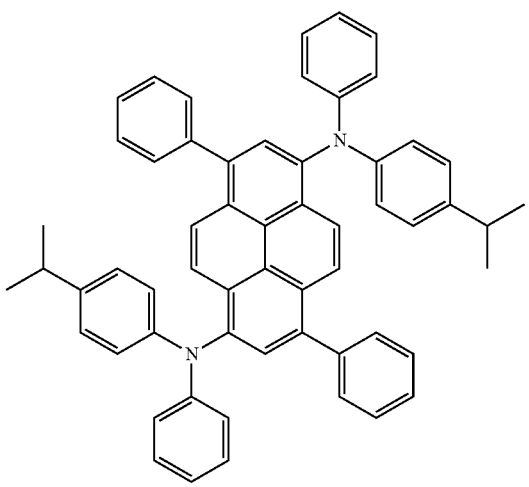
FD9
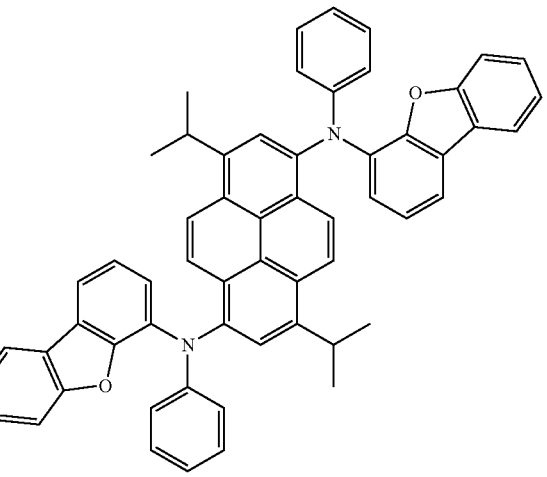

FD10 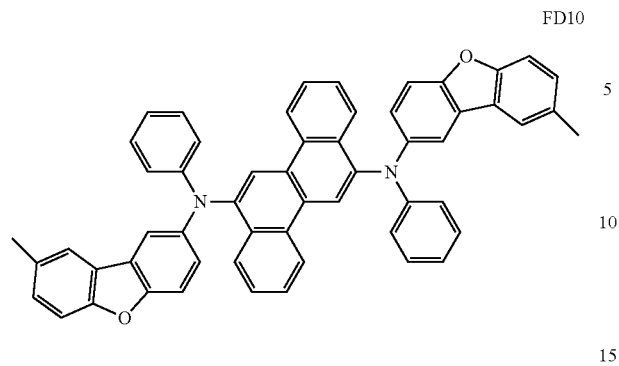
FD15 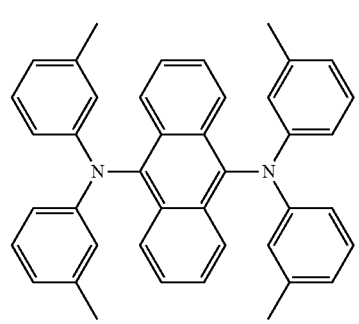
FD11 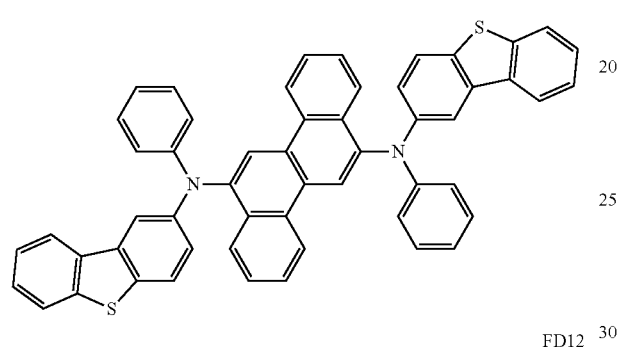
FD16 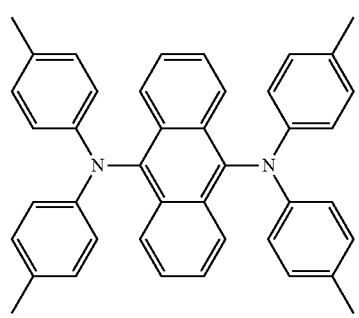
FD12 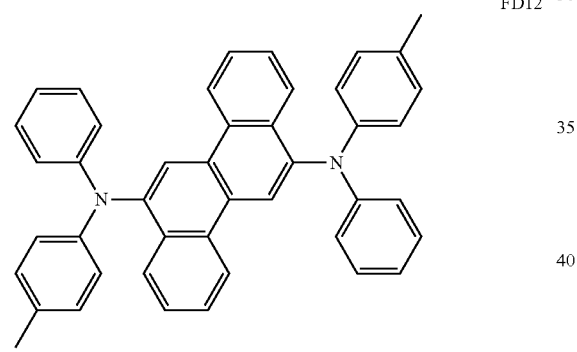
FD17 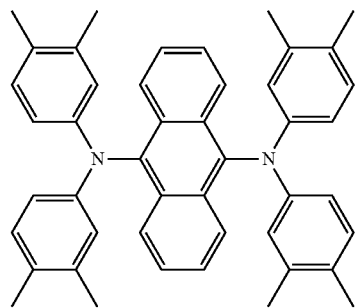
FD13 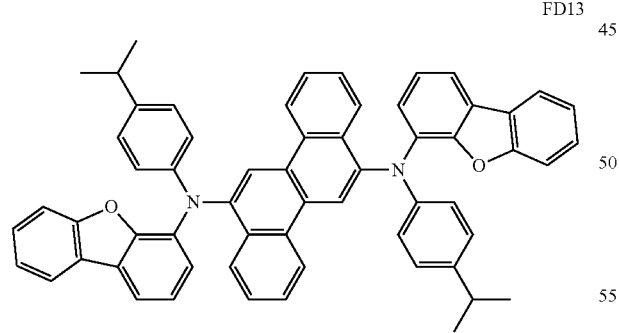
FD14 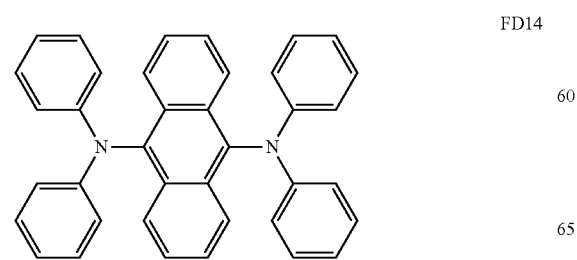
FD18 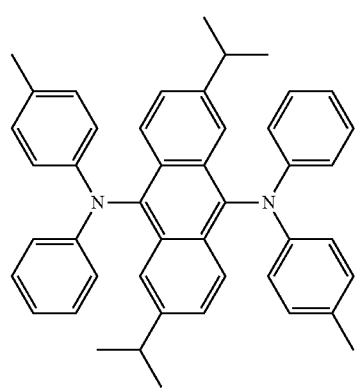

FD19
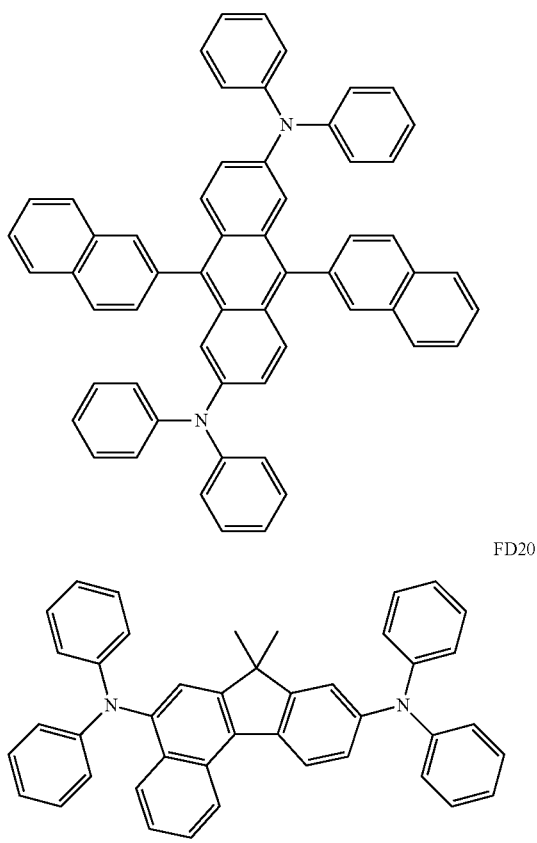
FD20
FD21
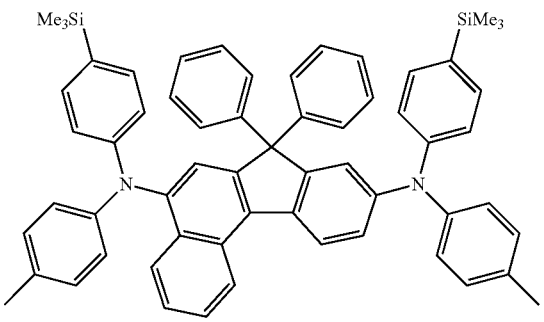
FD22
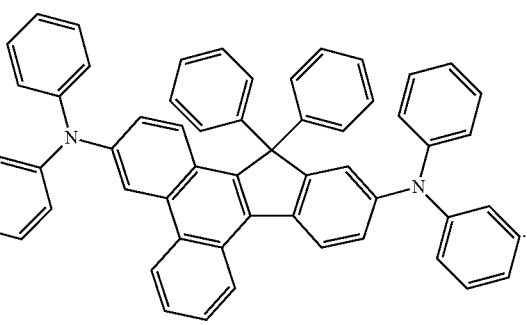
In various embodiments, the fluorescent dopant may be selected from compounds below, but embodiments are not limited thereto:
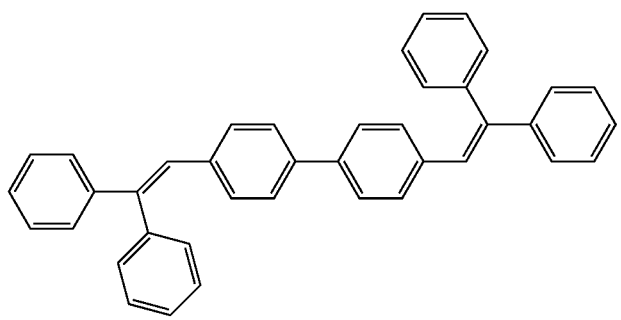
DPVBi
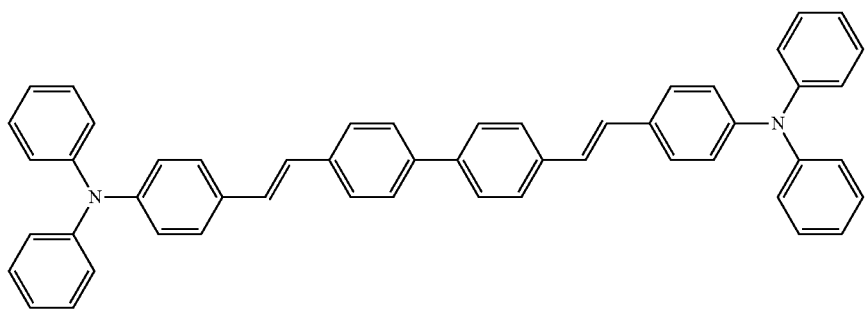
DPAVBi

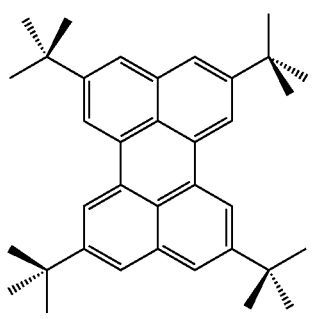
TBPe

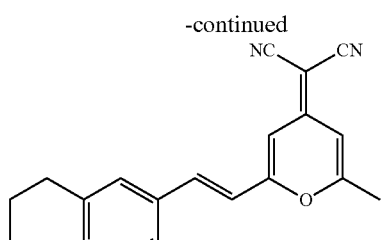
DCM

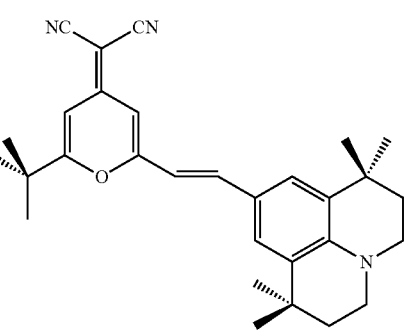
DCJTB

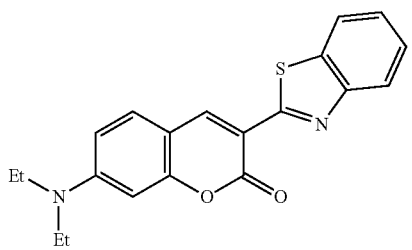
Coumarin 6

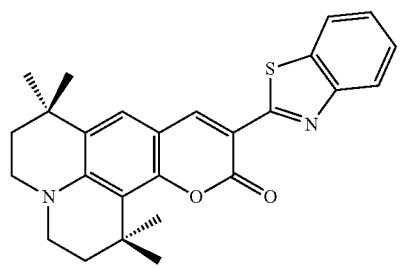
C545T

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one layer selected from a buffer layer, a hole blocking layer, an electron control layer, an electron transport layer, and an electron injection layer, but embodiments are not limited thereto.

For example, the electron transport region may have a structure of electron transport layer/electron injection layer, a structure of hole blocking layer/electron transport layer/electron injection layer, a structure of electron control layer/electron transport layer/electron injection layer, or a structure of buffer layer/electron transport layer/electron injection layer, wherein for each structure, constituting layers are sequentially stacked from the emission layer, but embodiments are not limited thereto.

In an embodiment, the electron transport region may include an electron transport layer and an electron injection layer, and the electron transport layer may be disposed between the emission layer and the electron injection layer and include the first compound described above.

In various embodiments, the electron transport region may include at least one compound selected from 2,9-dimethyl-4,7-diphenyl-1,10-phenanthroline (BCP), 4,7-diphenyl-1,10-phenanthroline (Bphen), Alq$_3$, BAlq, (3-(biphenyl-4-yl)-5-(4-tert-butylphenyl)-4-phenyl-4H-1,2,4-triazole (TAZ), and NTAZ:

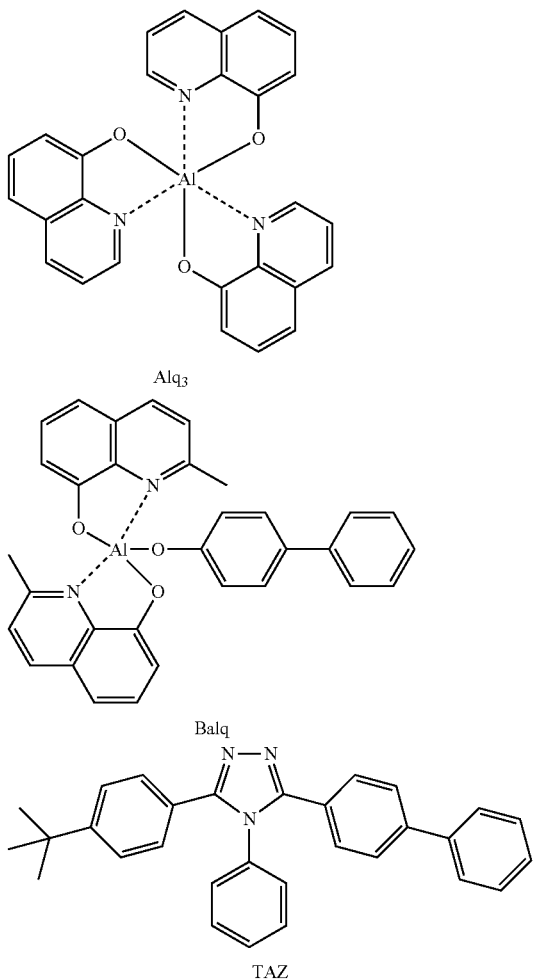

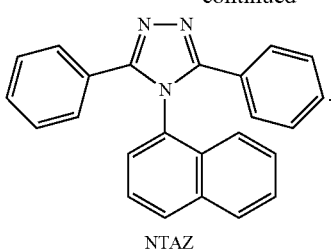

NTAZ

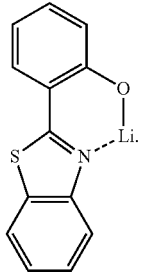

ET-D2

A thickness of the buffer layer, the hole blocking layer, or the electron control layer may each independently be in a range of about 20 Å to about 1,000 Å, for example, about 30 Å to about 300 Å. When the thicknesses of the buffer layer, the hole blocking layer, or the electron control layer are within these ranges, excellent hole blocking characteristics or electron controlling characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within these ranges, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from a Li ion, a Na ion, a K ion, a Rb ion, and a Cs ion, and the alkaline earth metal complex may include a metal ion selected from a Be ion, a Mg ion, a Ca ion, a Sr ion, and a Ba ion. A ligand coordinated with the metal ion of the alkali metal complex or the alkaline earth metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments are not limited thereto.

For example, the metal-containing material may include a Li complex. The Li complex may include, for example, Compound ET-D1 (lithium quinolate, LiQ) or Compound ET-D2:

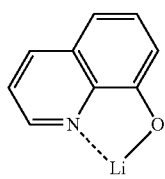

ET-D1

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare-earth-metal, an alkali metal compound, an alkaline earth metal compound, a rare-earth-metal compound, an alkali metal complex, an alkaline earth metal complex, a rare-earth-metal complex, or a combination thereof.

The alkali metal may be selected from Li, Na, K, Rb, and Cs. In an embodiment, the alkali metal may be Li, Na, or Cs. In various embodiments, the alkali metal may be Rb or Cs, but embodiments are not limited thereto.

The alkaline earth metal may be selected from Mg, Ca, Sr, and Ba.

The rare-earth-metal may be selected from Sc, Y, Ce, Tb, Yb, and Gd.

The alkali metal compound, the alkaline earth metal compound, and the rare-earth-metal compound may be selected from oxides and halides (for example, fluorides, chlorides, bromides, and iodines) of the alkali metal, the alkaline earth metal, and the rare-earth-metal.

The alkali metal compound may be selected from alkaline metal oxides, such as $Li_2O$, $Cs_2O$, and $K_2O$, and alkaline metal halides, such as LiF, NaF, CsF, KF, LiI, NaI, CsI, KI, and RbI. In an embodiment, the alkali metal compound may be selected from LiF, $Li_2O$, NaF, LiI, NaI, CsI, and KI, but embodiments are not limited thereto.

The alkaline earth metal compound may be selected from alkaline earth metal compounds, such as BaO, SrO, CaO, $Ba_xSr_{1-x}O$ (where 0<x<1), and $Ba_xCa_{1-x}O$ (where 0<x<1). In an embodiment, the alkaline earth metal compound may be selected from BaO, SrO, and CaO, but embodiments are not limited thereto.

The rare-earth-metal compound may be selected from $YbF_3$, $ScF_3$, $ScO_3$, $Y_2O_3$, $Ce_2O_3$, $GdF_3$, and $TbF_3$. In an embodiment, the rare-earth-metal compound may be selected from $YbF_3$, $ScF_3$, $TbF_3$, $YbI_3$, $ScI_3$, and $TbI_3$, but embodiments are not limited thereto.

The alkali metal complex, the alkaline earth metal complex, and the rare-earth-metal complex may include an ion of the alkali metal, the alkaline earth metal, and the rare-earth-metal, and a ligand coordinated with the metal ion of the alkali metal complex, the alkaline earth metal complex, and the rare-earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments are not limited thereto.

The electron injection layer may include the alkali metal, the alkaline earth metal, the rare-earth-metal, the alkali metal compound, the alkaline earth metal compound, the rare-earth-metal compound, the alkali metal complex, the alkaline earth metal complex, the rare-earth-metal complex, or a combination thereof. In various embodiments, the electron injection layer may further include an organic material. When the electron injection layer further includes an organic material, the alkali metal, the alkaline earth metal, the rare-earth-metal, the alkali metal compound, the alkaline earth metal compound, the rare-earth-metal compound, the alkali metal complex, the alkaline earth metal complex, the rare-earth-metal complex, or the combination thereof may be homogeneously or non-homogeneously dispersed in a matrix including the organic material.

A thickness of the electron injection layer may be in a range of about 1 Å to about 100 Å, for example, about 3 Å to about 90 Å. When thickness of the electron injection layer is within these ranges, satisfactory electron injecting characteristics may be obtained without a substantial increase in driving voltage.

[Second Electrode 190]

The second electrode 190 may be disposed on the organic layer 150 having such a structure described above. The second electrode 190 may be a cathode which is an electron injection electrode, and in this regard, a material for forming the second electrode 190 may be selected from a metal, an alloy, an electrically conductive compound, and a combination thereof, which may have a relatively low work function.

The second electrode 190 may include at least one selected from Ag, Li, Mg, Al, Al—Li, Ca, Mg—In, Mg—Ag, ITO, and IZO, but embodiments are not limited thereto. The second electrode 190 may be a reflective electrode, a semi-transmissive electrode, or a transmissive electrode.

The second electrode 190 may have a single-layered structure or a multi-layered structure having a plurality of layers.

Figure 3:
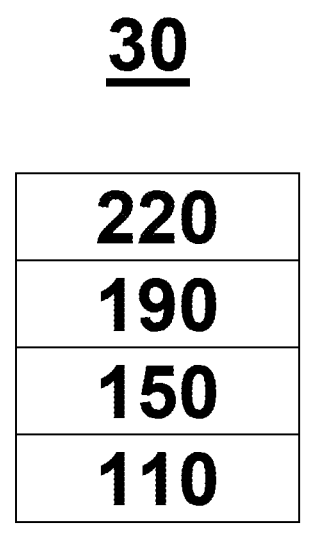
Figure 4:
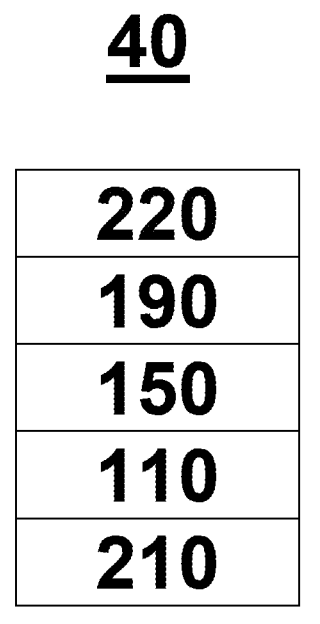

[Descriptions of FIGS. 2 to 4]

Figure 2:
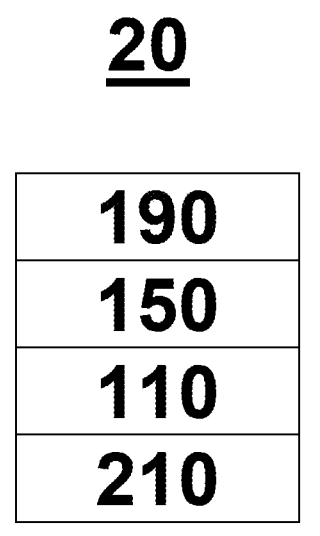

An organic light-emitting device 20 of FIG. 2 includes a first capping layer 210, a first electrode 110, an organic layer 150, and a second electrode 190, which are sequentially stacked in this stated order, an organic light-emitting device 30 of FIG. 3 includes a first electrode 110, an organic layer 150, a second electrode 190, and a second capping layer 220, which are sequentially stacked in this stated order, and an organic light-emitting device 40 of FIG. 4 includes a first capping layer 210, a first electrode 110, an organic layer 150, a second electrode 190, and a second capping layer 220, which are sequentially stacked in this stated order.

In FIGS. 2 to 4, the first electrode 110, the organic layer 150, and the second electrode 190 may each independently be the same as respectively described herein in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external brightness efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may include a carboxylic compound, a heterocyclic compound, an amine-based compound, a porphine derivative, a phthalocyanine derivative, a naphthalocyanine derivative, an alkali metal complex, and an alkaline earth metal complex. The carboxylic compound, the heterocyclic compound, and the amine-based compound may be optionally substituted with a substituent containing at least one element selected from O, N, S, Se, Si, F, Cl, Br, and I.

In an embodiment, at least one selected from the first capping layer 210 and the second capping layer 220 may include an amine-based compound.

In various embodiments, at least one selected from the first capping layer 210 and the second capping layer 220 may include a compound selected from Compounds CP1 to CP5, but embodiments are not limited thereto:

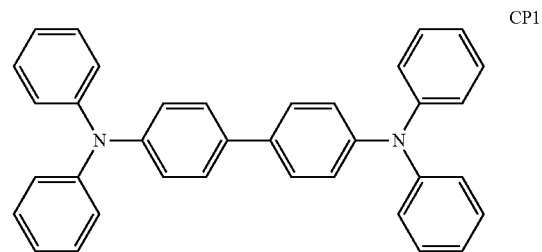

CP1

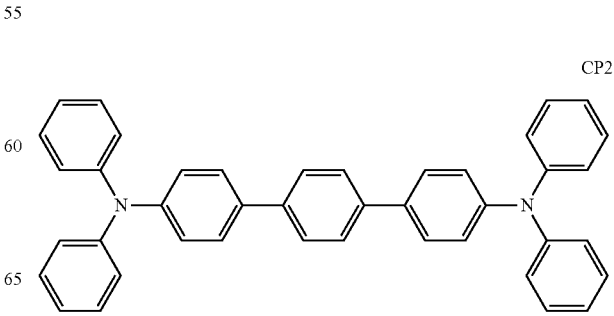

CP2

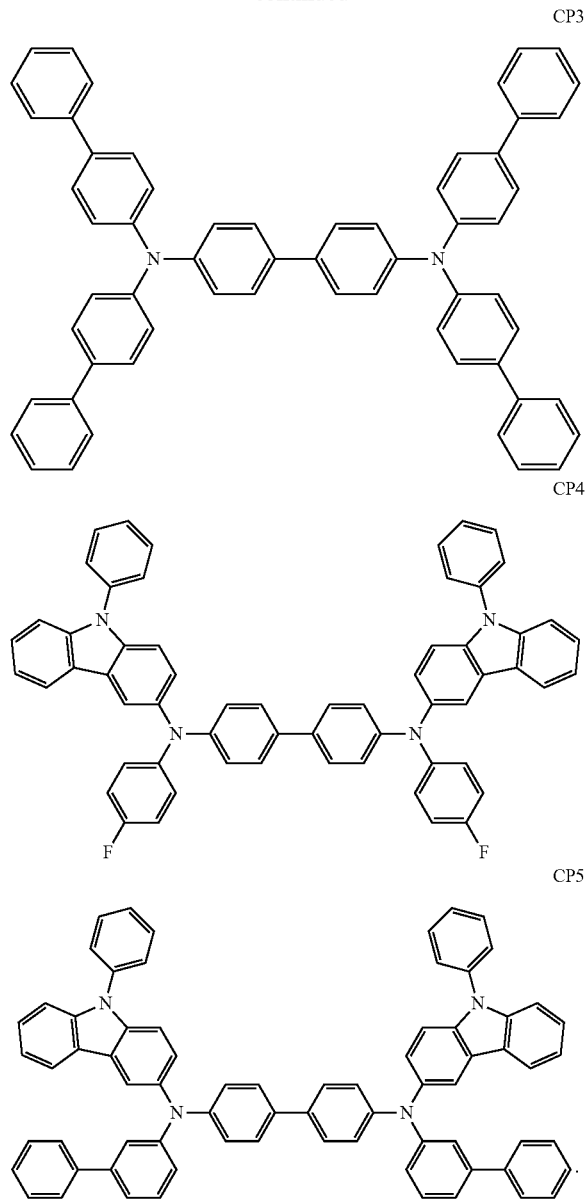

Hereinabove, the organic light-emitting device has been described with reference to FIGS. 1 to 4, but embodiments are not limited thereto.

Layers constituting the hole transport region, the emission layer, and layers constituting the electron transport region may each independently be formed in a certain region by utilizing one or more suitable methods such as vacuum deposition, spin coating, casting, a Langmuir-Blodgett (LB) method, ink-jet printing, laser-printing, and/or laser induced thermal imaging (LITI).

When layers constituting the hole transport region, the emission layer, and layers constituting the electron transport region are each independently formed by vacuum deposition, deposition conditions for the vacuum deposition may be, for example, performed at a deposition temperature of about 100° C. to about 500° C., at a vacuum degree of about $10^{-8}$ to about $10^{-3}$ torr, and at a deposition rate of about 0.01 to about 100 Å/sec, by taking into account a compound to be included in a layer to be formed and a structure of the layer to be formed.

When layers constituting the hole transport region, the emission layer, and layers constituting the electron transport region are each independently formed by spin coating, coating conditions for the spin coating may be, for example, performed at a coating rate of about 2,000 rpm to about 5,000 rpm and at a temperature of about 80° C. to 200° C., taking into account a compound to be included in a layer to be formed and a structure of the layer to be formed.

[General Definition of Substituents]

A "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a ter-butyl group, a pentyl group, an iso-amyl group, and a hexyl group. A "$C_1$-$C_{60}$ alkylene group," as used herein, refers to a divalent group having substantially the same structure as the $C_1$-$C_{60}$ alkyl group.

A "$C_2$-$C_{60}$ alkenyl group," as used herein, refers to a hydrocarbon group having at least one carbon-carbon double bond at one or more positions along the hydrocarbon chain (e.g., in the middle or at either terminal end of the $C_2$-$C_{60}$ alkyl group), and examples thereof include an ethenyl group, a propenyl group, and a butenyl group. A "$C_2$-$C_{60}$ alkenylene group," as used herein, refers to a divalent group having substantially the same structure as the $C_2$-$C_{60}$ alkenyl group.

A "$C_2$-$C_{60}$ alkynyl group," as used herein, refers to a hydrocarbon group having at least one carbon-carbon triple bond at one or more positions along the hydrocarbon chain (e.g., in the middle or at either terminal end of the $C_2$-$C_{60}$ alkyl group), and examples thereof include an ethynyl group and a propynyl group. A "$C_2$-$C_{60}$ alkynylene group," as used herein, refers to a divalent group having substantially the same structure as the $C_2$-$C_{60}$ alkynyl group.

A "$C_1$-$C_{60}$ alkoxy group," as used herein, refers to a monovalent group represented by -$OA_{101}$ (where $A_{101}$ is the $C_1$-$C_{60}$ alkyl group), and examples thereof include a methoxy group, an ethoxy group, and an isopropyloxy group.

A "$C_3$-$C_{10}$ cycloalkyl group," as used herein, refers to a monovalent saturated hydrocarbon monocyclic saturated group having 3 to 10 carbon atoms, and examples thereof include a cyclopropyl group, a cyclobutyl group, a cyclopentyl group, a cyclohexyl group, and a cycloheptyl group. A "$C_3$-$C_{10}$ cycloalkylene group," as used herein, refers to a divalent group having substantially the same structure as the $C_3$-$C_{10}$ cycloalkyl group.

A "$C_1$-$C_{10}$ heterocycloalkyl group," as used herein, refers to a monovalent saturated monocyclic group having at least one heteroatom selected from N, O, Si, P, and S as ring-forming atom in addition to 1 to 10 carbon atoms, and examples thereof include a 1,2,3,4-oxatriazolidinyl group, a tetrahydrofuranyl group, and a tetrahydrothiophenyl group. A "$C_1$-$C_{10}$ heterocycloalkylene group," as used herein, refers to a divalent group having substantially the same structure as the $C_1$-$C_{10}$ heterocycloalkyl group.

A "$C_3$-$C_{10}$ cycloalkenyl group," as used herein, refers to a monovalent saturated monocyclic group that has 3 to 10 carbon atoms and at least one carbon-carbon double bond in the ring thereof and does not have aromaticity, and examples thereof include a cyclopentenyl group, a cyclohexenyl group, and a cycloheptenyl group. A "$C_3$-$C_{10}$ cycloalkenylene group," as used herein, refers to a divalent group having substantially the same structure as the $C_3$-$C_{10}$ cycloalkenyl group.

A "$C_1$-$C_{10}$ heterocycloalkenyl group," as used herein, refers to a monovalent monocyclic group that has at least one heteroatom selected from N, O, Si, P, and S as a ring-forming atom in addition to 1 to 10 carbon atoms, and at least one carbon-carbon double bond in the ring. Examples of the $C_1$-$C_{10}$ heterocycloalkenyl group include a 4,5-dihydrothiophenyl group, a 2,3-hydrofuranyl group, and a 2,3-hydrothiophenyl group. A "$C_1$-$C_{10}$ heterocycloalkenylene group," as used herein, refers to a divalent group having substantially the same structure as the $C_1$-$C_{10}$ heterocycloalkenyl group.

A "$C_6$-$C_{60}$ aryl group," as used herein, refers to a monovalent group having a cyclic aromatic system having 6 to 60 carbon atoms, and a "$C_6$-$C_{60}$ arylene group," as used herein, refers to a divalent group having an aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other or may be linked with each other via a single bond.

A "$C_1$-$C_{60}$ heteroaryl group," as used herein, refers to a monovalent group having a heterocyclic aromatic system that has at least one heteroatom selected from N, O, Si, P, and S as a ring-forming atom in addition to 1 to 60 carbon atoms. A "$C_1$-$C_{60}$ heteroarylene group," as used herein, refers to a divalent group having a heterocyclic aromatic system that has at least one heteroatom selected from N, O, Si, P, and S as a ring-forming atom in addition to 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other or may be linked with each other via a single bond.

A "$C_6$-$C_{60}$ aryloxy group," as used herein, refers to a group represented by -O$A_{102}$ (where $A_{102}$ is the $C_6$-$C_{60}$ aryl group), and a "$C_6$-$C_{60}$ arylthio group," as used herein, refers to a group represented by -S$A_{103}$ (where $A_{103}$ is the $C_6$-$C_{60}$ aryl group).

A "monovalent non-aromatic condensed polycyclic group," as used herein, refers to a monovalent group that has two or more rings condensed to each other, has only carbon atoms as ring-forming atoms (for example, 8 to 60 carbon atoms), and has non-aromaticity in the entire molecular structure. An example of the monovalent non-aromatic condensed polycyclic group includes a fluorenyl group. A "divalent non-aromatic condensed polycyclic group," as used herein, refers to a divalent group having substantially the same structure as the monovalent non-aromatic condensed polycyclic group.

A "monovalent non-aromatic condensed heteropolycyclic group," as used herein, refers to a monovalent group that has two or more rings condensed to each other, has at least one heteroatom selected from N, O, Si, P, and S as a ring-forming atom in addition to carbon atoms (for example, 1 to 60 carbon atoms), and has non-aromaticity in the entire molecular structure. An example of the monovalent non-aromatic condensed heteropolycyclic group includes a carbazolyl group. A "divalent non-aromatic condensed heteropolycyclic group," as used herein, refers to a divalent group having substantially the same structure as the monovalent non-aromatic condensed heteropolycyclic group.

A "$C_5$-$C_{60}$ carbocyclic group," as used herein, refers to a monocyclic or polycyclic group having 5 to 60 carbon atoms in which the ring-forming atoms include only carbon atoms. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In various embodiments, depending on the number of substituents connected to the $C_5$-$C_{60}$ carbocyclic group, the $C_5$-$C_{60}$ carbocyclic group may be a trivalent group or a quadrivalent group.

A "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon atom (the number of carbon in the $C_1$-$C_{60}$ heterocyclic group may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), (=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group". The "biphenyl group" belongs to "a substituted phenyl group" having a "$C_6$-$C_{60}$ aryl group" as a substituent.

The term "terphenyl group," as used herein, refers to "a phenyl group substituted with a biphenyl group". The "terphenyl group" belongs to "a substituted phenyl group" having "a "$C_6$-$C_{60}$ aryl group substituted with a $C_6$-$C_{60}$ aryl group".

* and *', as used herein, unless defined otherwise, each indicate a binding site to a neighboring atom in a corresponding formula.

Hereinafter, a compound according to one or more embodiments and an organic light-emitting device according to one or more embodiments will be described in more detail with reference to Synthesis Examples and Examples.

EXAMPLES

Example 1-1

Blue Fluorescence

An anode was prepared by cutting a glass substrate, on which ITO having a thickness of 15 Ω/cm² (120 nm) was formed, to a size of 50 mm×50 mm×0.5 mm, ultrasonically cleaning the glass substrate by utilizing acetone, isopropyl alcohol, and pure water for 15 minutes each, and then irradiating UV light for 30 minutes thereto and exposing the glass substrate to ozone to clean the glass substrate. Then, the glass substrate was loaded into a vacuum deposition apparatus.

m-MTDATA was vacuum-deposited on the ITO anode of the glass substrate to form a hole injection layer having a thickness of 20 nm, and then, Compound HT3 was vacuum-deposited on the hole injection layer to form a hole transport layer having a thickness of 70 nm.

Compound 2-1 was vacuum-deposited on the hole transport layer to form an emission auxiliary layer having a thickness of 10 nm.

Compound ADN (as a host) and Compound FD1 (as a dopant having an amount of 5 wt %) were co-deposited on the emission auxiliary layer to form an emission layer having a thickness of 30 nm.

Compound 1-1 was vacuum-deposited on the emission layer to form an electron transport layer having a thickness of 30 nm, and then, LiF was deposited on the electron transport layer to form an electron injection layer having a thickness of 1 nm. Then, Al was vacuum-deposited on the electron injection layer to form a second electrode (i.e., a cathode) having a thickness of 200 nm, thereby completing the manufacture of an organic light-emitting device.

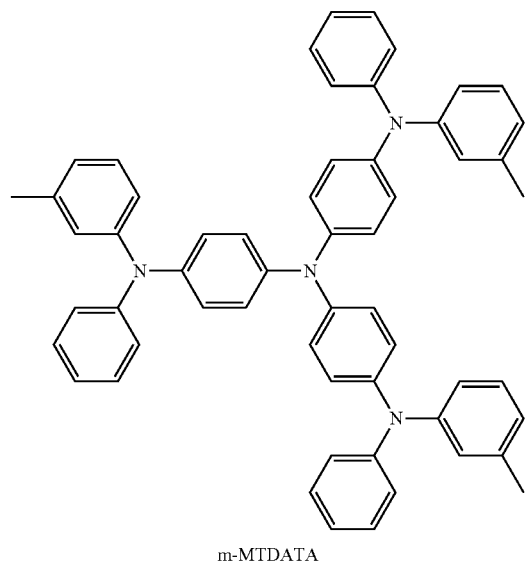

m-MTDATA

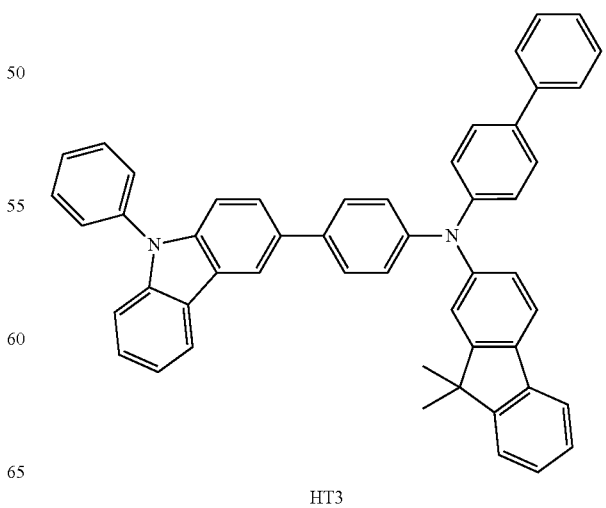

HT3

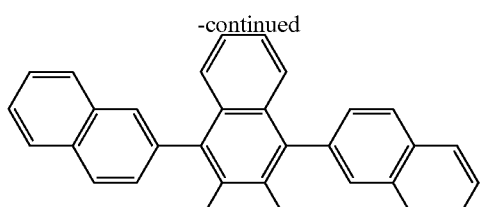

ADN

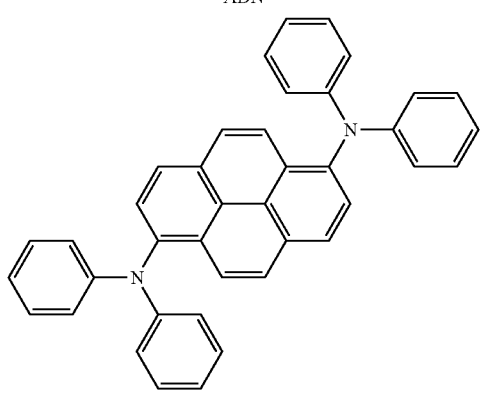

FD1

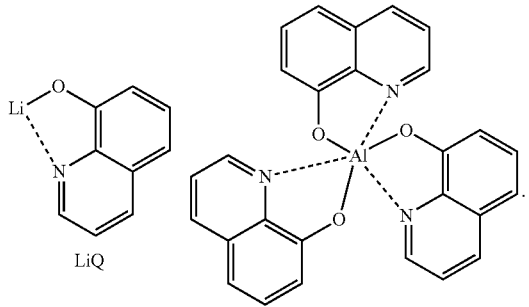

LiQ    Alq₃

Examples 1-2 to 1-7 and Comparative Examples 1-1 to 1-6

Blue Fluorescence

Organic light-emitting devices of Examples 1-2 to 1-7 and Comparative Examples 1-1 to 1-6 were each manufactured in substantially the same manner as in Example 1-1, except that compounds shown in Table 1 were utilized instead of the materials utilized for forming the emission auxiliary layer and the electron transport layer.

Evaluation Example 1

Blue Fluorescence

The driving voltage (V) and efficiency (cd/A) of the organic light-emitting devices manufactured in Examples 1-1 to 1-7 and Comparative Examples 1-1 to 1-6 were evaluated at a current density of 10 mA/cm² by utilizing a Keithley MU 236 and a PR650 luminance meter. The results are shown in Table 1.

TABLE 1

| | Material for emission auxiliary layer | Material for electron transport layer | Driving voltage (V) | Efficiency (cd/A) |
|---|---|---|---|---|
| Example1-1 | Compound 2-3 | Compound 1-1 | 5.4 | 5.1 |
| Example1-2 | Compound 2-18 | Compound 1-3 | 5.2 | 5.1 |
| Example1-3 | Compound 2-19 | Compound 1-14 | 5.3 | 4.9 |
| Example1-4 | Compound 2-20 | Compound 1-22 | 5.4 | 5.2 |
| Example1-5 | Compound 2-26 | Compound 1-25 | 5.4 | 5.0 |
| Example1-6 | Compound 2-37 | Compound 1-45:LiQ(5:5) | 5.2 | 5.2 |
| Example1-7 | Compound 2-41 | Compound 1-29:LiQ(5:5) | 5.3 | 5.1 |
| Comparative Example 1-1 | HT3 | Alq₃ | 5.8 | 4.5 |
| Comparative Example1-2 | HT3 | Compound A-1 | 5.4 | 4.7 |
| Comparative Example1-4 | Compound B-1 | Compound A-2 | 5.5 | 4.8 |
| Comparative Example1-5 | NPB | Compound A-3 | 5.7 | 4.5 |
| Comparative Example1-6 | Compound B-2 | Compound A-4 | 5.5 | 4.6 |

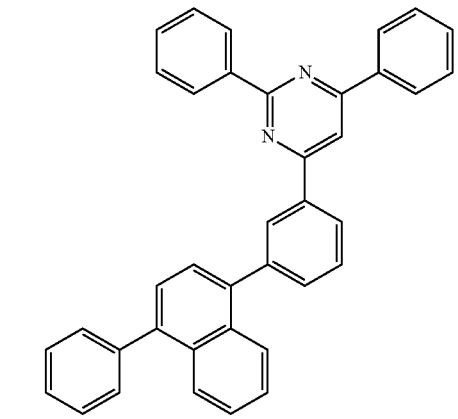

1-1

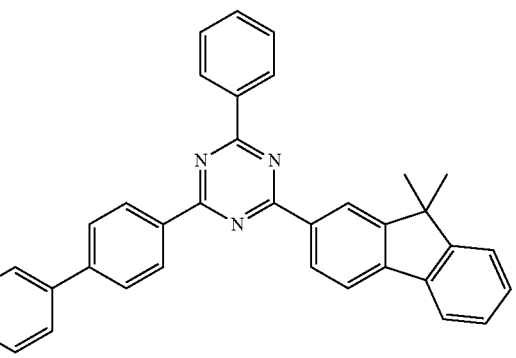

1-3

-continued
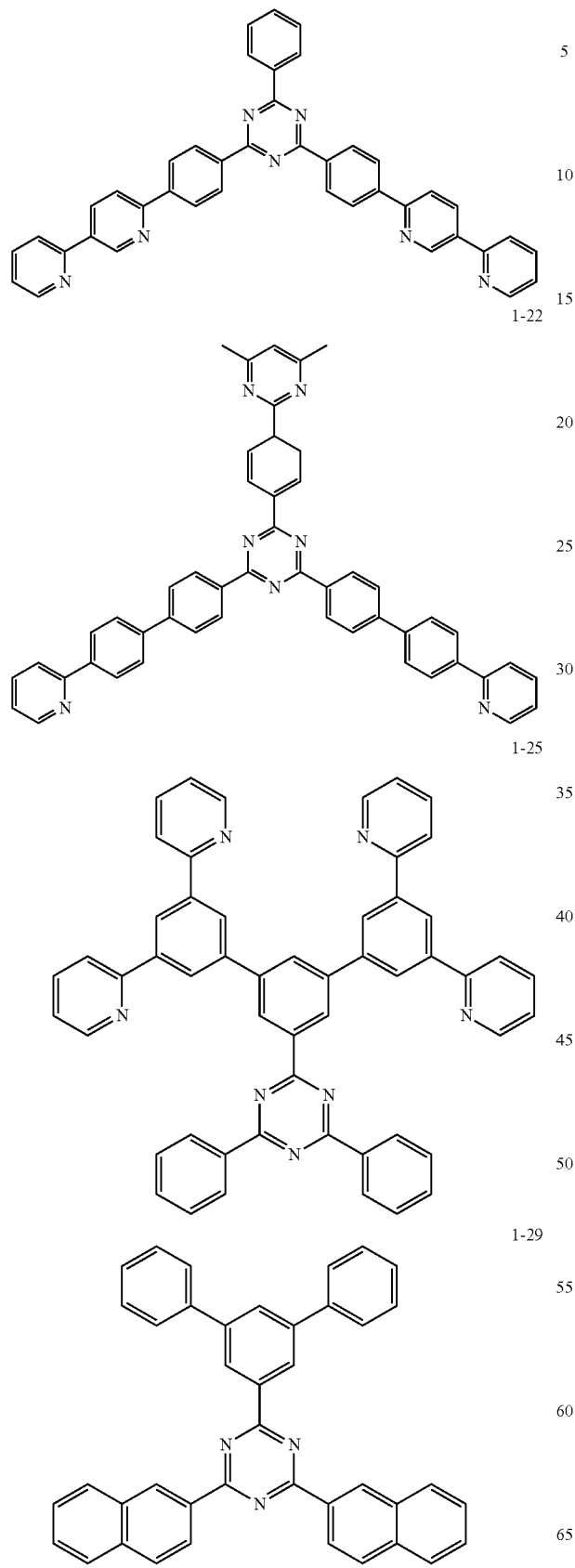
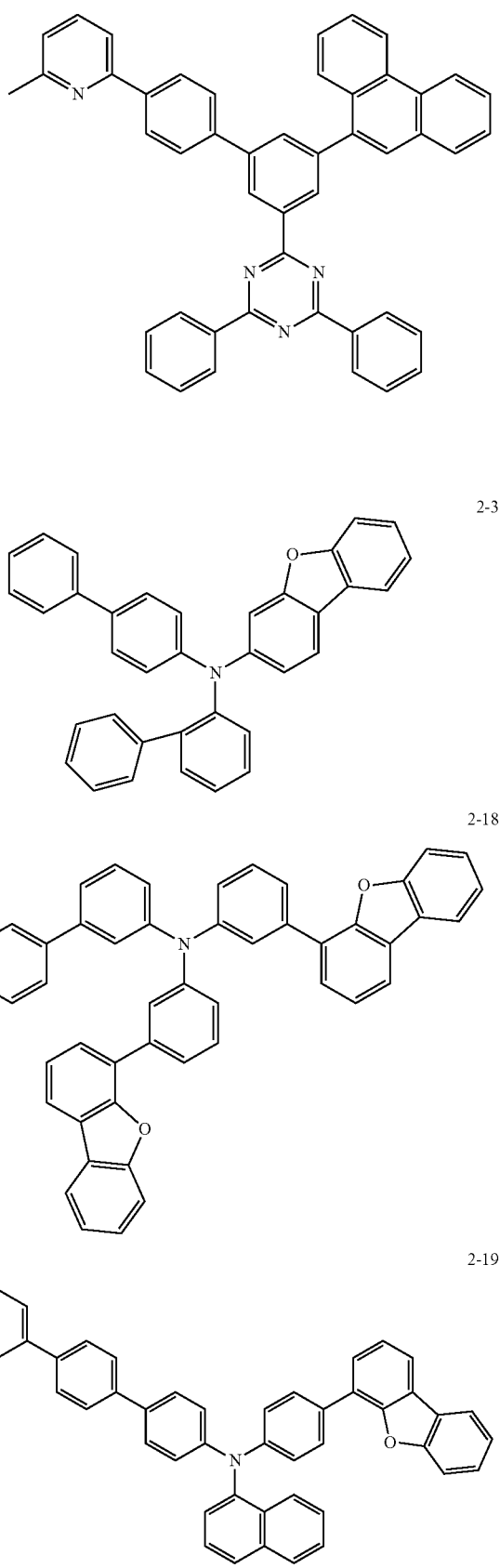

287
-continued
2-20
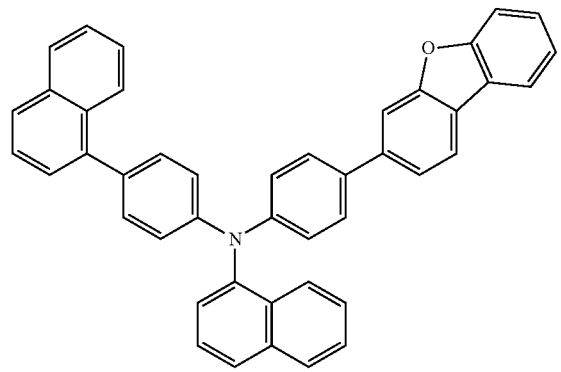
2-26
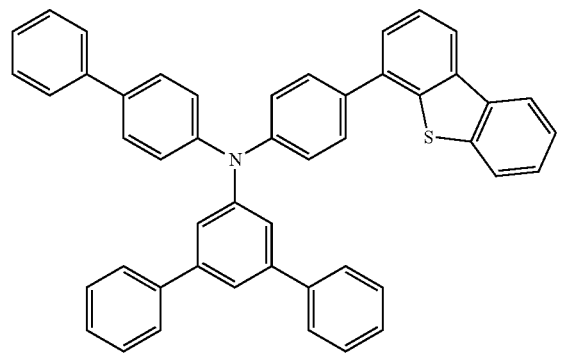
2-37
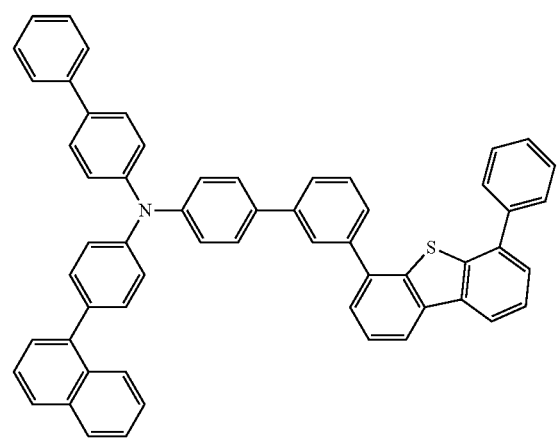
2-41
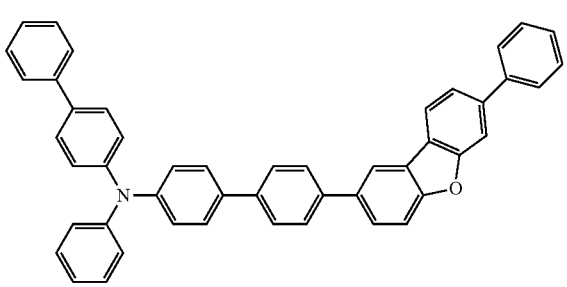
288
-continued
Compound A-1
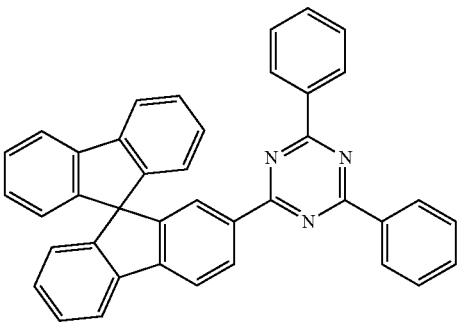
Compound A-2
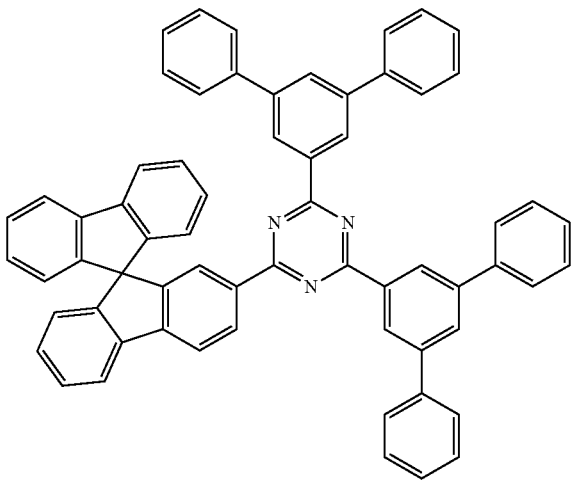
Compuond A-3
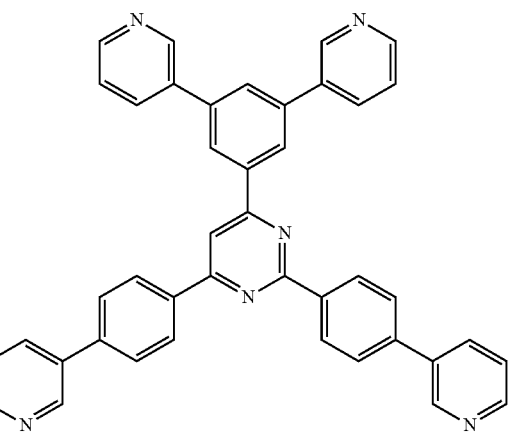
Compound A-4
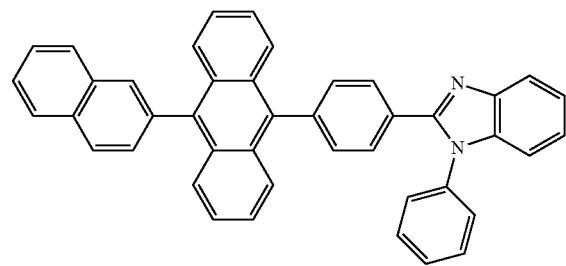

-continued

Compound B-1

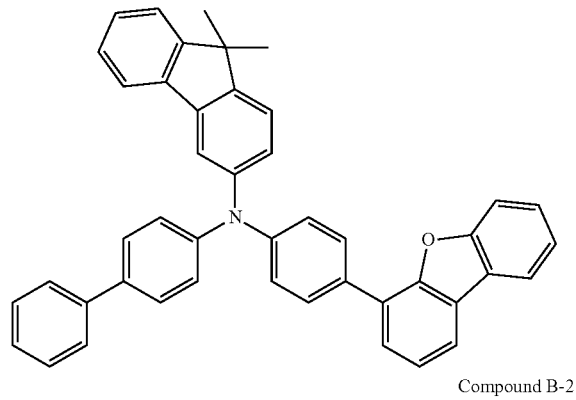

Compound B-2

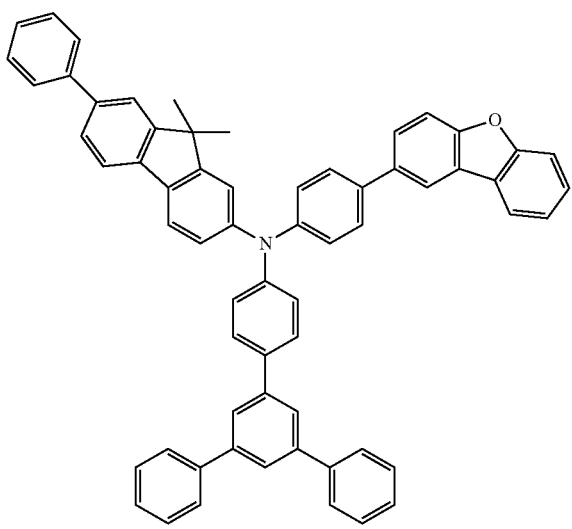

NPB

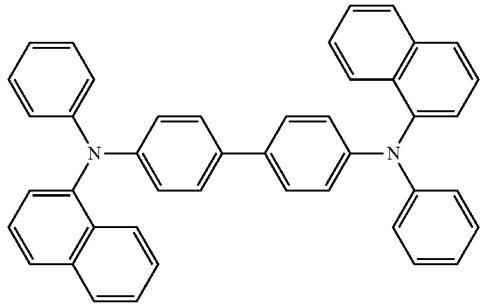

Referring to the results of Table 1, it was confirmed that the organic light-emitting devices manufactured in Examples 1-1 to 1-7 exhibited low driving voltage and high efficiency, as compared with the organic light-emitting devices manufactured in Comparative Examples 1-1 to 1-6.

Example 2-1

Green Phosphorescence

An anode was prepared by cutting a glass substrate, on which ITO having a thickness of 15 Ω/cm² (120 nm) was formed, to a size of 50 mm×50 mm×0.5 mm, ultrasonically cleaning the glass substrate by utilizing acetone, isopropyl alcohol, and pure water for 15 minutes each, and then irradiating UV light for 30 minutes thereto and exposing the glass substrate to ozone to clean the glass substrate. Then, the glass substrate was loaded into a vacuum deposition apparatus.

m-MTDATA was vacuum-deposited on the ITO anode of the glass substrate to form a hole injection layer having a thickness of 20 nm, and then, Compound HT3 was vacuum-deposited on the hole injection layer to form a hole transport layer having a thickness of 70 nm.

Compound 2-1 was vacuum-deposited on the hole transport layer to form an emission auxiliary layer having a thickness of 10 nm.

Compound CBP (as a host) and Compound PD13 (as a dopant having an amount of 10 wt %) were co-deposited on the emission auxiliary layer to form an emission layer having a thickness of 30 nm.

Balq was vacuum-deposited on the emission layer to form a buffer layer having a thickness of 10 nm.

Compound 1-1 was vacuum-deposited on the buffer layer to form an electron transport layer having a thickness of 30 nm, and then, LiF was deposited on the electron transport layer to form an electron injection layer having a thickness of 1 nm. Then, Al was vacuum-deposited on the electron injection layer to form a second electrode (i.e., a cathode) having a thickness of 200 nm, thereby completing the manufacture of an organic light-emitting device.

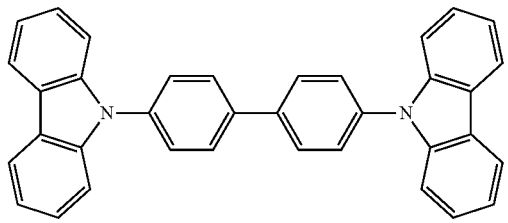

CBP

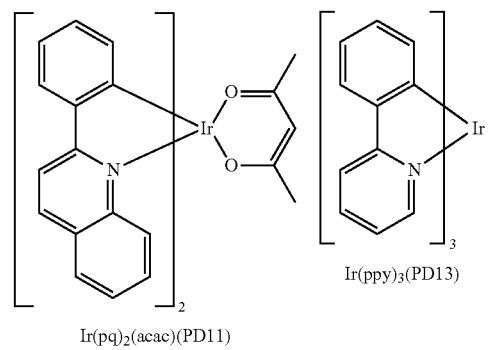

Ir(pq)$_2$(acac)(PD11)

Ir(ppy)$_3$(PD13)

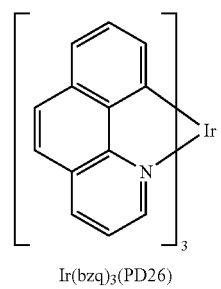

Ir(bzq)$_3$(PD26)

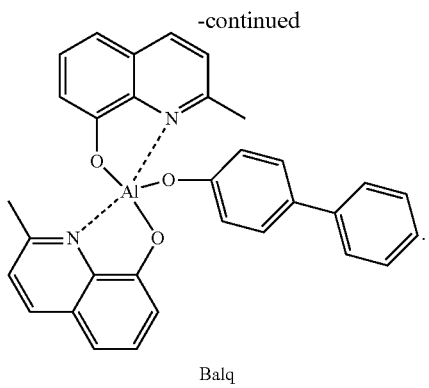

Balq

Examples 2-1 to 2-7 and Comparative Examples 2-1 to 2-6

Green Phosphorescence

Organic light-emitting devices of Examples 2-2 to 2-7 and Comparative Examples 2-2 to 2-6 were each manufactured in substantially the same manner as in Example 2-1, except that compounds shown in Table 2 were utilized instead of the materials utilized for forming the emission auxiliary layer and the electron transport layer.

Evaluation Example 2

Green Phosphorescence

The driving voltage (V) and efficiency (cd/A) of the organic light-emitting devices manufactured in Examples 2-1 to 2-7 and Comparative Examples 2-1 to 2-6 were evaluated at a current density of 10 mA/cm$^2$ by utilizing a Keithley MU 236 and a PR650 luminance meter. The results are shown in Table 2.

TABLE 2

|  | Material for emission auxiliary layer | Material for buffer layer | Material for electron transport layer | Driving voltage (V) | Efficiency (cd/A) |
| --- | --- | --- | --- | --- | --- |
| Example 2-1 | Compound 2-3 | BAlq | Compound 1-1 | 5.5 | 34 |
| Example 2-2 | Compound 2-18 | BAlq | Compound 1-3 | 5.4 | 35 |
| Example 2-3 | Compound 2-19 | BAlq | Compound 1-14 | 5.3 | 33.6 |
| Example 2-4 | Compound 2-20 | BAlq | Compound 1-22 | 5.5 | 34.4 |
| Example 2-5 | Compound 2-26 | BAlq | Compound 1-25 | 5.5 | 35 |
| Example 2-6 | Compound 2-37 | BAlq | Compound 1-45:LiQ (5:5) | 5.4 | 35.5 |
| Example 2-7 | Compound 2-41 | BAlq | Compound 1-29:LiQ(5:5) | 5.3 | 34 |
| Comparative Example 2-1 | HT3 | BAlq | Alq$_3$ | 5.9 | 30 |
| Comparative Example 2-2 | HT3 | BAlq | Compound A-1 | 5.7 | 32 |
| Comparative Example 2-3 | HT3 | — | Compound A-1 | 5.6 | 31.5 |
| Comparative Example 2-4 | Compound B-1 | — | Compound A-2 | 5.6 | 33.2 |
| Comparative Example 2-5 | NPB | — | Compound A-3 | 5.7 | 31.8 |
| Comparative Example 2-6 | Compound B-2 | — | Compound A-4 | 5.7 | 32 |

Referring to the results of Table 2, it was confirmed that the organic light-emitting devices manufactured in Examples 2-1 to 2-7 exhibited low driving voltage and high efficiency, as compared with the organic light-emitting devices manufactured in Comparative Examples 2-1 to 2-6.

Examples 3-1 to 3-4 and Comparative Examples 3-1 to 3-4

Red Phosphorescence

Organic light-emitting devices of Examples 3-1 to 3-4 and Comparative Examples 3-1 to 3-4 were each manufactured in substantially the same manner as in Example 2-1, except that compounds shown in Table 2 were utilized instead of the materials utilized for forming the emission auxiliary layer and the electron transport layer and Compound PD11 (as a dopant having an amount of 4 wt %) was used instead of Compound PD13 to form the emission layer.

Evaluation Example 3

Red Phosphorescence

The driving voltage (V) and efficiency (cd/A) of the organic light-emitting devices manufactured in Examples 3-1 to 3-4 and Comparative Examples 3-1 to 3-4 were evaluated at a current density of 10 mA/cm$^2$ by utilizing a Keithley MU 236 and a PR650 luminance meter. The results are shown in Table 3.

TABLE 3

| | Material for emission auxiliary layer | Material for buffer layer | Material for electron transport layer | Driving voltage (V) | Efficiency (cd/A) |
|---|---|---|---|---|---|
| Example 3-1 | Compound 2-18 | BAlq | Compound 1-1 | 5.8 | 20.7 |
| Example 3-2 | Compound 2-19 | BAlq | Compound 1-14 | 5.9 | 21 |
| Example 3-3 | Compound 2-20 | BAlq | Compound 1-25 | 6.0 | 20.5 |
| Example 3-4 | Compound 2-37 | BAlq | Compound 1-45:LiQ(5:5) | 5.8 | 22 |
| Comparative Example 3-1 | HT3 | BAlq | Alq$_3$ | 6.1 | 19.8 |
| Comparative Example 3-2 | Compound B-1 | — | Compound A-2 | 6.0 | 20.2 |
| Comparative Example 3-3 | NPB | — | Compound A-3 | 6.2 | 19.5 |
| Comparative Example 3-4 | Compound B-2 | — | Compound A-4 | 6.2 | 19.7 |

Referring to results of Table 3, it was confirmed that the organic light-emitting devices manufactured in Examples 3-1 to 3-4 exhibited low driving voltage and high efficiency, as compared with the organic light-emitting devices manufactured in Comparative Examples 3-1 to 3-4.

As described above, an organic light-emitting device according to one or more embodiments may have low driving voltage and high efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims

What is claimed is:
1. An organic light-emitting device comprising:
a first electrode;
a second electrode facing the first electrode;
an emission layer between the first electrode and the second electrode;
a hole transport region between the first electrode and the emission layer; and
an electron transport region between the emission layer and the second electrode,
wherein the electron transport region comprises a first compound represented by one selected from Formulae 1A, 1B(3), 1B(4), 1C, and 1D, and the hole transport region comprises a second compound represented by Formula 2:

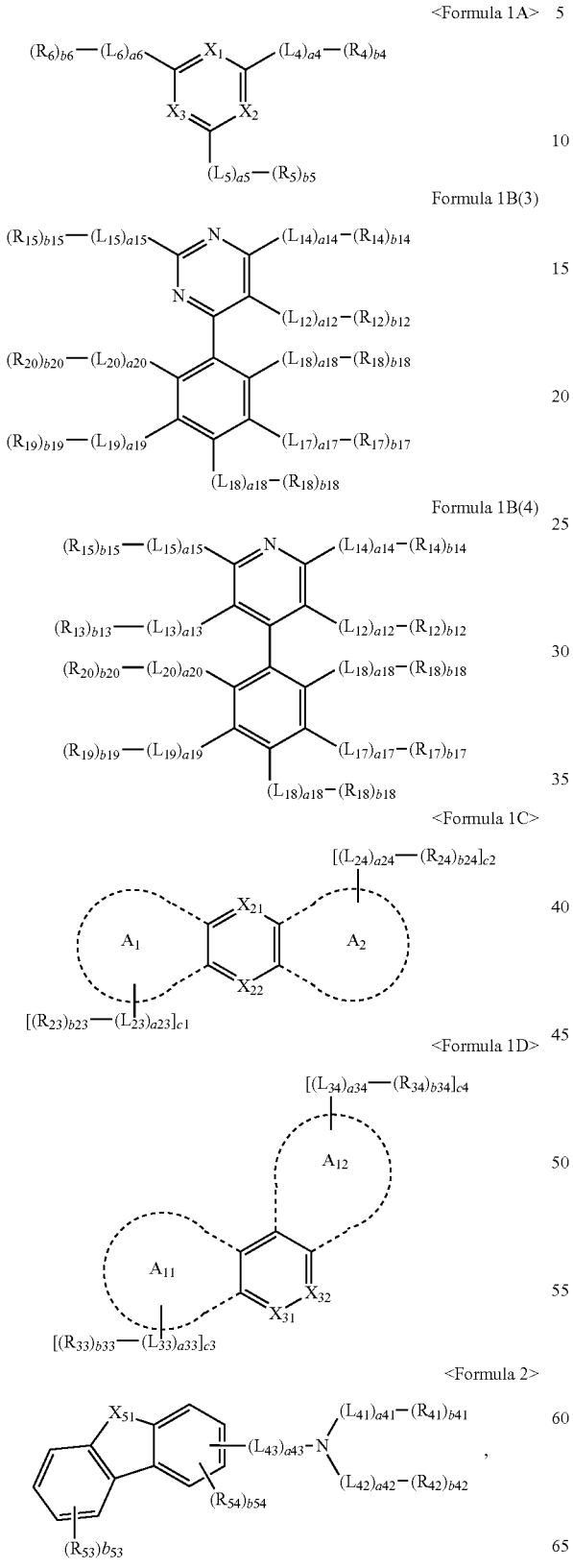

wherein, in Formula 1A, $X_1$ is N, $X_2$ is $C-[(L_2)_{a2}-(R_2)_{b2}]$, and $X_3$ is N, in Formulae 1A, 1B(3), 1B(4), 1C, 1D, and 2, each of ring $A_1$ and ring $A_2$ is independently a $C_5$-$C_{60}$ carbocyclic group or a $C_1$-$C_{30}$ heterocyclic group, each of ring $A_{11}$ and ring $A_{12}$ is independently a $C_1$-$C_{30}$ heterocyclic group, $X_{21}$ is selected from N and $C-[(L_{21})_{a21}-(R_{21})_{b21}]$, and $X_{22}$ is selected from N and $C-[(L_{22})_{a22}-(R_{22})_{b22}]$, wherein at least one of $X_{21}$ and $X_{22}$ is N, $X_{31}$ is selected from N and $C-[(L_{31})_{a31}-(R_{31})_{b31}]$, and $X_{32}$ is selected from N and $C-[(L_{32})_{a32}-(R_{32})_{b32}]$, $X_{51}$ is selected from O, S, Se, and $Si(R_{51})(R_{52})$, $L_1$ to $L_6$, $L_{11}$ to $L_{24}$, $L_{31}$ to $L_{34}$, and $L_{41}$ to $L_{43}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, each of a1 to a6, a11 to a24, a31 to a34, and a41 to a43 is independently an integer selected from 0 to 5, each of $R_1$ to $R_6$, $R_{11}$ to $R_{24}$, $R_{31}$ to $R_{34}$, and $R_{51}$ to $R_{54}$ is independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, except that $R_4$ to $R_6$ and $R_{18}$ are not a substituted or unsubstituted fluorenyl group, each of $R_{41}$ and $R_{42}$ is independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, each of b1 to b3, b11 to b17, b19 to b24, b31 to b34, b53, and b54 is independently an integer selected from 0 to 5, each of b4 to b6, b18, b41, and b42 is independently an integer selected from 1 to 5, each of c1 to c4 is independently an integer selected from 1 to 10, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group, wherein in Formula 1B(4), $L_{17}$ and $L_{19}$ are each independently selected from a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group; and a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $R_{17}$ and $R_{19}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), in Formula 1D, $R_{33}$ and $R_{34}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), and —S(=O)$_2$($Q_{31}$), neither of a carbazole ring and a spiro-bifluorene ring is comprised in Formulae 1A, 1B(3), 1B(4), 1C, and 1D, and neither of a carbazole ring and a fluorene ring is comprised in Formula 2.

2. The organic light-emitting device of claim 1, wherein each of ring $A_1$ and ring $A_2$ in Formula 1C is independently selected from a benzene group, a naphthalene group, an anthracene group, an indene group, a fluorene group, a pyridine group, a pyrimidine group, a pyrazine group, a pyridazine group, a quinoline group, and an isoquinoline group, and each of ring $A_{11}$ and ring $A_{12}$ in Formula 1D is independently selected from a pyridine group, a pyrimidine group, a pyrazine group, a pyridazine group, a quinoline group, and an isoquinoline group.

3. The organic light-emitting device of claim 1, wherein, in Formula 1C,
i) $X_{21}$ is C-[($L_{21}$)$_{a21}$-($R_{21}$)$_{b21}$], and $X_{22}$ is N, or
ii) $X_{21}$ is N, and $X_{22}$ is C-[($L_{22}$)$_{a22}$-($R_{22}$)$_{b22}$]; and
in Formula 1D,
i) $X_{31}$ is C-[($L_{31}$)$_{a31}$-($R_{31}$)$_{b31}$], and $X_{32}$ is C-[($L_{32}$)$_{a32}$-($R_{32}$)$_{b32}$],
ii) $X_{31}$ is N, and $X_{32}$ is C-[($L_{32}$)$_{a32}$-($R_{32}$)$_{b32}$]; or
iii) $X_{31}$ is C-[($L_{31}$)$_{a31}$-($R_{31}$)$_{b31}$], and $X_{32}$ is N.

4. The organic light-emitting device of claim 1, wherein, in Formula 2, $X_{51}$ is O or S.

5. The organic light-emitting device of claim 1, wherein each of $L_1$ to $L_6$, $L_{11}$ to $L_{24}$, and $L_{31}$ to $L_{34}$ in Formulae 1A, 1B(3), 1C, and 1D, and $L_1$ to $L_6$, $L_{11}$ to $L_{16}$, $L_{18}$, $L_{20}$ to $L_{24}$, and $L_{31}$ to $L_{34}$ in Formula 1B(4) is independently selected from:

a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group; and a phenylene group, a pentalenylene group, an indenylene group, a naphthylene group, an azulenylene group, an indacenylene group, an acenaphthylene group, a fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), each of $L_{41}$ to $L_{43}$ in Formula 2 is independently selected from:

a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group; and a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, —Si($Q_{31}$)($Q_{32}$)($Q_{33}$), —N($Q_{31}$)($Q_{32}$), and —B($Q_{31}$)($Q_{32}$), and each of $Q_{31}$ to $Q_{33}$ is independently selected from:

a $C_1$-$C_{10}$ alkyl group, a $C_1$-$C_{10}$ alkoxy group, a phenyl group, a biphenyl group, terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

6. The organic light-emitting device of claim 1, wherein each of $L_1$ to $L_6$, $L_{11}$ to $L_{24}$, and $L_{31}$ to $L_{34}$ in Formulae 1A, 1B(3), 1B(4), 1C, and 1D, and $L_1$ to $L_6$, $L_{11}$ to $L_{16}$, $L_{18}$, $L_{20}$ to $L_{24}$, and $L_{31}$ to $L_{34}$ in Formula 1B(4) is independently a group represented by one selected from Formulae 3-1 to 3-100, $L_{17}$ and $L_{19}$ in Formula 1B(4) are each independently selected from Formulae 3-1 to 3-24 and 3-31 to 3-100, and $L_{41}$ to $L_{43}$ in Formula 2 are each independently group represented by one selected from Formulae 3-1 to 3-30 (wherein Yi in Formulae 3-17 to 3-20 is O or S):

Formula 3-1

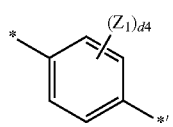

Formula 3-2

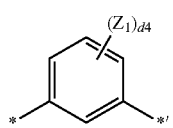

Formula 3-3

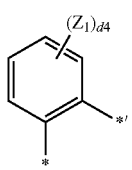

Formula 3-4

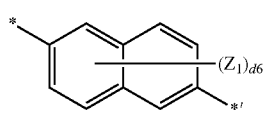

Formula 3-5

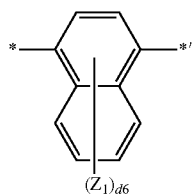

Formula 3-6

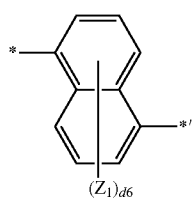

-continued

Formula 3-7

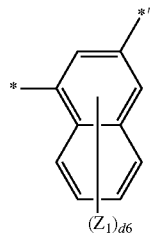

Formula 3-8

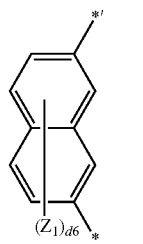

Formula 3-9

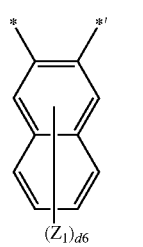

Formula 3-10

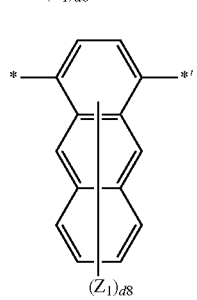

Formula 3-11

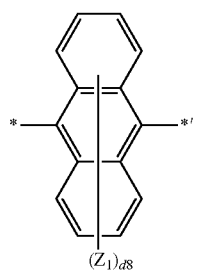

Formula 3-12

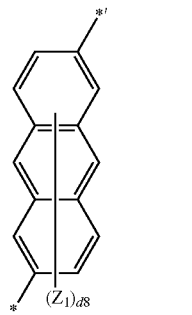

307
-continued
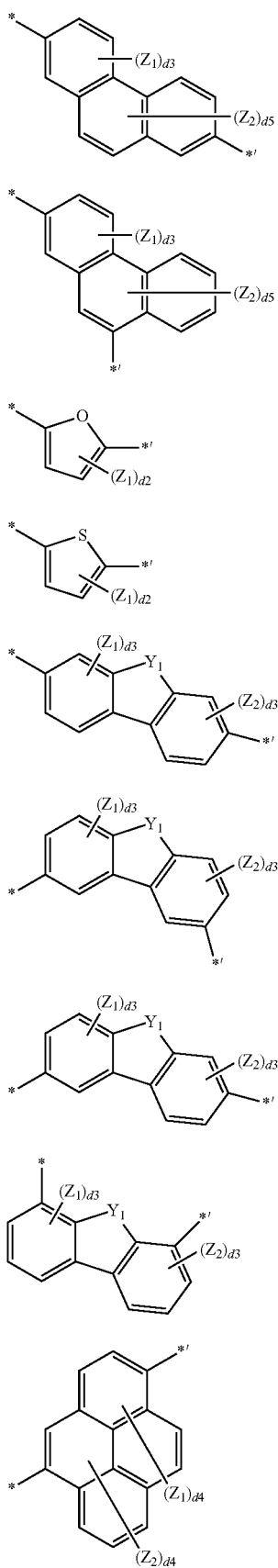
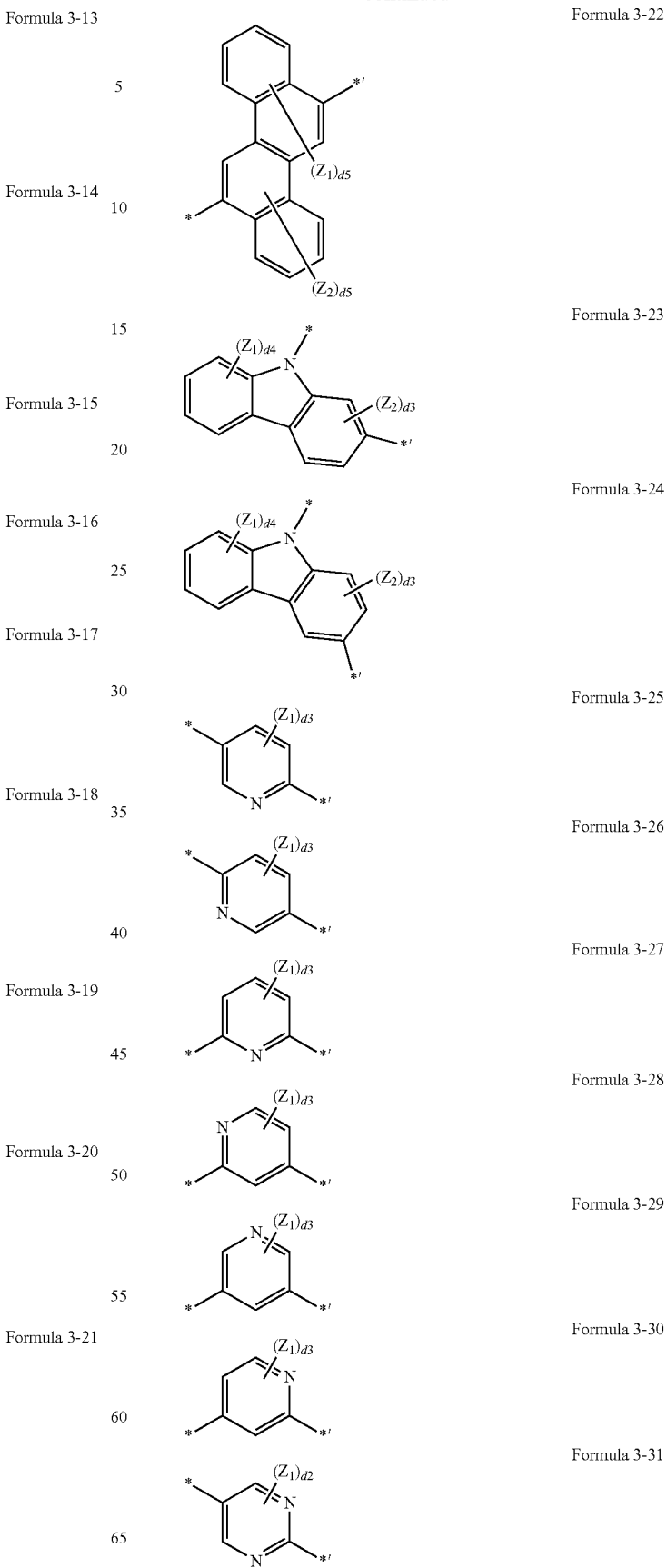

Formula 3-32
Formula 3-33
Formula 3-34
Formula 3-35
Formula 3-36
Formula 3-37
Formula 3-38
Formula 3-39
Formula 3-40
Formula 3-41
Formula 3-42
Formula 3-43
Formula 3-44
Formula 3-45
Formula 3-46
Formula 3-47
Formula 3-48
Formula 3-49

-continued
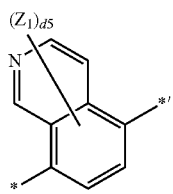
Formula 3-50
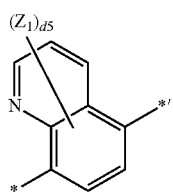
Formula 3-51
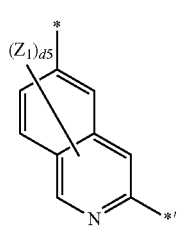
Formula 3-52
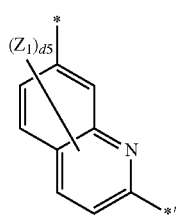
Formula 3-53
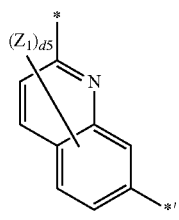
Formula 3-54
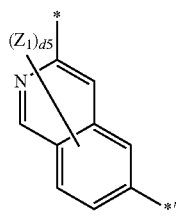
Formula 3-55
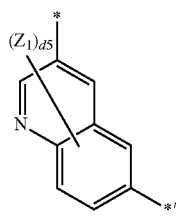
Formula 3-56
-continued
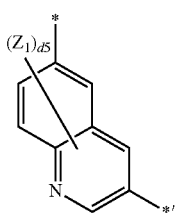
Formula 3-57
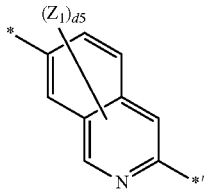
Formula 3-58
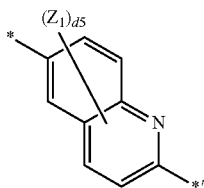
Formula 3-59
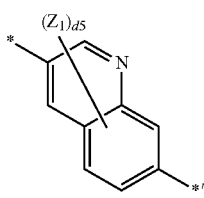
Formula 3-60
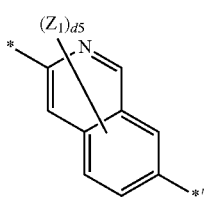
Formula 3-61
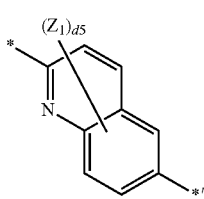
Formula 3-62
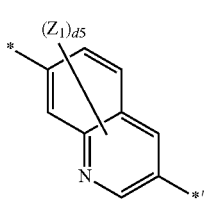
Formula 3-63
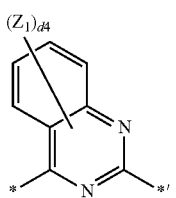
Formula 3-64

313
-continued
Formula 3-65
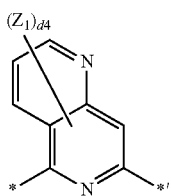
Formula 3-66
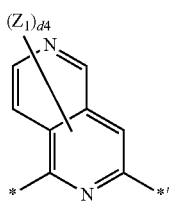
Formula 3-67
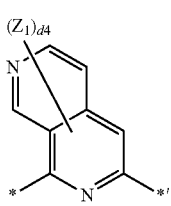
Formula 3-68
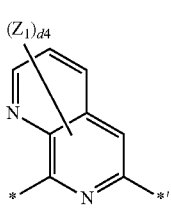
Formula 3-69
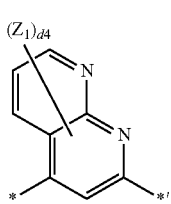
Formula 3-70
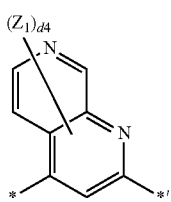
Formula 3-71
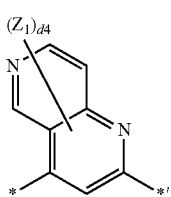
Formula 3-72
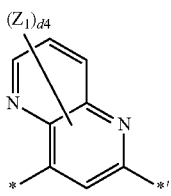
314
-continued
Formula 3-73
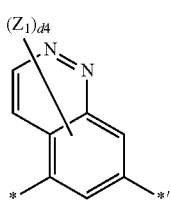
Formula 3-74
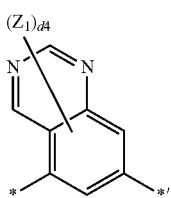
Formula 3-75
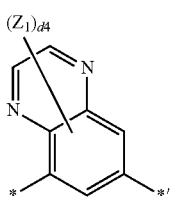
Formula 3-76
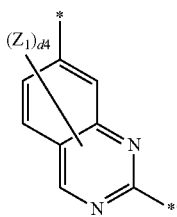
Formula 3-77
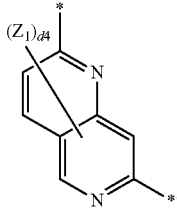
Formula 3-78
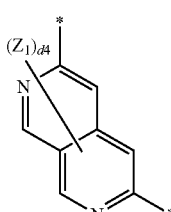
Formula 3-79
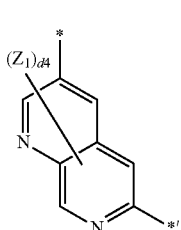

Formula 3-80
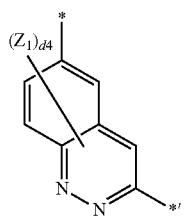
Formula 3-81
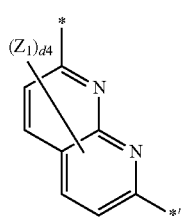
Formula 3-82
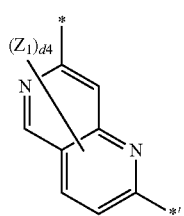
Formula 3-83
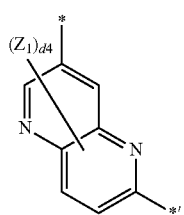
Formula 3-84
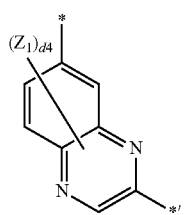
Formula 3-85
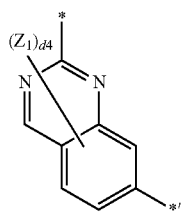
Formula 3-86
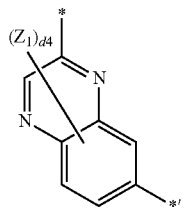
Formula 3-87
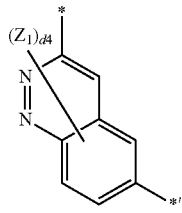
Formula 3-88
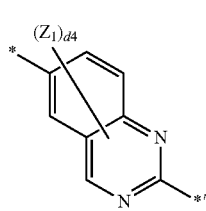
Formula 3-89
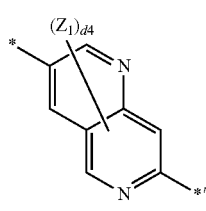
Formula 3-90
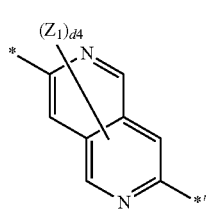
Formula 3-91
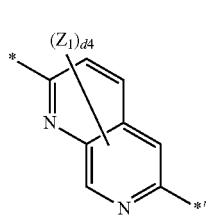
Formula 3-92
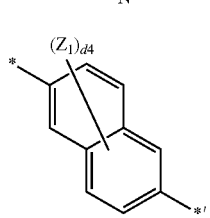
Formula 3-93
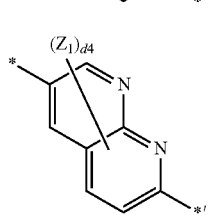
Formula 3-94
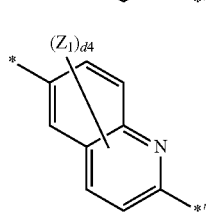

-continued

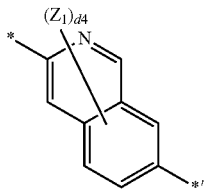

Formula 3-95

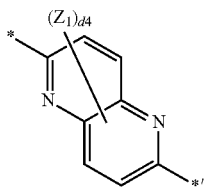

Formula 3-96

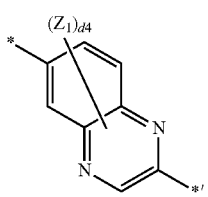

Formula 3-97

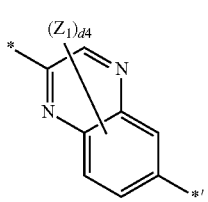

Formula 3-98

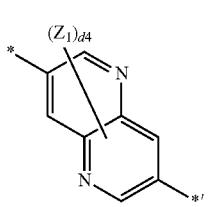

Formula 3-99

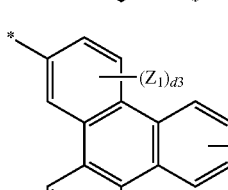

Formula 3-100 wherein, in Formulae 3-1 to 3-100, $Y_1$ is O, S, $C(Z_4)(Z_5)$, or $Si(Z_6)(Z_7)$, each of $Z_1$ to $Z_7$ is independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a dibenzofluorenyl group, a phenalenyl group, a phenanthrenyl group, an anthracenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, a benzonaphthyridinyl group, an azafluorenyl group, an azadibenzofuranyl group, an azadibenzothiophenyl group, an azadibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), each of $Q_{31}$ to $Q_{33}$ is independently selected from:
a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 is an integer selected from 0 to 2,
d3 is an integer selected from 0 to 3,
d4 is an integer selected from 0 to 4,
d5 is an integer selected from 0 to 5,
d6 is an integer selected from 0 to 6,
d8 is an integer selected from 0 to 8, and
* and *' each indicate a binding site to a neighboring atom.

7. The organic light-emitting device of claim 1, wherein each of $R_1$ to $R_6$, $R_{11}$ to $R_{24}$, and $R_{31}$ to $R_{34}$ in Formulae 1A, 1B(3), and 1C, and $R_1$ to $R_6$, $R_{11}$ to $R_{16}$, $R_{18}$, and $R_{20}$ to $R_{24}$, and $R_{31}$ to $R_{34}$ in Formulae 1B(4), and $R_1$ to $R_6$, $R_{11}$ to $R_{24}$, $R_{31}$, and $R_{32}$ in Formula 1D independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and each of $Q_{31}$ to $Q_{33}$ is independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, except that $R_4$ to $R_6$ and $R_{18}$ are not a substituted or unsubstituted fluorenyl group.

8. The organic light-emitting device of claim 1, wherein, in Formula 2, each of $R_{41}$ and $R_{42}$ is independently selected from:

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, —Si($Q_{31}$)($Q_{32}$)($Q_{33}$), —N($Q_{31}$)($Q_{32}$), and —B($Q_{31}$)($Q_{32}$), and each of $Q_{31}$ to $Q_{33}$ is independently selected from a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

9. The organic light-emitting device of claim 1, wherein, each of $R_1$ to $R_6$, $R_{11}$ to $R_{24}$, and $R_{31}$ to $R_{34}$ in Formulae 1A, 1B(3), 1B(4), and 1C, and $R_1$ to $R_6$, $R_{11}$ to $R_{16}$, $R_{18}$, and $R_{20}$ to $R_{24}$, and $R_{31}$ to $R_{34}$ in Formulae 1B(4), and $R_1$ to $R_6$, $R_{11}$ to $R_{24}$, $R_{31}$, and $R_{32}$ in Formula 1D is independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group, groups represented by Formulae 5-1 to 5-38, groups represented by Formulae 6-1 to 6-123, Si($Q_1$)($Q_2$)($Q_3$), —S(=O)$_2$($Q_1$), and —P(=O)($Q_1$)($Q_2$), $R_{17}$ and $R_{19}$ in Formula 1B(4) are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group, groups represented by Formulae 5-1 to 5-38, groups represented by Formulae 6-4 to 6-123, Si($Q_1$)($Q_2$)($Q_3$), —S(=O)$_2$($Q_1$), and —P(=O)($Q_1$)($Q_2$), $R_{33}$ and $R_{34}$ in Formula 1D are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, groups represented by Formulae 5-1 to 5-38, groups represented by Formulae 6-1 to 6-123, Si($Q_1$)($Q_2$)($Q_3$), —S(=O)$_2$($Q_1$), each of $R_{41}$ and $R_{42}$ in Formula 2 is independently selected from groups represented by Formulae 5-1 to 5-38 (wherein $Y_{31}$ in Formulae 5-13 to 5-36 is O or S):

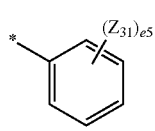

Formula 5-1

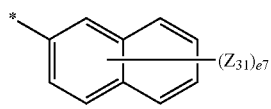

Formula 5-2

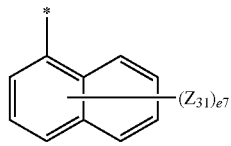

Formula 5-3

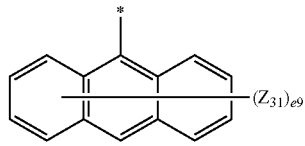

Formula 5-4

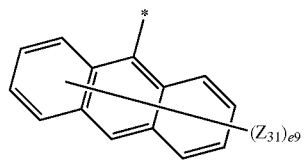

Formula 5-5

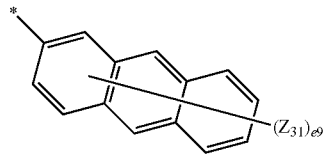

Formula 5-6

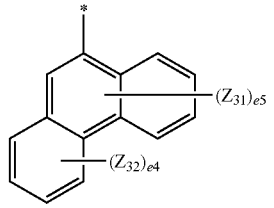

Formula 5-7

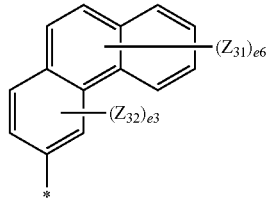

Formula 5-8

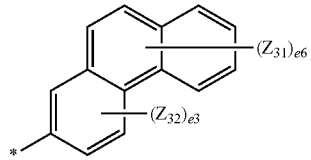

Formula 5-9

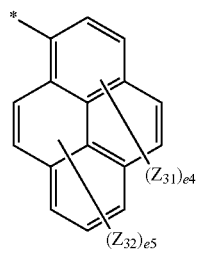

Formula 5-10

Formula 5-11 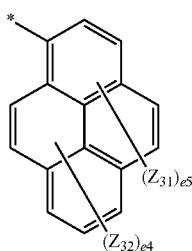
Formula 5-12 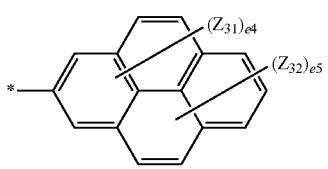
Formula 5-13 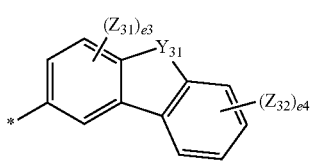
Formula 5-14 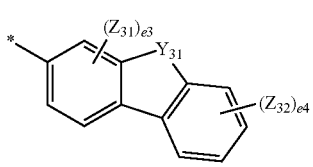
Formula 5-15 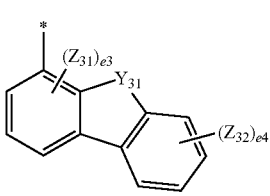
Formula 5-16 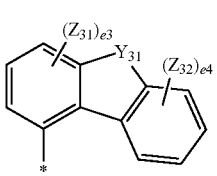
Formula 5-17 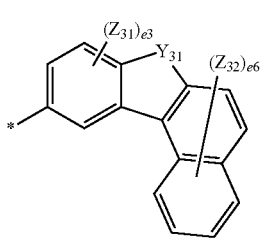
Formula 5-18 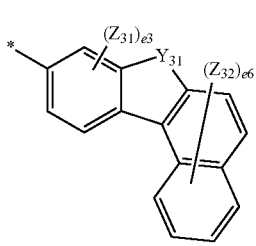
Formula 5-19 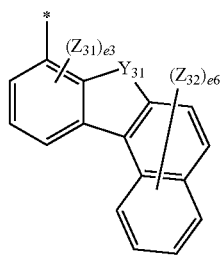
Formula 5-20 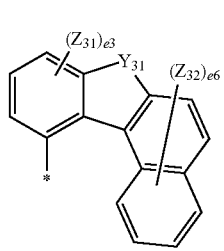
Formula 5-21 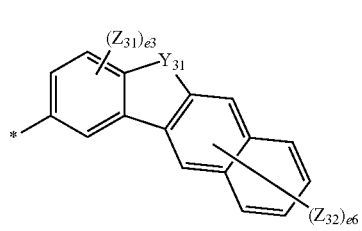
Formula 5-22
Formula 5-23
Formula 5-24
Formula 5-25

-continued
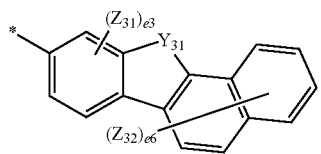
Formula 5-26
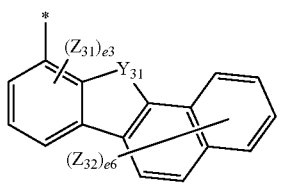
Formula 5-27
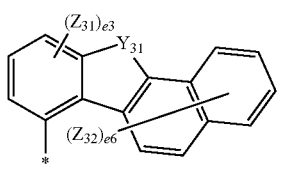
Formula 5-28
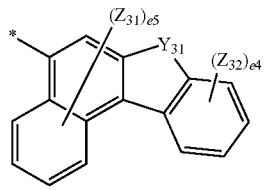
Formula 5-29
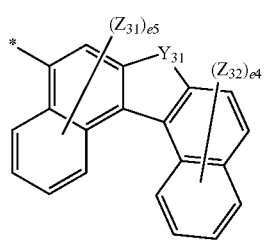
Formula 5-30
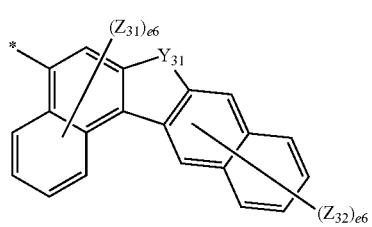
Formula 5-31
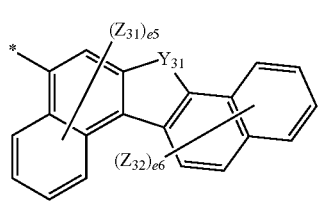
Formula 5-32
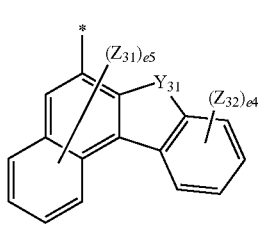
Formula 5-33
-continued
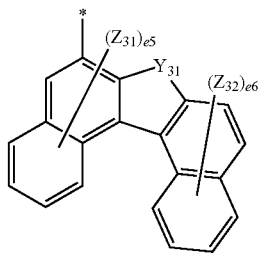
Formula 5-34
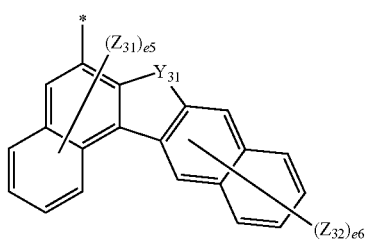
Formula 5-35
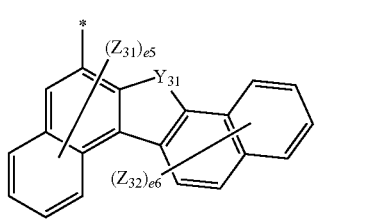
Formula 5-36
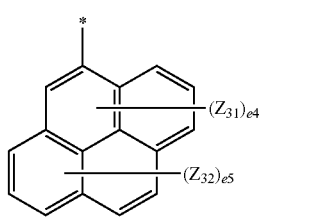
Formula 5-37
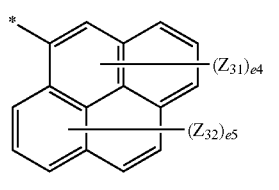
Formula 5-38
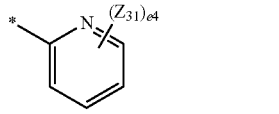
Formula 6-1
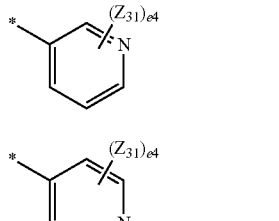
Formula 6-2
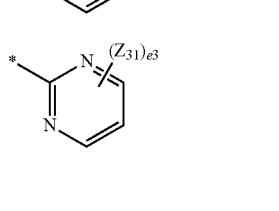
Formula 6-3
Formula 6-4

-continued
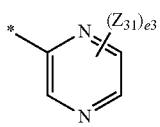
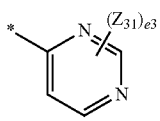
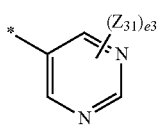
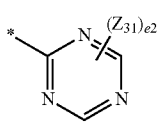
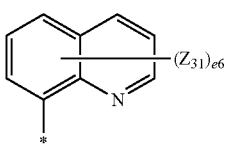
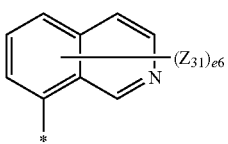
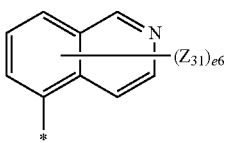
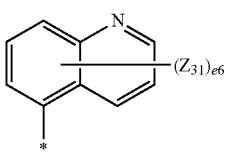
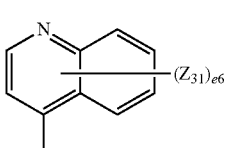
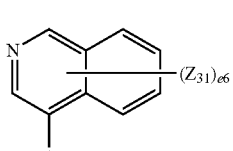
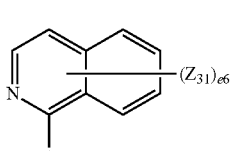
-continued
Formula 6-5
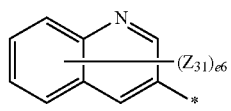
Formula 6-6
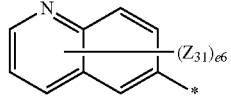
Formula 6-7
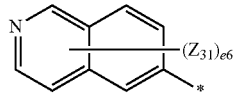
Formula 6-8
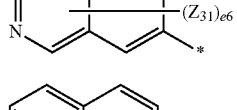
Formula 6-9
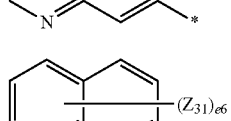
Formula 6-10
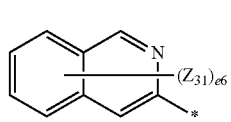
Formula 6-11
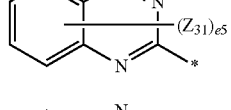
Formula 6-12
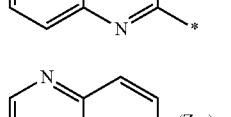
Formula 6-13
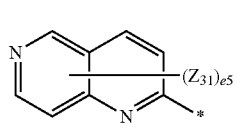
Formula 6-14
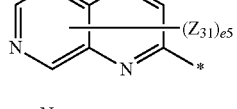
Formula 6-15
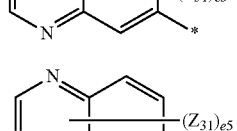
Formula 6-16
Formula 6-17
Formula 6-18
Formula 6-19
Formula 6-20
Formula 6-21
Formula 6-22
Formula 6-23
Formula 6-24
Formula 6-25
Formula 6-26
Formula 6-27
Formula 6-28
Formula 6-29

-continued
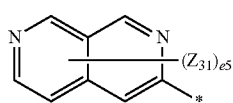 Formula 6-30
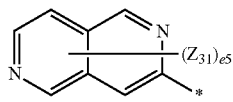 Formula 6-31
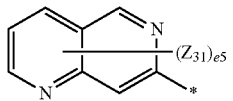 Formula 6-32
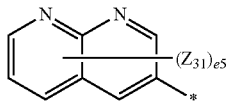 Formula 6-33
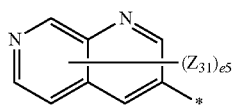 Formula 6-34
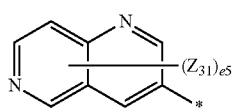 Formula 6-35
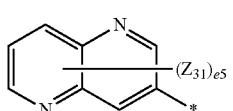 Formula 6-36
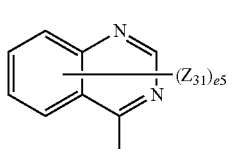 Formula 6-37
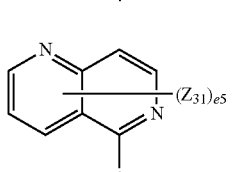 Formula 6-38
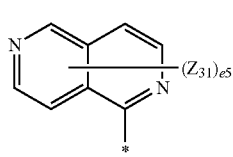 Formula 6-39
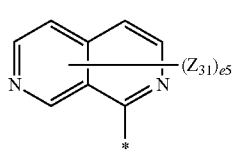 Formula 6-40
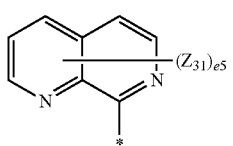 Formula 6-41
-continued
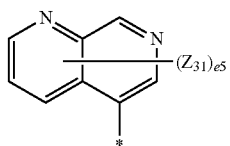 Formula 6-42
Formula 6-43
Formula 6-44
Formula 6-45
Formula 6-46
Formula 6-47
Formula 6-48
Formula 6-49
Formula 6-50
Formula 6-51

Formula 6-52 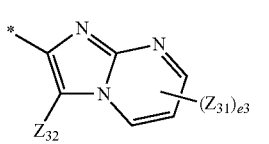
Formula 6-53 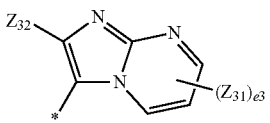
Formula 6-54 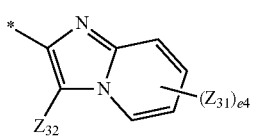
Formula 6-55 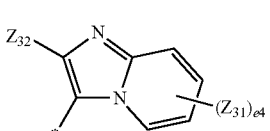
Formula 6-56 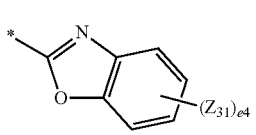
Formula 6-57 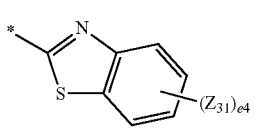
Formula 6-58 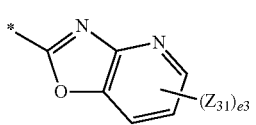
Formula 6-59 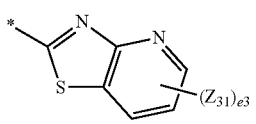
Formula 6-60 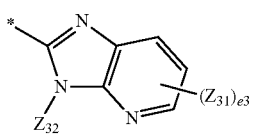
Formula 6-61 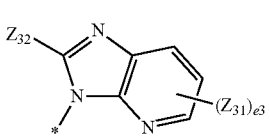
Formula 6-62 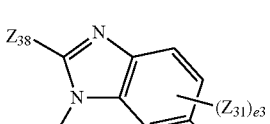
Formula 6-63 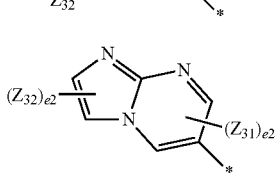
Formula 6-64 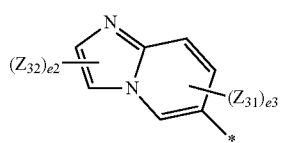
Formula 6-65 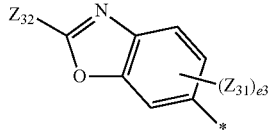
Formula 6-66 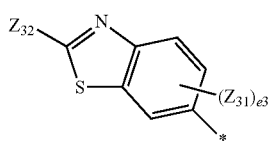
Formula 6-67 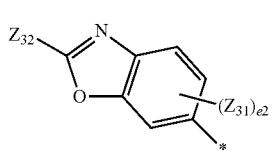
Formula 6-68 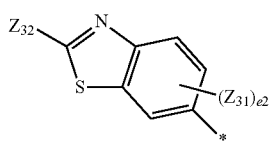
Formula 6-69 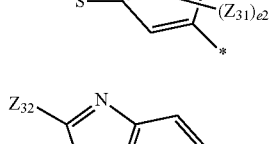
Formula 6-70 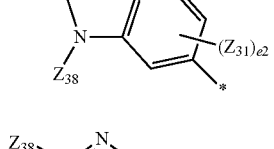
Formula 6-71 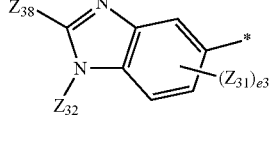
Formula 6-72 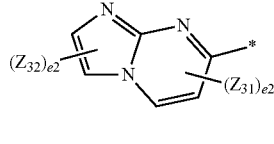
Formula 6-73 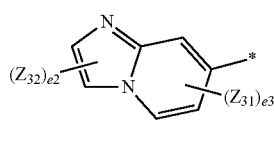
Formula 6-74 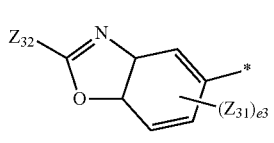

333
-continued
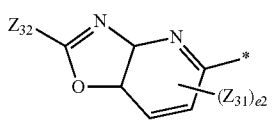
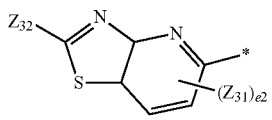
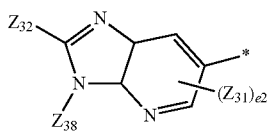
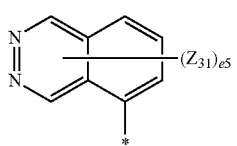
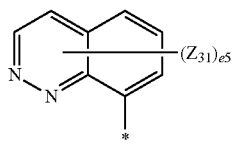
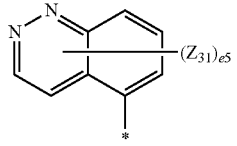
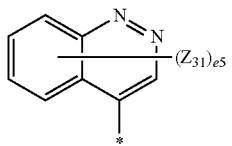
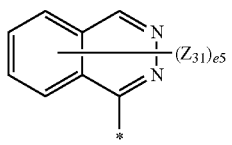
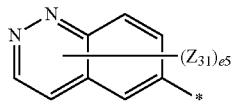
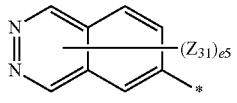
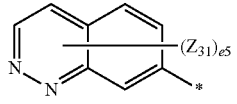
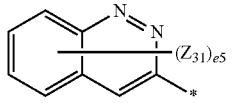
334
-continued
Formula 6-75
Formula 6-76
Formula 6-77
Formula 6-78
Formula 6-79
Formula 6-80
Formula 6-81
Formula 6-82
Formula 6-83
Formula 6-84
Formula 6-85
Formula 6-86
Formula 6-87
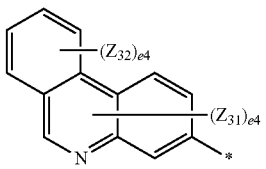
Formula 6-88
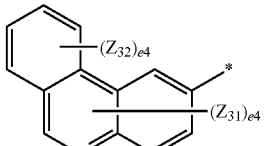
Formula 6-89
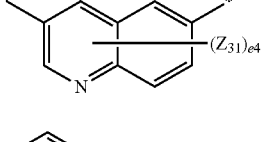
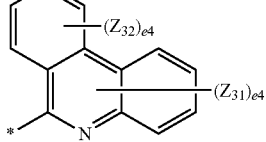
Formula 6-90
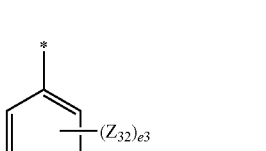
Formula 6-91
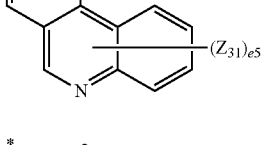
Formula 6-92
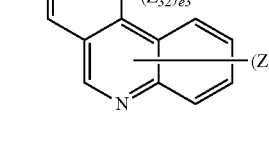
Formula 6-93
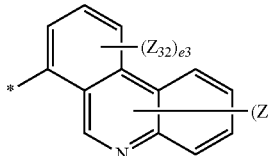
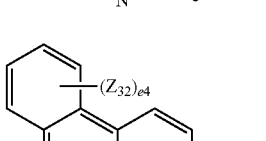
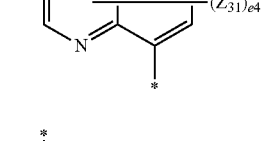
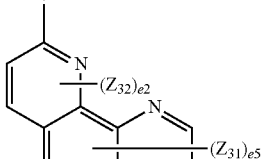
Formula 6-94
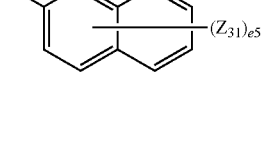

Formula 6-95
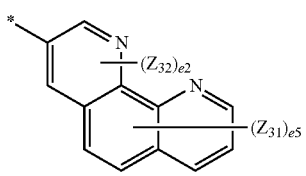
Formula 6-96
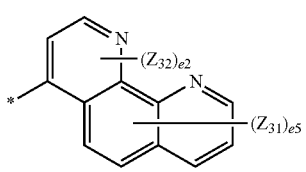
Formula 6-97
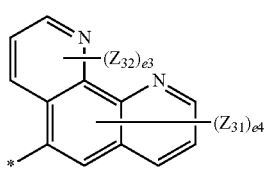
Formula 6-98
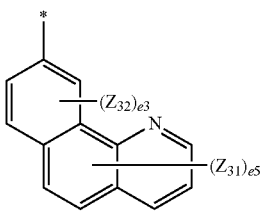
Formula 6-99
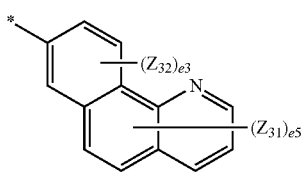
Formula 6-100
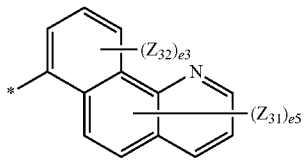
Formula 6-101
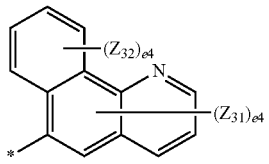
Formula 6-102
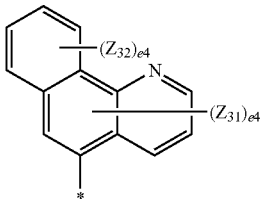
Formula 6-103
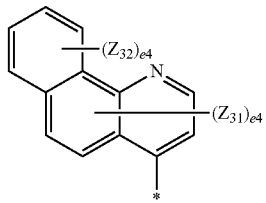
Formula 6-104
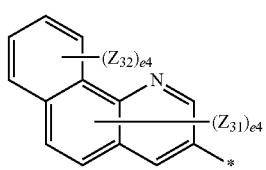
Formula 6-105
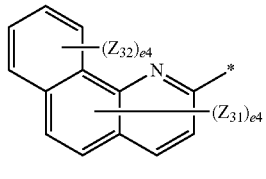
Formula 6-106
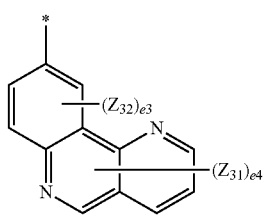
Formula 6-107
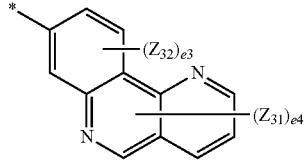
Formula 6-108
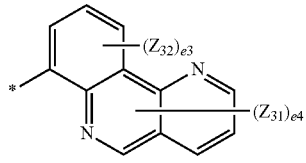
Formula 6-109
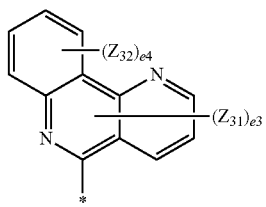
Formula 6-110
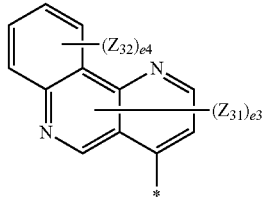

-continued

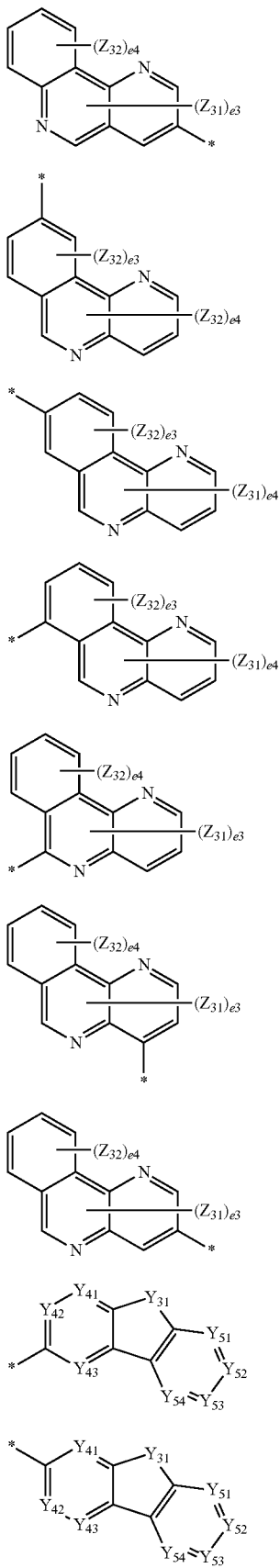

Formula 6-111

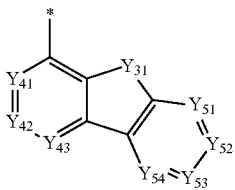

Formula 6-112

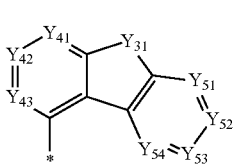

Formula 6-113

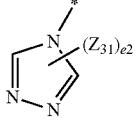

Formula 6-114

Formula 6-115

Formula 6-116

Formula 6-117

Formula 6-118

Formula 6-119

Formula 6-120

Formula 6-121

Formula 6-122

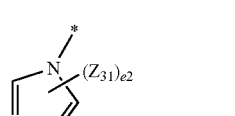

Formula 6-123

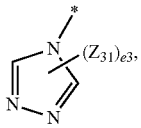

wherein, in Formulae 5-1 to 5-38 and 6-1 to 6-123,
each of $Y_{31}$ and $Y_{32}$ is independently O, S, $C(Z_{33})(Z_{34})$, or $Si(Z_{35})(Z_{36})$,
$Y_{41}$ is N or $C(Z_{41})$, $Y_{42}$ is N or $C(Z_{42})$, $Y_{43}$ is N or $C(Z_{43})$, $Y_{44}$ is N or $C(Z_{44})$, $Y_{51}$ is N or $C(Z_{51})$, $Y_{52}$ is N or $C(Z_{52})$, $Y_{53}$ is N or $C(Z_{53})$, $Y_{54}$ is N or $C(Z_{54})$,
each of $Z_{31}$ to $Z_{36}$, $Z_{41}$ to $Z_{44}$, and $Z_{51}$ to $Z_{54}$ is independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a thiadiazolyl group, an imidazopyridinyl group, an imidazopyrimidinyl group, a benzonaphthyridinyl group, an azafluorenyl group, an azadibenzofuranyl group, an azadibenzothiophenyl group, an azadibenzosilolyl group, and —Si($Q_{31}$)($Q_{32}$)($Q_{33}$), each of $Q_1$ to $Q_3$ and $Q_{31}$ to $Q_{33}$ is independently selected from a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, each of $Q_1$ to $Q_3$ and $Q_{31}$ to $Q_{33}$ is independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, e3 is an integer selected from 0 to 3, e4 is an integer selected from 0 to 4, e5 is an integer selected from 0 to 5, e6 is an integer selected from 0 to 6, e7 is an integer selected from 0 to 7, e8 is an integer selected from 0 to 8, e9 is an integer selected from 0 to 9, and

* indicates a binding site to a neighboring atom.

10. The organic light-emitting device of claim 1, wherein, in Formula 2, each of $R_{51}$ to $R_{54}$ is independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, and a pyridinyl group; and a phenyl group, a biphenyl group, a terphenyl group, a naphthyl group, and a pyridinyl group, each substituted with at least one selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and a pyridinyl group.

11. The organic light-emitting device of claim 1, wherein the first compound is represented by one selected from Formulae 1A(2), 1C(1) to 1C(3), and 1D(1) to 1D(4):

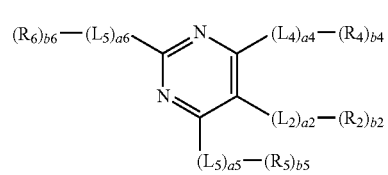

Formula 1A(2)

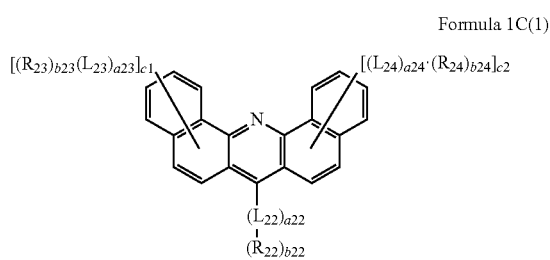

Formula 1C(1)

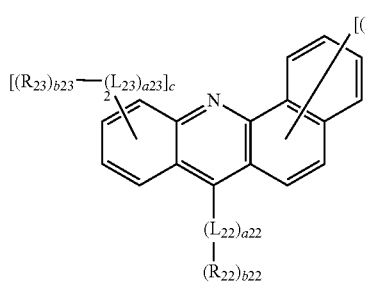

Formula 1C(2)

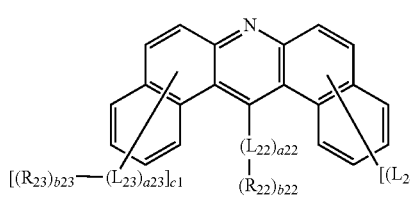

Formula 1C(3)

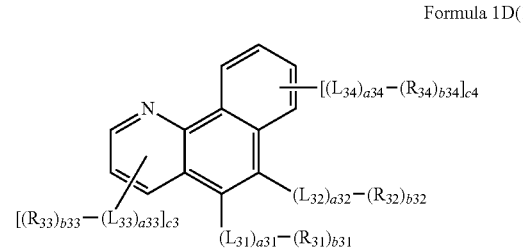

Formula 1D(1)

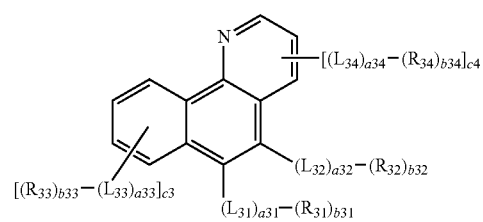

Formula 1D(2)

-continued

Formula 1D(3)

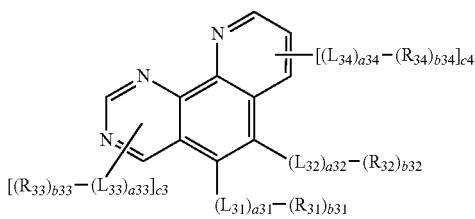

Formula 1D(4)

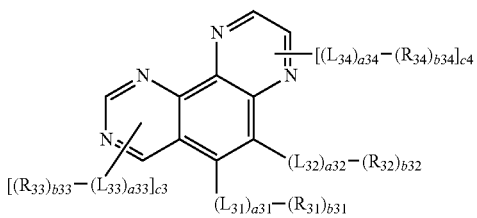

wherein, in Formulae 1A(2), 1C(1) to 1C(3), and 1D(1) to 1D(4), $L_2$ to $L_6$, $L_{11}$ to $L_{20}$, $L_{22}$ to $L_{24}$, $L_{31}$ to $L_{34}$, a2 to a6, a11 to a20, a22 to a24, a31 to a34, $R_3$ to $R_6$, $R_{11}$ to $R_{20}$, $R_{22}$ to $R_{24}$, $R_{31}$ to $R_{34}$, b3 to b6, b11 to b20, b22 to b24, b31 to b34, and c1 to c4 are understood by referring to the descriptions thereof provided in claim 1.

12. The organic light-emitting device of claim 1, wherein the second compound is represented by one selected from Formulae 2A to 2D:

Formula 2A

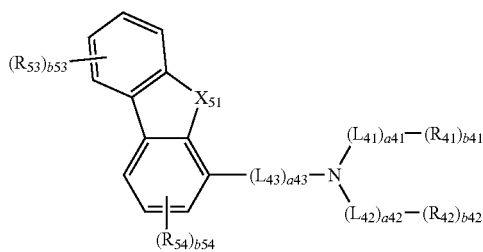

Formula 2B

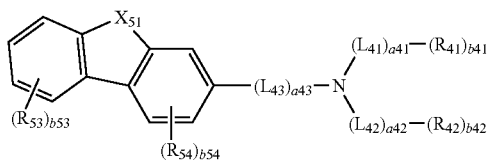

Formula 2C

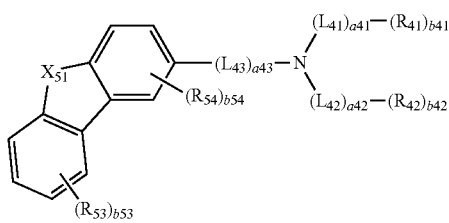

-continued

Formula 2D

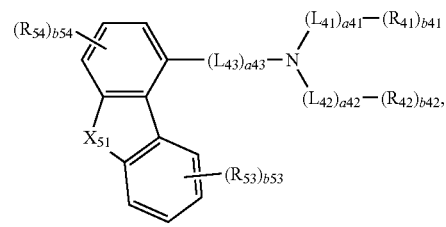

wherein, in Formulae 2A to 2D, $X_{51}$, $L_{41}$ to $L_{43}$, a41 to a43, $R_{41}$, $R_{42}$, $R_{53}$, $R_{54}$, b41, b42, b53, and b54 are understood by referring to the descriptions thereof provided in claim 1.

13. The organic light-emitting device of claim 1, wherein the electron transport region comprises an electron transport layer and an electron injection layer,
wherein the electron transport layer is disposed between the emission layer and the electron injection layer, and the electron transport layer comprises the first compound.

14. The organic light-emitting device of claim 13, wherein the electron transport layer further comprises an alkali metal, an alkaline earth metal, a rare-earth-metal, an alkali metal compound, an alkaline earth metal compound, a rare-earth-metal compound, an alkali metal complex, an alkaline earth metal complex, a rare-earth-metal complex, or a combination thereof.

15. The organic light-emitting device of claim 13, wherein the electron injection layer comprises an alkali metal, an alkaline earth metal, a rare-earth-metal, alkali metal compound, an alkaline earth metal compound, a rare-earth-metal compound, an alkali metal complex, an alkaline earth metal complex, a rare-earth-metal complex, or a combination thereof.

16. The organic light-emitting device of claim 15, wherein the electron injection layer comprises Li, Na, K, Rb, Cs, Mg, Ca, Er, Tm, Yb, or a combination thereof.

17. The organic light-emitting device of claim 15, wherein the hole transport region comprises an emission auxiliary layer,
wherein the emission auxiliary layer directly contacts the emission layer and comprises the second compound.

18. The organic light-emitting device of claim 1, wherein the hole transport region comprises a p-dopant,
wherein a lowest unoccupied molecular orbital (LUMO) level of the p-dopant is about −3.5 eV or less.

19. The organic light-emitting device of claim 18, wherein the p-dopant comprises a cyano group-containing compound.

20. The organic light-emitting device of claim 1, wherein the emission layer is a first-color-light emission layer, and the organic light-emitting device comprises, between the first electrode and the second electrode, i) at least one second-color-light emission layer or ii) at least one second-color-light emission layer and at least one third-color-light emission layer,
wherein a maximum emission wavelength of the first-color-light emission layer, a maximum emission wavelength of the second-color-light emission layer, and a maximum emission wavelength of the third-color-light emission are identical to or different from each other, and
the organic light-emitting device emits mixed light including first-color-light and second-color-light, or mixed light including first-color-light, second-color-light, and third-color-light.

21. An organic light-emitting device comprising:
a first electrode;
a second electrode facing the first electrode;
an emission layer between the first electrode and the second electrode;
a hole transport region between the first electrode and the emission layer; and
an electron transport region between the emission layer and the second electrode,
wherein the electron transport region comprises a first compound represented by one selected from Formulae 1A to 1D, and
the hole transport region comprises a second compound represented by Formula 2:

<Formula 1A>

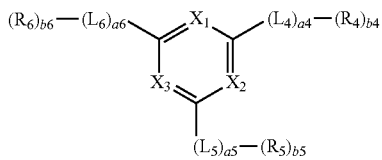

<Formula 1B>

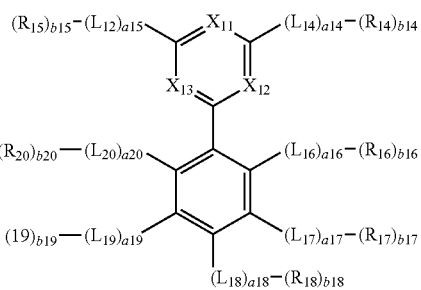

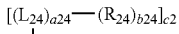

<Formula 1C>

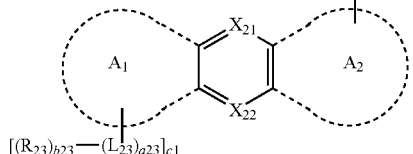

<Formula 1D>

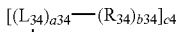

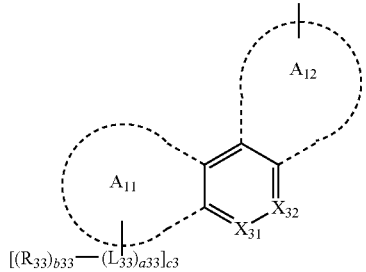

<Formula 2>

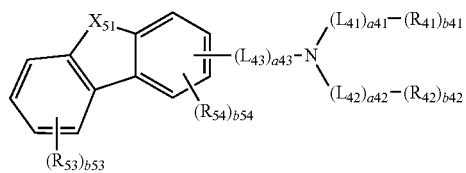

wherein, in Formulae 1A to 1D and 2,
each of ring $A_1$ and ring $A_2$ is independently a $C_5$-$C_{60}$ carbocyclic group or a $C_1$-$C_{30}$ heterocyclic group,
each of ring $A_{11}$ and ring $A_{12}$ is independently a $C_1$-$C_{30}$ heterocyclic group,
$X_1$ is selected from N and C-[$(L_1)_{a1}$-$(R_1)_{b1}$], $X_2$ is selected from N and C-[$(L_2)_{a2}$-$(R_2)_{b2}$], and $X_3$ is selected from N and C-[$(L_3)_{a3}$-$(R_3)_{b3}$], wherein at least one selected from $X_1$ to $X_3$ is N,
$X_{11}$ is selected from N and C-[$(L_{11})_{a11}$-$(R_{11})_{b11}$], $X_{12}$ is selected from N and C-[$(L_{12})_{a12}$-$(R_{12})_{b12}$], $X_{13}$ is selected from N and C-[$(L_{13})_{a13}$-$(R_{13})_{b13}$], wherein at least one selected from $X_{11}$ to $X_{13}$ is N,
$X_{21}$ is selected from N and C-[$(L_{21})_{a21}$-$(R_{21})_{b21}$], and $X_{22}$ is selected from N and C-[$(L_{22})_{a22}$-$(R_{22})_{b22}$], wherein at least one of $X_{21}$ and $X_{22}$ is N,
$X_{31}$ is selected from N and C-[$(L_{31})_{a31}$-$(R_{31})_{b31}$], and $X_{32}$ is selected from N and C-[$(L_{32})_{a32}$-$(R_{32})_{b32}$],
$X_{51}$ is selected from Se, and Si($R_{51}$)($R_{52}$),
$L_1$ to $L_6$, $L_{11}$ to $L_{24}$, $L_{31}$ to $L_{34}$, and $L_{43}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
each of $L_{41}$ and $L_{42}$ in Formula 2 is independently selected from:
a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group; and
a phenylene group, a pentalenylene group, an indenylene group, a naphthylene group, an azulenylene group, an indacenylene group, an acenaphthylene group, a phenalenylene group, a phenanthrenylene group, an anthracenylene group, a triphenylenylene group, a pyrenylene group, a chrysenylene group, a perylenylene group, a pentaphenylene group, a pyrrolylene group, a thiophenylene group, a furanylene group, a silolylene group, a pyridinylene group, an indolylene group, an isoindolylene group, a purinylene group, a benzofuranylene group, a benzothiophenylene group, a benzosilolylene group, a dibenzofuranylene group, a dibenzothiophenylene group, and a dibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, $-Si(Q_{31})(Q_{32})(Q_{33})$, $-N(Q_{31})(Q_{32})$, and $-B(Q_{31})(Q_{32})$, each of a1 to a6, a11 to a24, a31 to a34, and a41 to a43 is independently an integer selected from 0 to 5, each of $R_1$ to $R_6$, $R_{11}$ to $R_{24}$, $R_{31}$ to $R_{34}$, and $R_{51}$ to $R_{54}$ is independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, each of $R_{41}$ and $R_{42}$ is independently selected from a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a phenalenyl group, a phenanthrenyl group, an anthracenyl group, a triphenylenyl group, a pyrenyl group, a chrysenyl group, a perylenyl group, a pentaphenyl group, a pyrrolyl group, a thiophenyl group, a furanyl group, a silolyl group, a pyridinyl group, an indolyl group, an isoindolyl group, a purinyl group, a benzofuranyl group, a benzothiophenyl group, a benzosilolyl group, a dibenzofuranyl group, a dibenzothiophenyl group, a dibenzosilolyl group, $-Si(Q_{31})(Q_{32})(Q_{33})$, $-N(Q_{31})(Q_{32})$, and $-B(Q_{31})(Q_{32})$, each of b1 to b6, b11 to b24, b31 to b34, b53, and b54 is independently an integer selected from 0 to 5, each of b41 and b42 is independently an integer selected from 1 to 5, each of c1 to c4 is independently an integer selected from 1 to 10, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group, wherein neither of a carbazole ring and a spiro-bifluorene ring is comprised in Formulae 1A to 1D, and neither of a carbazole ring and a fluorene ring is comprised in Formula 2, and the carbazole ring that is not comprised in Formulae 1A to 1D and 2 includes:

a carbazolylene group, a benzocarbazolylene group, a dibenzocarbazolylene group, an azacarbazolylene group, a carbazolyl group, a benzocarbazolyl group, a dibenzocarbazolyl group, and an azacarbazolyl group; and a carbazolylene group, a benzocarbazolylene group, a dibenzocarbazolylene group, an azacarbazolylene group, a carbazolyl group, a benzocarbazolyl group, a dibenzocarbazolyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$).

22. An organic light-emitting device comprising:

a first electrode;

a second electrode facing the first electrode;

an emission layer between the first electrode and the second electrode;

a hole transport region between the first electrode and the emission layer; and an electron transport region between the emission layer and the second electrode, wherein the electron transport region comprises a first compound represented by one selected from Compounds 1-1 to 1-24, 1-26 to 1-241, 1-243, and 1-245 to 1-261, and the hole transport region comprises a second compound selected from Compounds 2-1 to 2-6, 2-8 to 2-14, 2-17, 2-18, 2-20 to 2-25, and 2-27 to 2-110:

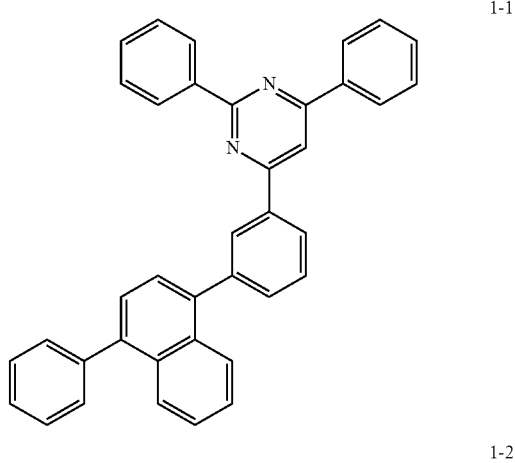

1-1

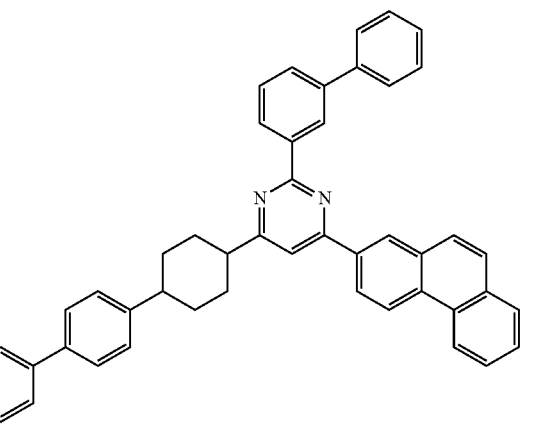

1-2

1-3
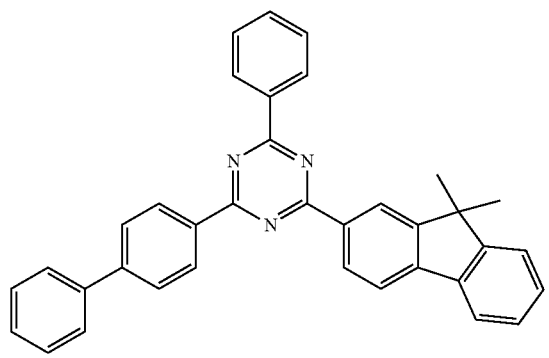
1-4
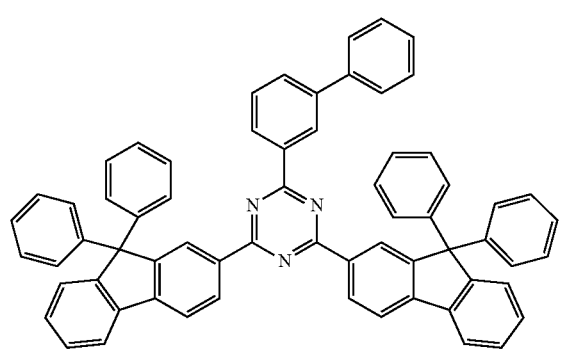
1-5
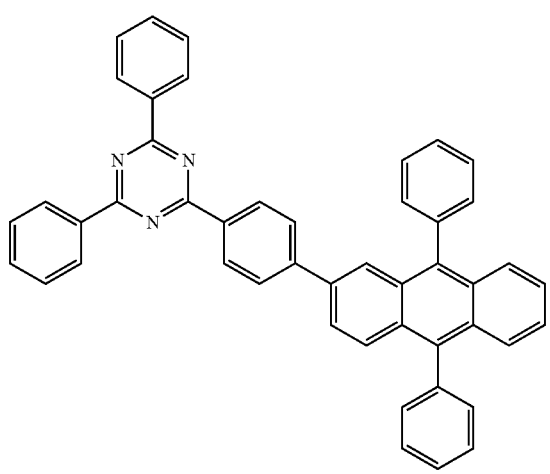
1-6
1-7
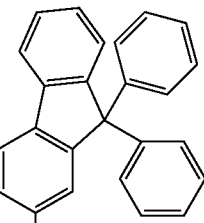
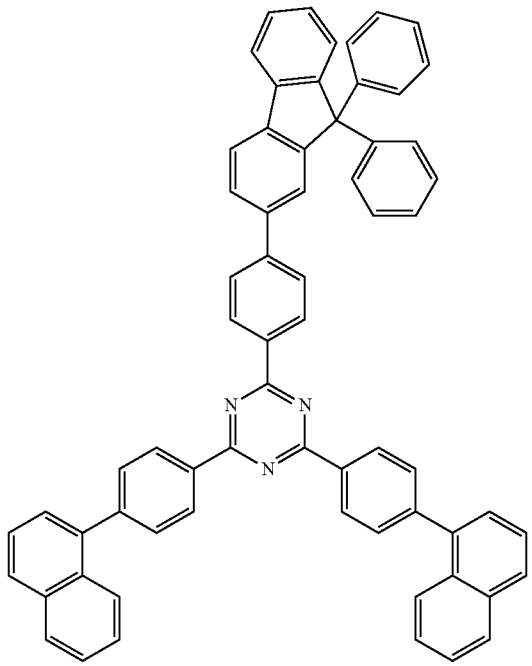
1-8
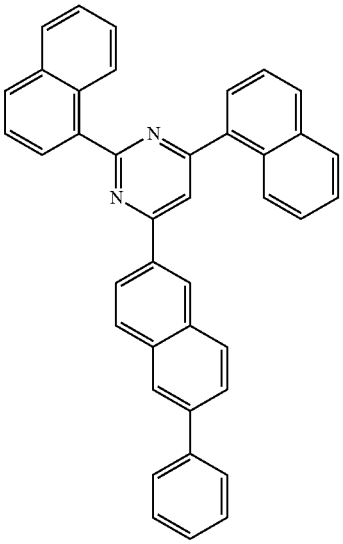
1-9
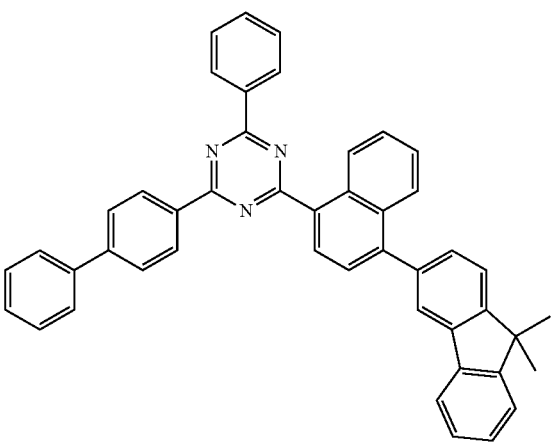

1-10
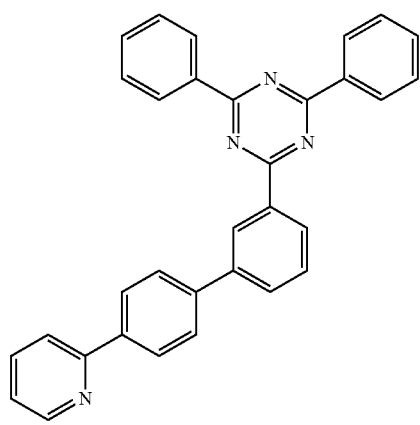
1-11
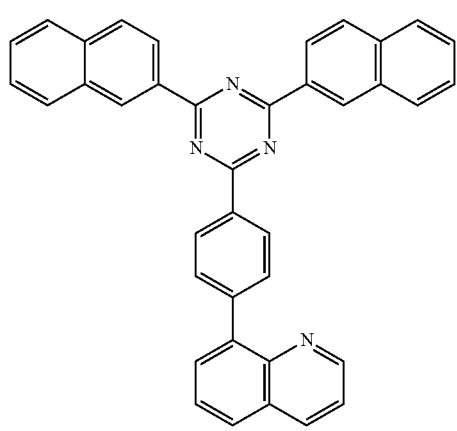
1-12
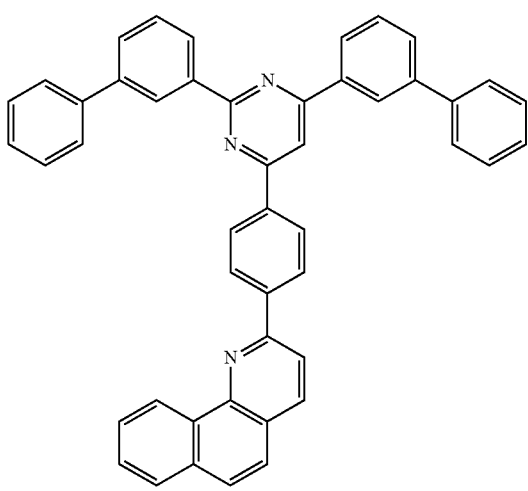
1-13
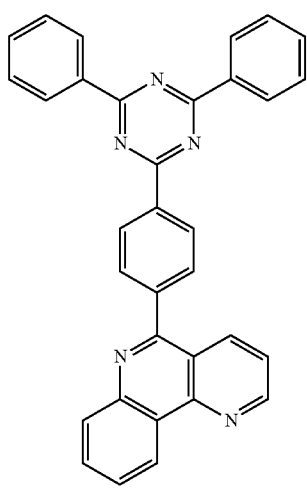
1-14
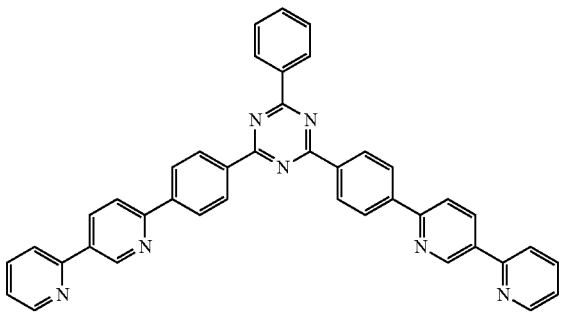
1-15
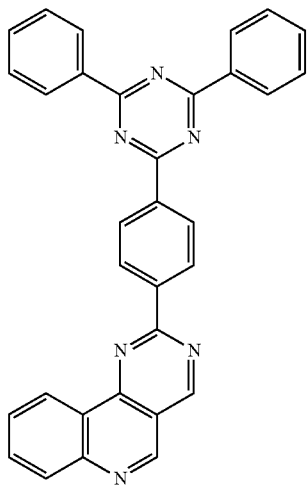

1-16
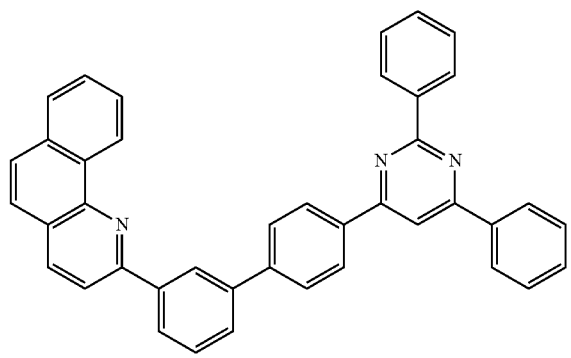
1-17
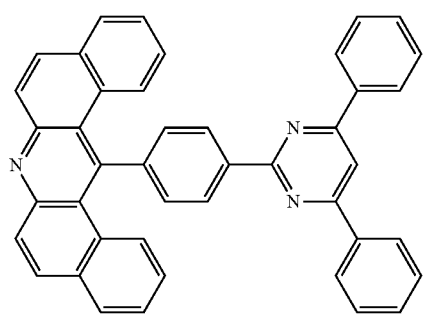
1-18
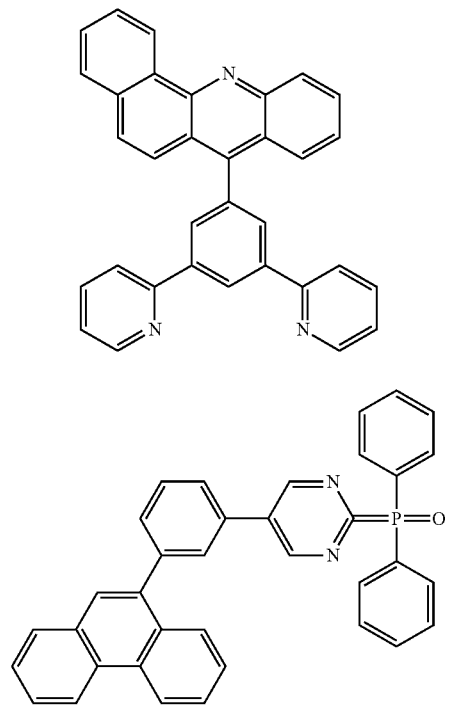
1-19
1-20
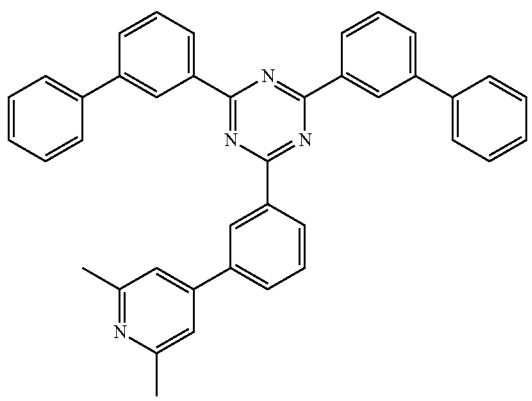
1-21
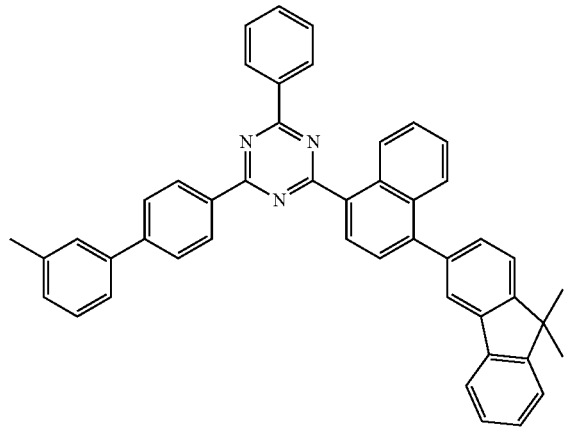
1-22
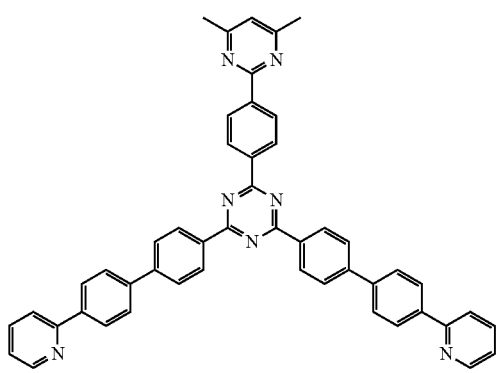

1-23
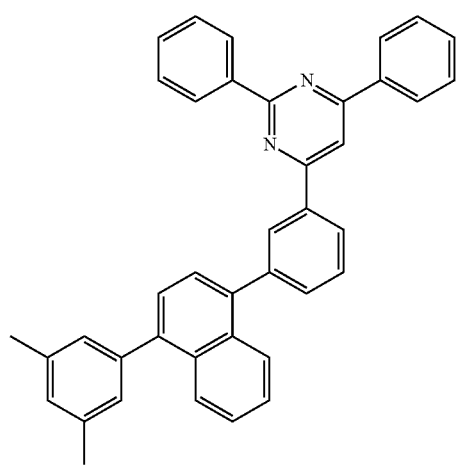
1-24
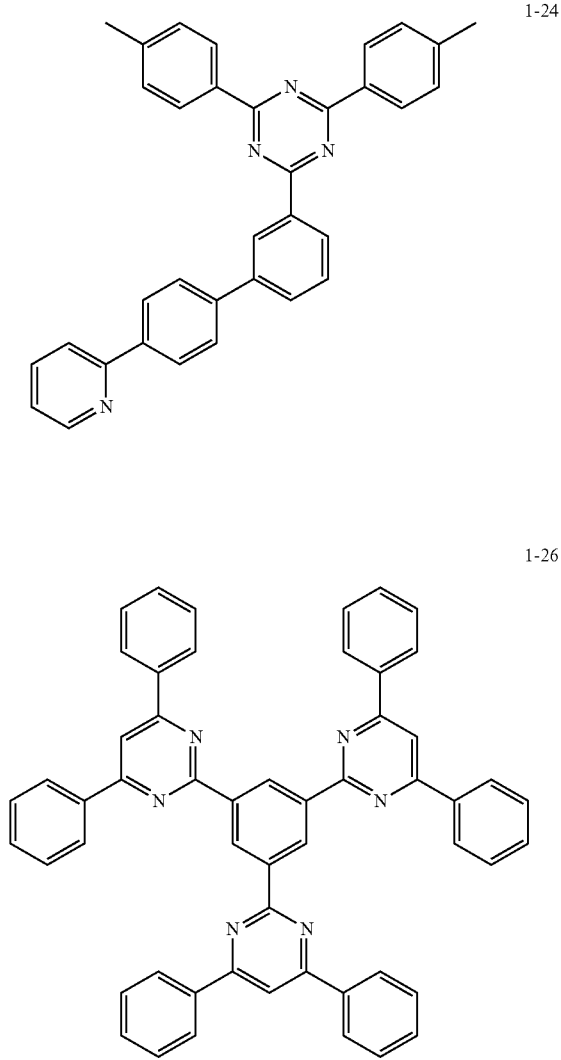
1-26
1-27
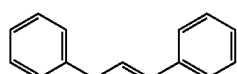
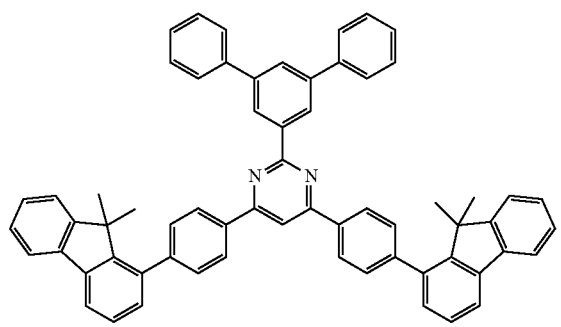
1-28
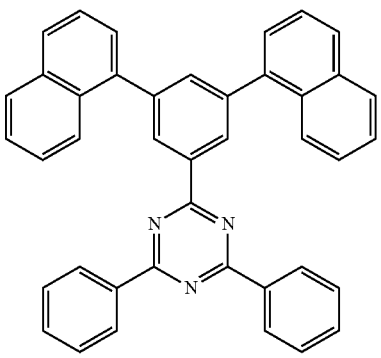
1-29
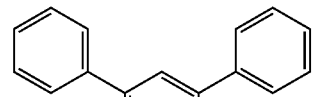
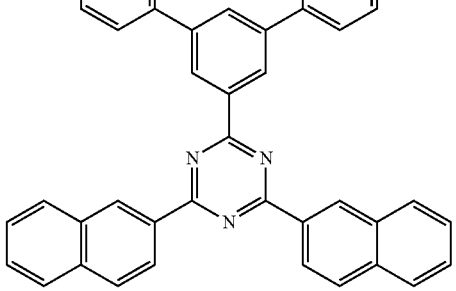
1-30
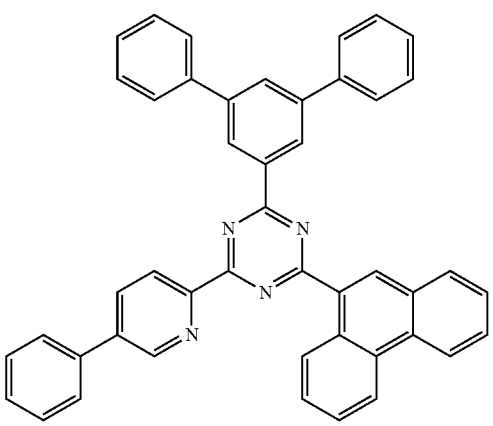

1-31
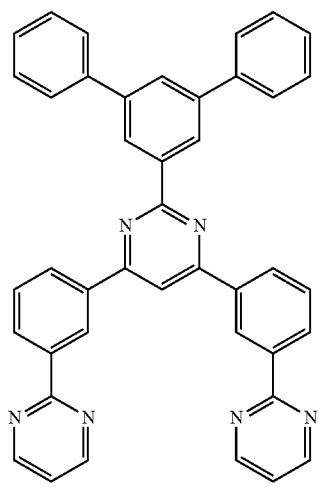
1-32
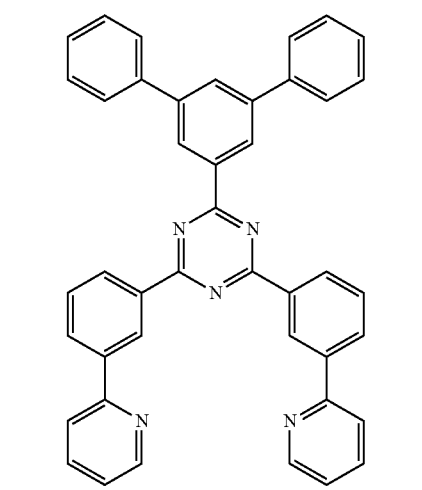
1-33
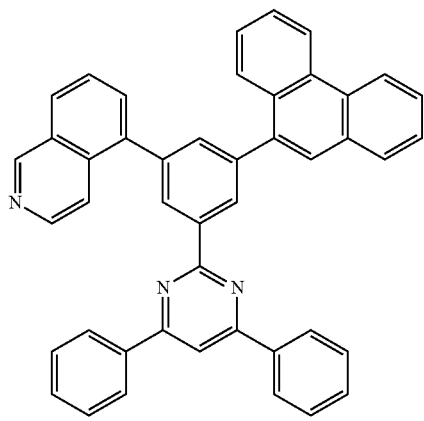
1-34
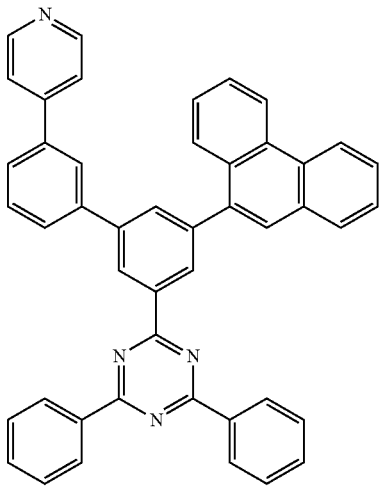
1-35
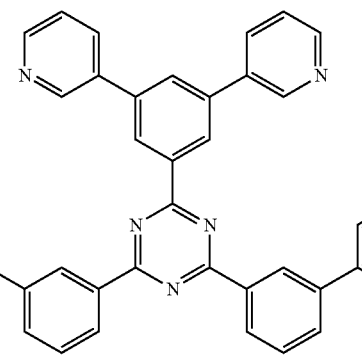
1-36
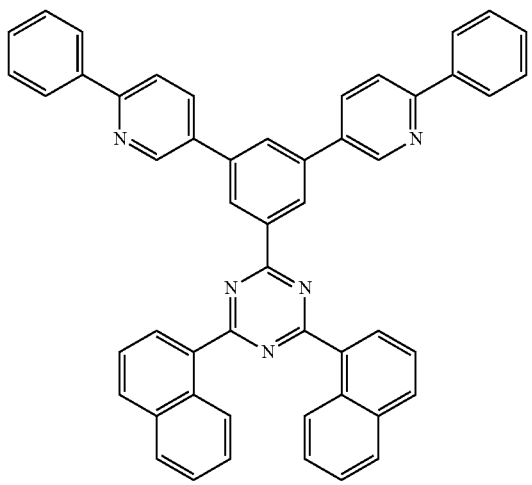

1-37
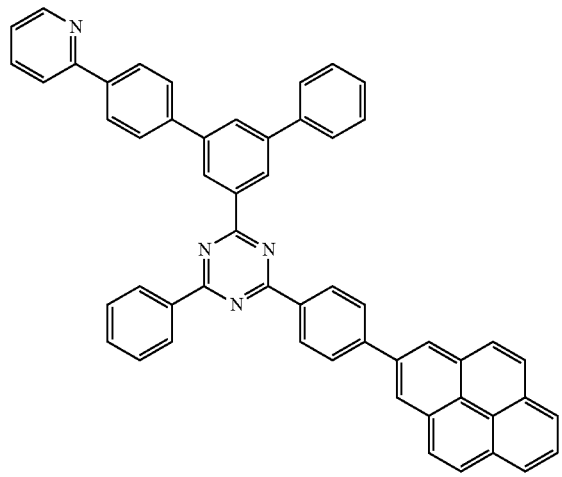
1-40
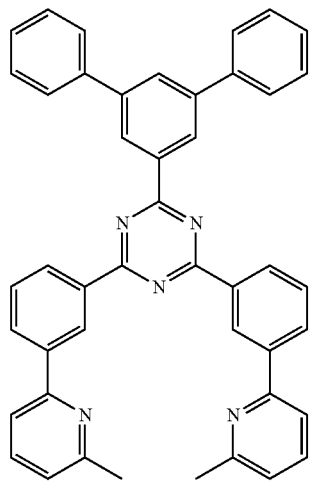
1-38
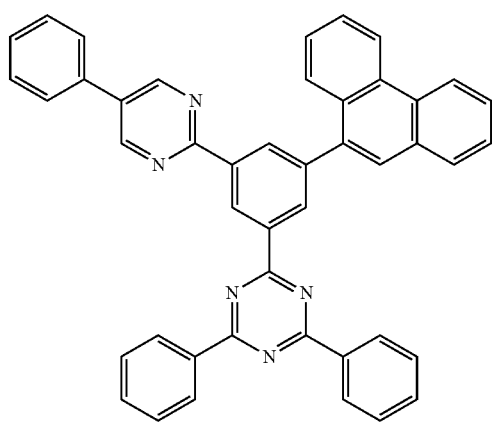
1-41
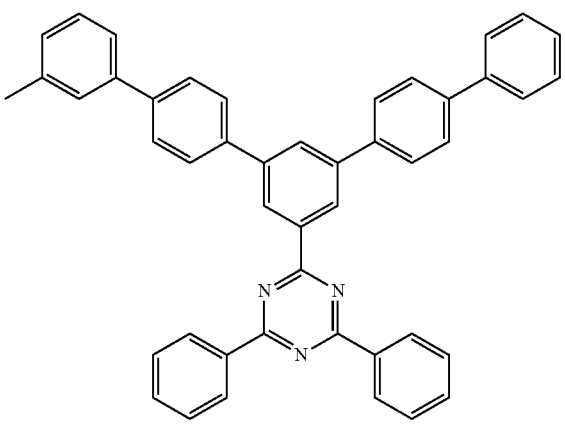
1-39
1-42
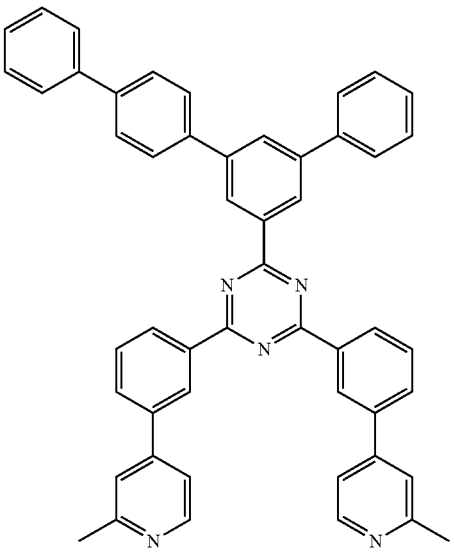

1-43
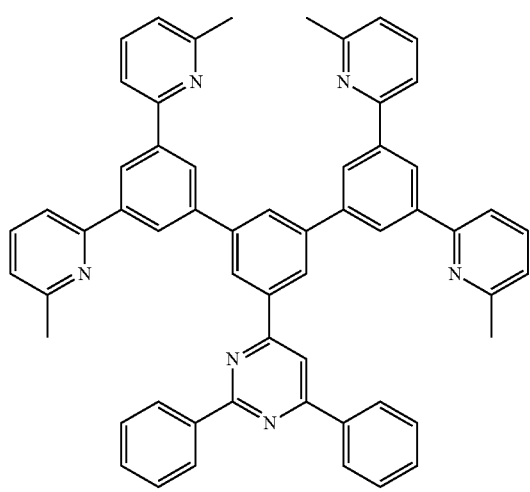
1-44
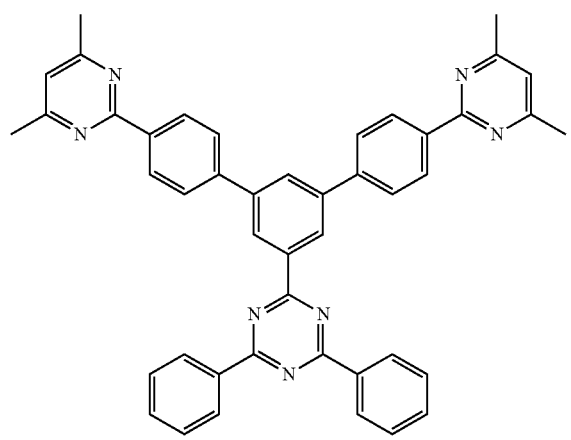
1-45
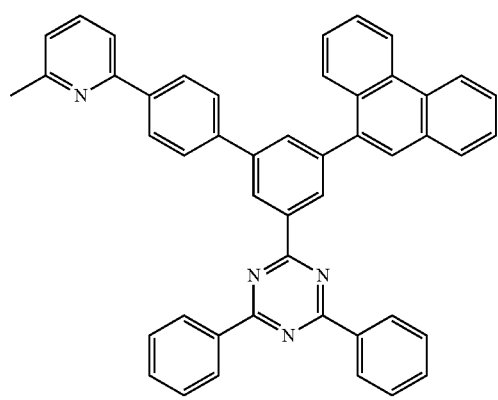
1-46
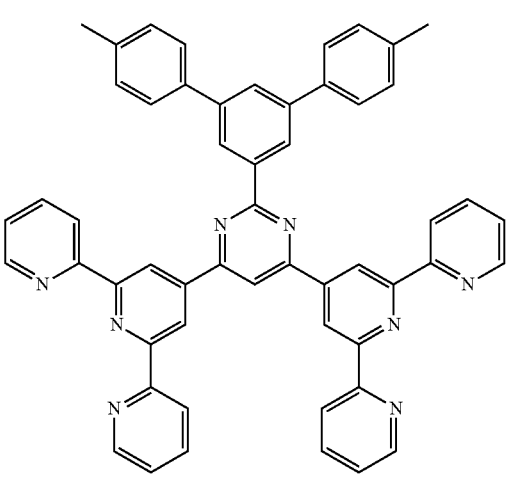
1-47
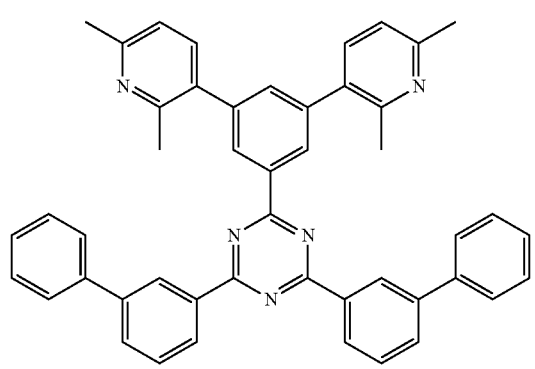
1-48
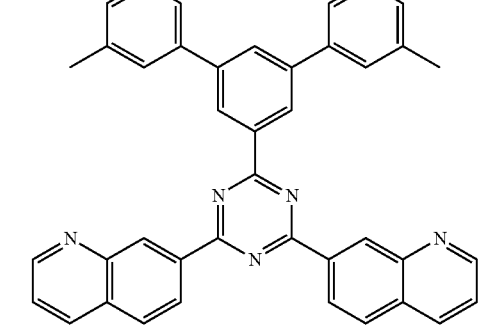
1-49
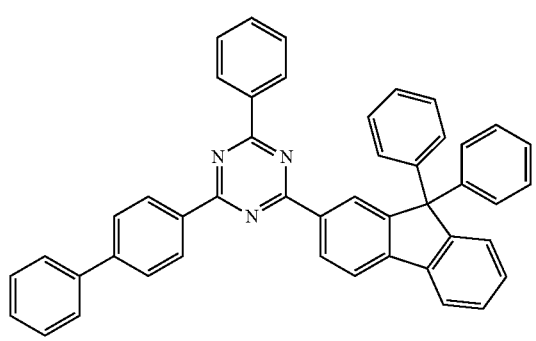

1-50 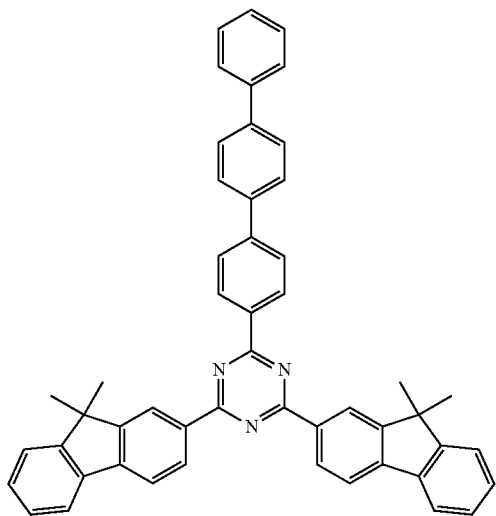
1-51 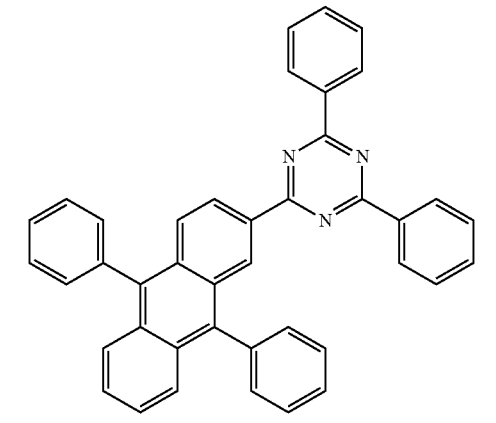
1-52 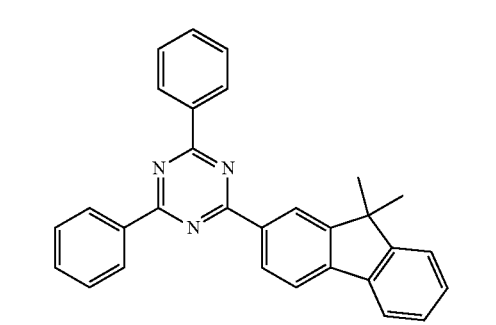
1-53 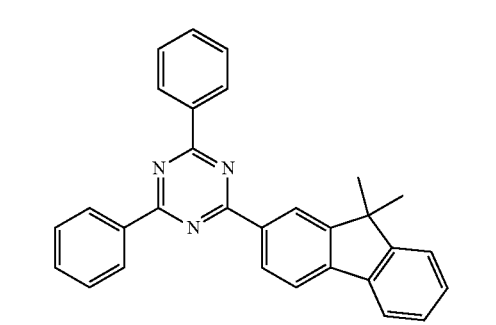
1-54 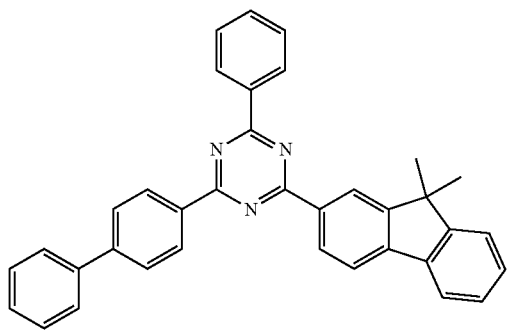
1-55 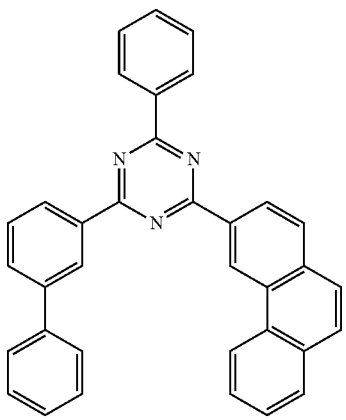
1-56 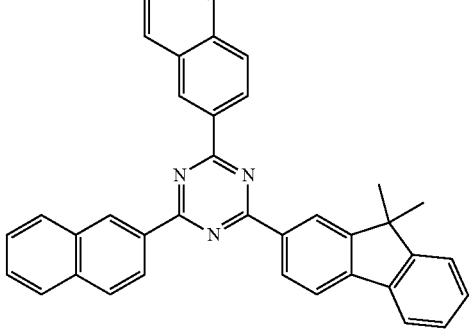
1-57 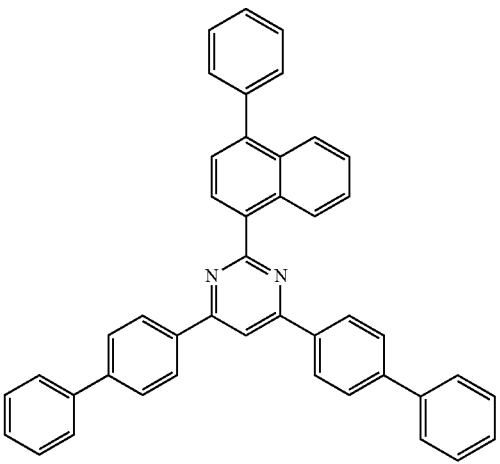

1-58
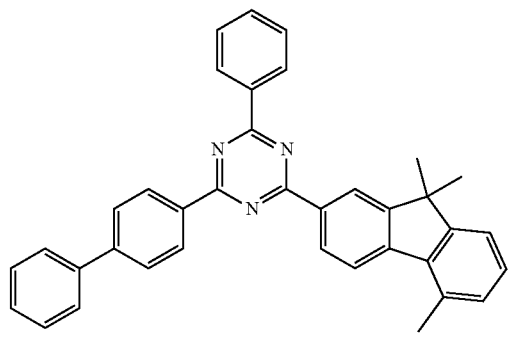
1-59
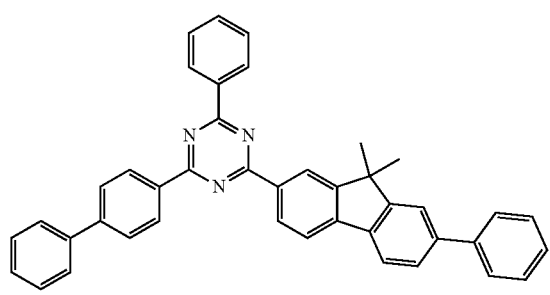
1-60
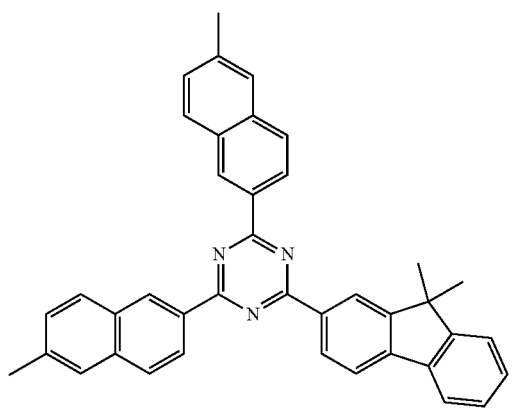
1-61
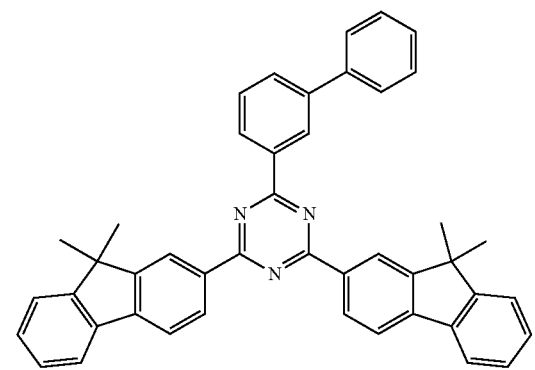
1-62
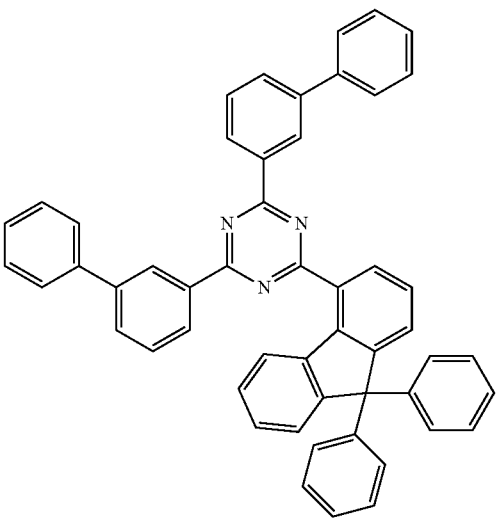
1-63
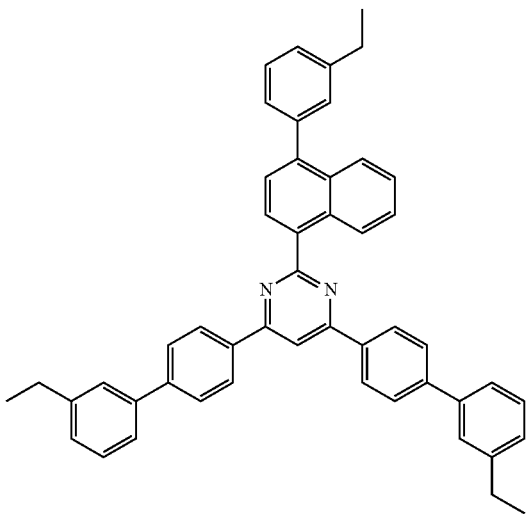
1-64
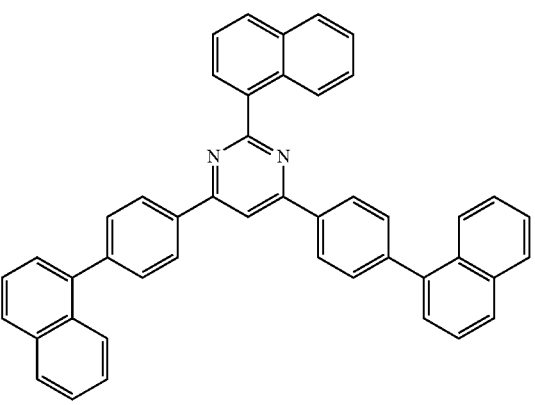

1-65
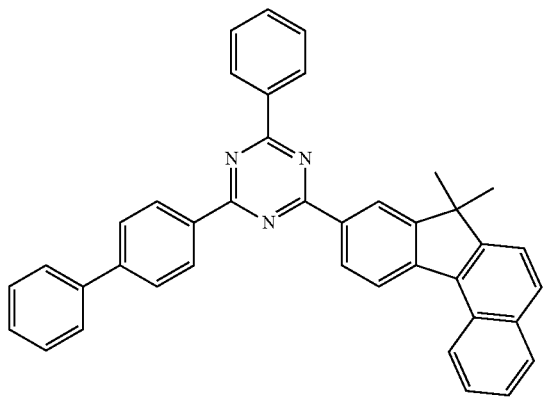
1-66
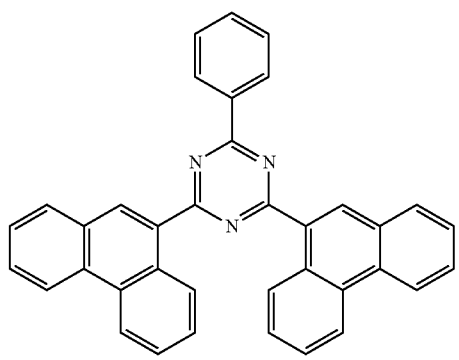
1-67
1-68
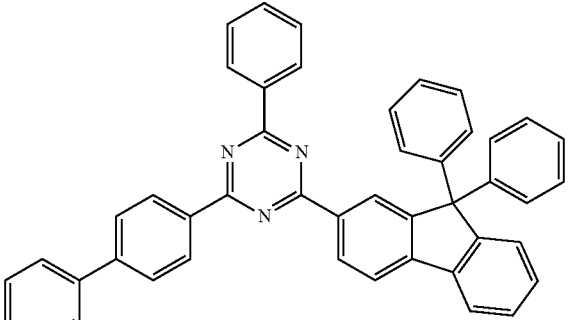
1-69
1-70
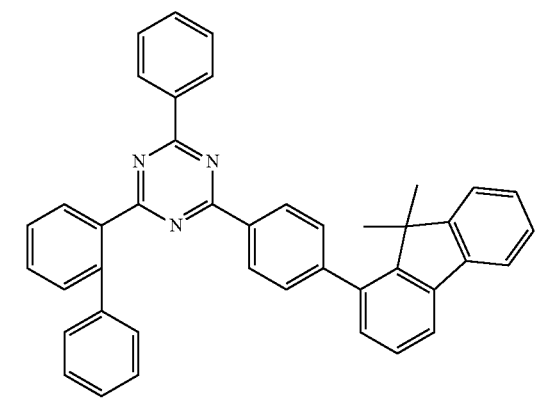
1-71
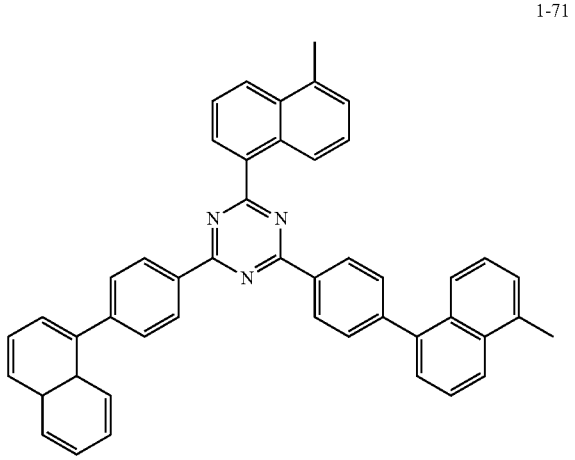

1-72
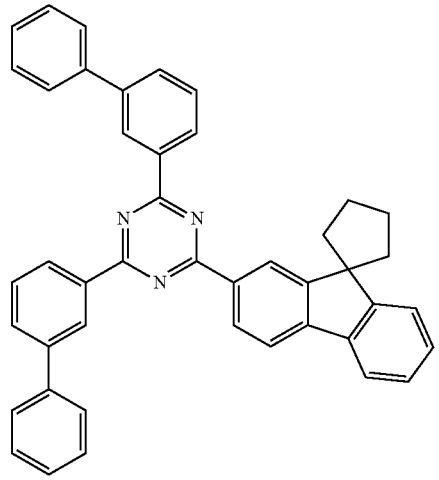
1-73
1-75
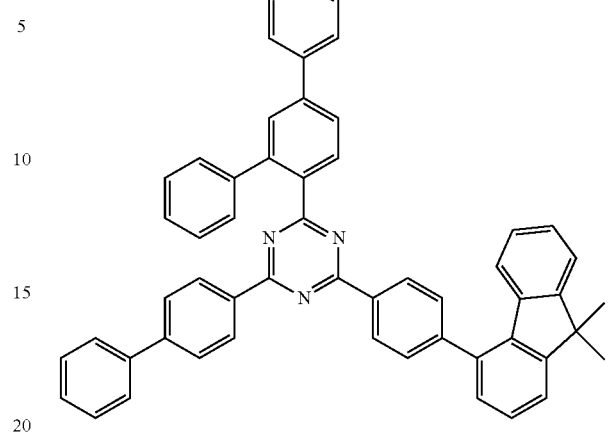
1-76
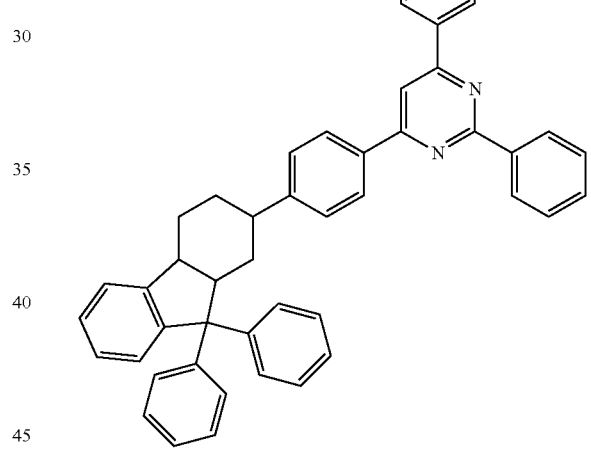
1-74
1-77
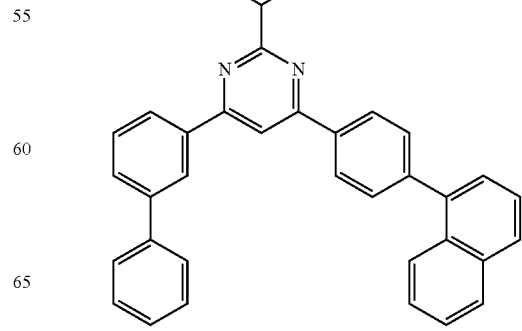

1-78
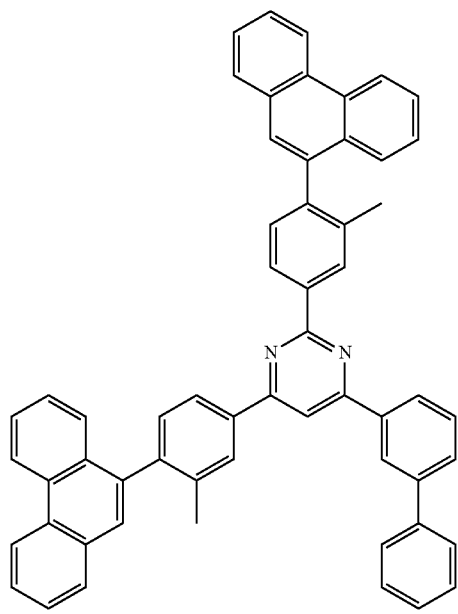
1-79
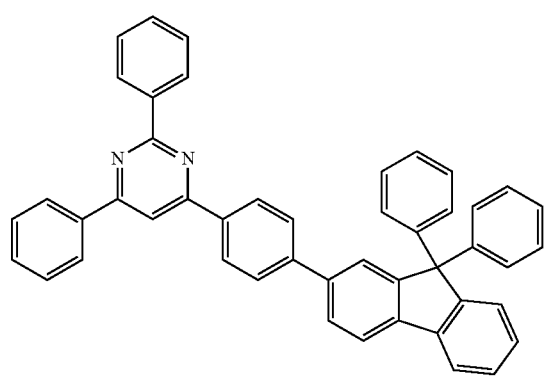
1-80
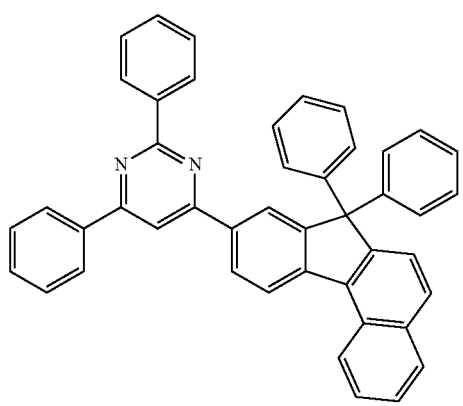
1-81
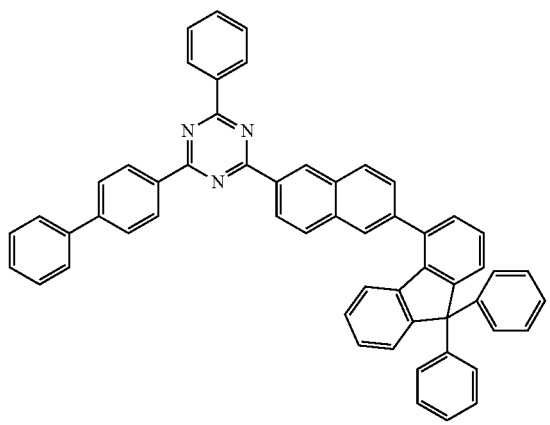
1-82
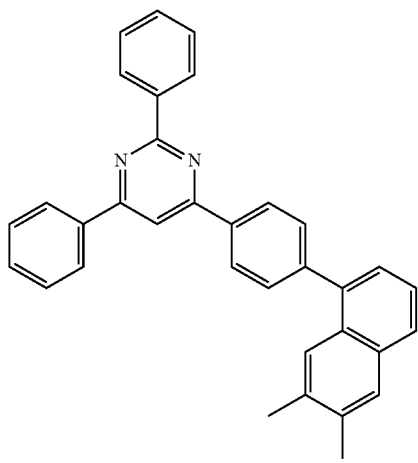
1-83
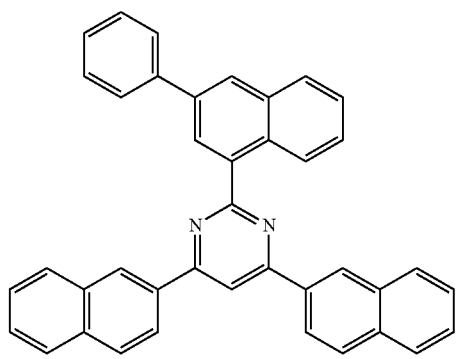

1-84
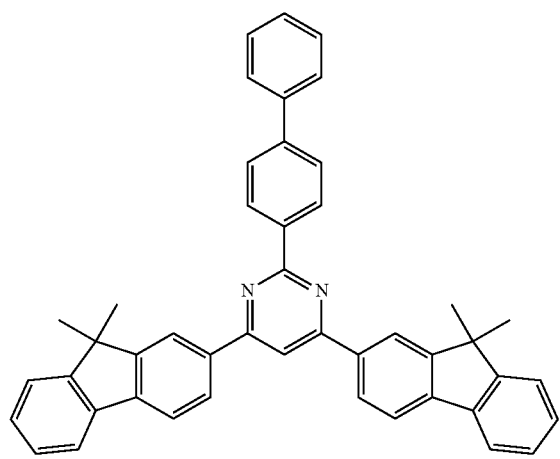
1-85
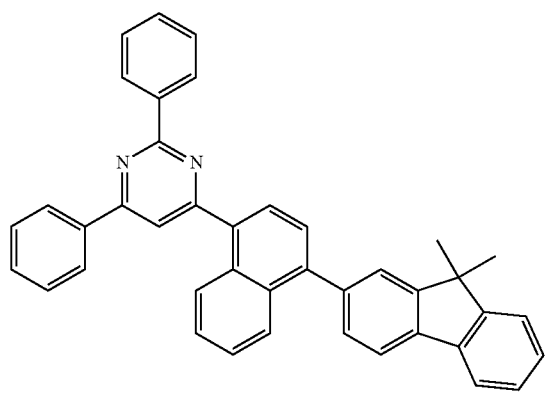
1-86
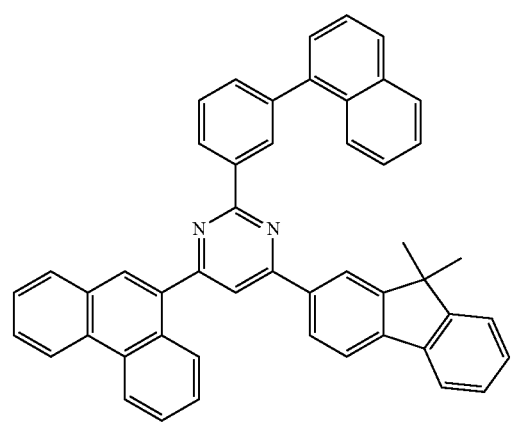
1-87
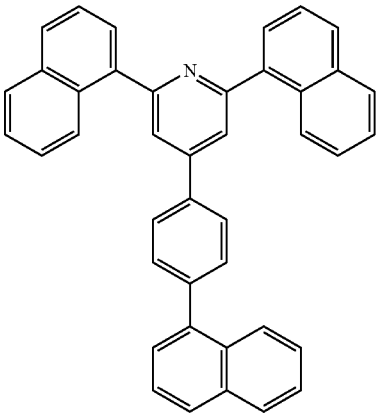
1-88
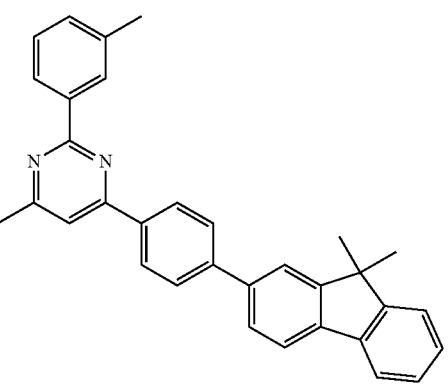
1-89
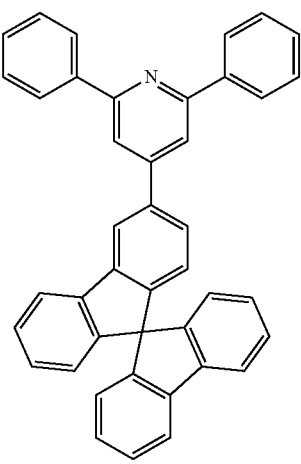

1-90
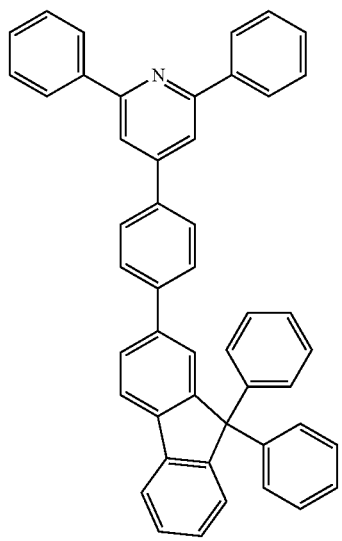
1-91
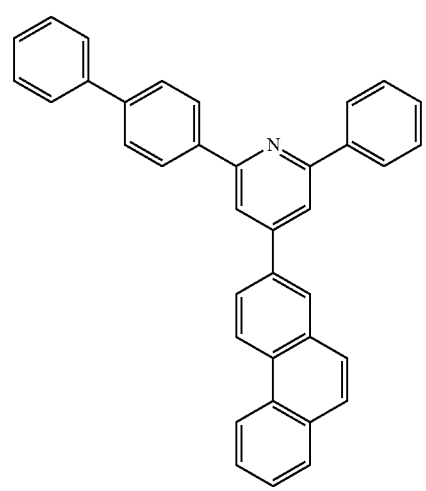
1-92
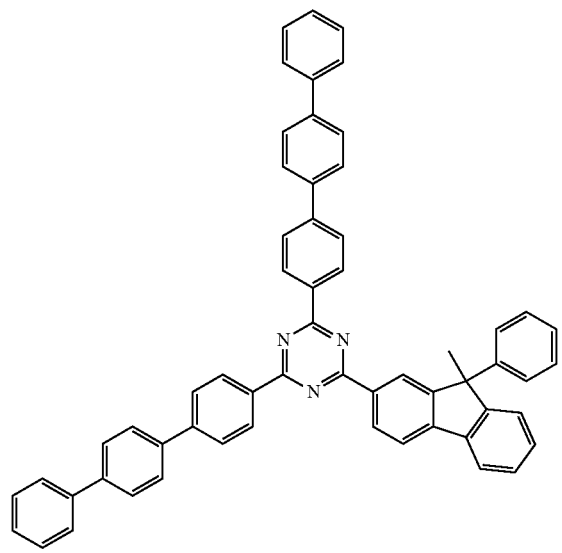
1-93
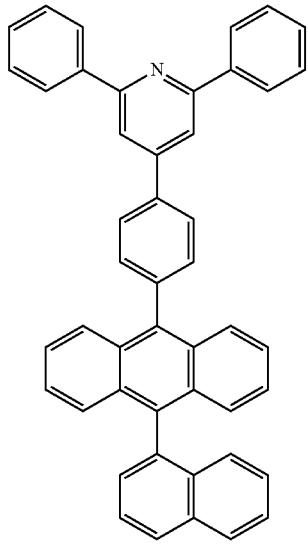
1-94
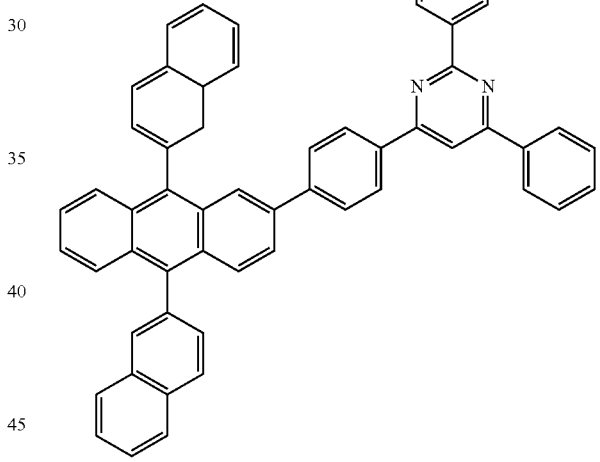
1-95
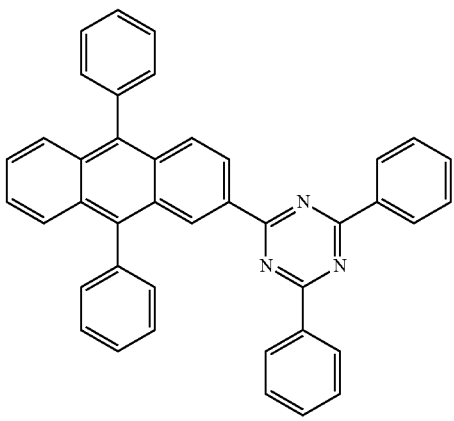

1-96
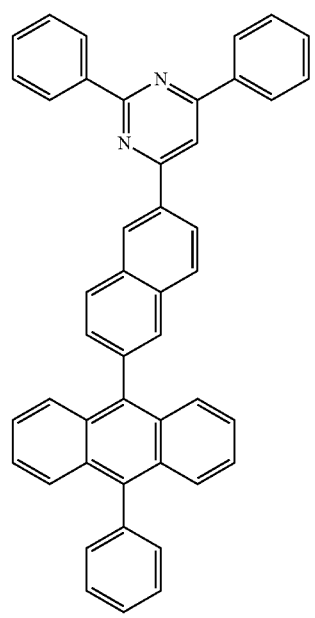
1-97
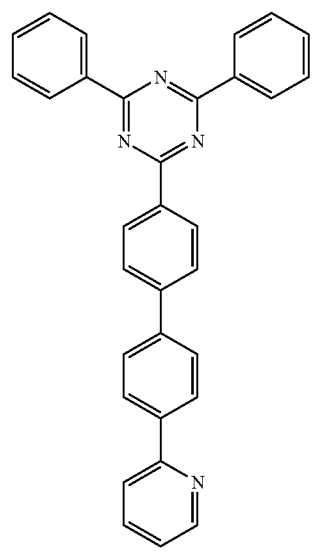
1-98
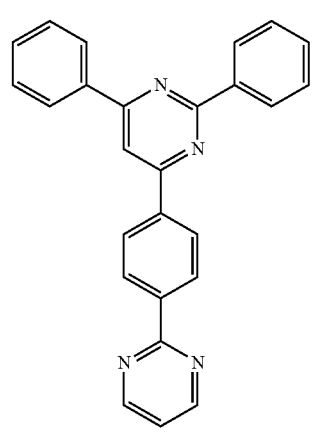
1-99
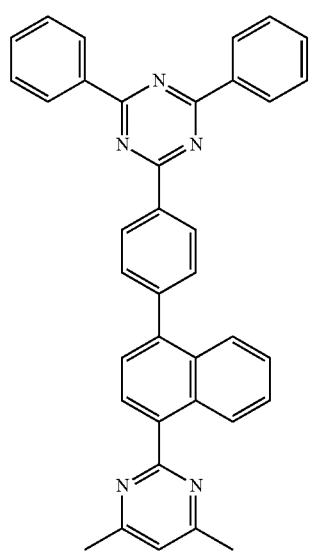
1-100
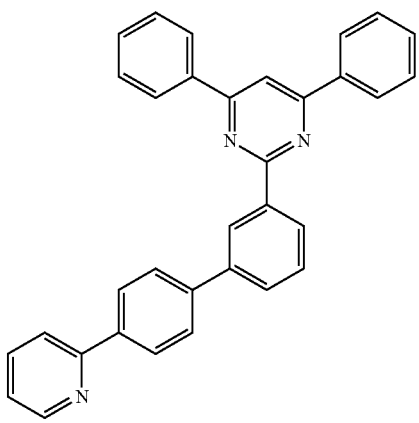
1-101
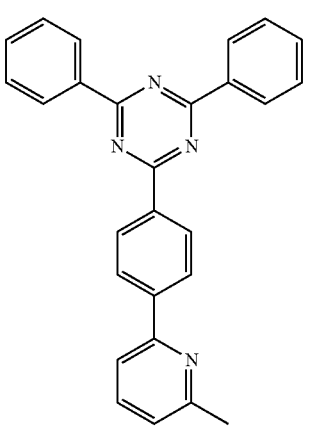

1-102
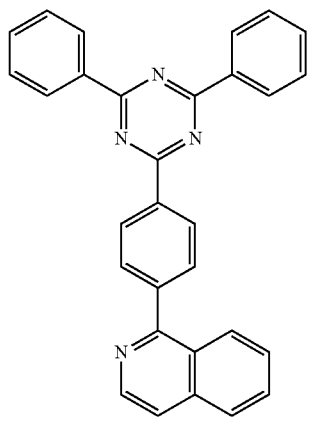
1-103
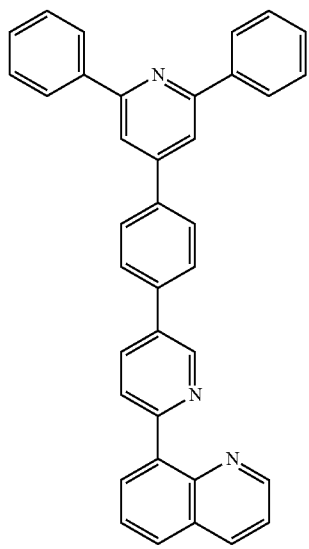
1-104
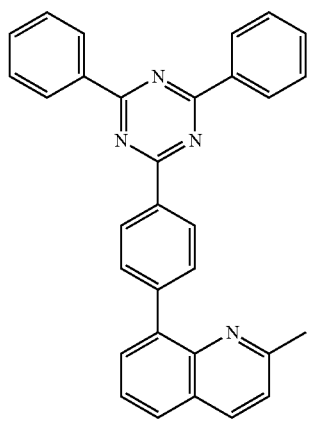
1-105
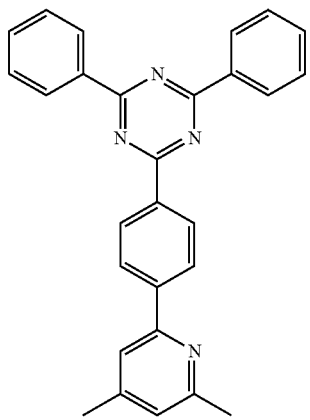
1-106
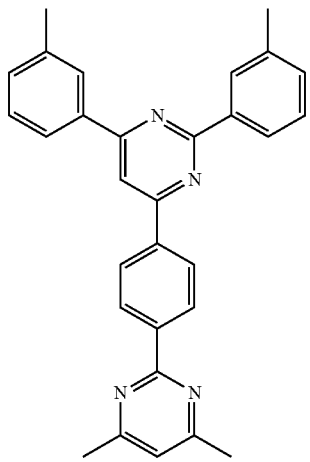
1-107
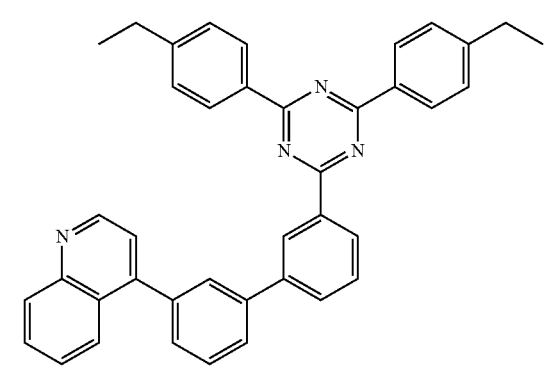

1-108
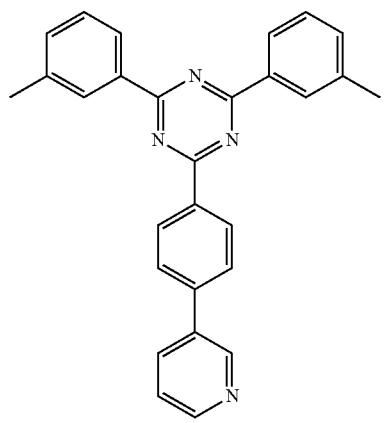
1-109
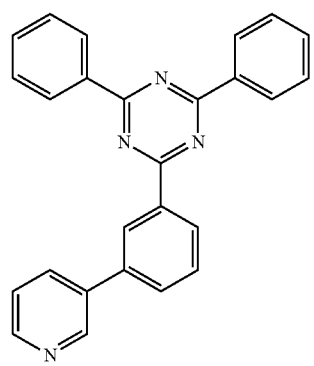
1-110
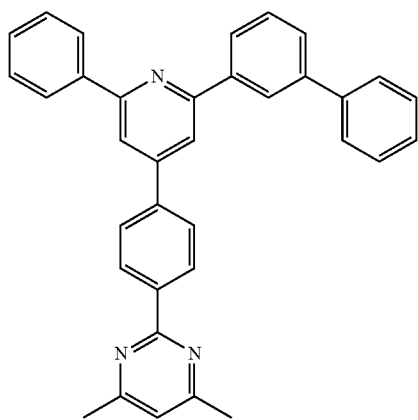
1-111
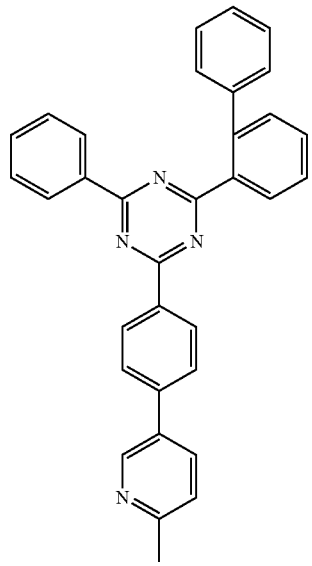
1-112
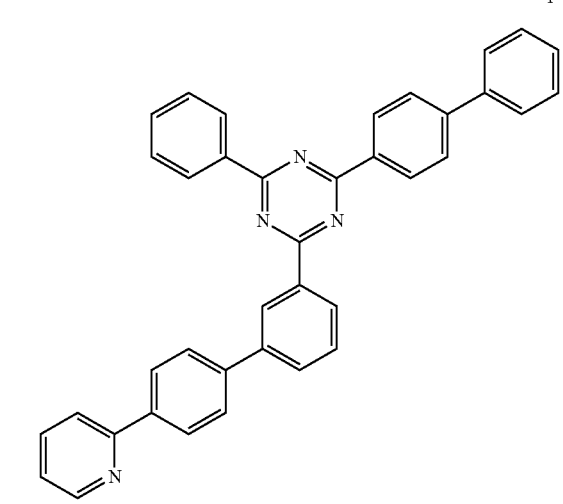
1-113
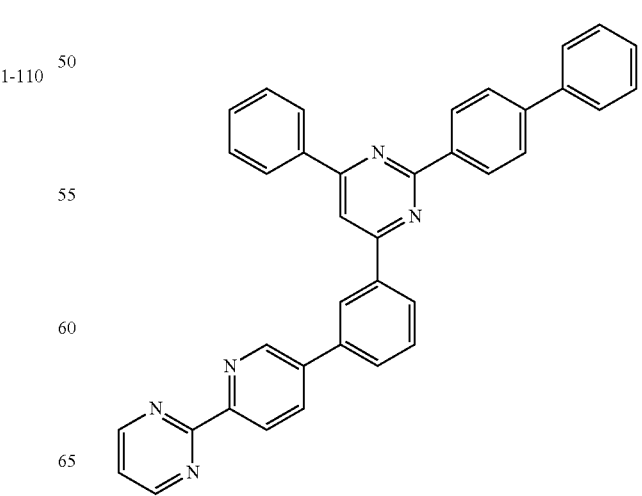

1-114
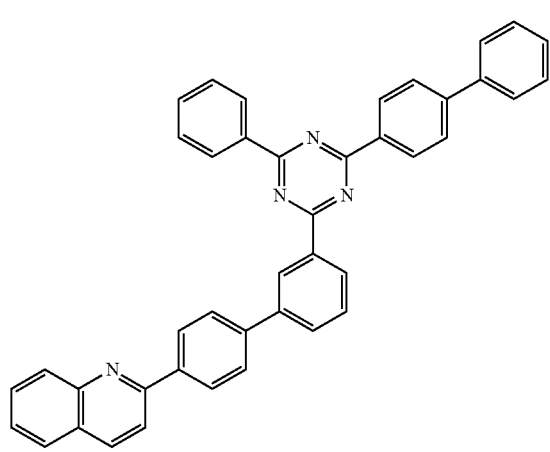
1-115
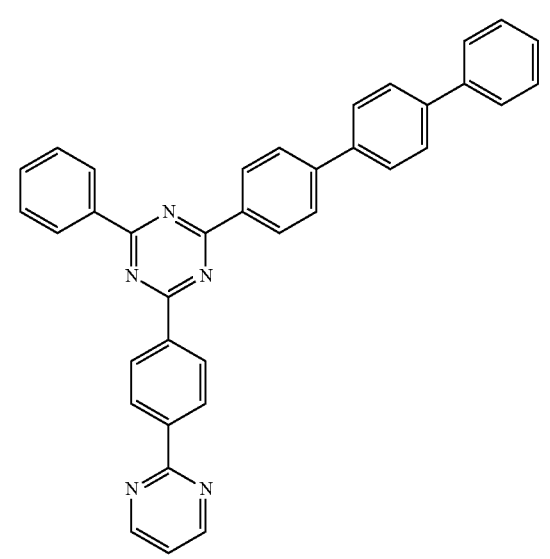
1-116
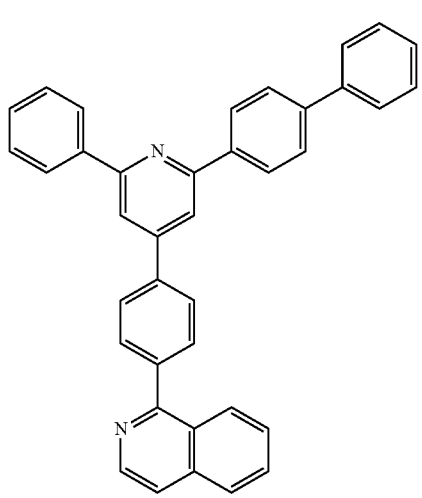
1-117
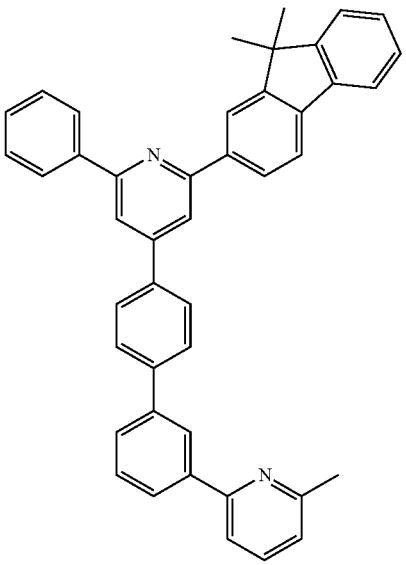
1-118
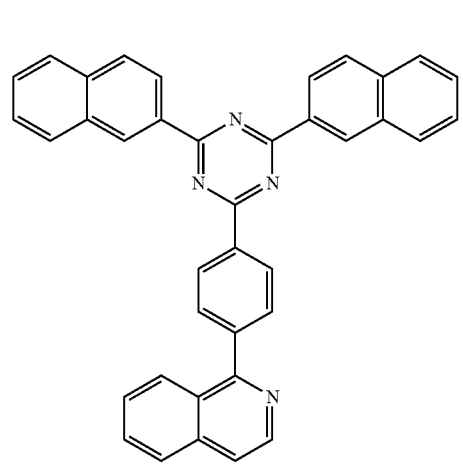
1-119
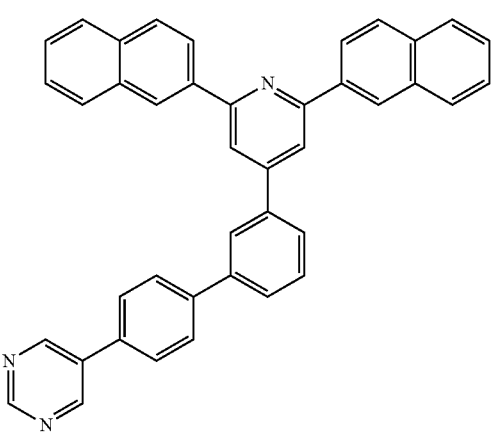

-continued
1-120
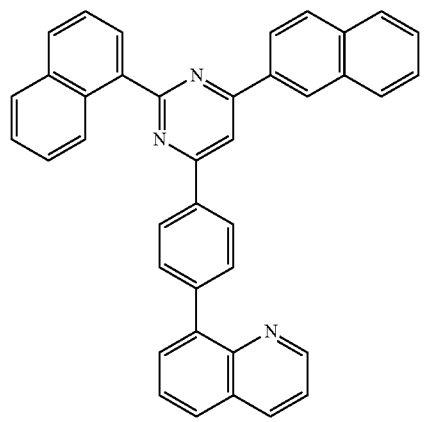
1-121
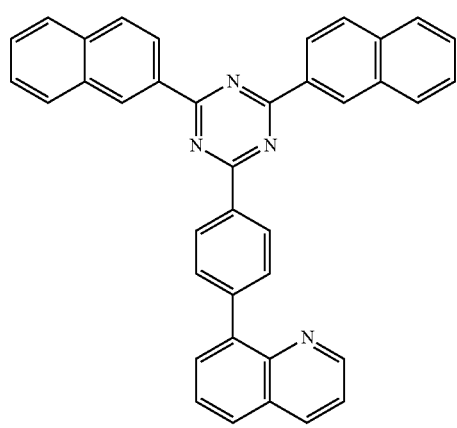
1-122
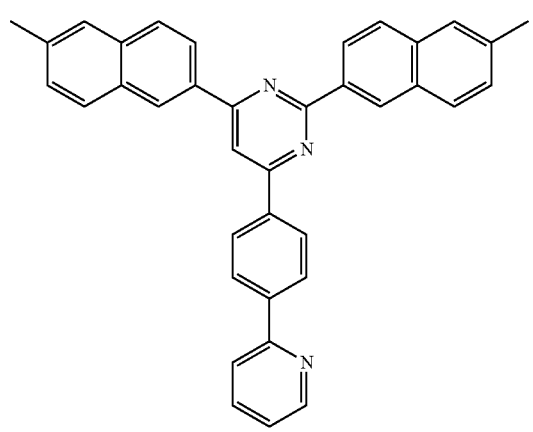
-continued
1-123
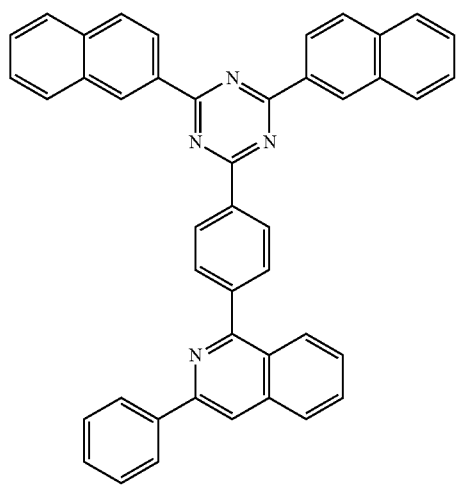
1-124
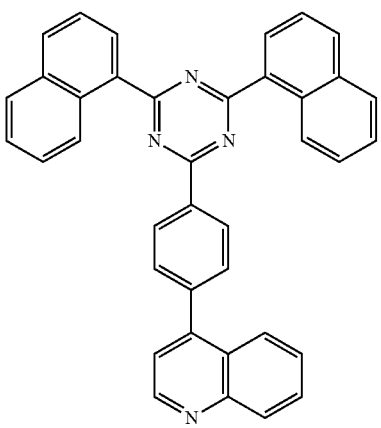
1-125
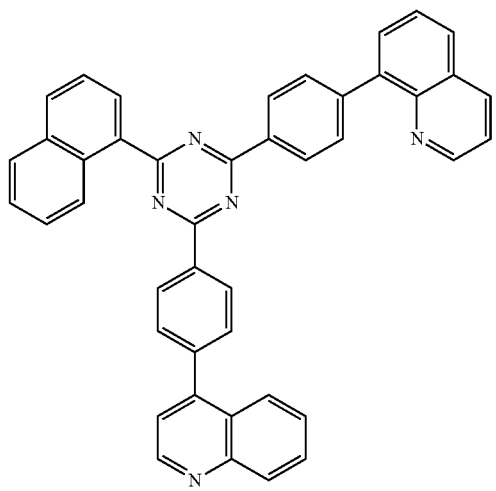

387
-continued
1-126
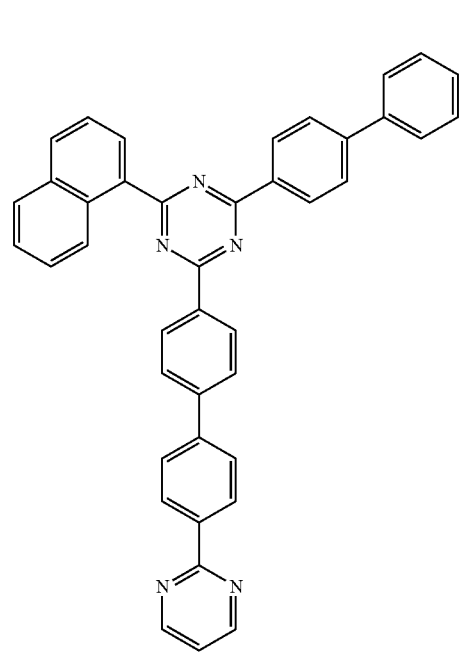
388
-continued
1-128
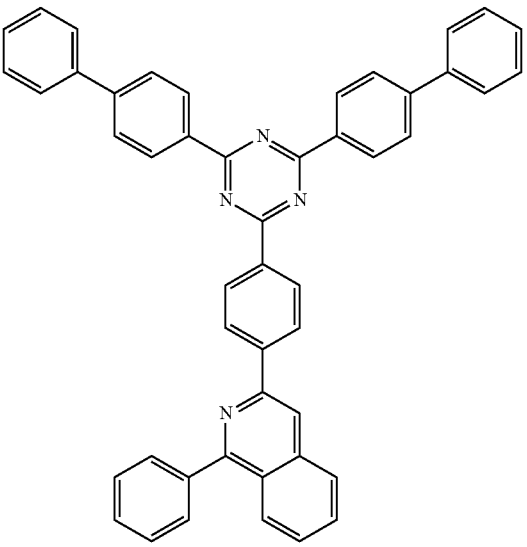
1-127
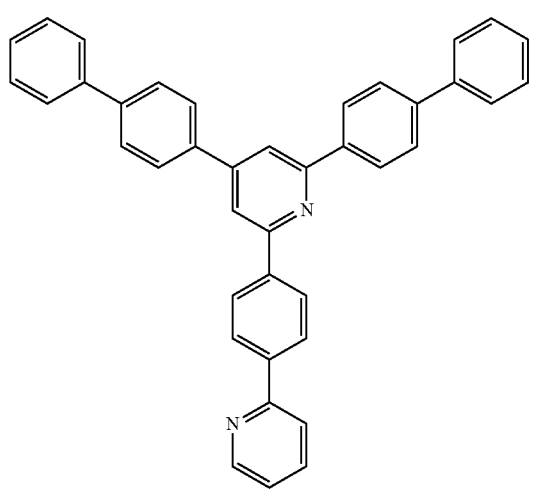
1-129
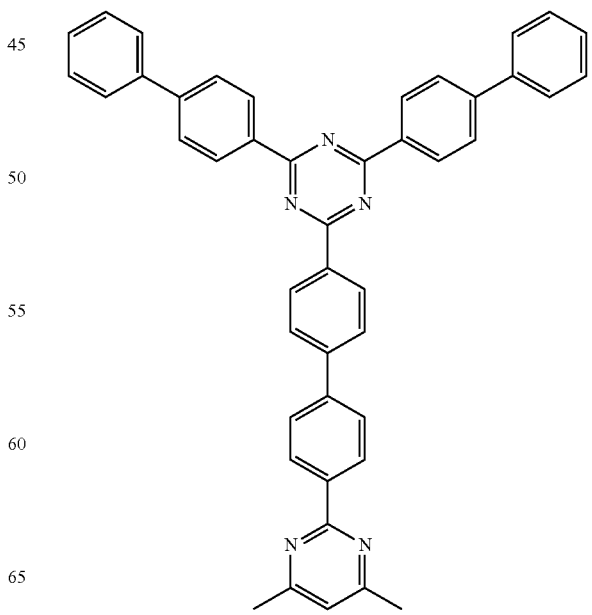

389
-continued
1-130
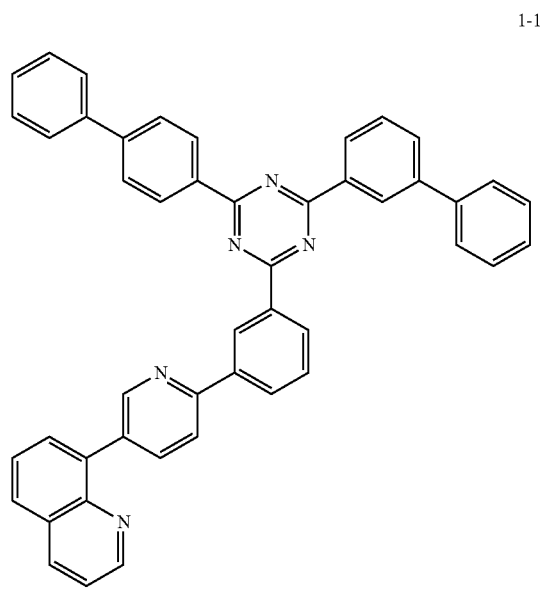
1-131
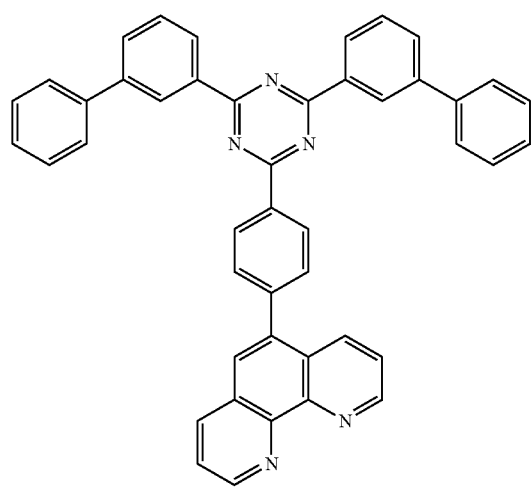
390
-continued
1-132
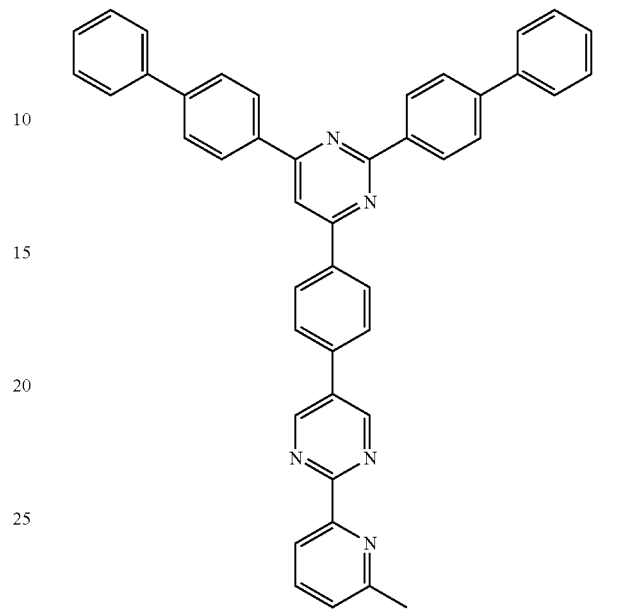
1-133
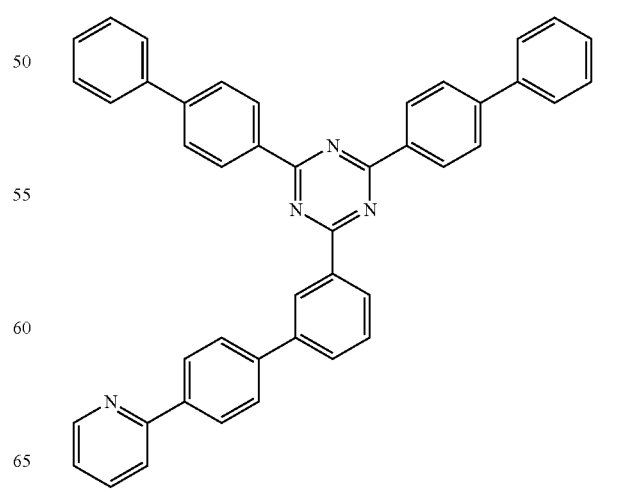

1-134
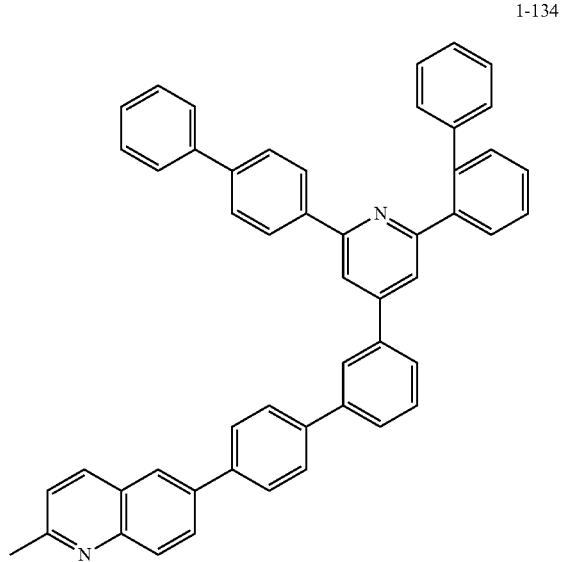
1-135
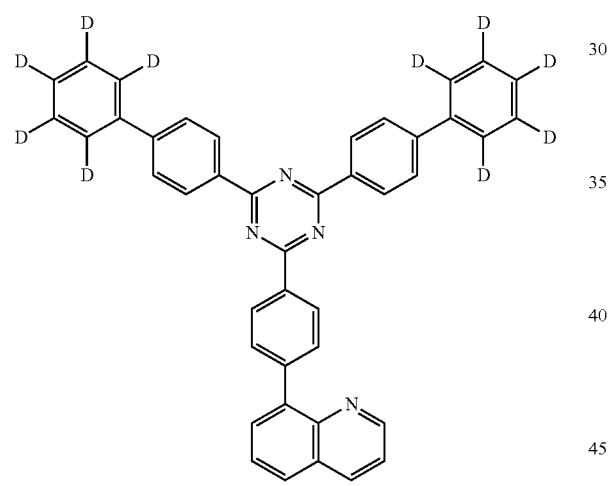
1-136
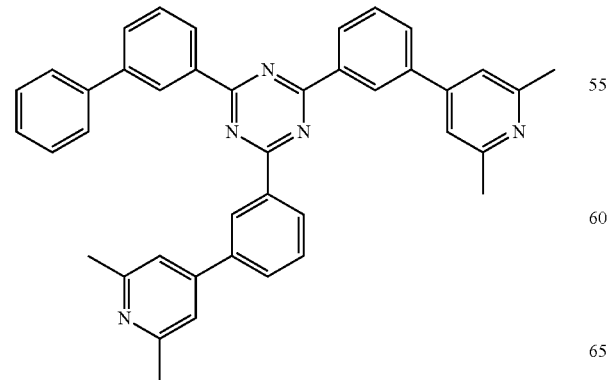
1-137
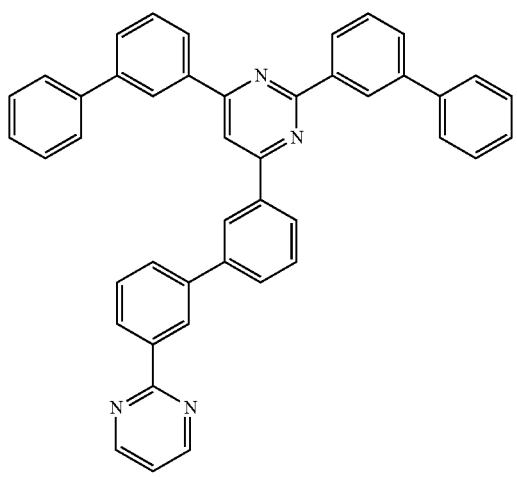
1-138
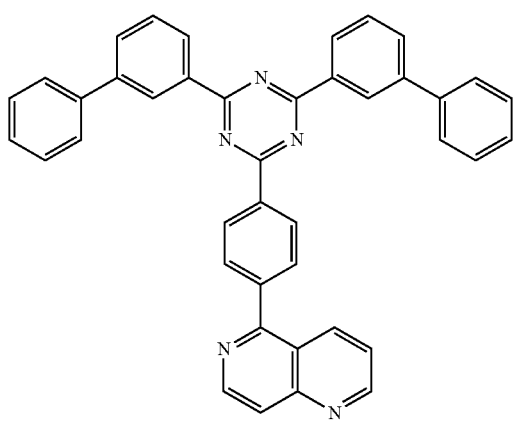
1-139
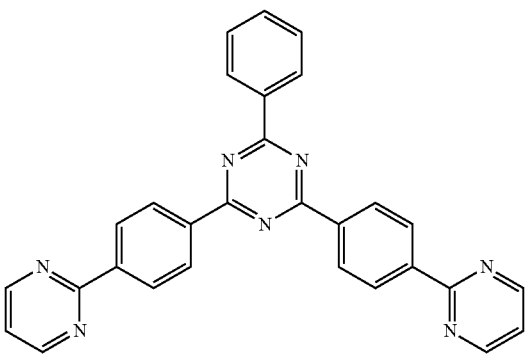
1-140
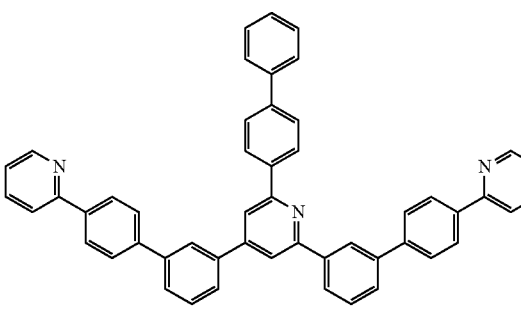

-continued
1-141
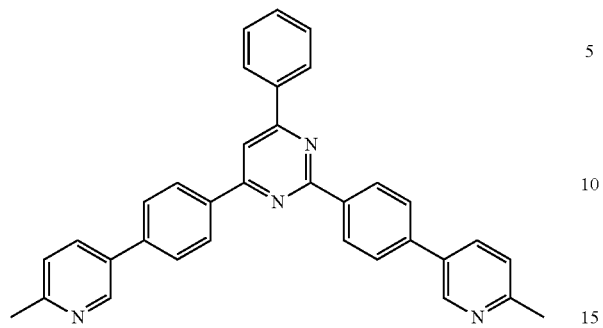
1-142
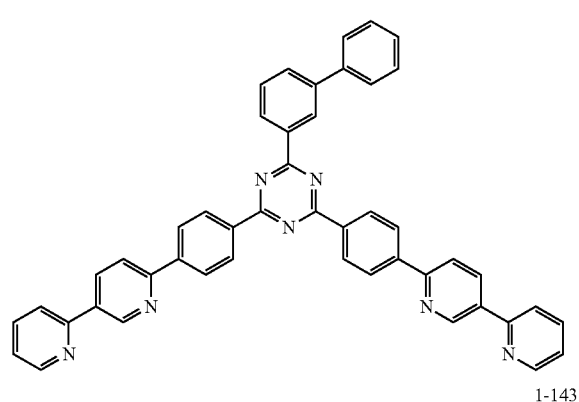
1-143
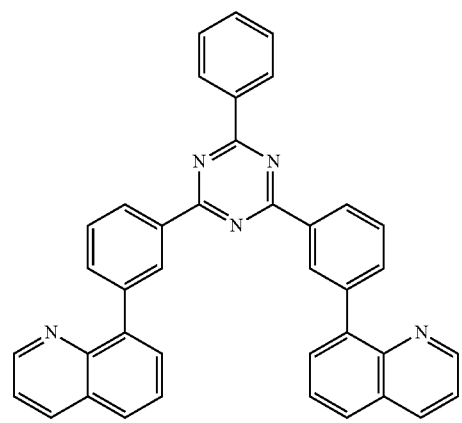
1-144
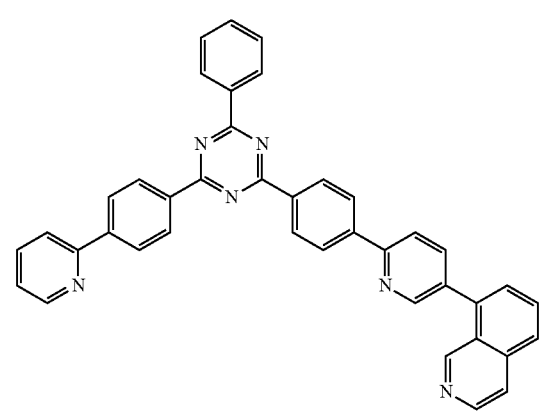
-continued
1-145
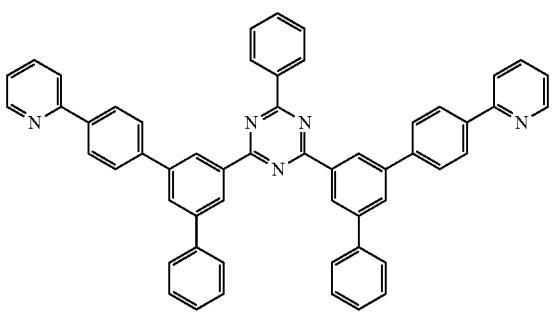
1-146
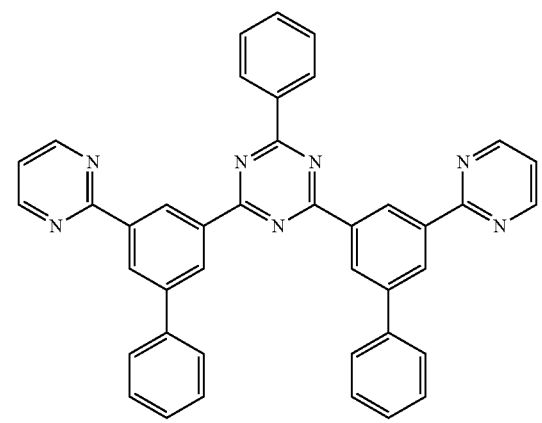
1-147
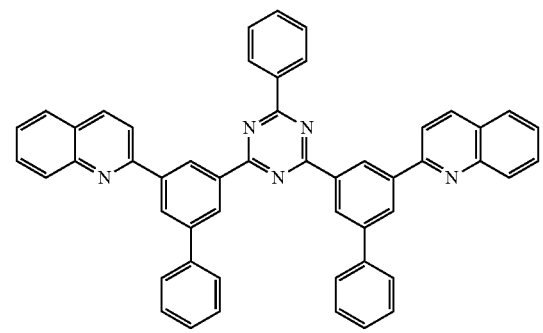
1-148
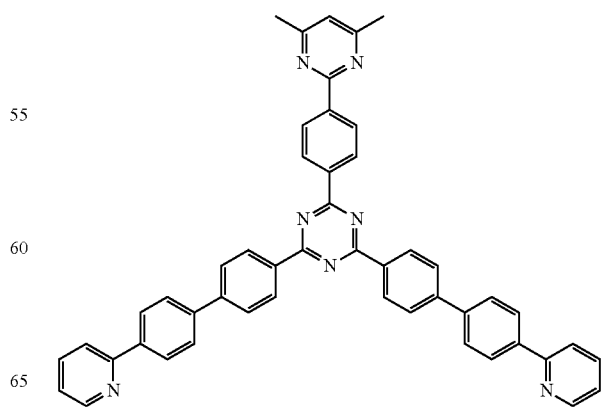

1-149
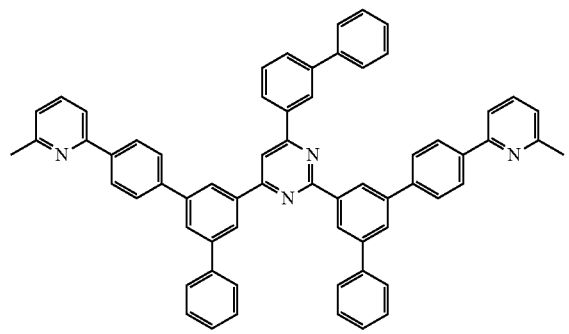
1-150
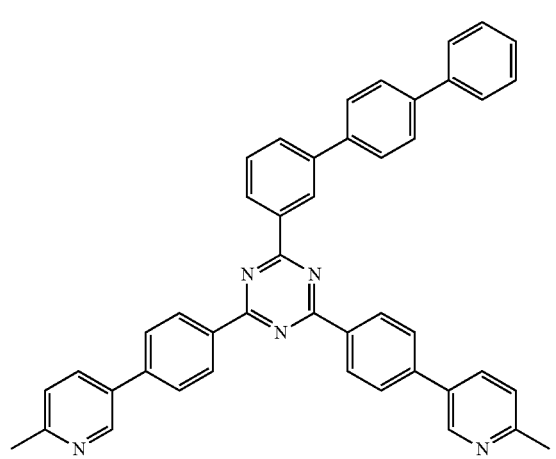
1-151
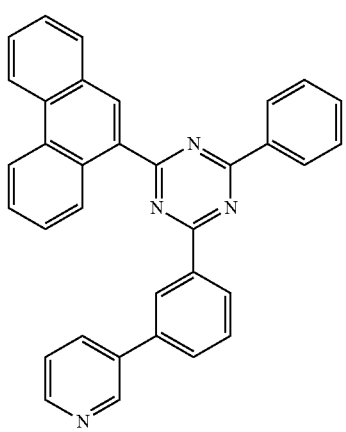
1-152
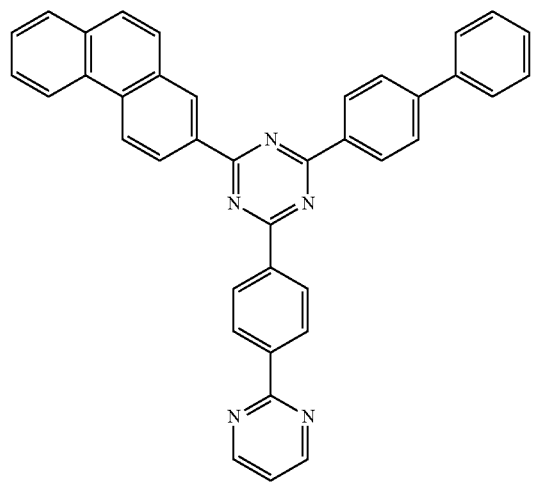
1-153
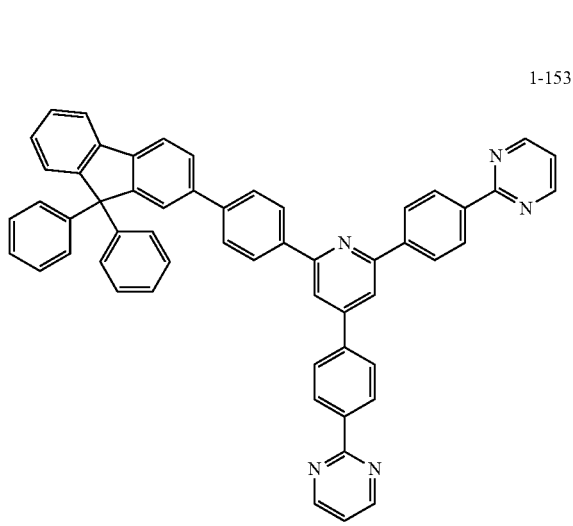
1-154
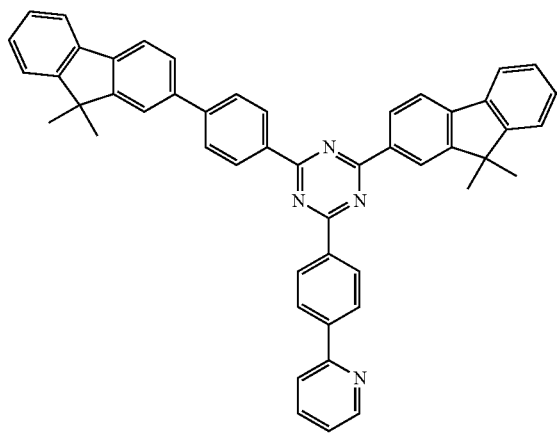

1-155
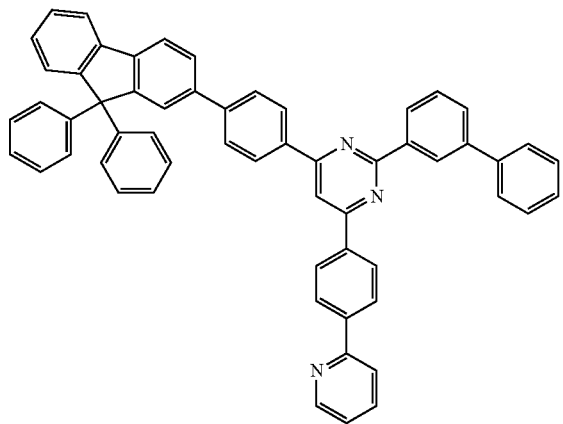
1-156
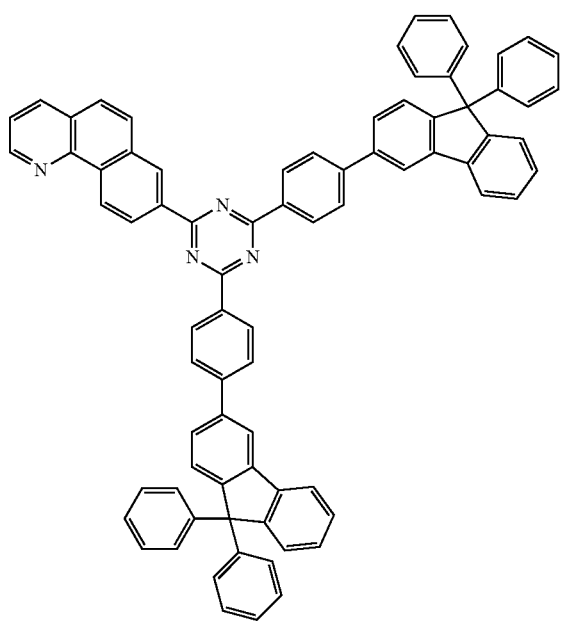
1-157
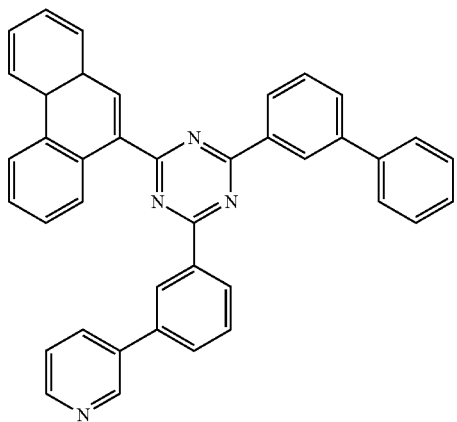
1-158
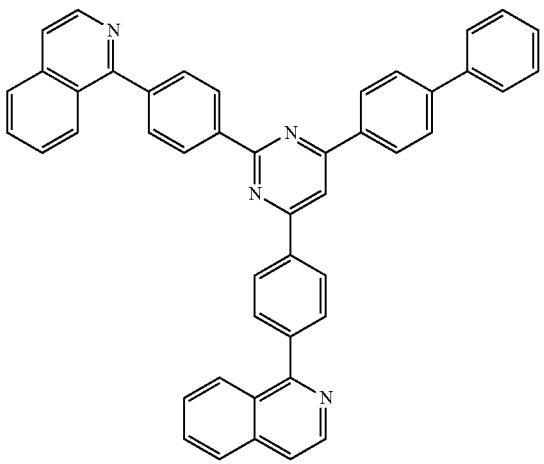
1-159
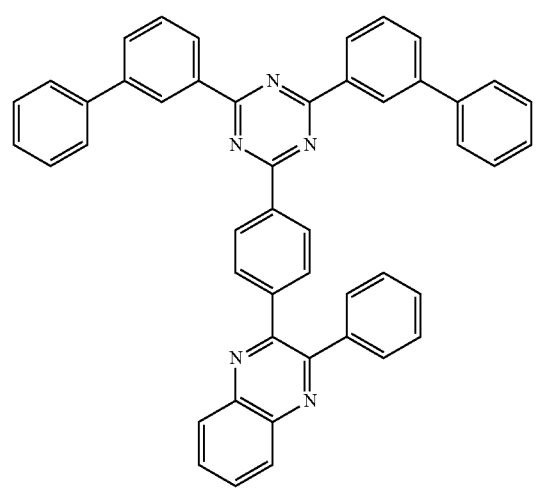
1-160
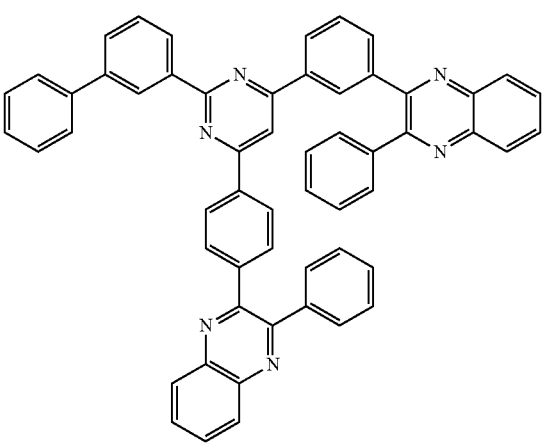

399
-continued
1-161
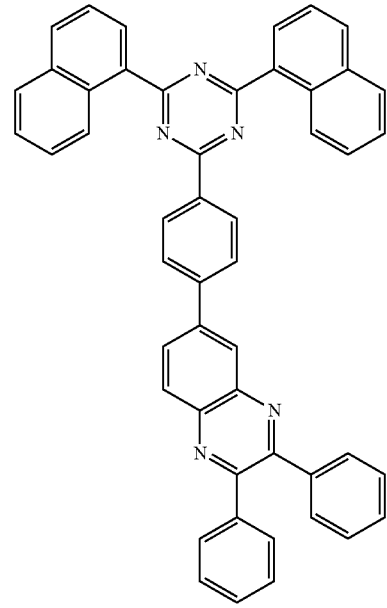
1-162
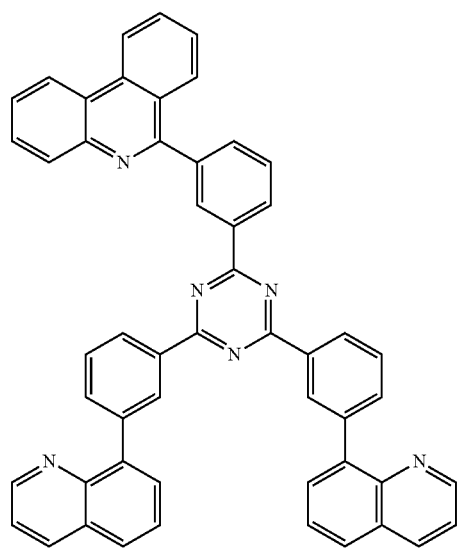
1-163
400
-continued
1-164
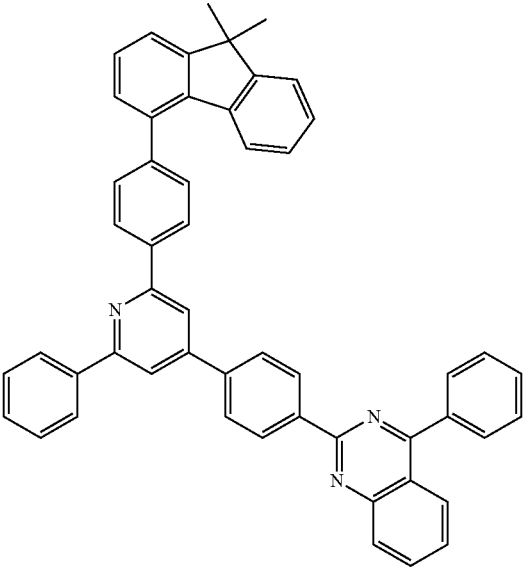
1-165

1-166
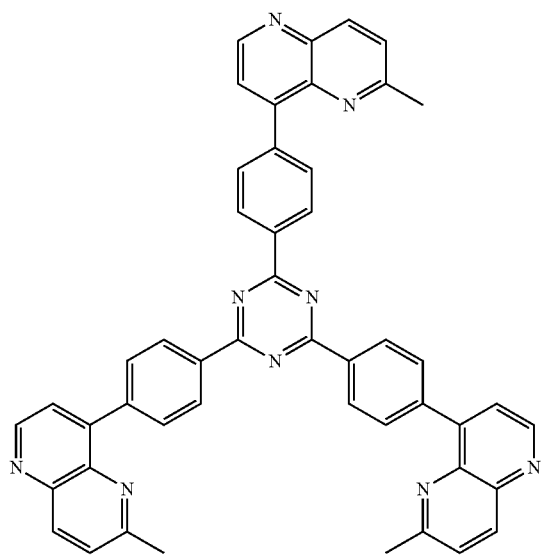
1-168
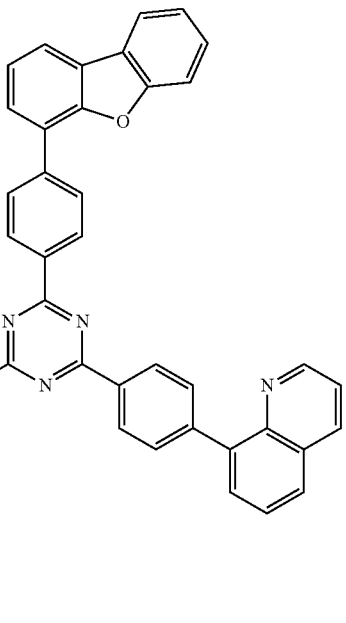
1-167
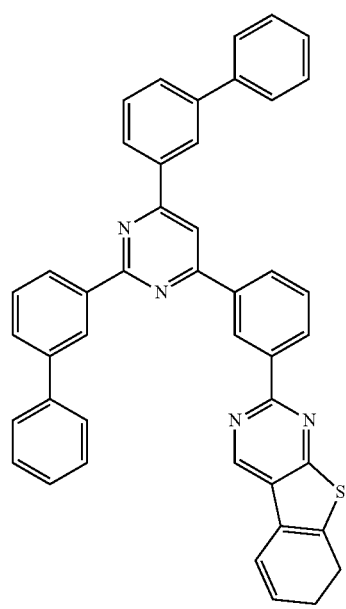
1-169
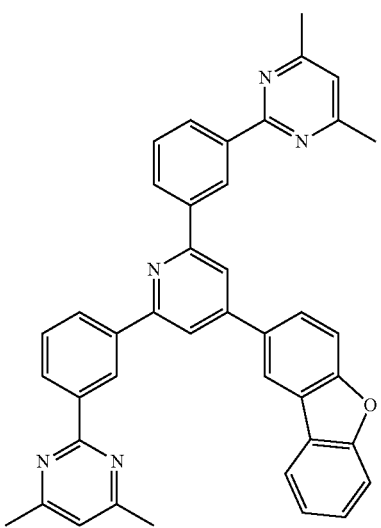
1-170
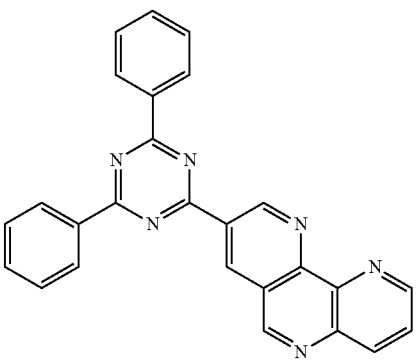

1-171 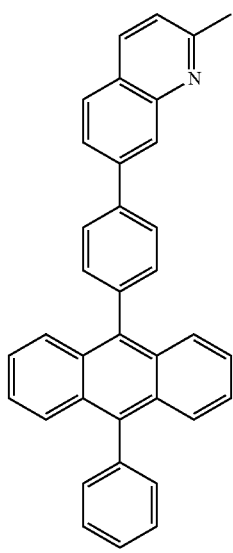
1-172 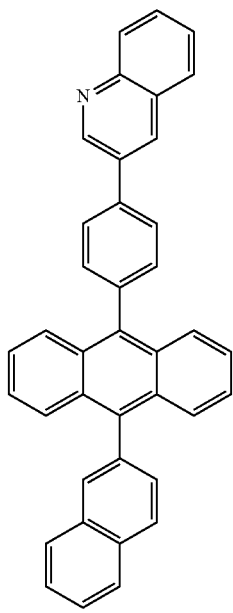
1-173 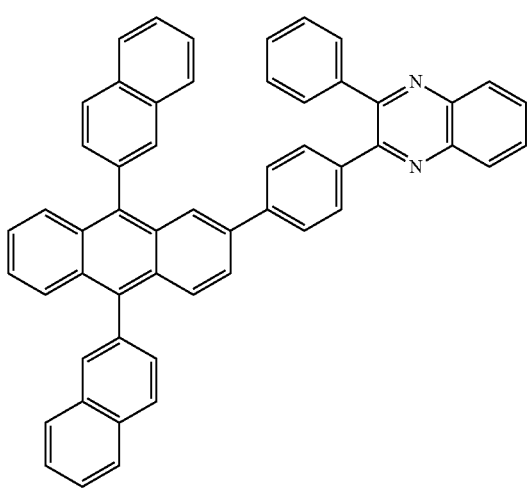
1-174 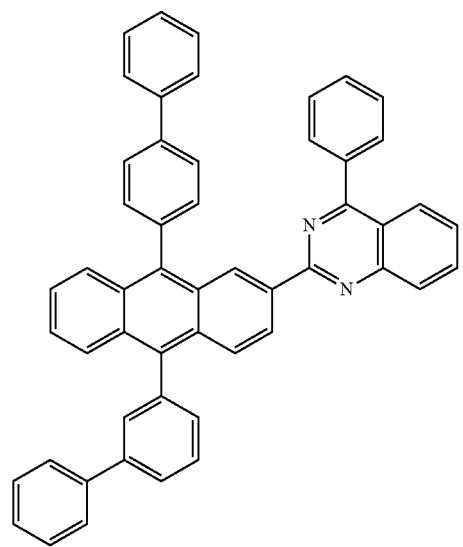
1-175 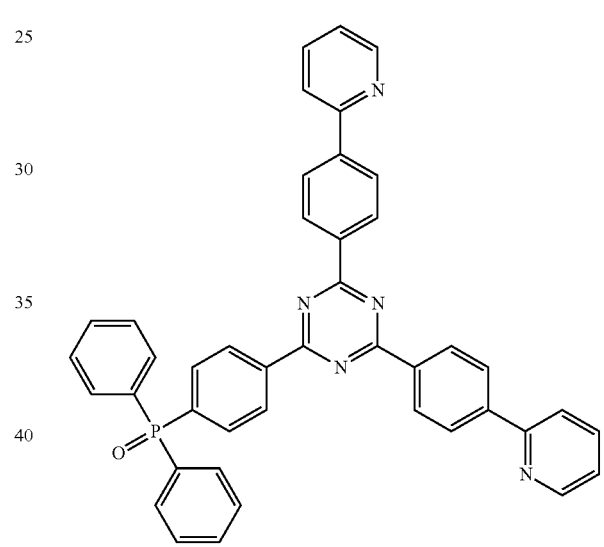
1-176 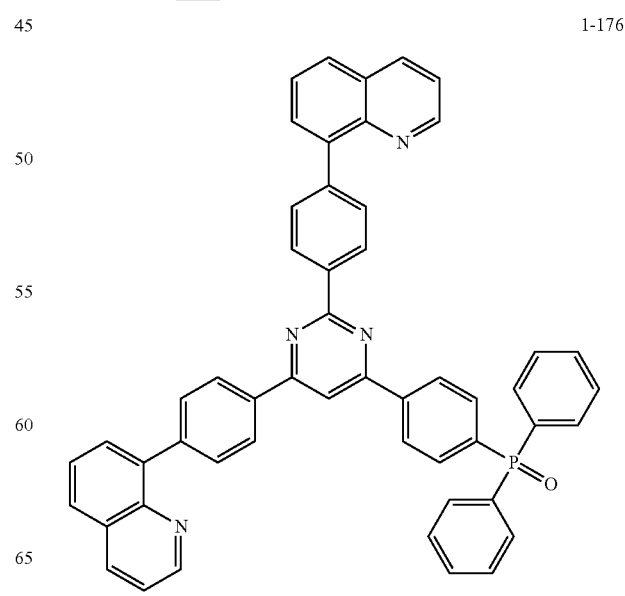

1-177

1-178

1-179

1-180

1-181

1-182

1-183

1-184
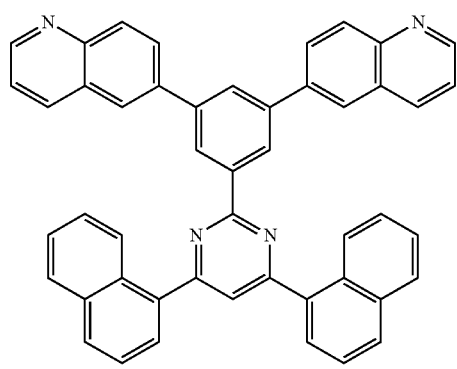
1-185
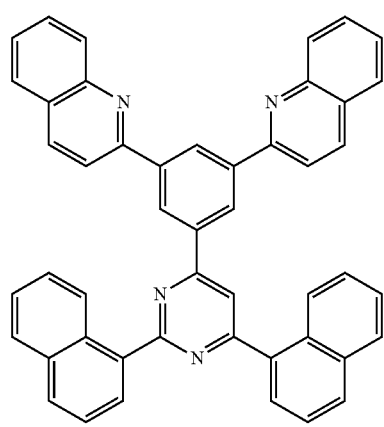
1-186
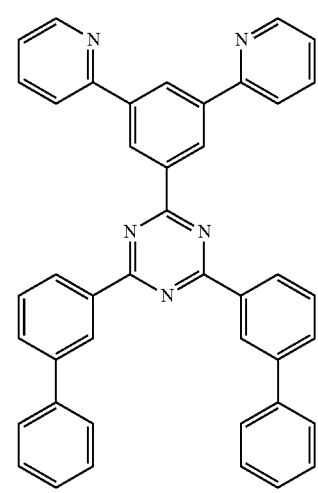
1-187
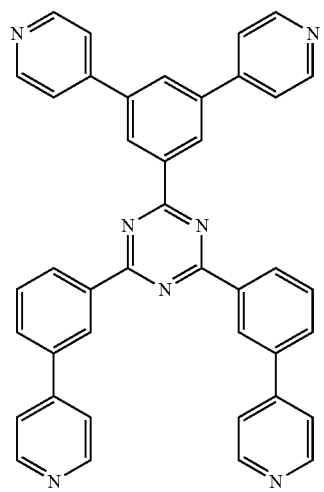
1-188
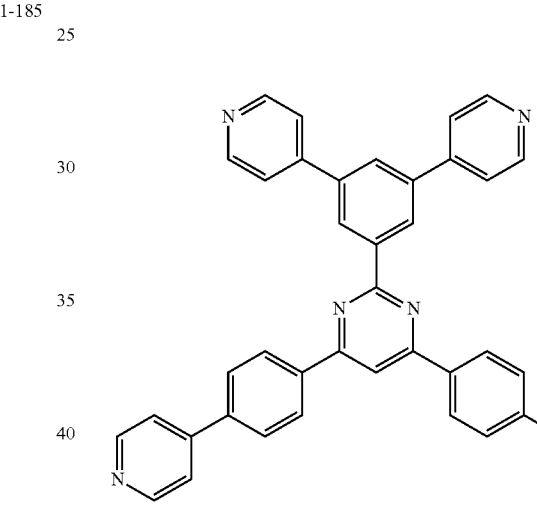
1-189
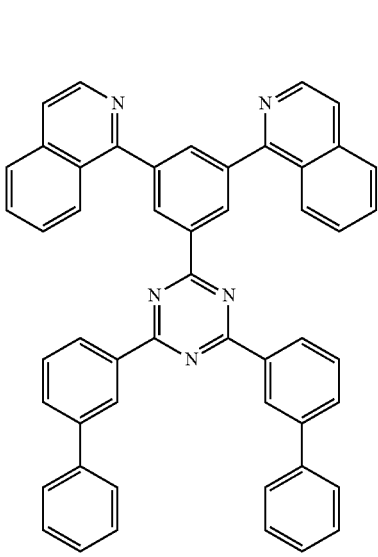

409
-continued
1-190
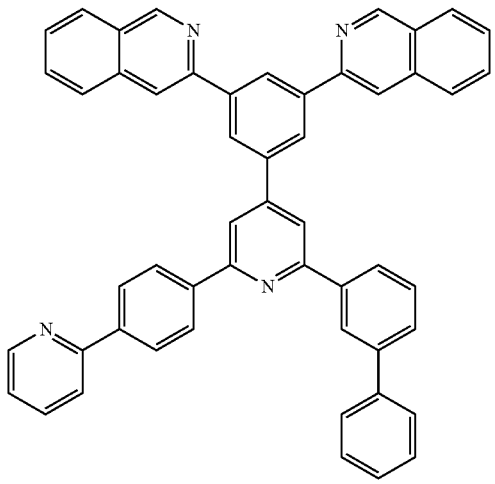
1-191
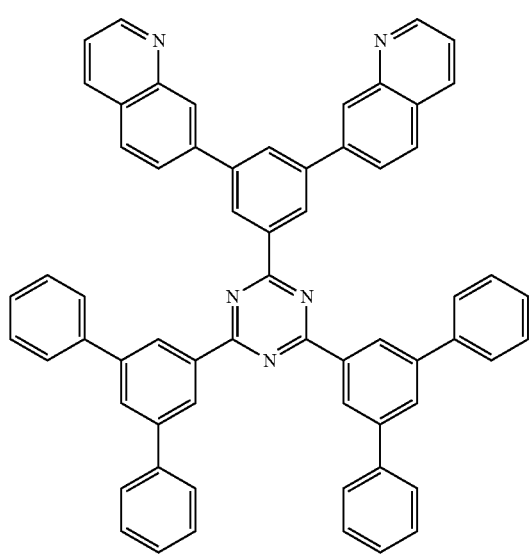
1-192
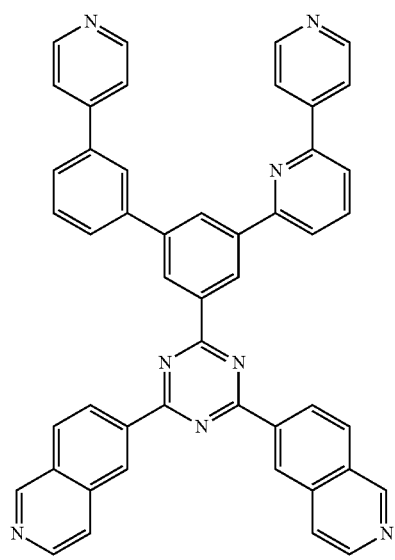
410
-continued
1-193
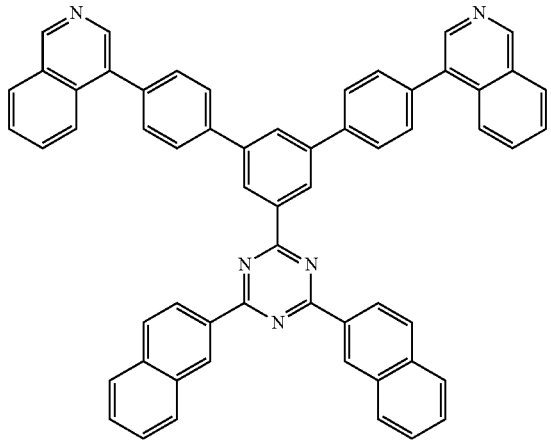
1-194
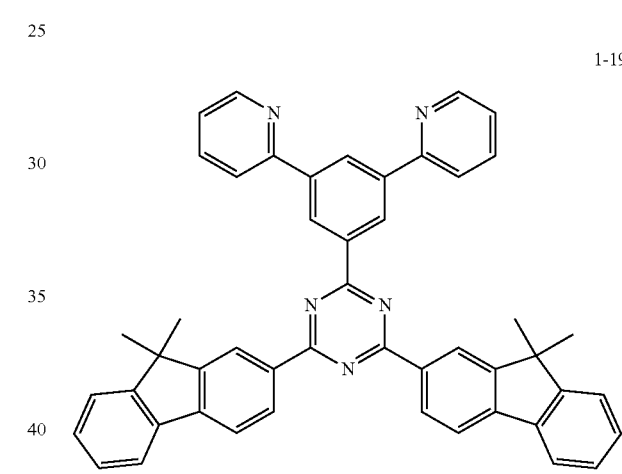
1-195
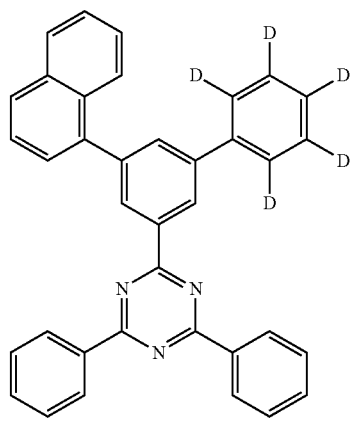

411
-continued
1-196
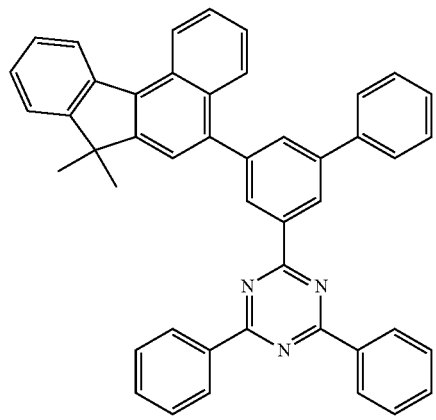
1-197
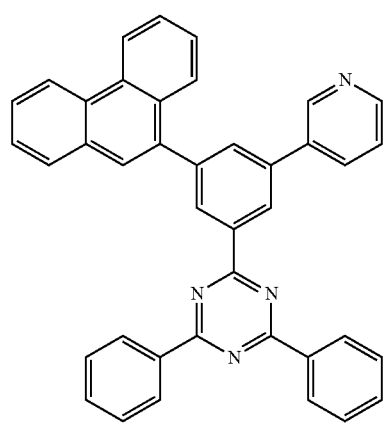
1-198
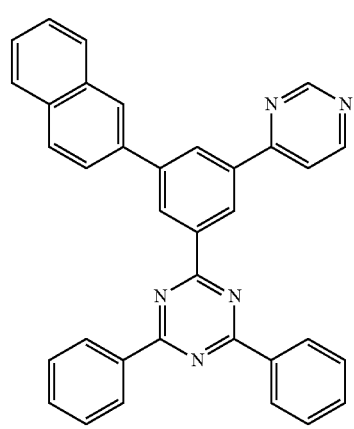
412
-continued
1-199
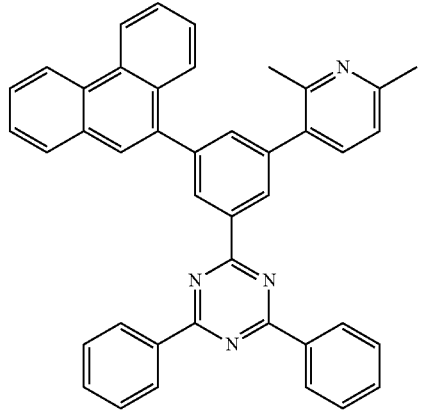
1-200
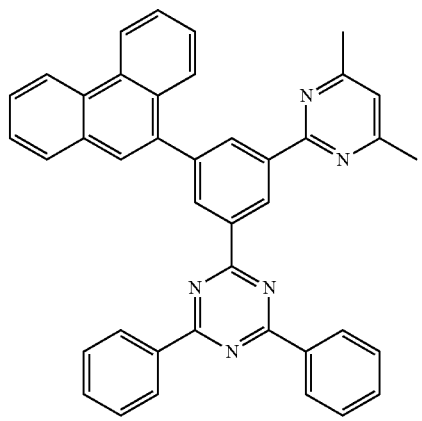
1-201
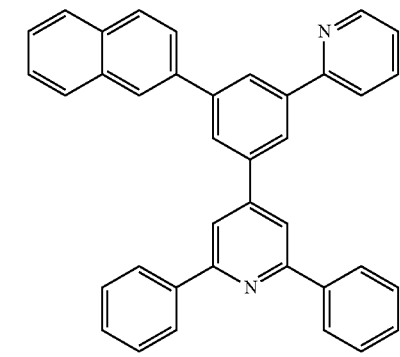
1-202
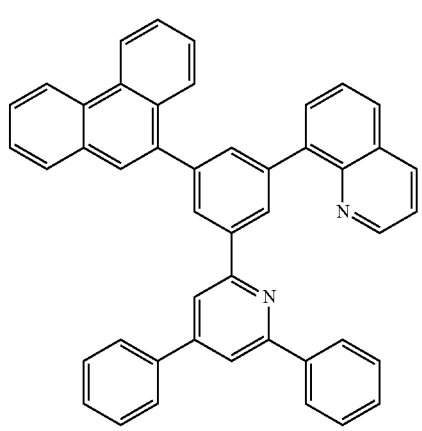

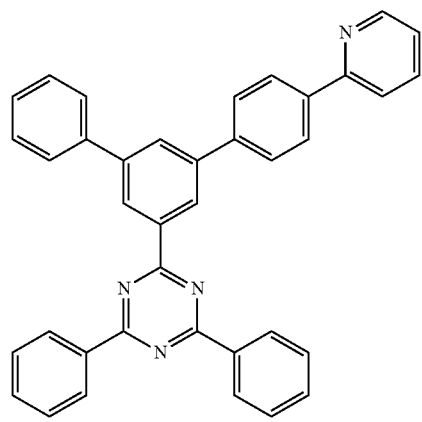
1-203
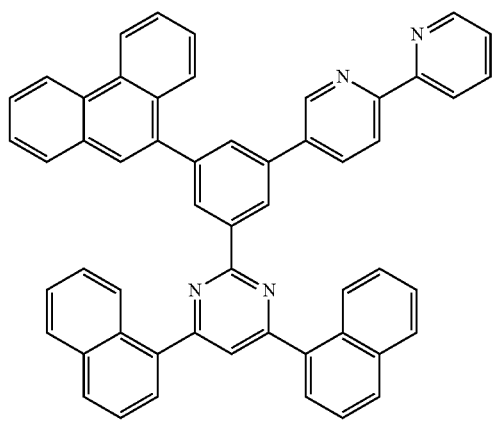
1-206
1-204
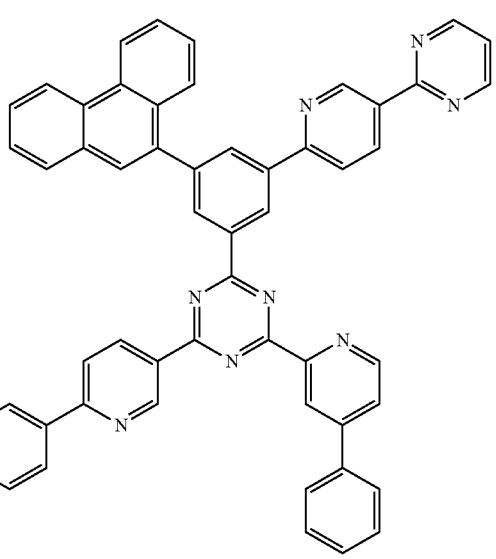
1-205
1-207
1-208
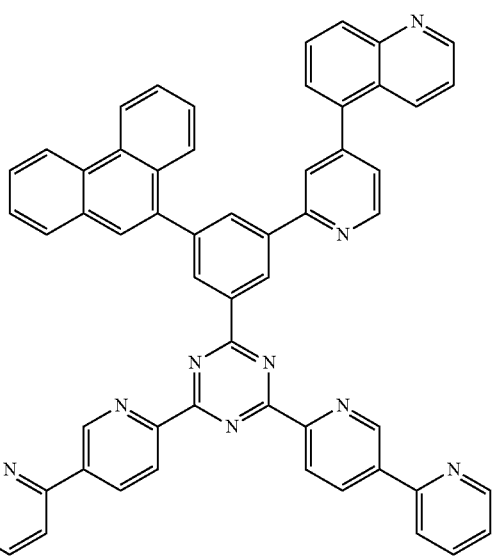

1-209
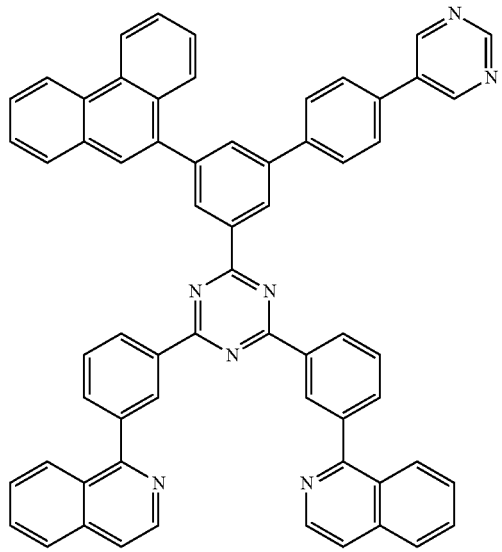
1-210
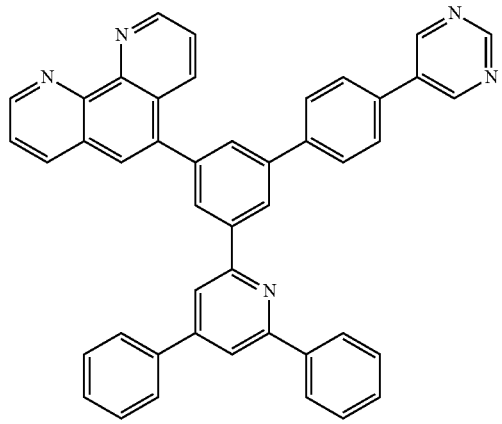
1-211
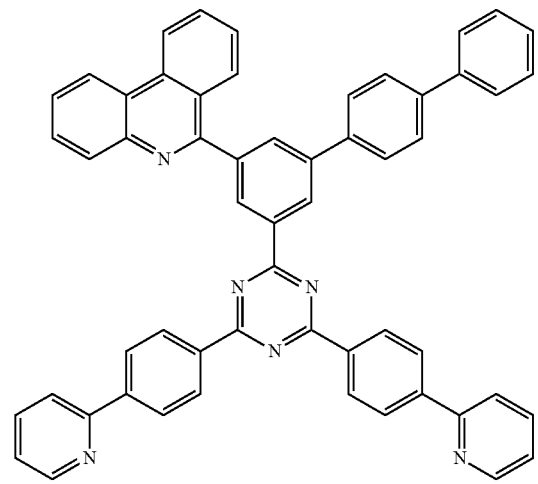
1-212
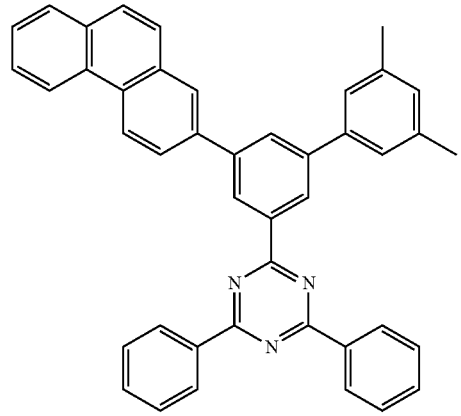
1-213
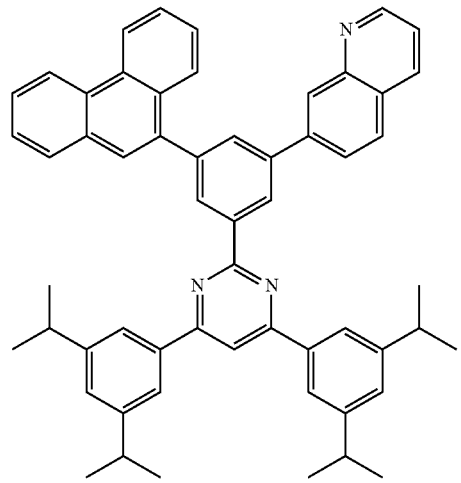
1-214
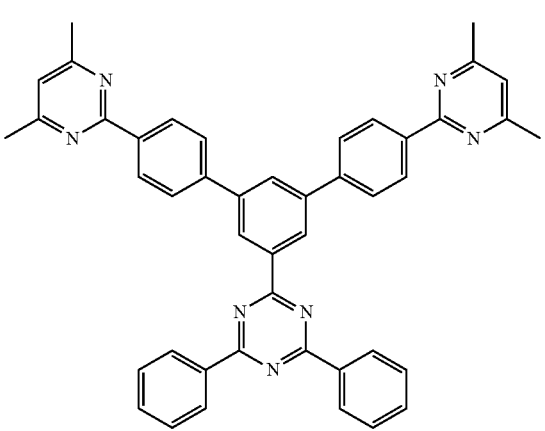

1-215
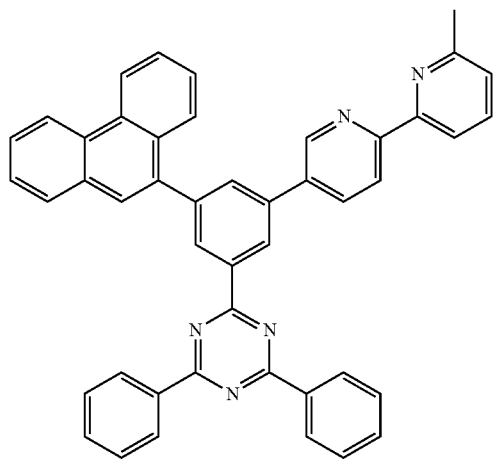
1-216
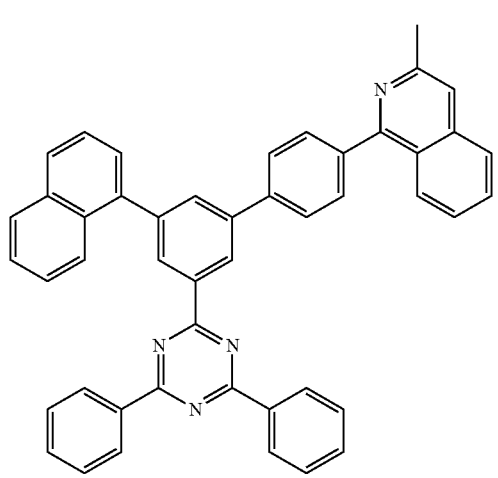
1-217
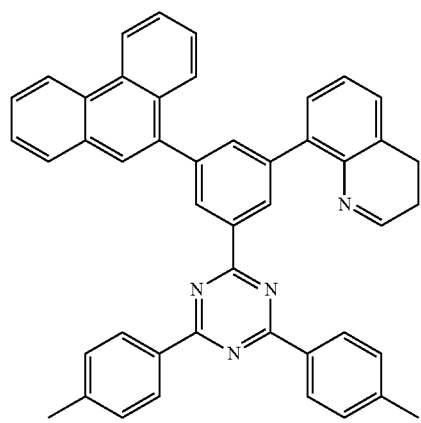
1-218
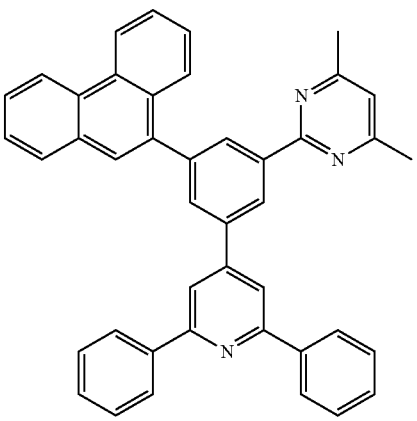
1-219
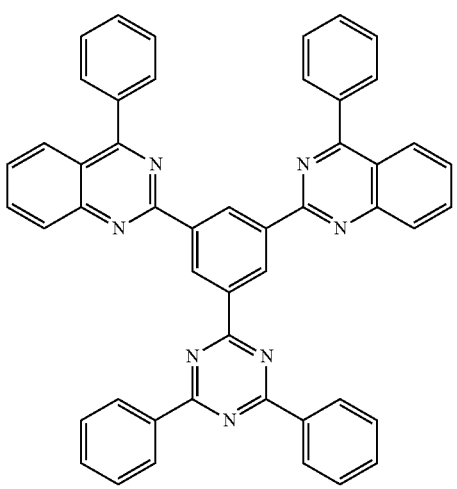
1-220
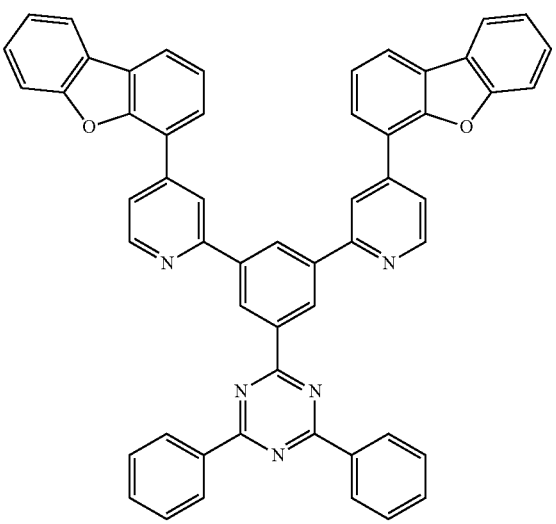

419
-continued
1-221
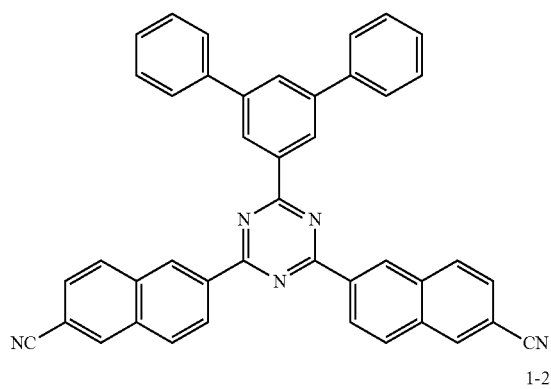
1-222
1-223
1-224
420
-continued
1-225
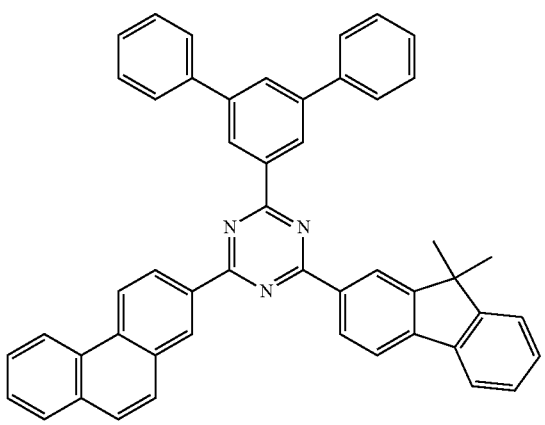
1-226
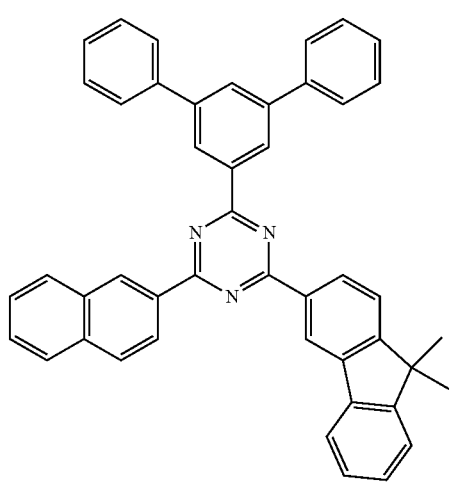
1-227
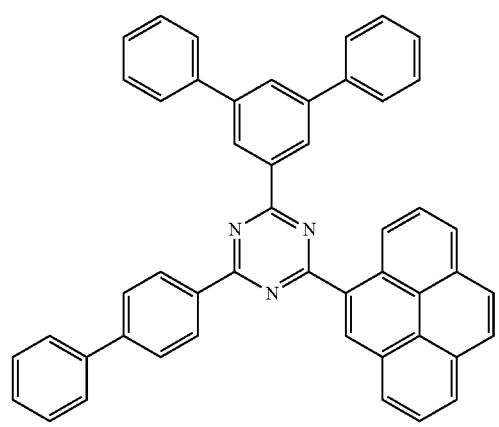

-continued
1-228
1-229
1-230
1-231
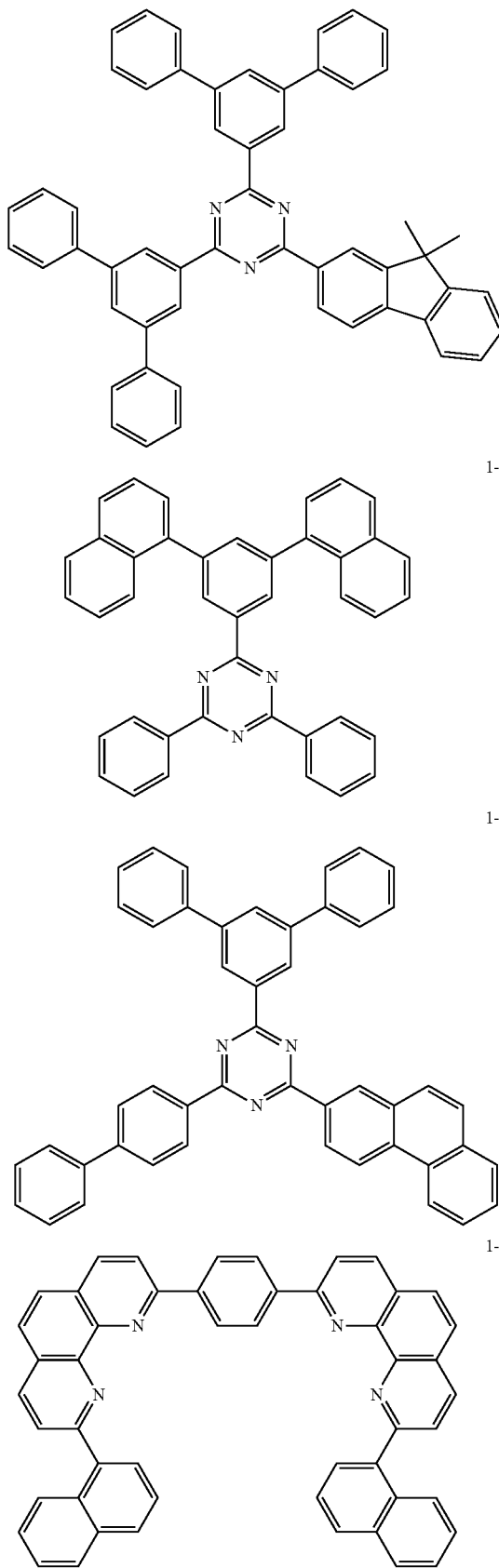
-continued
1-232
1-233
1-234
1-235
1-236
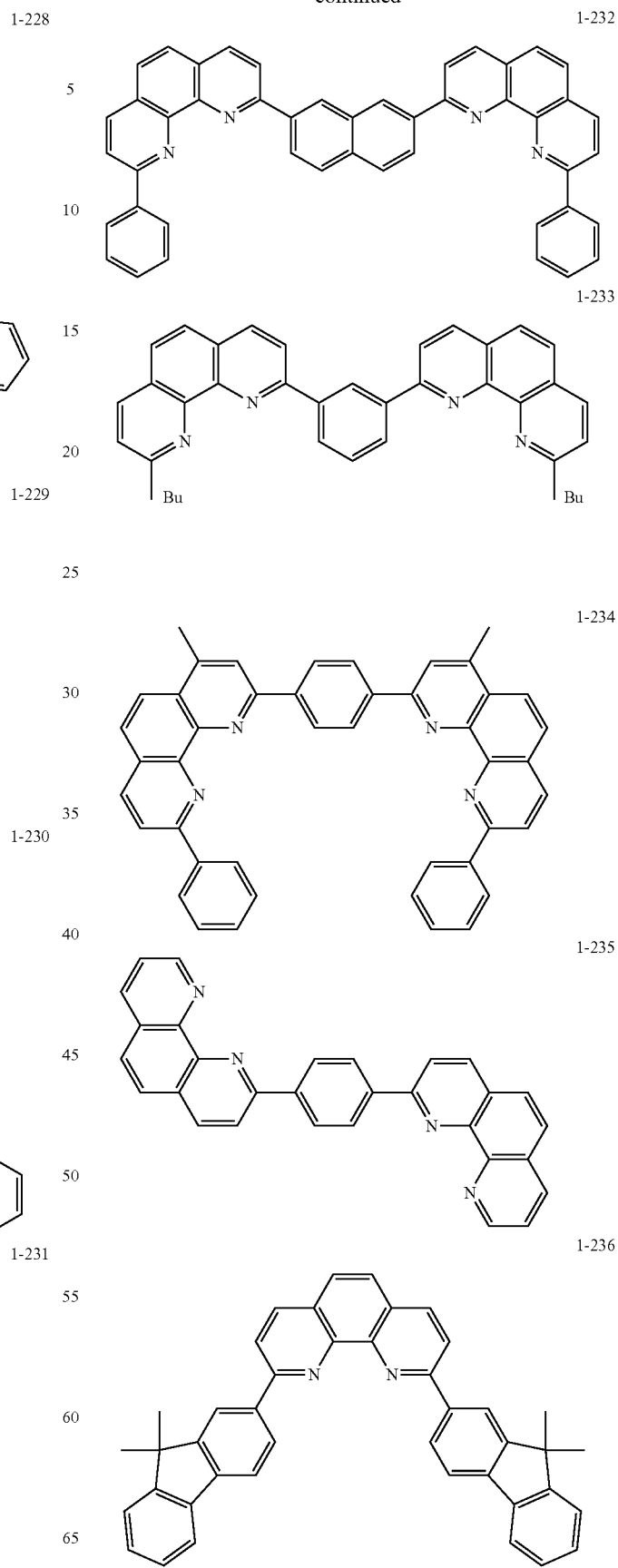

1-237
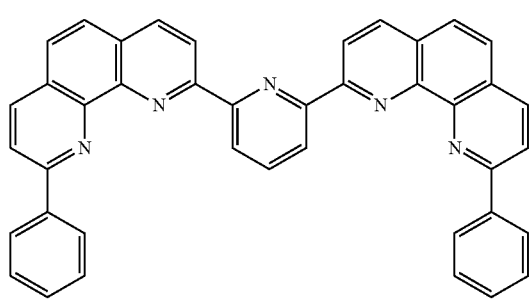
1-238
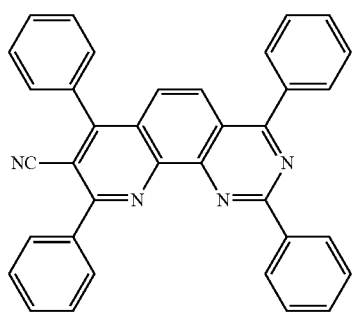
1-239
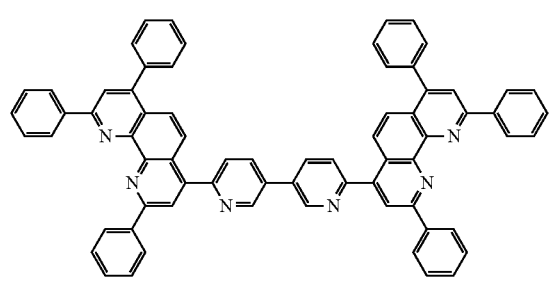
1-240
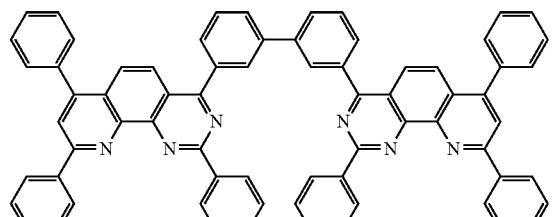
1-241
1-243
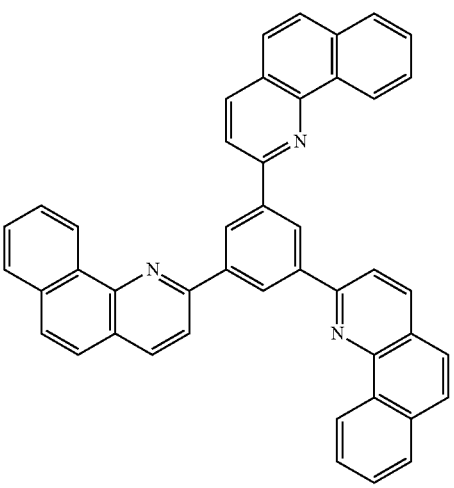
1-245
1-246
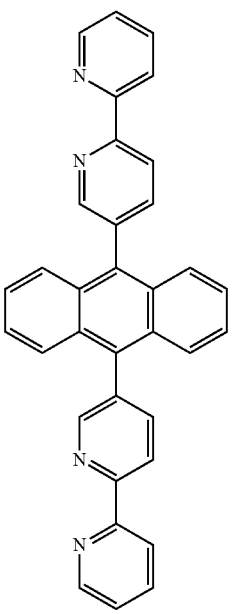

425
-continued
1-247
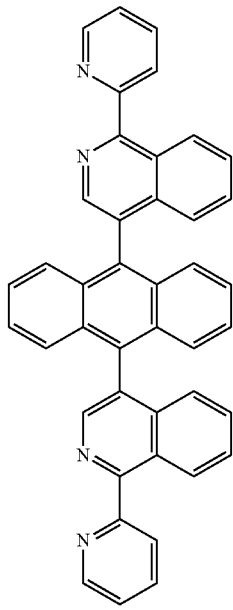
1-248
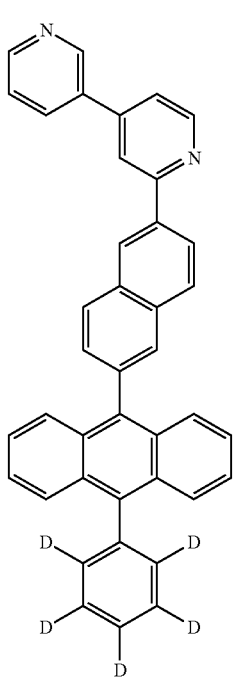
426
-continued
1-249
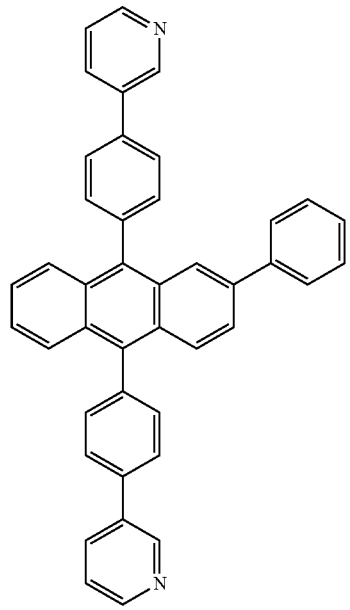
1-250
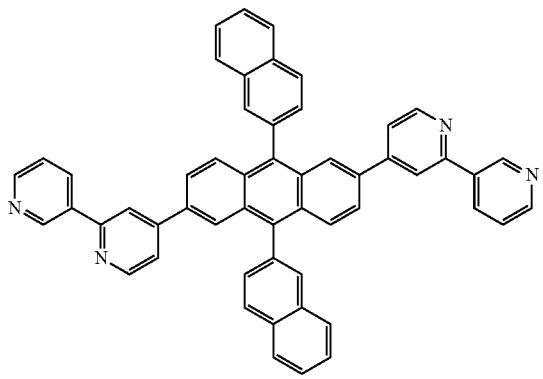
1-251
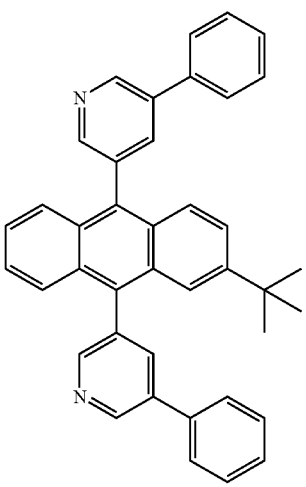

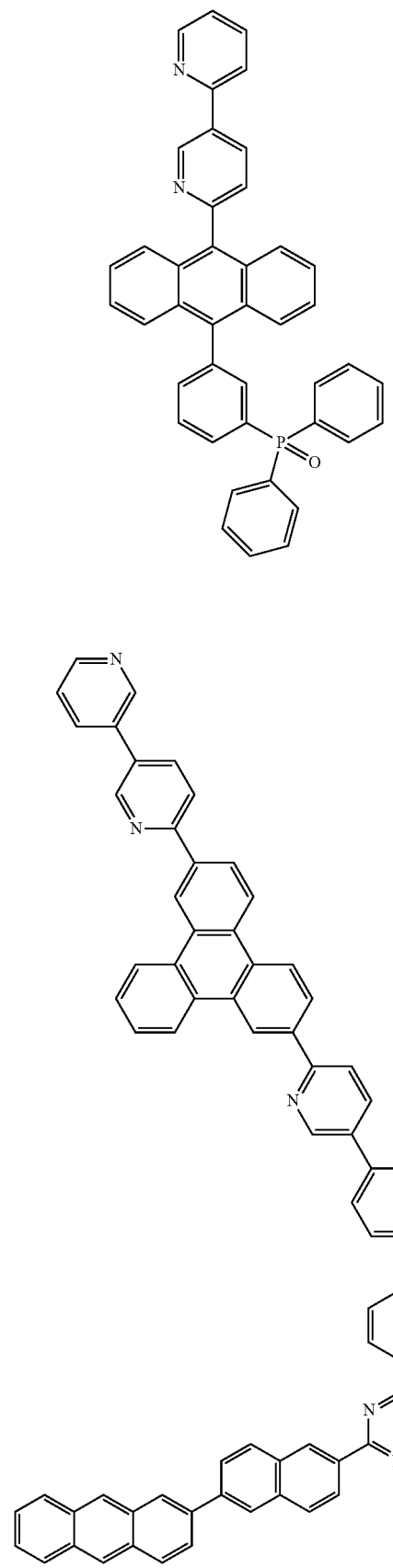
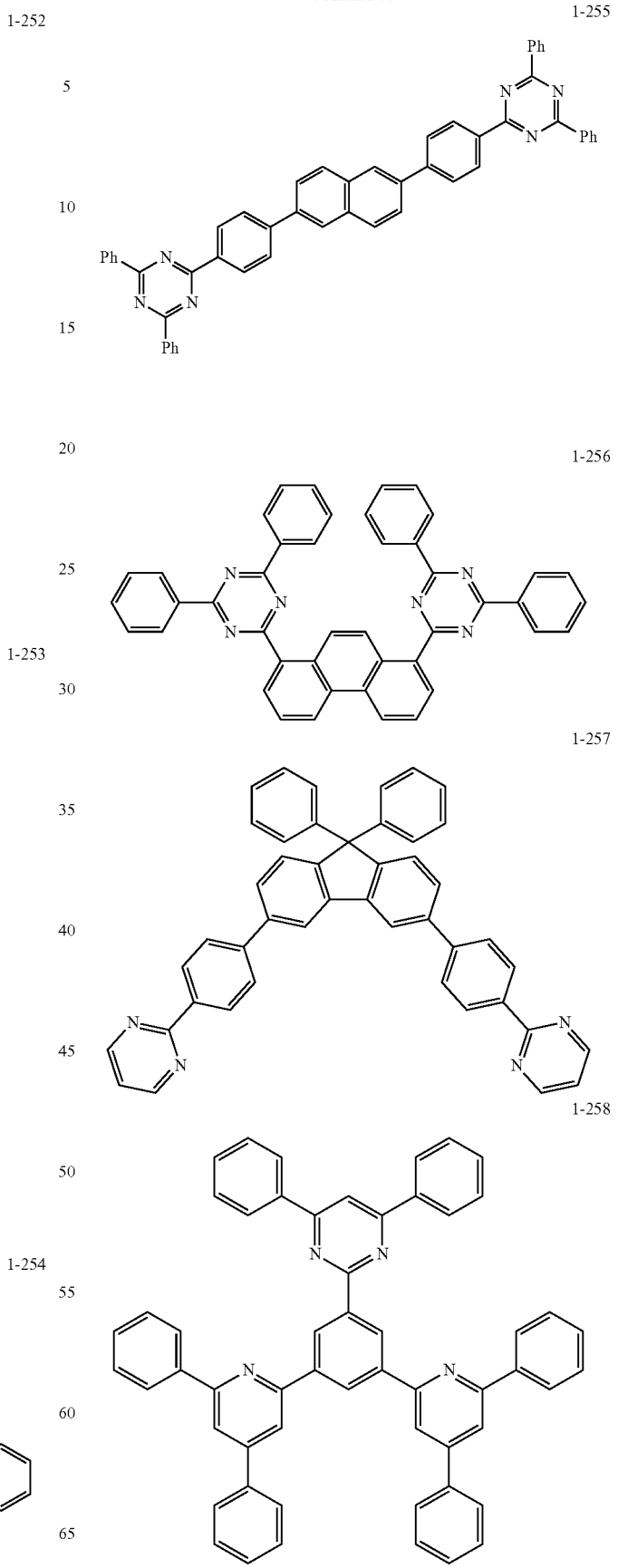

429
-continued
1-259
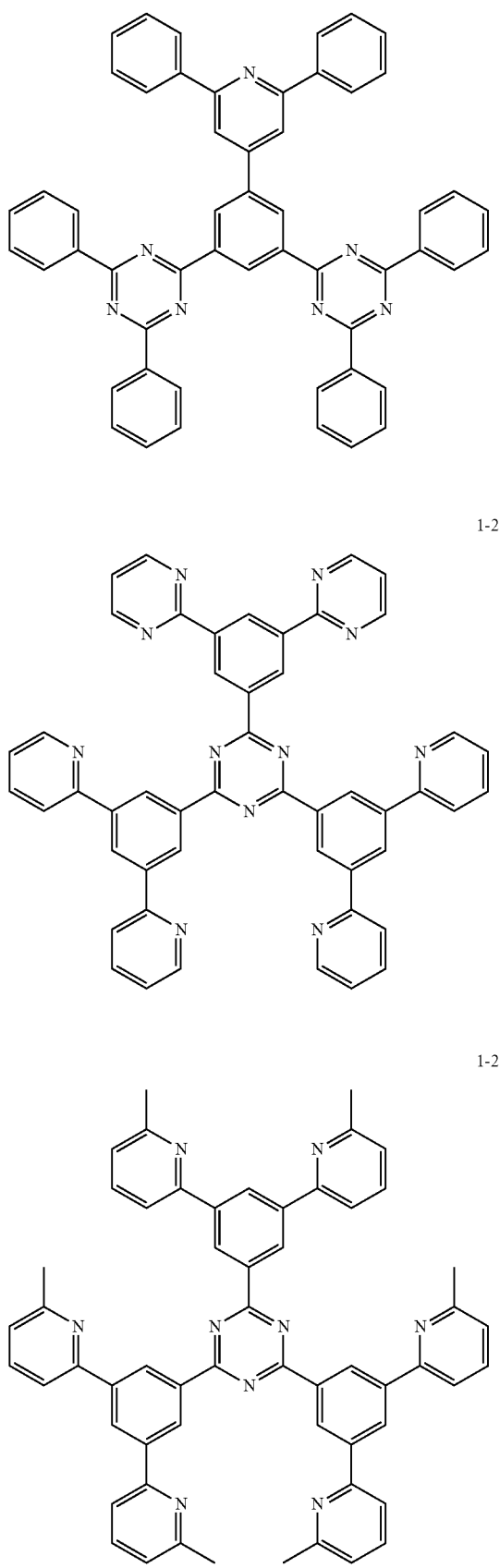
1-260
1-261
430
-continued
2-1
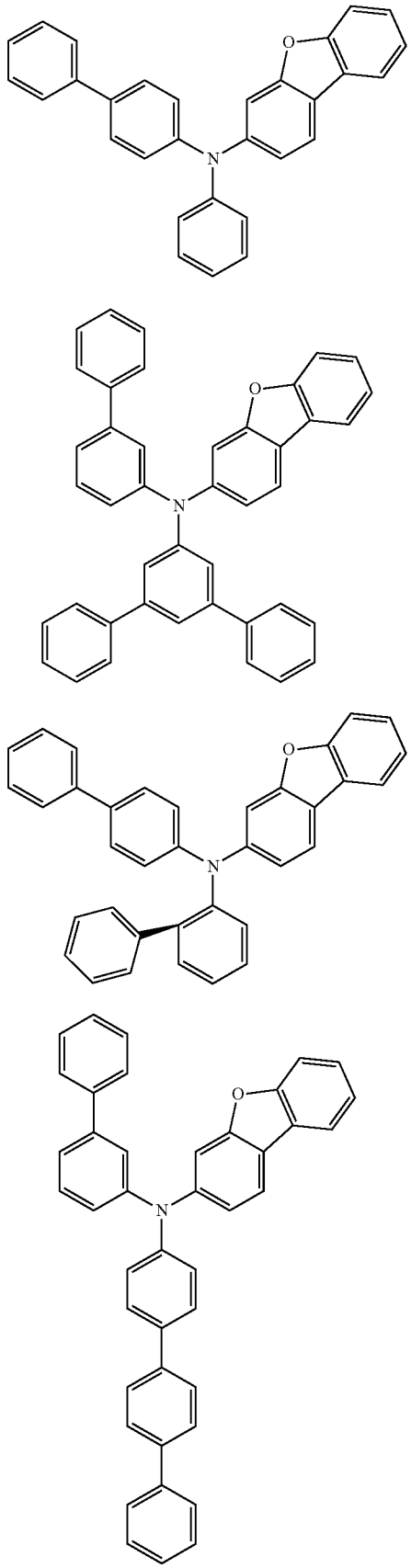
2-2
2-3
2-4

431
-continued
2-5
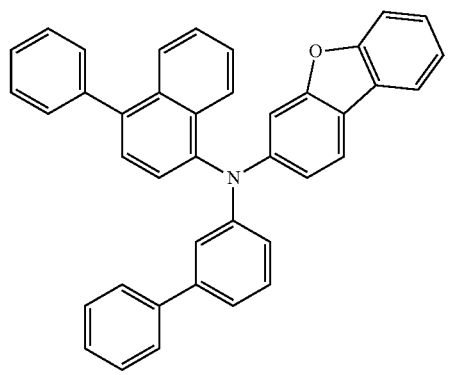
2-6
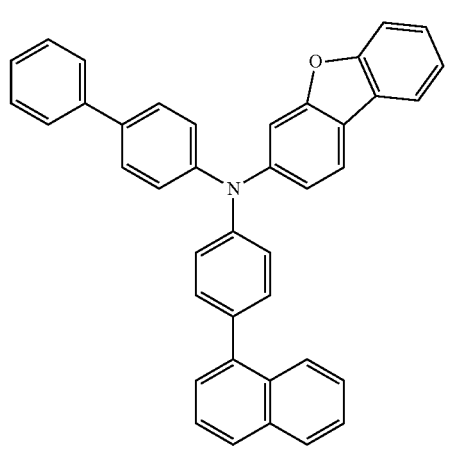
2-8
432
-continued
2-9
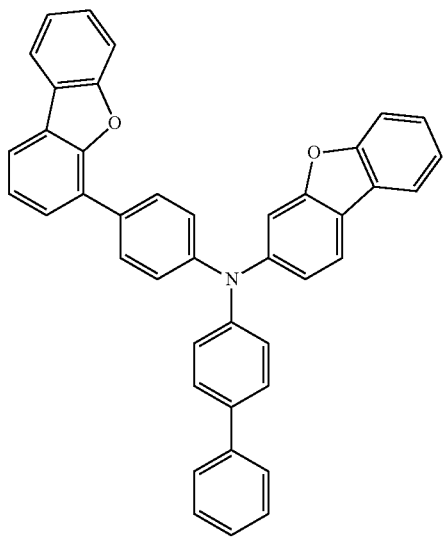
2-10
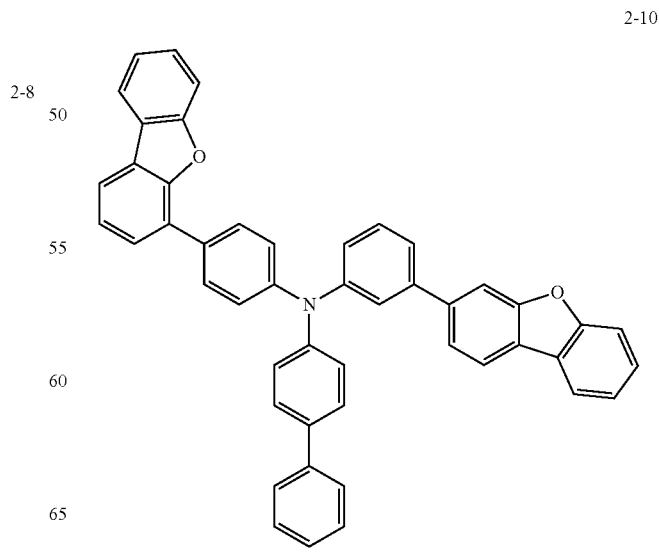

2-11
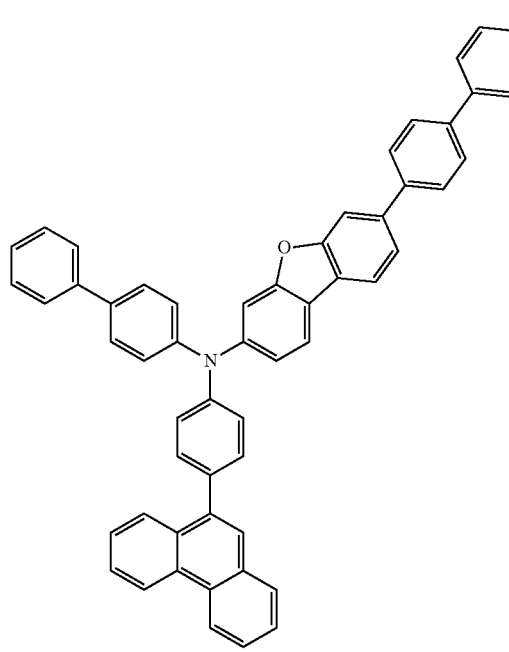
2-12
2-13
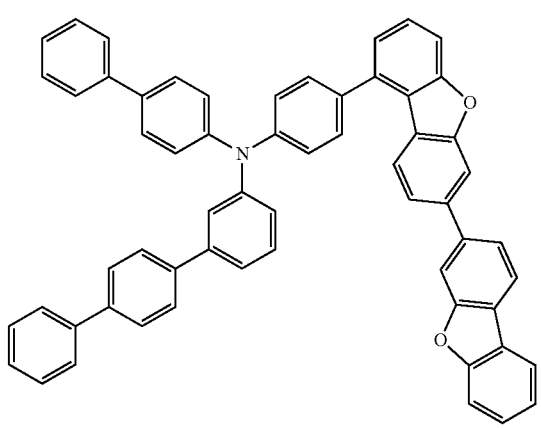
2-14
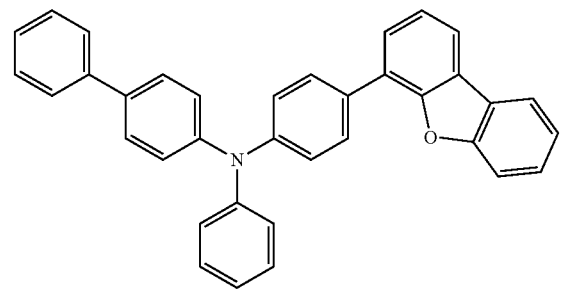
2-17
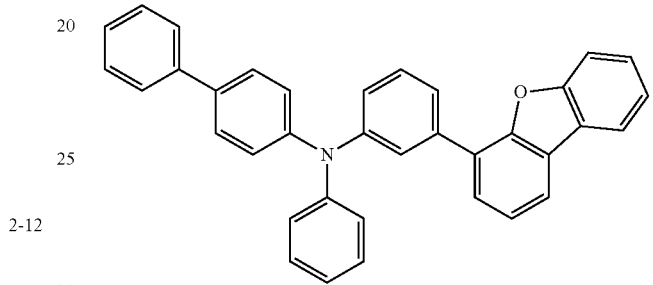
2-18
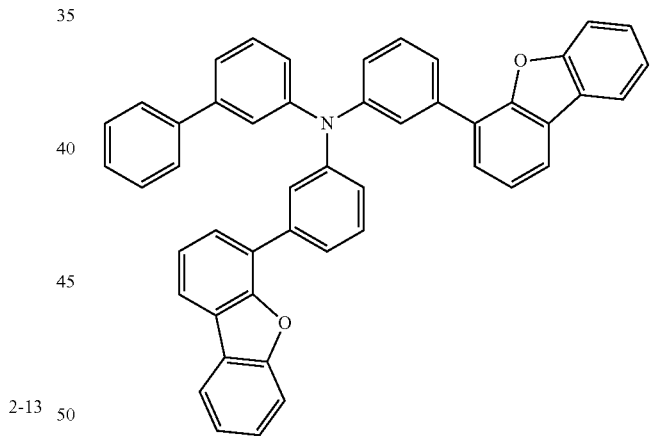
2-20

2-21
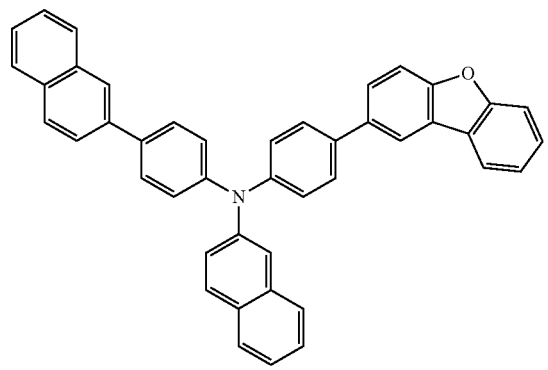
2-25
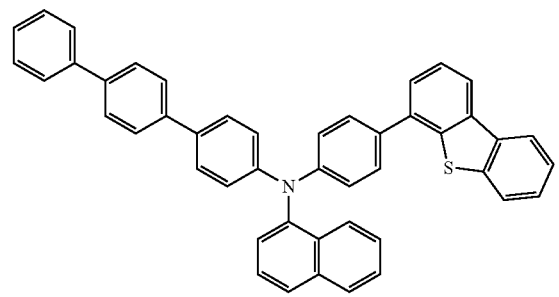
2-22
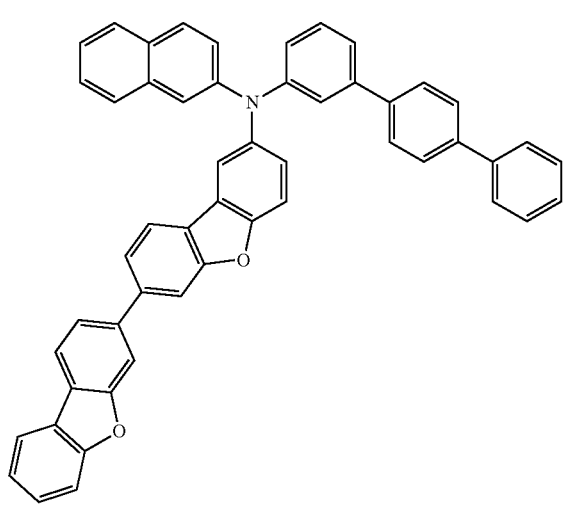
2-27
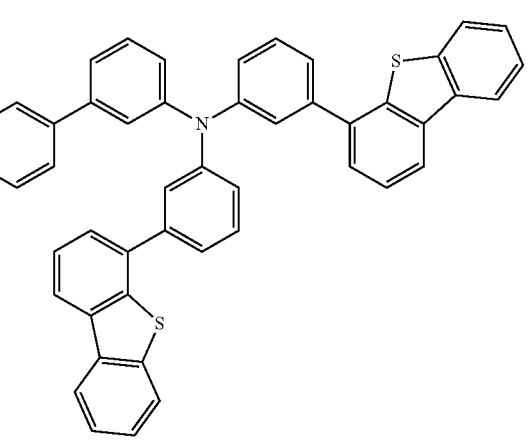
2-23
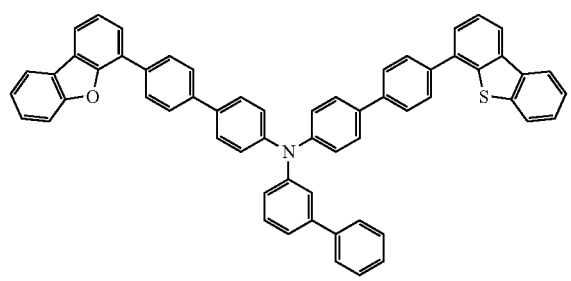
2-28
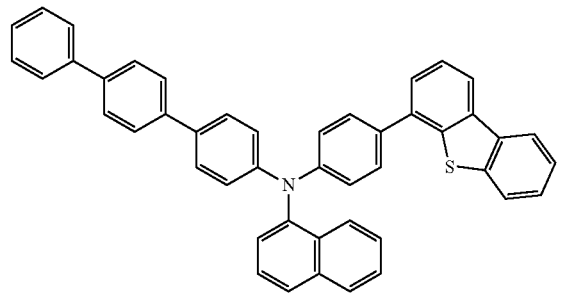
2-24
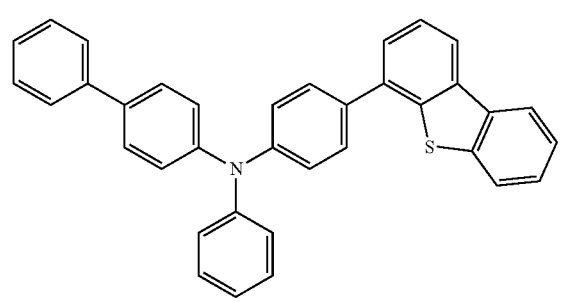
2-29
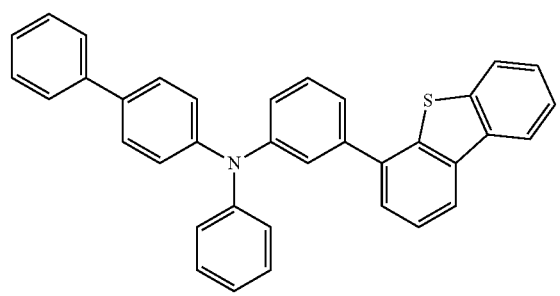

2-30
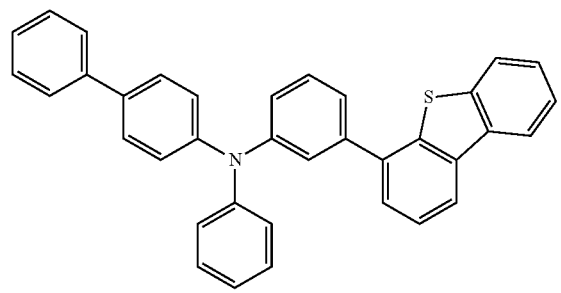
2-34
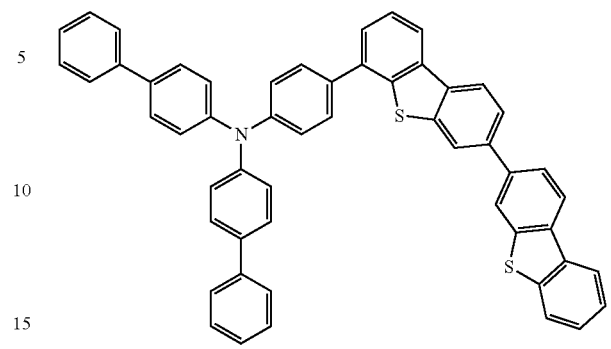
2-31
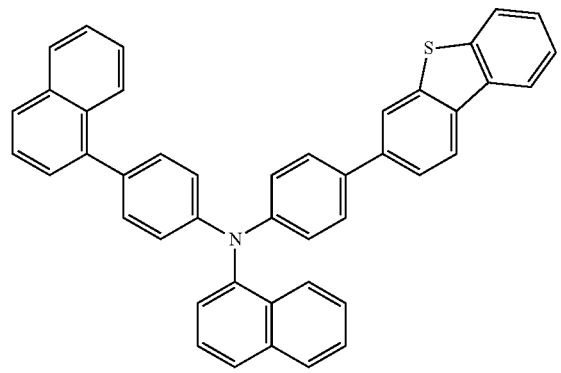
2-35
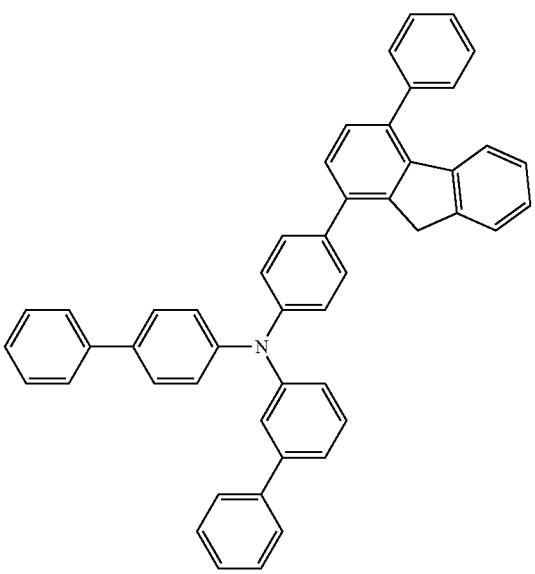
2-32
2-33
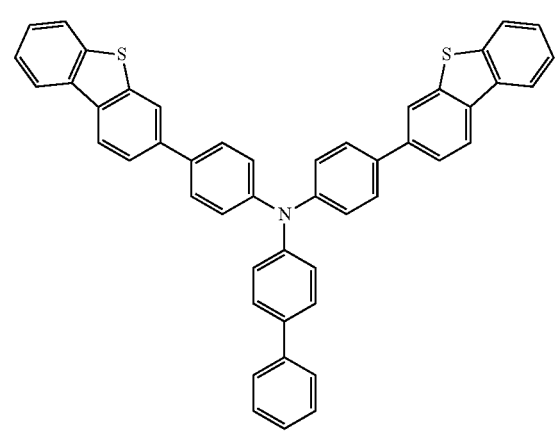
2-36
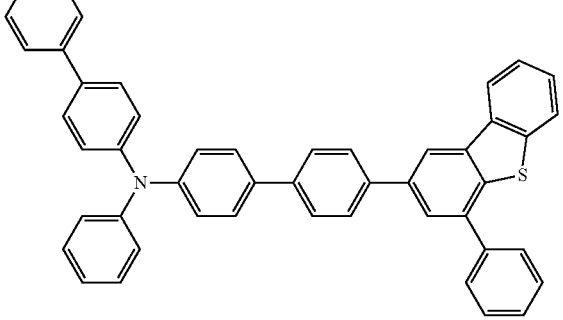

2-37
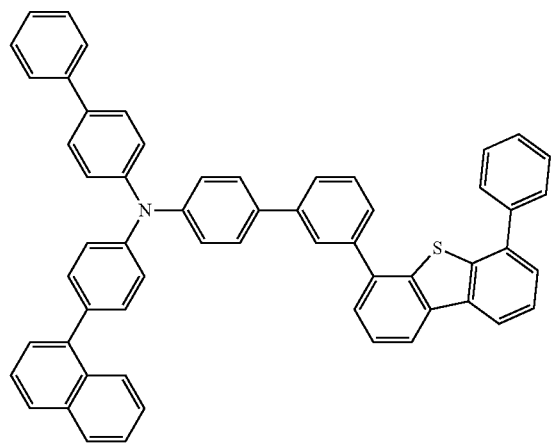
2-40
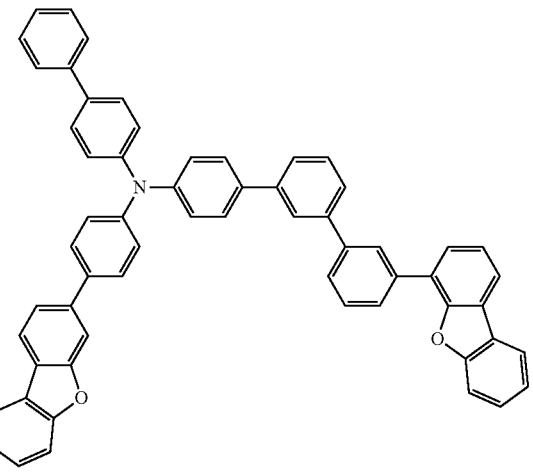
2-38
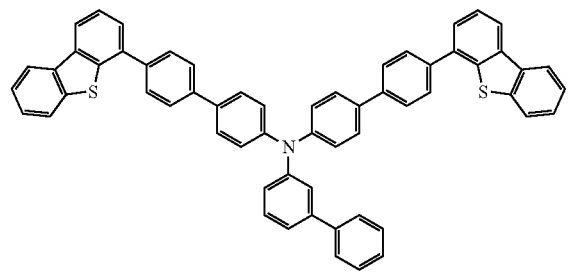
2-41
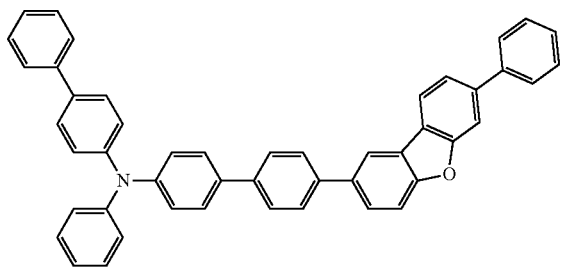
2-39
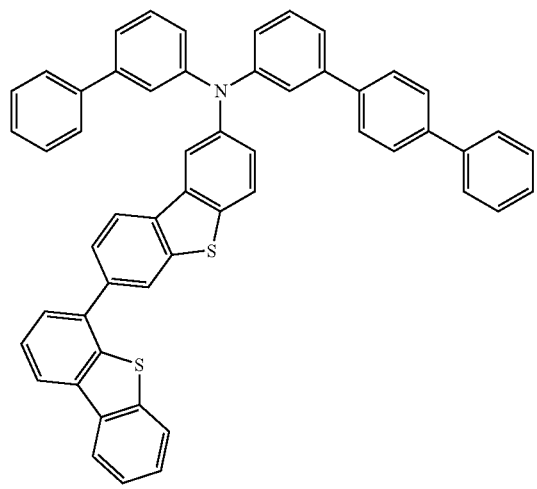
2-42
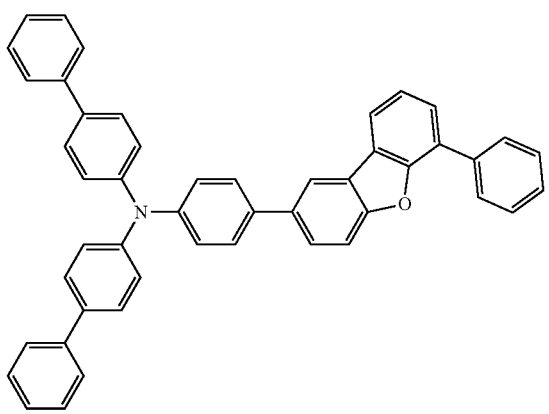

2-43
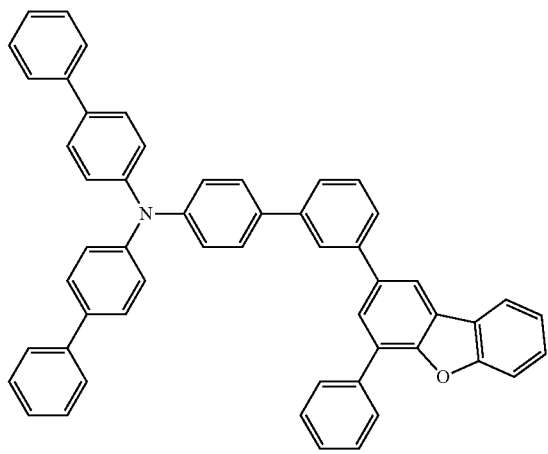
2-44
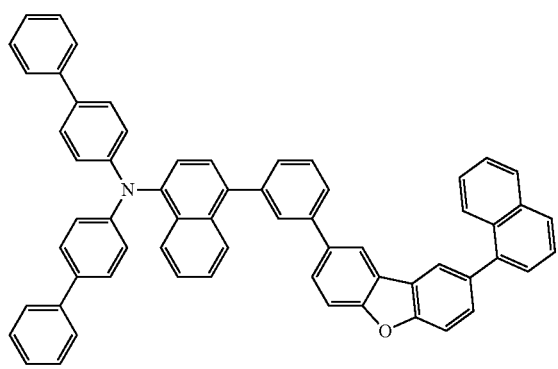
2-45
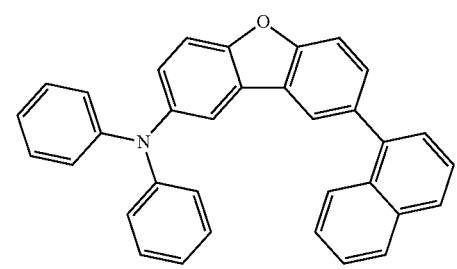
2-46
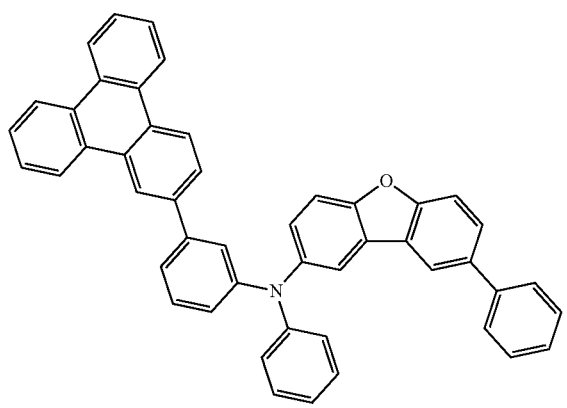
2-47
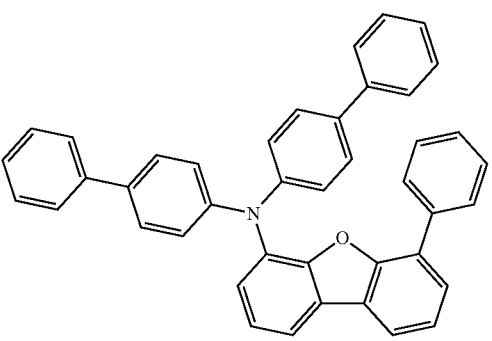
2-48
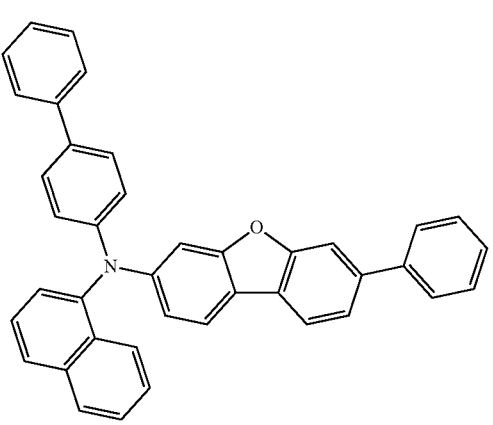
2-49
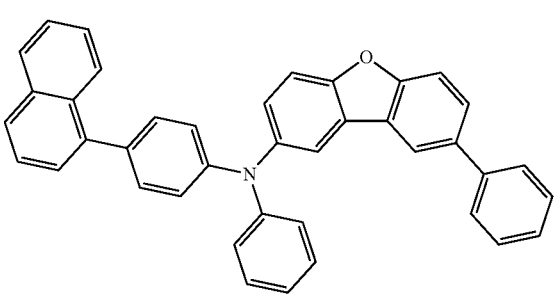
2-50
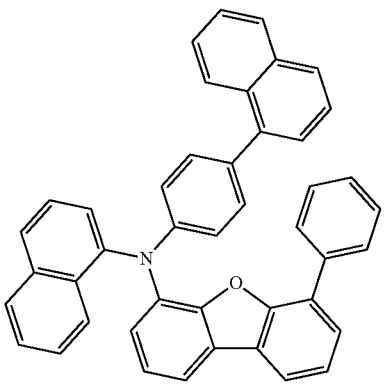

2-51
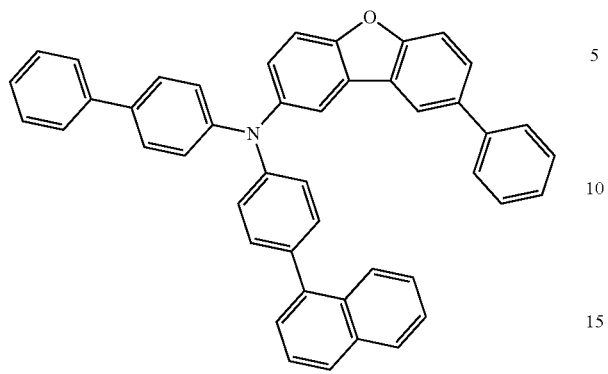
2-52
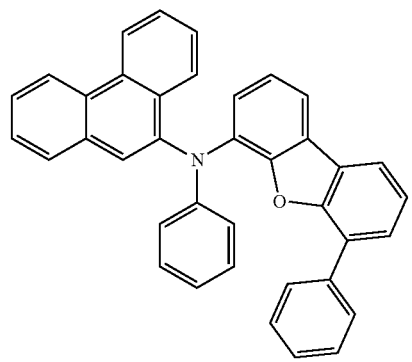
2-53
2-54
2-55
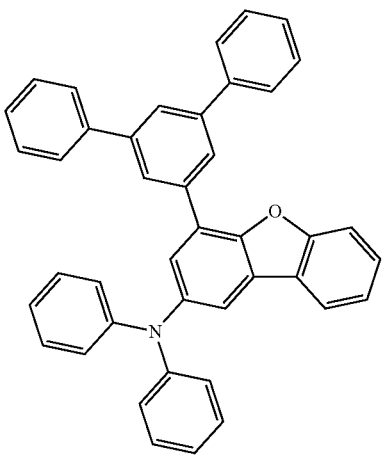
2-56
2-57
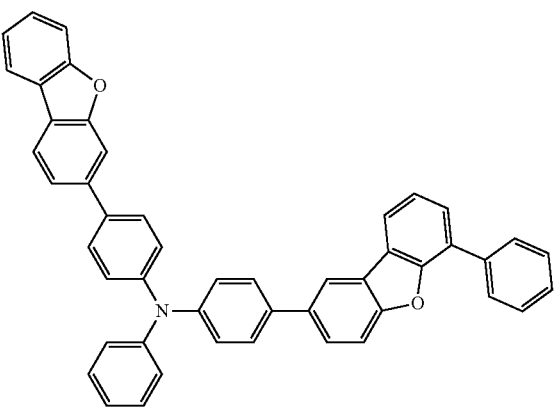

2-58
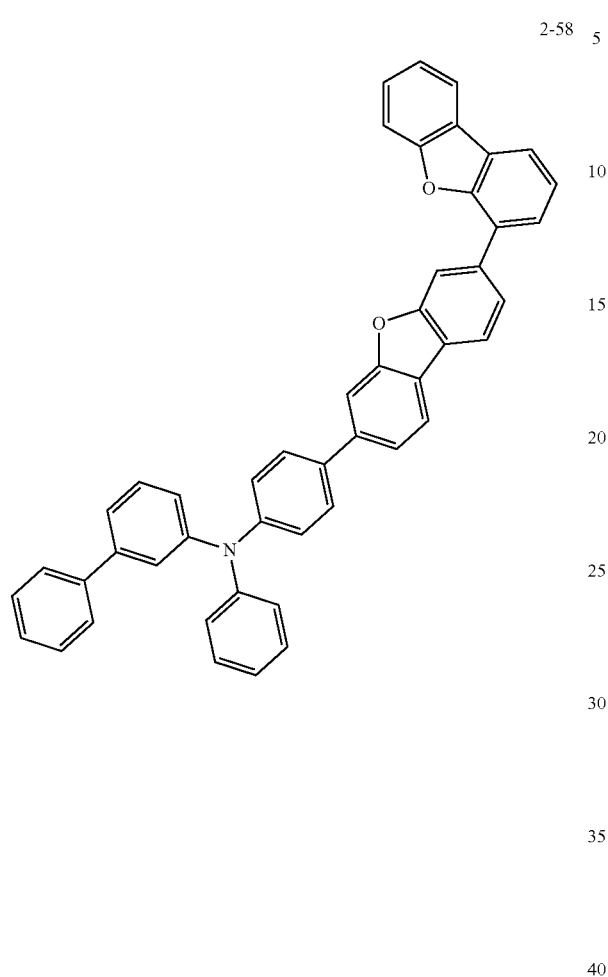
2-59
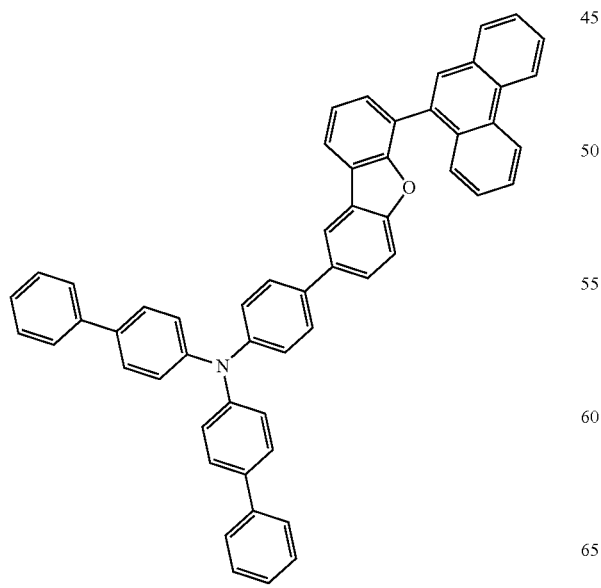
2-60
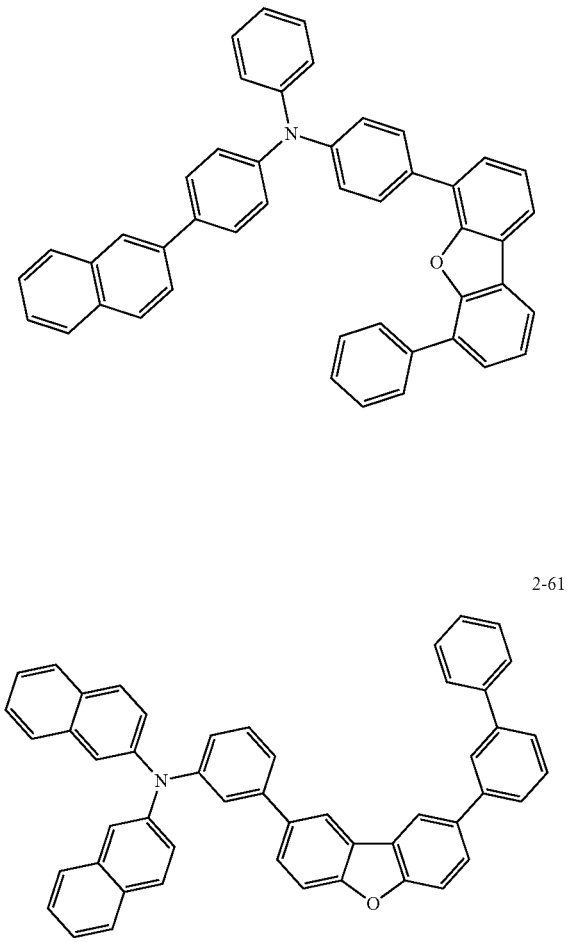
2-61
2-62
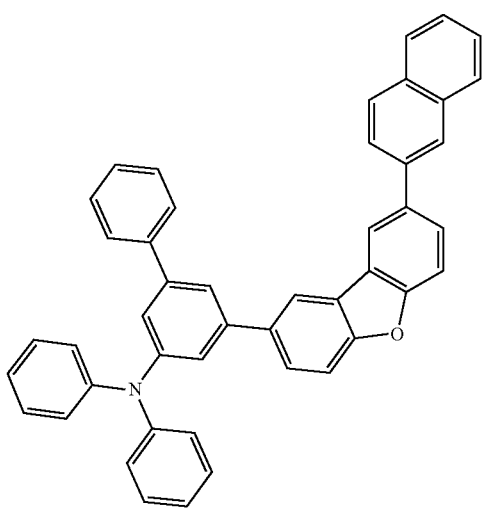

2-63
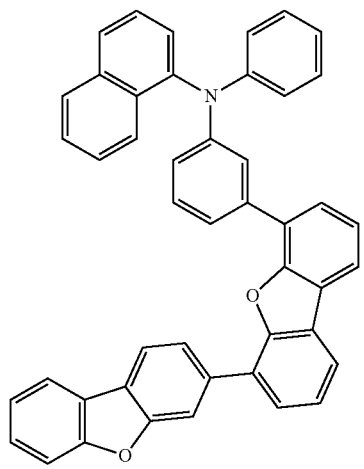
2-66
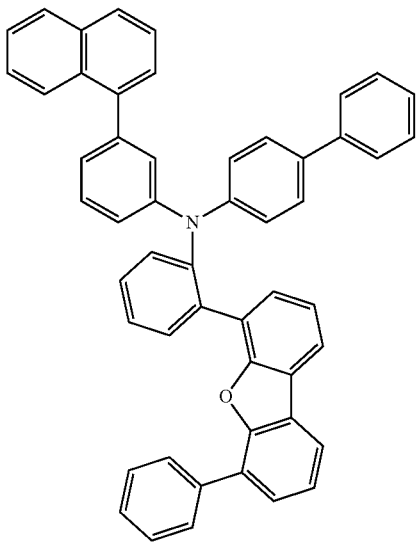
2-64
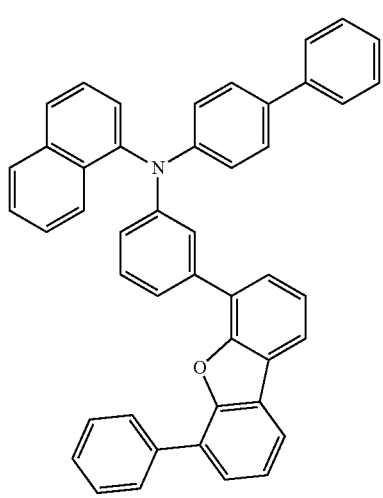
2-67
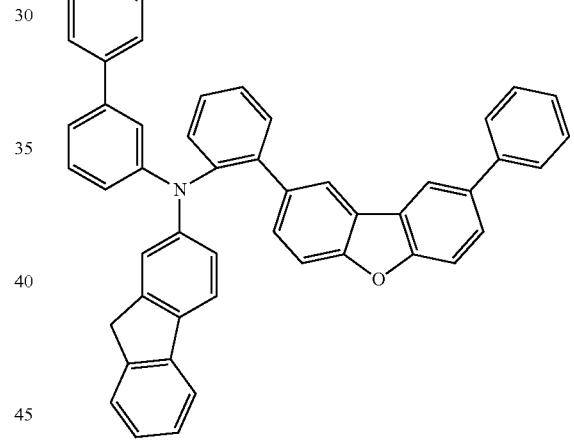
2-65
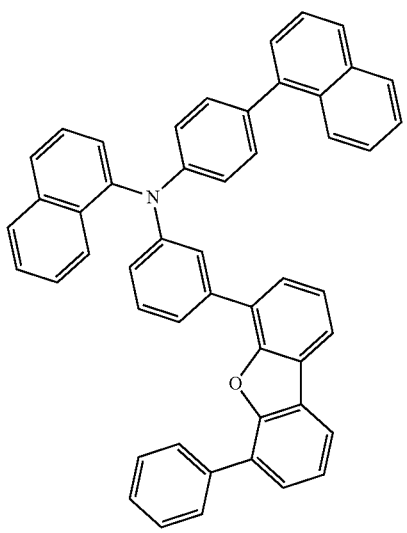
2-68
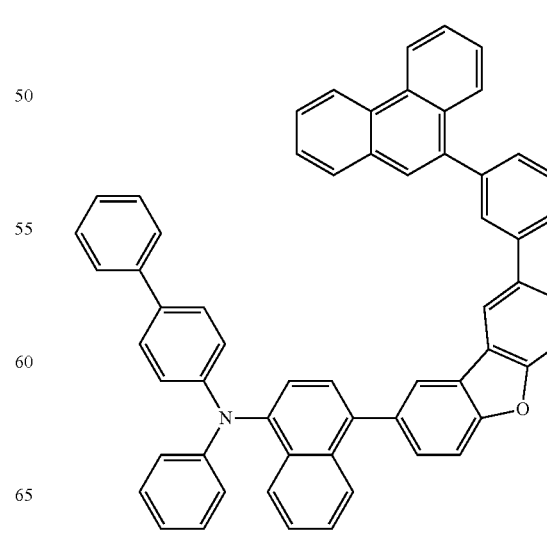

-continued
2-69
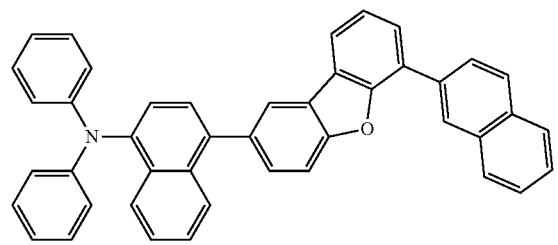
2-70
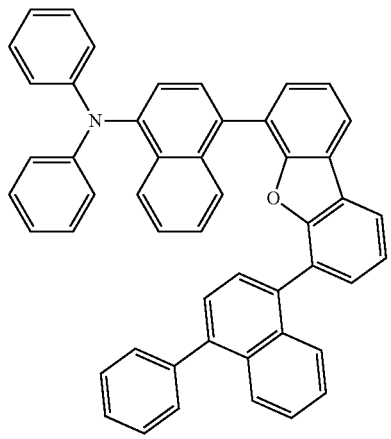
2-71
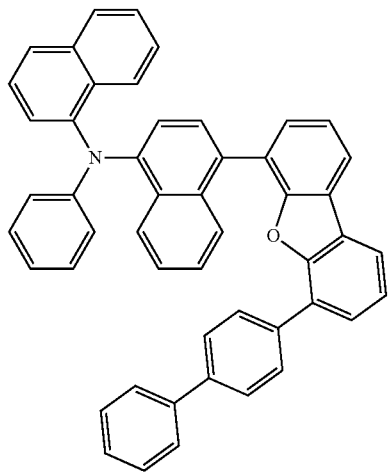
2-72
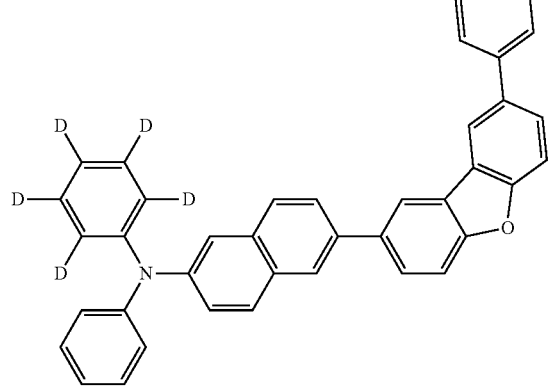
-continued
2-73
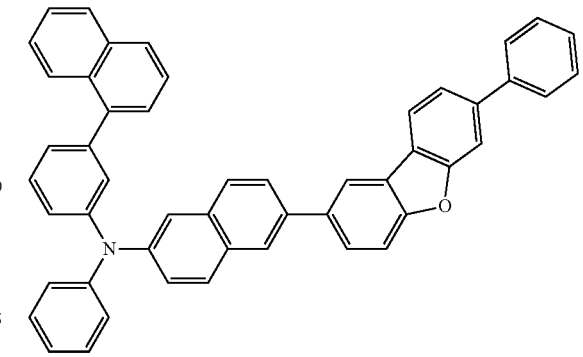
2-74
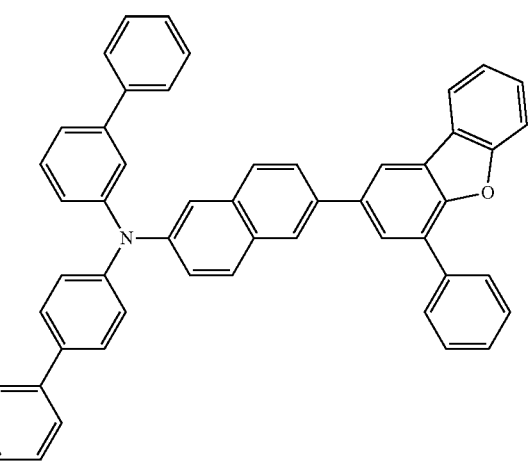
2-75
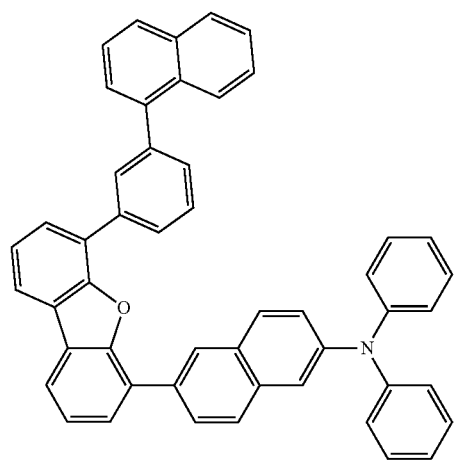

2-76
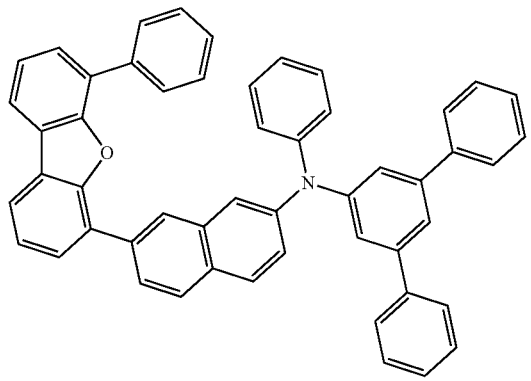
2-80
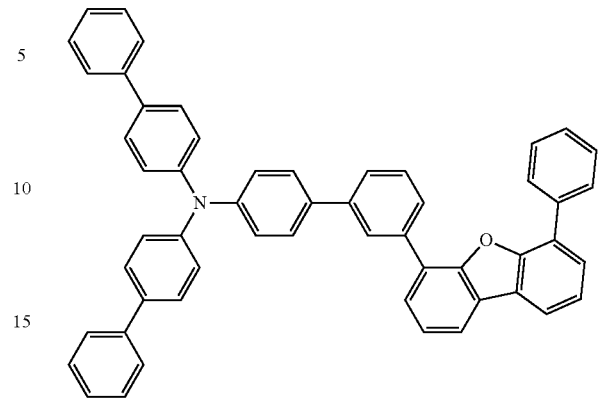
2-77
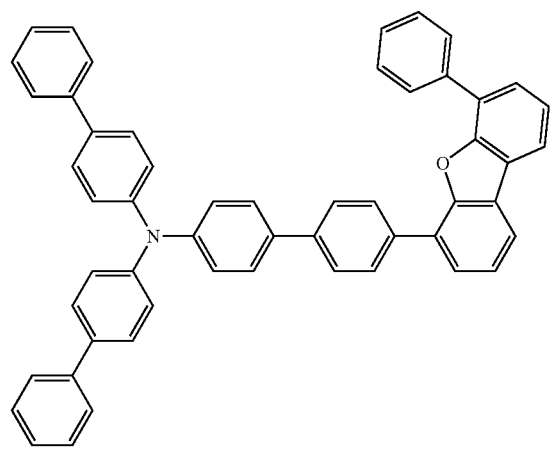
2-81
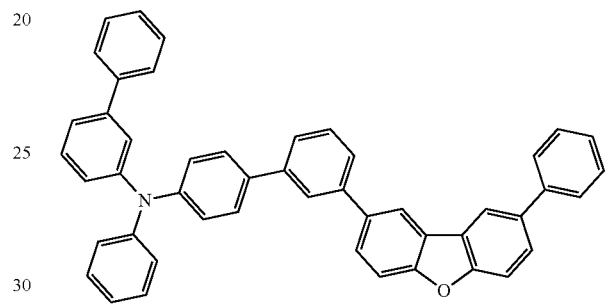
2-78
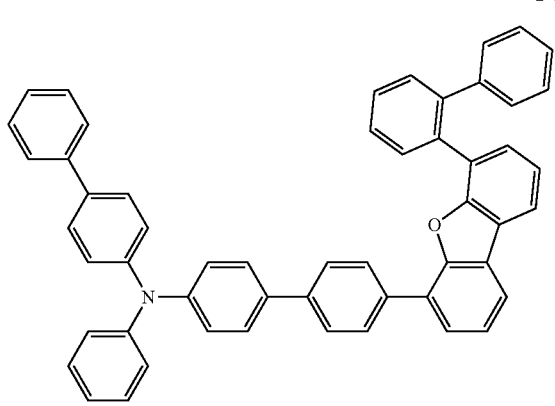
2-82
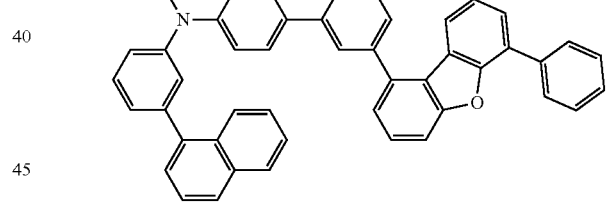
2-79
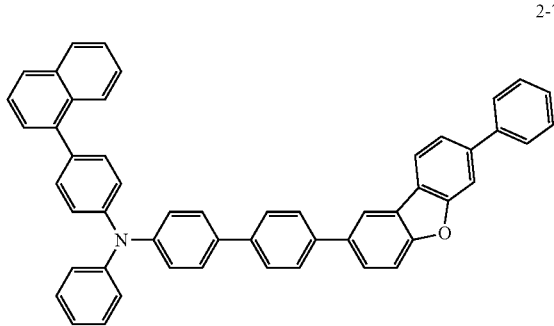
2-83
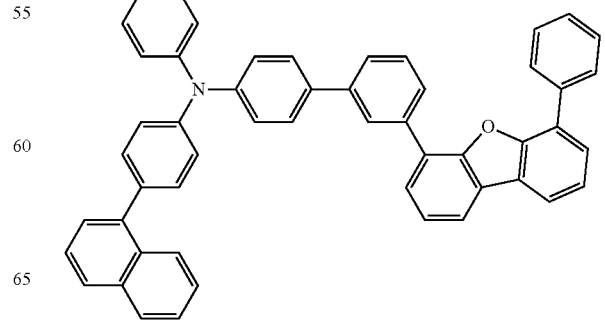

-continued
2-84
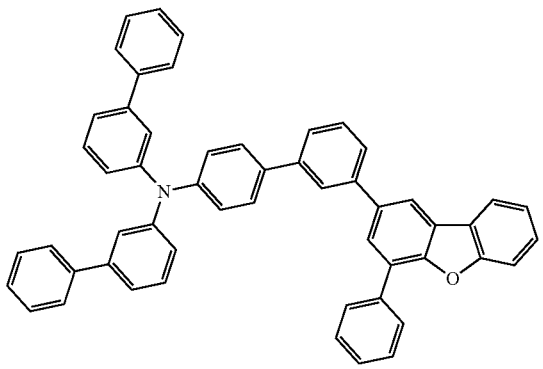
2-85
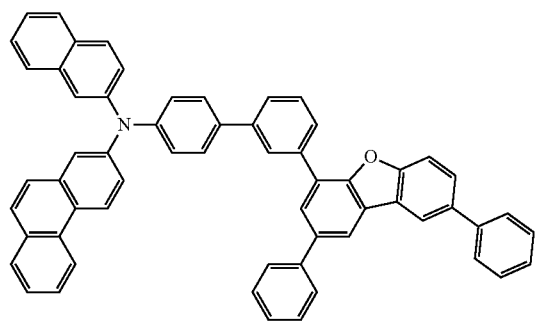
2-86
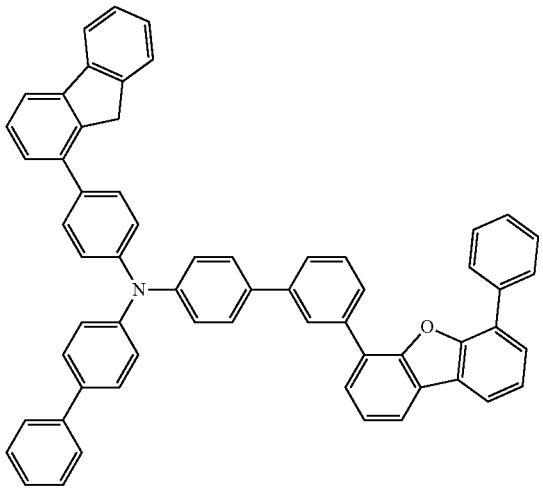
2-87
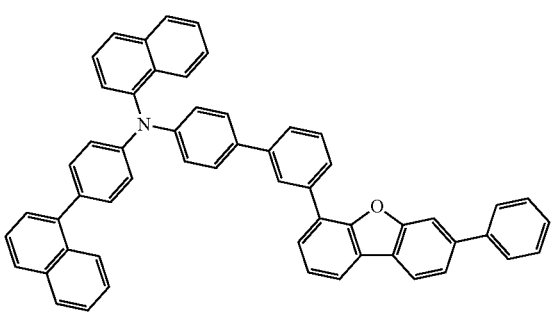
-continued
2-88
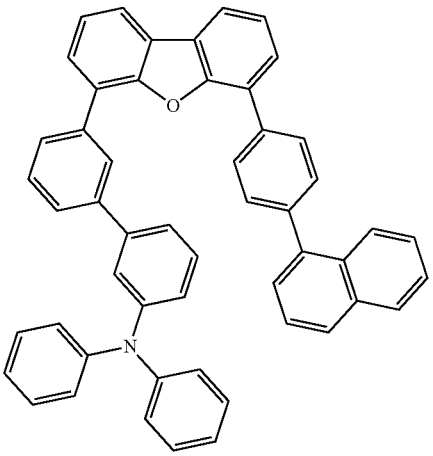
2-89
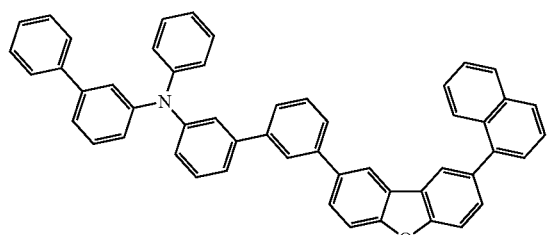
2-90
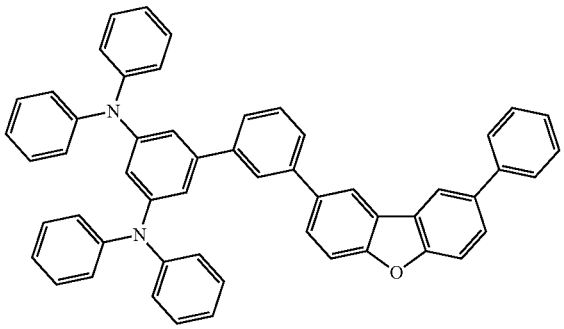
2-91
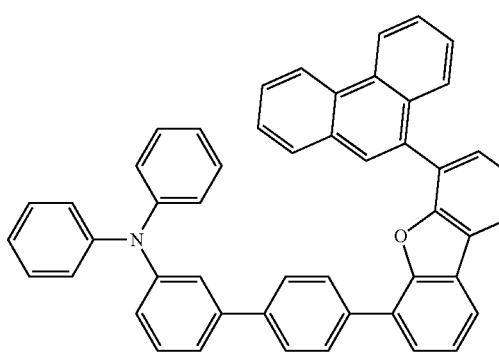

2-92
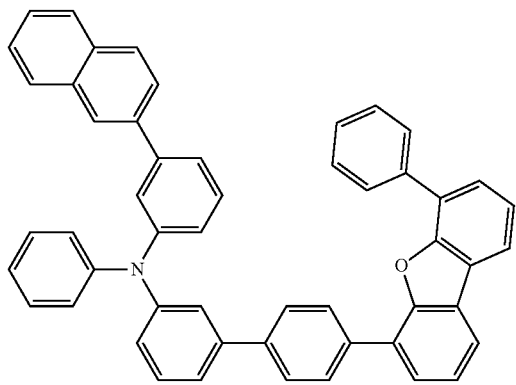
2-93
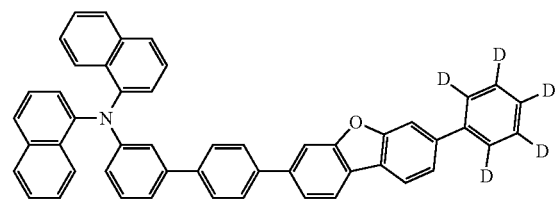
2-94
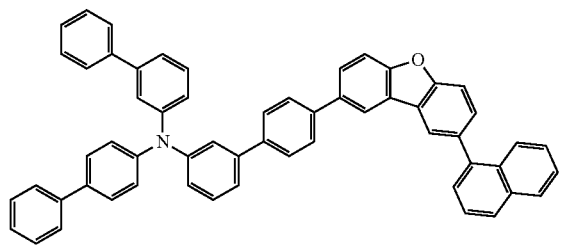
2-95
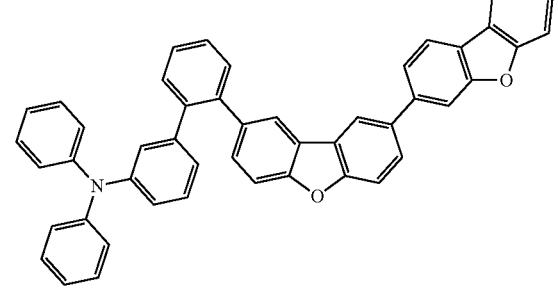
2-96
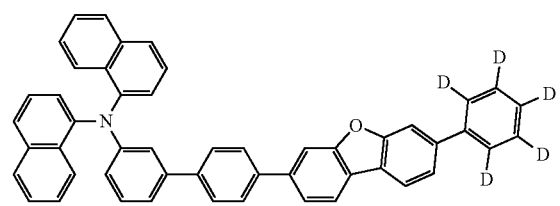
2-97
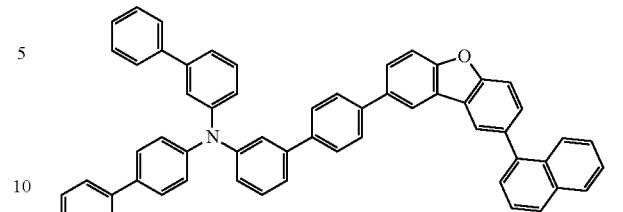
2-98
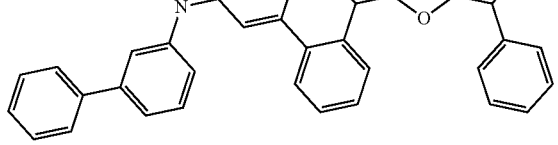
2-99
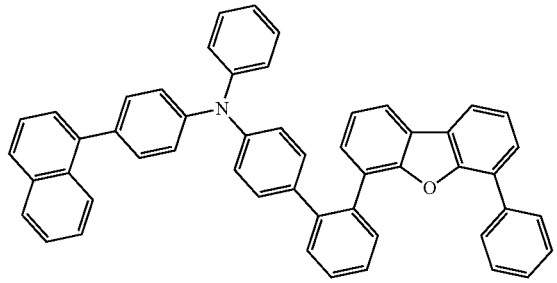
2-100
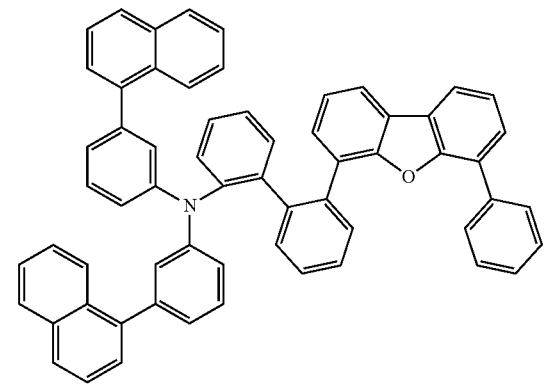
2-101

2-102
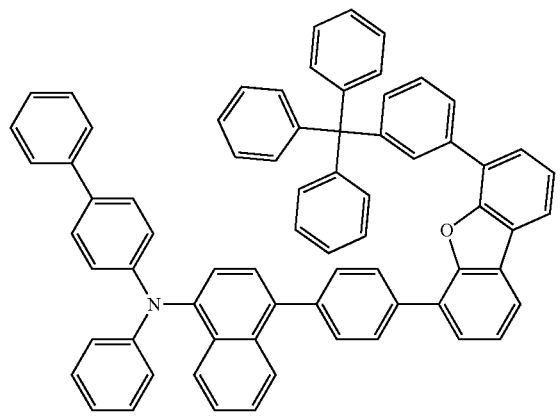
2-105
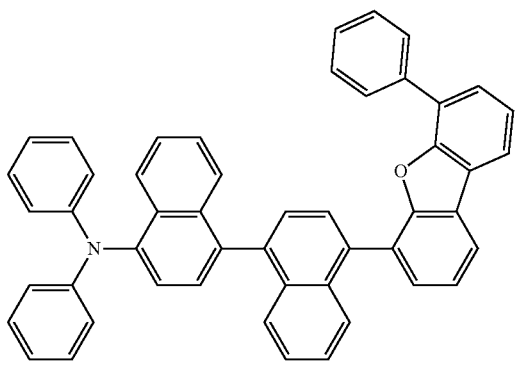
2-103
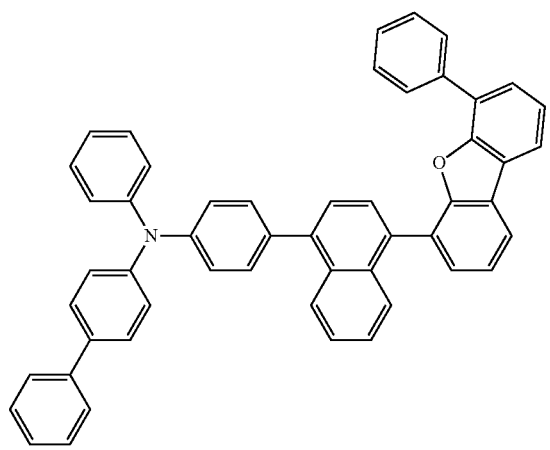
2-106
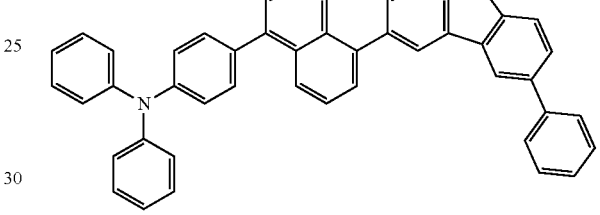
2-107
2-104
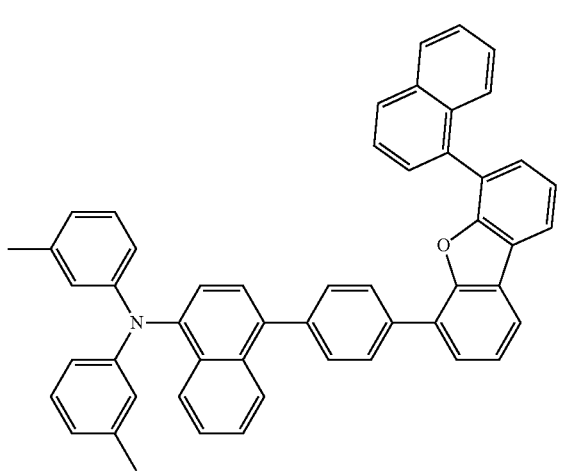
2-108
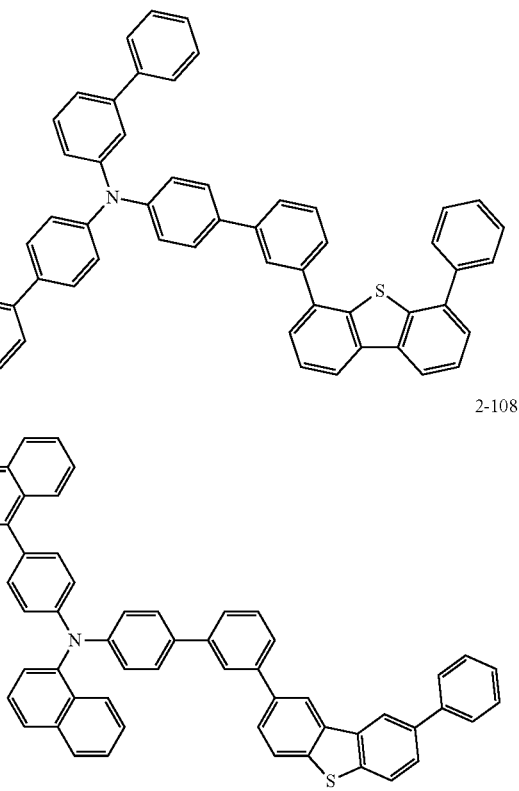

459
-continued
2-109
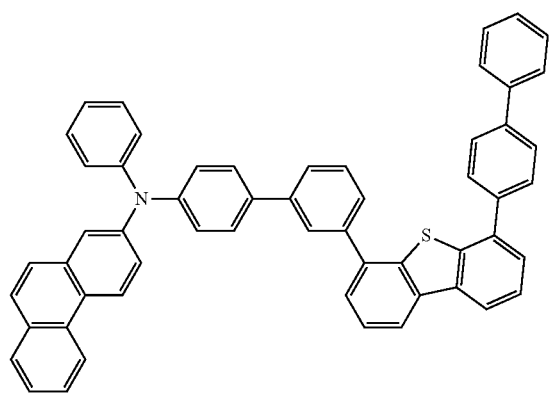
460
-continued
2-110
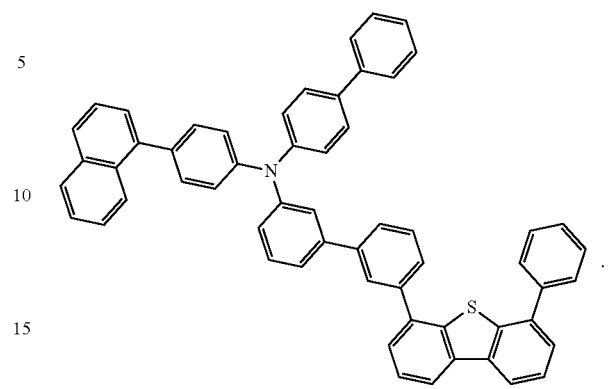
* * * * *